United States Patent
Sutkowski et al.

(10) Patent No.: US 9,709,574 B2
(45) Date of Patent: *Jul. 18, 2017

(54) HUMAN MONOCLONAL ANTIBODIES AND METHODS FOR PRODUCING THE SAME

(71) Applicant: MUSC Foundation for Research Development, Charleston, SC (US)

(72) Inventors: Natalie Sutkowski, Charleston, SC (US); Semyon Rubinchik, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/205,983

(22) Filed: Mar. 12, 2014

(65) Prior Publication Data

US 2014/0275492 A1    Sep. 18, 2014

Related U.S. Application Data

(63) Continuation of application No. 12/671,936, filed as application No. PCT/US2008/072124 on Aug. 4, 2008, now Pat. No. 8,715,743.

(60) Provisional application No. 60/953,739, filed on Aug. 3, 2007.

(51) Int. Cl.

| | | |
|---|---|---|
| C12N 5/10 | (2006.01) |
| C12N 5/00 | (2006.01) |
| C12N 5/02 | (2006.01) |
| G01N 33/68 | (2006.01) |
| C07K 16/00 | (2006.01) |
| C07K 16/10 | (2006.01) |
| C07K 16/12 | (2006.01) |
| C07K 16/16 | (2006.01) |
| C07K 16/22 | (2006.01) |
| C07K 16/24 | (2006.01) |
| C12N 5/0781 | (2010.01) |
| A61K 39/00 | (2006.01) |

(52) U.S. Cl.
CPC ......... *G01N 33/6854* (2013.01); *C07K 16/00* (2013.01); *C07K 16/1018* (2013.01); *C07K 16/1271* (2013.01); *C07K 16/16* (2013.01); *C07K 16/22* (2013.01); *C07K 16/244* (2013.01); *C12N 5/0635* (2013.01); *A61K 2039/505* (2013.01); *C07K 2317/21* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,464,465 A | 8/1984 | Lostrom | |
| 4,574,116 A | 3/1986 | Kaplan et al. | |
| 4,632,761 A | 12/1986 | Bowers et al. | |
| 4,634,664 A | 1/1987 | Oestberg | |
| 4,634,666 A | 1/1987 | Engleman et al. | |
| 4,693,975 A | 9/1987 | Kozbor et al. | |
| 4,804,627 A * | 2/1989 | Hammerling | C12N 5/0635 435/347 |
| 5,024,946 A | 6/1991 | Abe et al. | |
| 5,223,417 A * | 6/1993 | Dalla-Favera | C07K 14/82 435/326 |
| 5,229,275 A | 7/1993 | Goroff | |
| 5,534,423 A | 7/1996 | Palsson et al. | |
| 5,641,622 A | 6/1997 | Lake et al. | |
| 5,667,998 A | 9/1997 | Dougherty et al. | |
| 5,681,729 A | 10/1997 | Kudo et al. | |
| 5,702,892 A | 12/1997 | Mulligan-Kehoe | |
| 5,798,230 A | 8/1998 | Bornkamm et al. | |
| 5,814,318 A | 9/1998 | Lonberg et al. | |
| 5,874,085 A | 2/1999 | Mond et al. | |
| 5,906,928 A | 5/1999 | Dougherty et al. | |
| 5,939,598 A | 8/1999 | Kucherlapati et al. | |
| 6,884,613 B2 | 4/2005 | Le Doux et al. | |
| 6,900,052 B1 | 5/2005 | Ozaki et al. | |
| 7,592,170 B2 | 9/2009 | Le Doux et al. | |
| 7,741,077 B2 | 6/2010 | Grawunder et al. | |
| 7,807,415 B2 | 10/2010 | Groen et al. | |
| 7,960,145 B2 | 6/2011 | Paciotti et al. | |
| 2003/0059763 A1 | 3/2003 | Saxon et al. | |
| 2003/0165483 A1 | 9/2003 | Zimmermann et al. | |
| 2003/0180286 A1 | 9/2003 | Carmeliet et al. | |

(Continued)

FOREIGN PATENT DOCUMENTS

| | | |
|---|---|---|
| EP | 0 161 941 | 11/1985 |
| EP | 0 218 158 | 4/1987 |

(Continued)

OTHER PUBLICATIONS

Moosmann et al Blood, 2002, v.100 pp. 1755-1764.).*

(Continued)

*Primary Examiner* — Michail Belyavskyi

(74) *Attorney, Agent, or Firm* — Drinker Biddle & Reath LLP

(57) ABSTRACT

The present invention provides for methods of producing human monoclonal antibodies against a wide variety of antigens including bacterial and viral antigens, as well as tumor antigens, and various autoantigens. Also provided are the antibodies themselves, nucleic acids encoding such antibodies, cells producing such antibodies, and methods of using such antibodies for diagnostic assays and passive immunity against disease states such as infection and cancer.

18 Claims, 89 Drawing Sheets

(56) References Cited

U.S. PATENT DOCUMENTS

| | | | |
|---|---|---|---|
| 2005/0196755 | A1 | 9/2005 | Zauderer et al. |
| 2005/0208628 | A1* | 9/2005 | Duan ............... C07K 14/005 435/70.21 |
| 2006/0188502 | A1 | 8/2006 | Giles-Komar et al. |
| 2006/0252124 | A1 | 11/2006 | Li |
| 2007/0009510 | A1 | 1/2007 | Dertzbaugh |
| 2009/0270268 | A1 | 10/2009 | Funaro et al. |
| 2010/0021470 | A1 | 1/2010 | Lanzavecchia |
| 2010/0113745 | A1 | 5/2010 | Spits et al. |
| 2010/0248971 | A1 | 9/2010 | Inagaki et al. |
| 2011/0081642 | A1 | 4/2011 | Bachmann et al. |
| 2013/0115674 | A1 | 5/2013 | Sutkowski et al. |

FOREIGN PATENT DOCUMENTS

| | | |
|---|---|---|
| EP | 0454225 A1 | 10/1991 |
| EP | 1285577 A1 | 2/2003 |
| WO | WO 0020460 | 4/2000 |
| WO | WO 2004087914 | 3/2004 |
| WO | WO 2004/076677 | 9/2004 |
| WO | WO 2007/067046 A1 | 6/2007 |
| WO | WO 2007/068758 | 6/2007 |

OTHER PUBLICATIONS

Dorner et al., J of Virol., 2008, 82, pp. 4400-4412.*
Kotowitz et al., "Human immunoglobulin class and IgG subclass regulation: dual action of interleukin-4," Eur. J. Immunol., 1993, 23, pp. 2250-2256.
Malisan, et al., "Interleukin-10 Induces Immunoglobulin G Isotype Switch Recombination in Human CD40-Activated Naive B Lymphocytes," J. of Exper. Med., 1996, 183(9), pp. 937-947.
Patent Cooperation Treaty (PCT) International Preliminary Report on Patentability date of issuance Feb. 9, 2010.
Patent Cooperation Treaty (PCT) International Search Report including Written Opinion of the International Searching Authority dated Nov. 18, 2008.
Extended Search Report, EP Application No. 07971313 dated Mar. 25, 2013.
Duvall et al., "A novel platform to produce human monoclonal antibodies, the next generation of therapeutic human monoclonal antibodies discovery," MAbs 3(2) 203-208 (2011).
Sutkowski et al., "Production of fully human monoclonal antibodies to therapeutic self-antigenic targets (P3285)," The Journal of Immunology, 192(28)(2013)(abstract only).
Sullivan et al., Harnessing the Immune System's Arsenal: Producing Human Monoclonal Antibodies for Therapeutics and Investigating Immune Responses, F1000 Biology Reports 3(17) 2011.
Australian Office Action dated Jan. 18, 2013, for Australian Patent Application No. 2008284015.
Notice of Reasons of Rejection with English Language Translation dated Jul. 10, 2013, issued in Japanese Patent Application No. 2010-519273.
Hu et al., (J of Immunol, 2004, v. 173, pp. 2834-2841.
Chung et al., Clinical Immunol, 2010, v. 135, S137.
Agematsu et al., "Plasma cell generation from B-lymphocytes via CD27/CD70 interaction," Leuk. Lymphoma, 35:219-25, 1999.
Akahori et al., Homo sapiens IGL mRNA for immunoglobulin lambda light chain VLJ region, partial cds, clone:L66, GeneBank Accession No. AB064206.1, Jul. 2, 2002.
Arpin et al., "Generation of memory B cells and plasma cells in vitro," Science, 268:720-2, 1995.
Audigé et al., "Anti-HIV state but not apoptosis depends on IFN signature in CD4+T cells," J. Immunol., 177:227-37, 2006.
Bernasconi et al., "Maintenance of serological memory by polyclonal activation of human memory B cells," Science, 298:2199-202, 2002.
Bourke et al., "The toll-like receptor repertoire of human B lymphocytes: inducible and selective expression of TLR9 and TLR10 in normal and transformed cells," Blood, 102:956-63, 2003.
Cattoretti et al., "Stages of germinal center transit are defined by B cell transcription factor coexpression and relative abundance," J. Immunol., 177:6930-9, 2006.
Cerutti et al., "CD40 ligand and appropriate cytokines induce switching to IgG, IgA, and IgE and coordinated germinal center and plasmacytoid phenotypic differentiation in a human monoclonal IgM+IgD+B cell line," J. Immunol., 160:2145-57, 1998.
Chen et al., "Specific history of heterologous virus infections determines anti-viral immunity and immunopathology in the lung," Am. J. Pathol., 163:1341-55, 2003.
Choe et al., "Cellular and molecular factors that regulate the differentiation and apoptosis of germinal center B cells. Anti-Ig down-regulates Fas express of CD40 ligand-stimulated germinal center B cells and inhibits Fas-mediated apoptosis," J. Immunol., 157:1006-16, 1996.
Clute et al., "Cross-reactive influenza virus-specific CD8+ T cells contribute to lymphoproliferation in Epstein-Bar virus-associated infectious mononucleosis," J. Clin. Invest., 115:3602-12, 2005.
Combriato and Kloeck, "Ig lambda chain—human," GeneBank Accession No. S25752, Jan. 21, 2000.
Dechanet et al., "The ability of synoviocytes to support terminal differentiation of activated B cells may explain plasma cell accumulation in rheumatoid synovium," J. Clin. Invest., 95:456-63, 1995.
Ettinger et al., "IL-21 induces differentiation of human naïve and memory B cells into antibody-secreting plasma cells," J. Immunol., 175:7867-79, 2005.
Gansuvd et al., "Expansion of CD4+CD25+ suppressive *regulatory* T cells from rhesus macaque peripheral blood by FN18/antihuman CD28-coated Dynal beads," Hum. Immunol., 68:478-90, 2007.
Gearhart et al., "Successive switching of antibody isotypes expressed within the lines of a B-cell clone," Proc. Natl. Acad. Sci. USA, 77:5424-8, 1980.
Gosselin et al., "Epstein-Barr virus primes human polymorphonuclear leucocytes for the biosynthesis of leukotriene B4," Clin. Exp. Immunol., 126:494-502, 2001.
Hamilton-Williams et al., "Cutting edge: TLR ligands are not sufficient to break cross-tolerance to self-antigens," J. Immunol., 174:1159-63, 2005.
He et al., "Detection of H5 avian influenza viruses by antigen-capture enzyme-linked immunosorbent assay using HS-specific monoclonal antibody," Clin. Vaccine Immunol., 14:617-23, 2007.
Hodgkin et al., "Murine cytomegalovirus binds reversibly to mouse embryo fibroblasts: implications for quantitation and explanation of centrifugal enhancement," J. Virol. Methods, 22:215-30, 1988.
Hudson et al., "Cytomegalovirus infectivity: analysis of the phenomenon of centrifugal enhancement of infectivity," Virology, 72:235-43, 1976.
Hudson, "Further studies on the mechanism of centrifugal enhancement of cytomegalovirus infectivity," J. Virol. Methods, 19:97-108, 1988.
Huggins et al., "CpG DNA activation and plasma-cell differentiation of CD27- naive human B cells," Blood, 109:1611-9, 2007.
Jabara et al., "CD40 and IgE: synergism between anti-CD40 monoclonal antibody and interleukin 4 in the induction of IgE synthesis by highly purified human B cells," J. Exp. Med., 172:1861-4, 1990.
Johannessen et al., "Essential role for T cells in human B-cell lymphoproliferative disease development in severe combined immunodeficient mice," Br. J. Haernatol, 109:600-10, 2000.
Kanbe and Zhang, "A simple and quick method to concentrate MSCV retrovirus," Blood Cells Mol. Dis., 33:64-7, 2004.
Kim et al., "Production of polyclonal antibodies against peptide antigens using polystyrene beads as a carrier," Biotechnol. Lett., 29:1735-40, 2007.
Kindler and Zubler, "Memory, but not naive, peripheral blood B lymphocytes differentiate into Ig-secreting cells after CD40 ligation and costimulation with IL-4 and the differentiation factors IL-2, IL-10, and IL-3," J. Immunol., 159:2085-90, 1997.
Kozbor and Roder, "Requirements for the establishment of high-titered human monoclonal antibodies against tetanus toxoid using the Epstein-Barr virus technique," J. Immunol., 127:1275-80, 1981.
Kracker and Radbruch, "Immunoglobulin class switching: in vitro induction and analysis," Methods Mol. Biol., 271:149-59, 2004.

(56) References Cited

OTHER PUBLICATIONS

Lanzavecchia et al., "Understanding and making use of human memory .B cells," *Immunol. Rev.*, 211:303-9, 2006.

Miller and Lipman, "Release of infectious Epstein-Barr virus by transformed marmoset leukocytes," *Proc. Natl. Acad. Sci. USA*, 70:190-194, 1973.

Munch et al., "Detection and subtyping (H5 and H7) of avian type A influenza virus by reverse transcription-PCR and PCR-ELISA," *Arch. Virol.*, 146:87-97, 2001.

Murphy et al., "Antibodies to CD40 prevent Epstein-Barr virus-mediated human B-cell lymphomagenesis in severe combined immune deficient mice given human peripheral blood lymphocytes," *Blood*, 86:1946-53, 1995.

Nemerow and Cooper, "Isolation of Epstein Barr-virus and studies of its neutralization by human IgG and complement," *J. Immunol.*, 127:272-8, 1981.

O'Connor et al., "BCMA is essential for the survival of long-lived bone marrow plasma cells," *J. Exp. Med.*, 199:91-8, 2004.

O'Doherty et al., "Human immunodeficiency virus type 1 spinoculation enhances infection through virus binding," *J. Virol.*, 74:10074-80, 2000.

Poeck et al., "Plasmacytoid dendritic cells, antigen, and CpG-C license human B cells for plasma cell differentiation and immunoglobulin production in the absence of T-cell help," *Blood*, 103:3058-64, 2004.

Pugh-Bernard et al., "Regulation of inherently autoreactive VH4-34 B cells in the maintenance of human B cell tolerance," *J. Clin. Invest.*, 108:1061-70, 2001.

Rabin et al., "Loss of CD23 is a consequence of B-cell activation. Implications for the analysis of B-cell lineages," *Ann. N.Y. Acad. Sci.*, 651:130-42, 1992.

Rowe et al., "Detection of antibody to avian influenza A (H5N1) virus in human serum by using a combination of serologic assays," *J. Clin. Microbiol*, 37:937-43, 1999.

Sadek et al., "Ebola hemorrhagic fever, Democratic Republic of the Congo, 1995: determinants of survival," *J. Infect. Dis.*, 179(Suppl. 1):S24-7, 1999.

Sanyal and Schuening, "Increased gene transfer into human cord blood cells by centrifugation-enhanced transduction in fibronectin fragment-coated tubes," *Hum. Gene. Ther.*, 10:2859-68, 1999.

Sia et al., "Optimal purification method for Herpes-based viral vectors that confers minimal cytotoxicity for systemic route of vector administration," *J. Virol. Methods*, 139:166-74, 2007.

Simmons et al., "Prophylactic and therapeutic efficacy of human monoclonal antibodies against H5N1 influenza," *PLoS Med.*, 4:e178, 2007.

Speck et al., "Epstein-Barr virus lacking latent membrane protein 2 immortalizes B cells with efficiency indistinguishable from that of wild-type virus," *J. Gen. Virol*, 80(Pt. 8):2193-203, 1999.

Stauffer et al., "Interferon-alpha-induced endogenous superantigen. a model linking environment and autoimmunity," *Immunity*, 15:591-601, 2001.

Stashenko et al., "Expression of cell surface markers after human B lymphocyte activation," *Proc. Natl. Acad. Sci. USA*, 78:3848-52, 1981.

Steinitz et al., "EB virus-induced B lymphocyte cell lines producing specific antibody," *Nature*, 269:420-2, 1977.

Sutkowski et al., "An Epstein-Barr virus-associated superantigen," *J. Exp. Med.*, 184:971-80, 1996.

Sutkowski et al., "Epstein-Barr virus latent membrane protein LMP-2A is sufficient for transactivation of the human endogenous retrovirus HERV-K1 8 superantigen," *J. Virol.*, 78:7852-60, 2004.

Sutkowski et al., "Epstein-Barr virus transactivates the human endogenous retrovirus HERV-K18 that encodes a superantigen," *Immunity*, 15:579-89, 2001.

Traggiai et al., "An efficient method to make human monoclonal antibodies from memory B cells: potent neutralization of SARS coronavirus," *Nat. Med.*, 10:871-5, 2004.

Veronese et al., "Lymphoproliferative disease in human peripheral blood mononuclear cell-injected SCID mice. I. T lymphocyte requirement for B cell tumor generation," *J. Exp. Med.*, 176:1763-7, 1992.

Welschof et al., "Amino acid sequence based PCR primers for amplification of rearranged human heavy and light chain immunoglobulin variable region genes," *J. Immunol. Methods*, 179:203-14, 1995.

Yune et al., "Medical imaging in cochlear implant candidates," *Am. J. Otol.*, 12 Suppl:11-7, discussion 18-21, 1991.

Australian Office Action dated Feb. 23, 2015, for Australian Patent Application No. 2014213523.

* cited by examiner

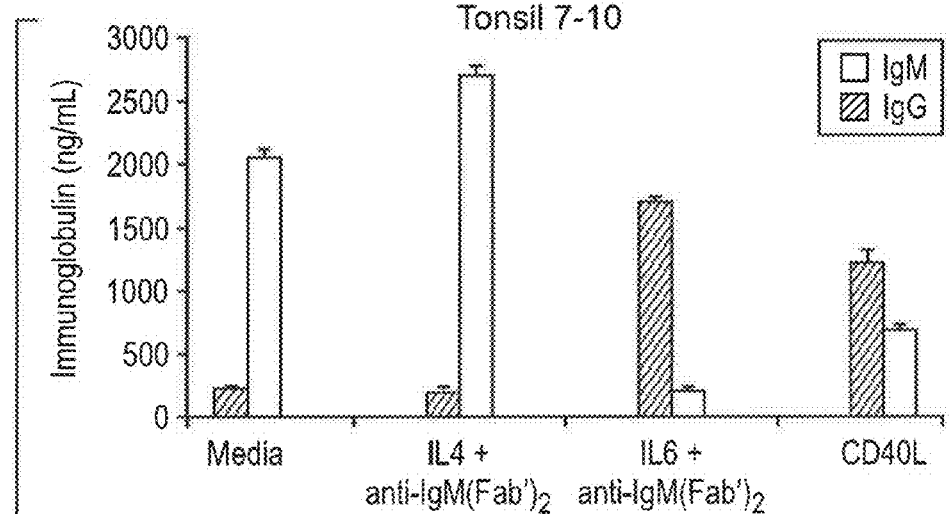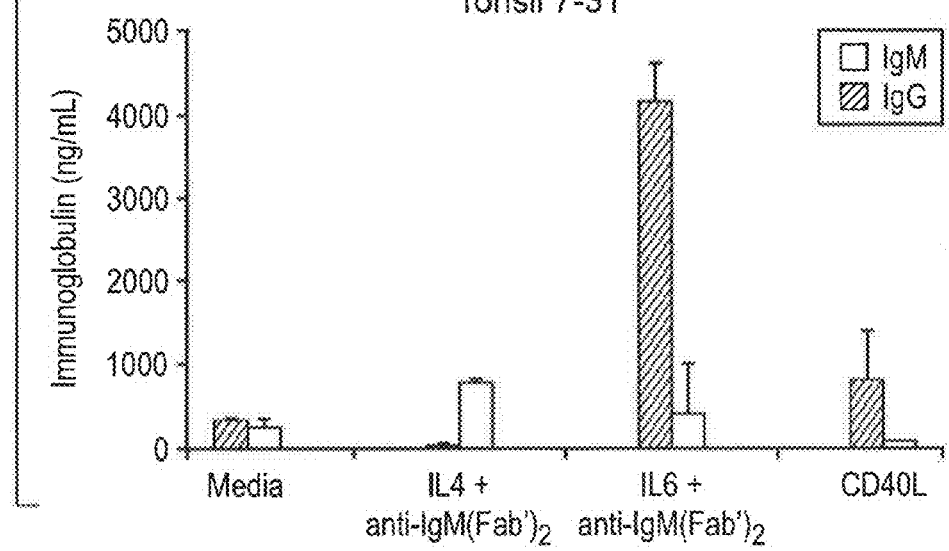
FIG. 5A

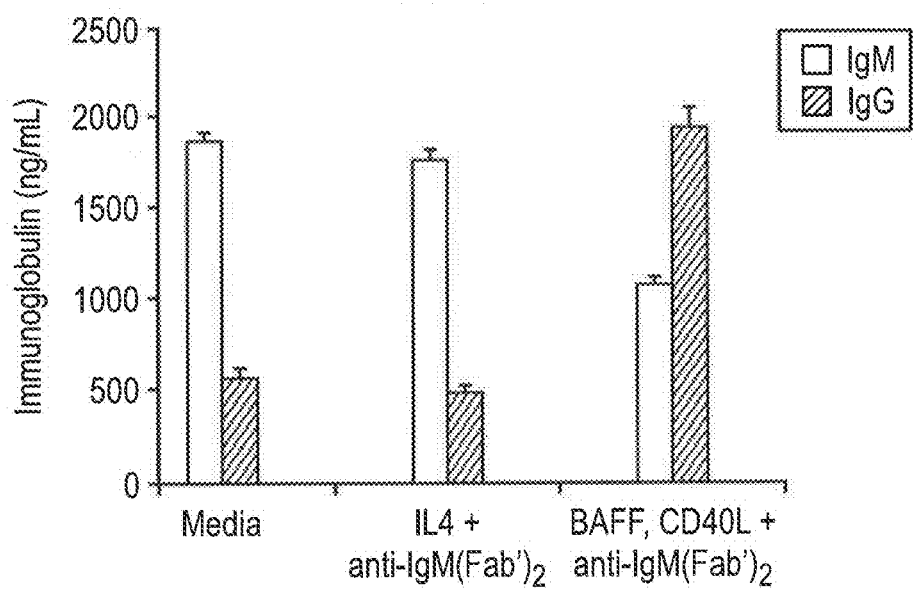

| | | | 4 | | 6 | |
|---|---|---|---|---|---|---|
| — | — | — | — | + | — | Week 1 (3-22) |
| — | — | | + | E | + | Week 2 rows (3-30) |
| | D+/- | | G | 1,2 | C | Week 3 rows |
| | — | | 8 | 1 | 2 | and wells (4-3) |
| | 1 10 100 1000 | | | 1 10 100 1000 | 1 10 100 1000 | Week 4 Subclone (4-11) |
| | — — — — | | | — — — — | — — — — | Week 5 (4-16) |
| | — — — +/- | | | — — — — | — +/- — — | Week 6 (4-19) |
| | — + — — | | | — — — — | — +/- — | Week 7 (4-25) |
| | — E | | | +/- — — — | — G | Week 8 (5-2) |
| | — — | | | +/- — — — | — 8 | Week 9 (5-7) |

PBMC A2: H5 HA ELISA analysis

FIG. 15

TNSL A: H5 HA ELISA analysis

| | 1 | 2 | 3 | 4 | 5 | 6 | 7 | 8 | 9 | 10 |
|---|---|---|---|---|---|---|---|---|---|---|
| Week 1 plates (2-8) | – | – | – | – | – | – | – | – | – | – |
| Week 2 rows and plates (2-15) | – | – | – | – | – | +/- | – | – | + | – |
| Week 3 rows and plates (2-22) | – | – | – | – | – | – | – | – | C,F | – |

*Sample lost due to fungal contamination

FIG. 16

TNSL B: H5 HA ELISA analysis

| | 1 | 2 | 3 | 4 | 5 | 6 | 7 | 8 | 9 | 10 |
|---|---|---|---|---|---|---|---|---|---|---|
| Week 1 (4-3) | — | — | + | — | — | — | — | — | — | — |
| Week 2 plates and rows (4-11) | — | — | D+/- | — | — | — | — | — | — | — |
| Week 3 plates and wells (4-18) | — | — | — | — | — | — | — | — | — | — |
| Week 4 plates and wells (4-25) | — | — | — | — | — | — | — | — | — | — |

FIG. 17

| | 1 | 2 | 3 | 4 | 5 | 6 | 7 | 8 | 9 | 10 |
|---|---|---|---|---|---|---|---|---|---|---|
| Week 1 plates (4-19) | — | — | — | — | — | — | +/- | +/- | +/- | +/- |
| Week 2 plates and wells (4-25) | — | — | — | — | — | — | — | — | — | — |
| Week 3 plates and wells (5-2) | — | — | — | — | — | — | — | — | — | — |

TNSL C: Subcloning Scheme

TNSL D: H5 HA ELISA analysis

| | 1 | 2 | 3 | 4 | 5 | 6 | 7 | 8 | 9 | 10 |
|---|---|---|---|---|---|---|---|---|---|---|
| Week 1 (4-26) | — | — | — | — | — | — | — | — | — | — |
| Week 2 (5-3) | + | — | — | — | — | — | + | + | | ++ |
| Week 3 rows wells (5-9) | +/- | — | — | — | — | — | — | +/- | +/- | G 3 [4] |
| Week 4 (5-15) subclones | — | — | — | — | — | — | — | — | | 1 10

| Primer | Sequence (5' → 3') |
|---|---|
| λ1-xba | TCTAGACAGTCTGTGYTGACKCAGCCGCCCTCA |
| λ2/5-xba | TCTAGACAGTCTGCGCTGACTCARCCGSCCTCT |
| λ3-xba | TCTAGATCCTATGAACTGACTCAGCCACCYT |
| λ4a-xba | TCTAGATCTGAACTGACTCAGCCDSCCTC |
| λ4b-xba | TCTAGATCTGAACTGACTCAGGACCCTGYT |
| λ6-xba | TCTAGARATTTTATGCTGACTCAGCCCCACTCT |
| Clλ-sal | GTCGACAGAGGASGGYGGGAACAGAGTGAC |
| κ1/4-xba | TCTAGAC ATCSRGATGACCCAGTCTCC |
| κ2-xba | TCTAGATATTGTGATGACYCAGWCTCCACTCT |
| κ3-xba | TCTAGAAATTGTRWTGACRCAGTCTCCA |
| CLκ-sal | GTCGACGAAGACAGATGGTGCAGCCACAGT |
| VH1-xba | TCTAGASAGGTGCAGCTGGTGCAGTCT |
| VH2-xba | TCTAGACAGGTRCAGCTGCAGSAGTC |
| VH3-xba | TCTAGAGGTGCAGCTGKTGGAGTCT |
| Chγ1-sal | GTCGACSGATGGGCCCTTGGTGGA |

WOBBLE CODE:
Y = C+T; R = A+G; K = G+T; S = C+G; W = A+T; D = A+G+T

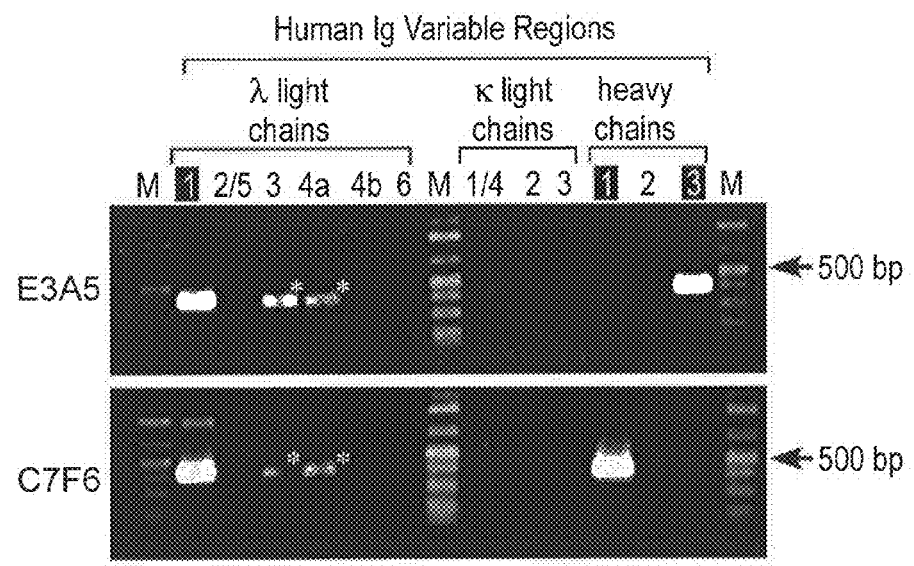

FIG. 34B

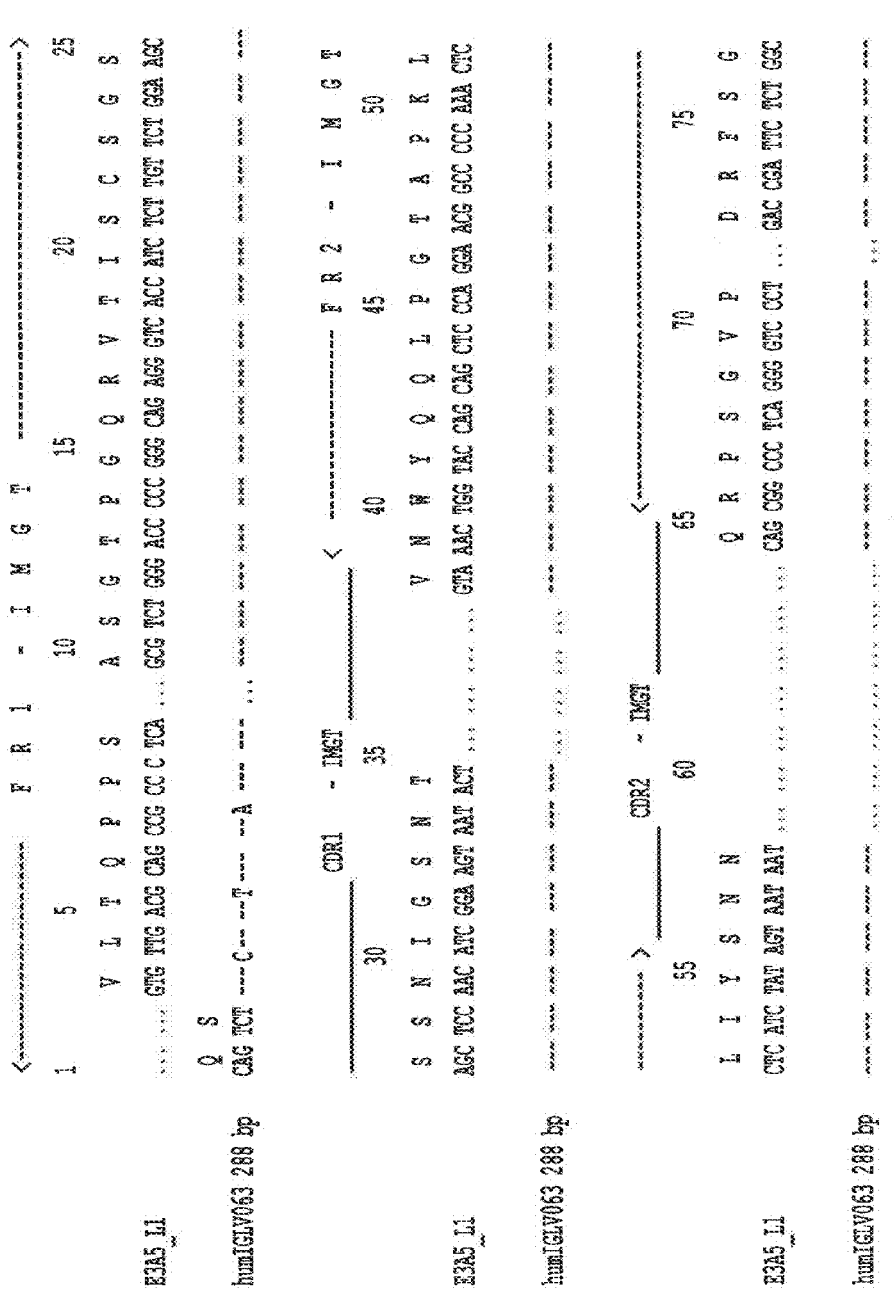
FIG. 35A1

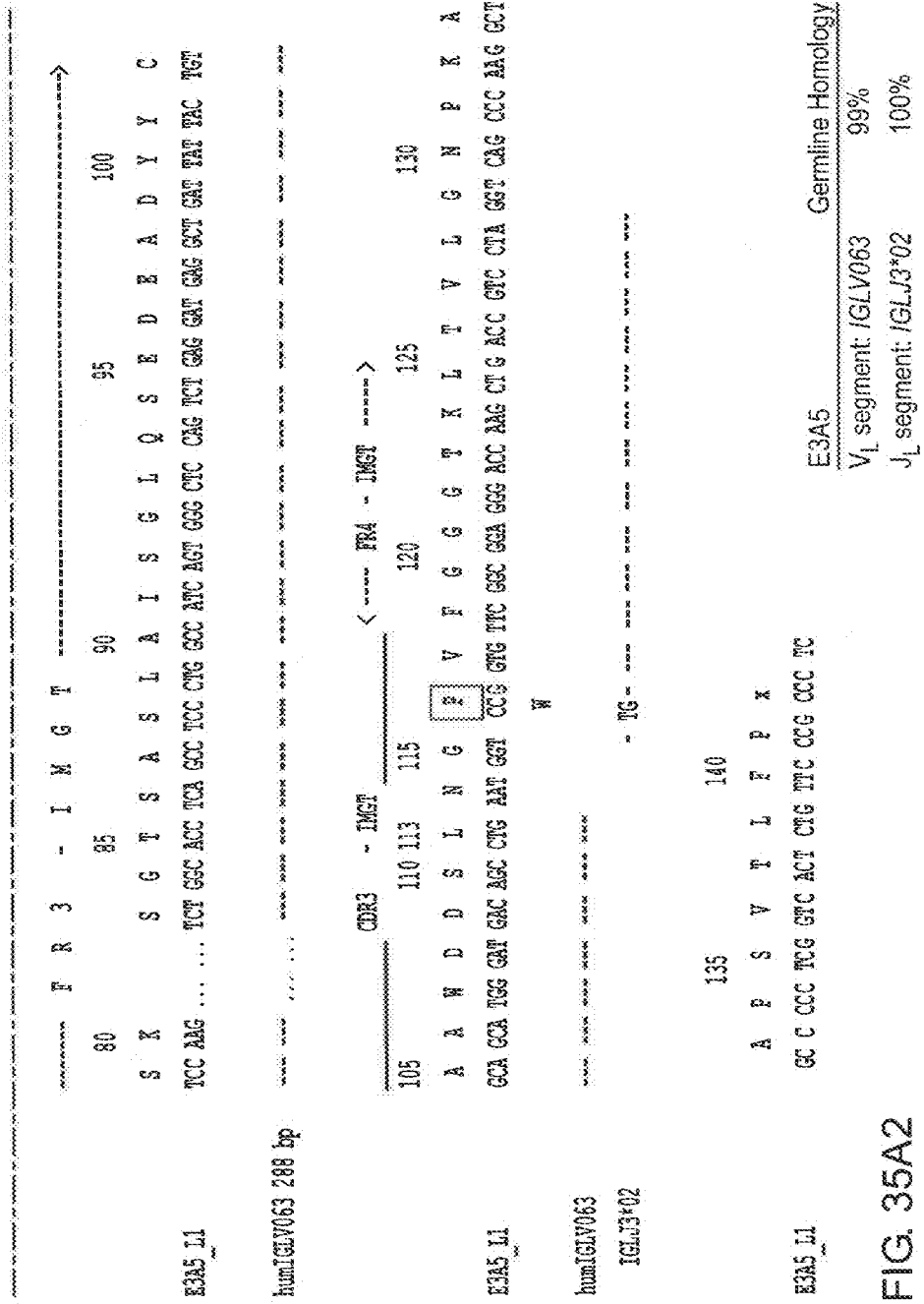
FIG. 35A2

FIG. 35B1

```
                          <------------------- F R 1 - I M G T ----------------->
            1           5              10             15           20            25
            X  L  T  Q  P  P  S       V  S  G  A  P  G  Q  R  V  T  I  S  C  T  G  S
CTF6_l1    ..G TTG ACG CAG CCG CCC TCA .... GTG TCT GGG GCC CCA GGG CAG AAG GTC ACC ATC TCC TGC ACT GGG AGC
            Q  S  V                                           R
humIGLV067 291 bp  CAG TCT GT- C---  ----  ----  ----  ----  ----  ---G- ----  ----  ----  ----  ----  ----

<-- CDR1 - IMGT -->              <-------- F R 2 - I M G T -------->
                   30              35              40              45              50
            S  S  N  I  G  A  G  Y  D           V  H  W  Y  Q  Q  L  P  G  T  A  P  K  L
CTF6_l1    AGC TCC AAC ATC GGG GCA GGT TAT GAT ...... GTA CAC TGG TAC CAG CAG CTT CCA GGA ACA GCC CCC AAA CTC
humIGLV067 291 bp  ----  ----  ----  ----  ----  ----  ----  ----  ...... ----  ----  ----  ----  ----  ----

<--- CDR2 - IMGT --->
              55              60              65              70              75
            L  I  Y  G  N  S                    N  R  P  S  G  V  P   D  R  F  S  G
CTF6_l1    CTC ATC TAT GGT AAC AGC ......        AAT CGG CCC TCA GGG GTC CCT ... GAC CGA TTC TCT GGC
humIGLV067 291 bp  ----  ----  ----  ----  ----  ----  ......  ----  ----  ----  ----  ----  ----  ----  ----
```

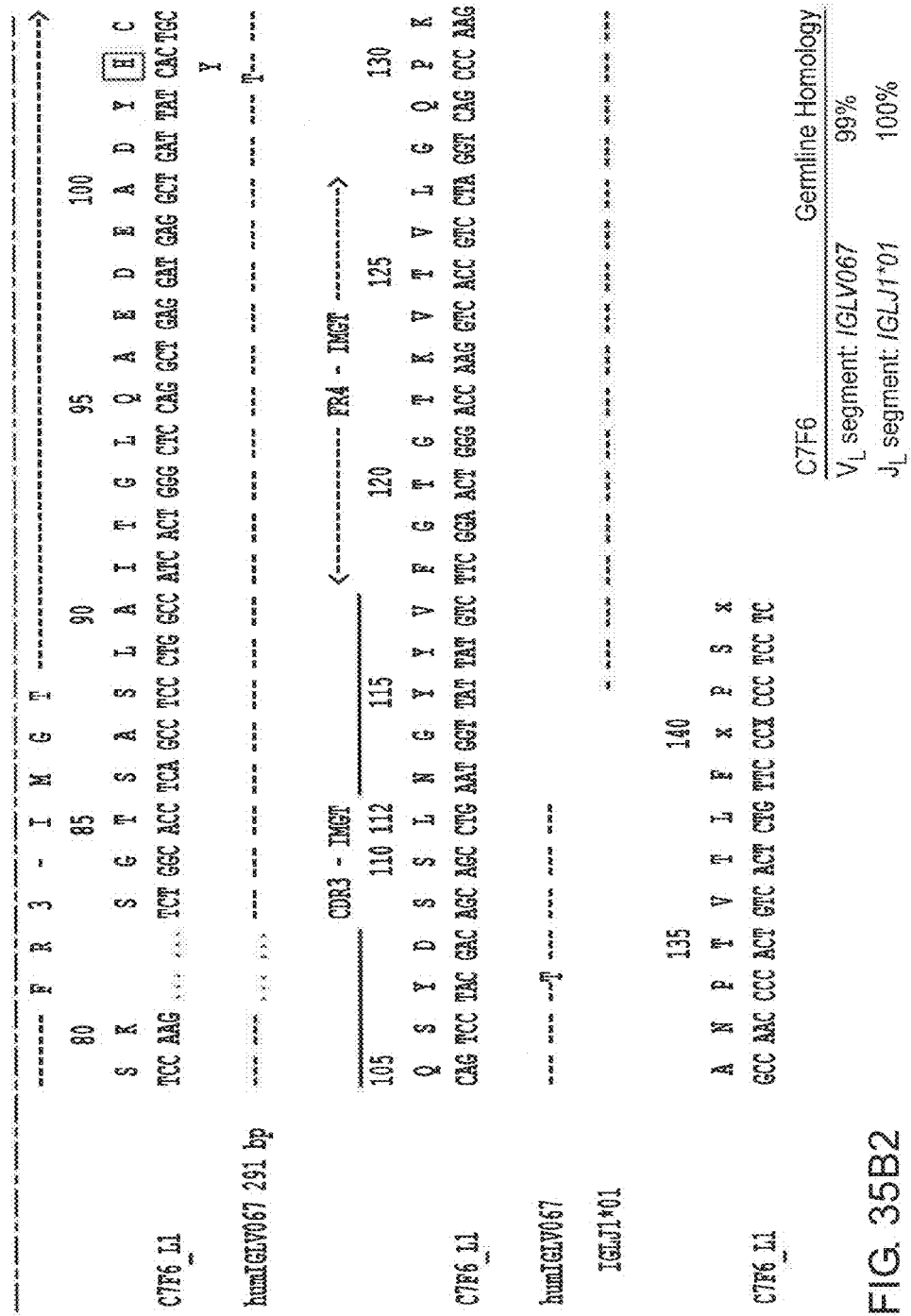
FIG. 35B2

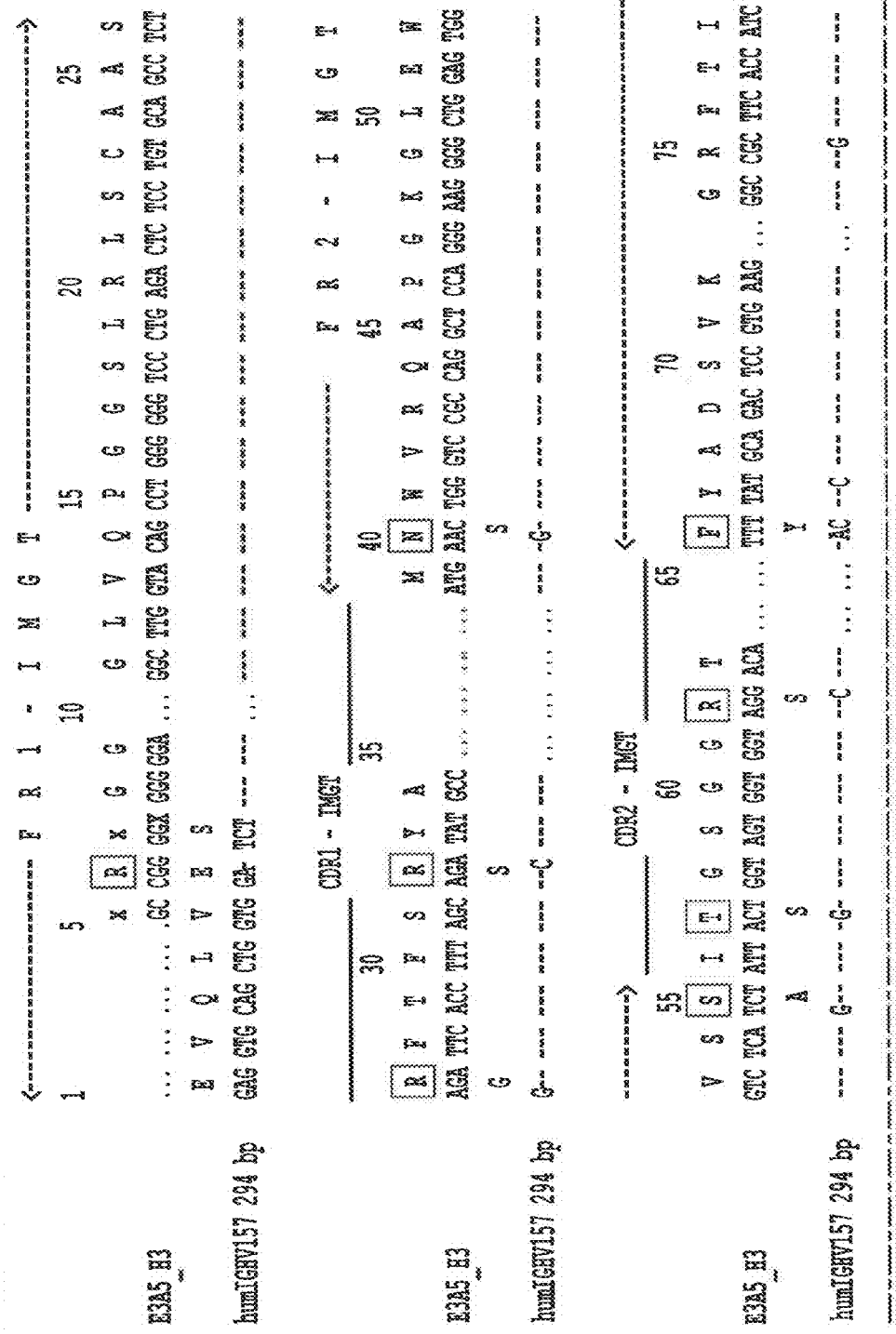
FIG. 35C1

```
                        - F R 3 - I M G T -------------------------->
                    80              85              90              95             100
                    S R D N S K N T L Y L Q M N S L R A E D T A  L  Y Y C
E3A5_H3             TCC AGA GAC AAT TCC AAG AAC ACA TTG TAT CTG CAA ATG AAC AGC CTG AGA GCC GAG GAC ACG GCC CTT TAT TAC TGT
                                                                                                         V
humIGHV157 294 bp   --- --- --- --- --- --- --- --- --- --- --- --- --- --- --- --- --G C-- --- --- G-A --- --- --- ---

---- CDR3 - IMGT -----------------<-------- FR4 - IMGT --------->
                    105             110             112.1       115             120              125
                    A K  P  T V T G D  P  F D I W G Q G T M V T V S S  P 
E3A5_H3             GCG AAA CCC ACG GTG ACT ACG GGG GAT CCT TTT GAT ATC TGG GGC CAA GGG ACA ATG GTC ACC GTC TCT TCA CCC
                        L   T                A
humIGHV157          --- --TG A-- --- --- --- --- --- --- --- --- --- --- --- --- --- --- --- --- --- --- --- --- ---
IGHD4-17*01                                  G---
IGHJ3*02                                                                                                     G---    A E3A5                      Germline Homology
                    V_H segment: IGHV157           90%
                    D_H segment: IGHD4-17*1        93%
                    J_H segment: IGHJ3*02          96%
```

FIG. 35C2

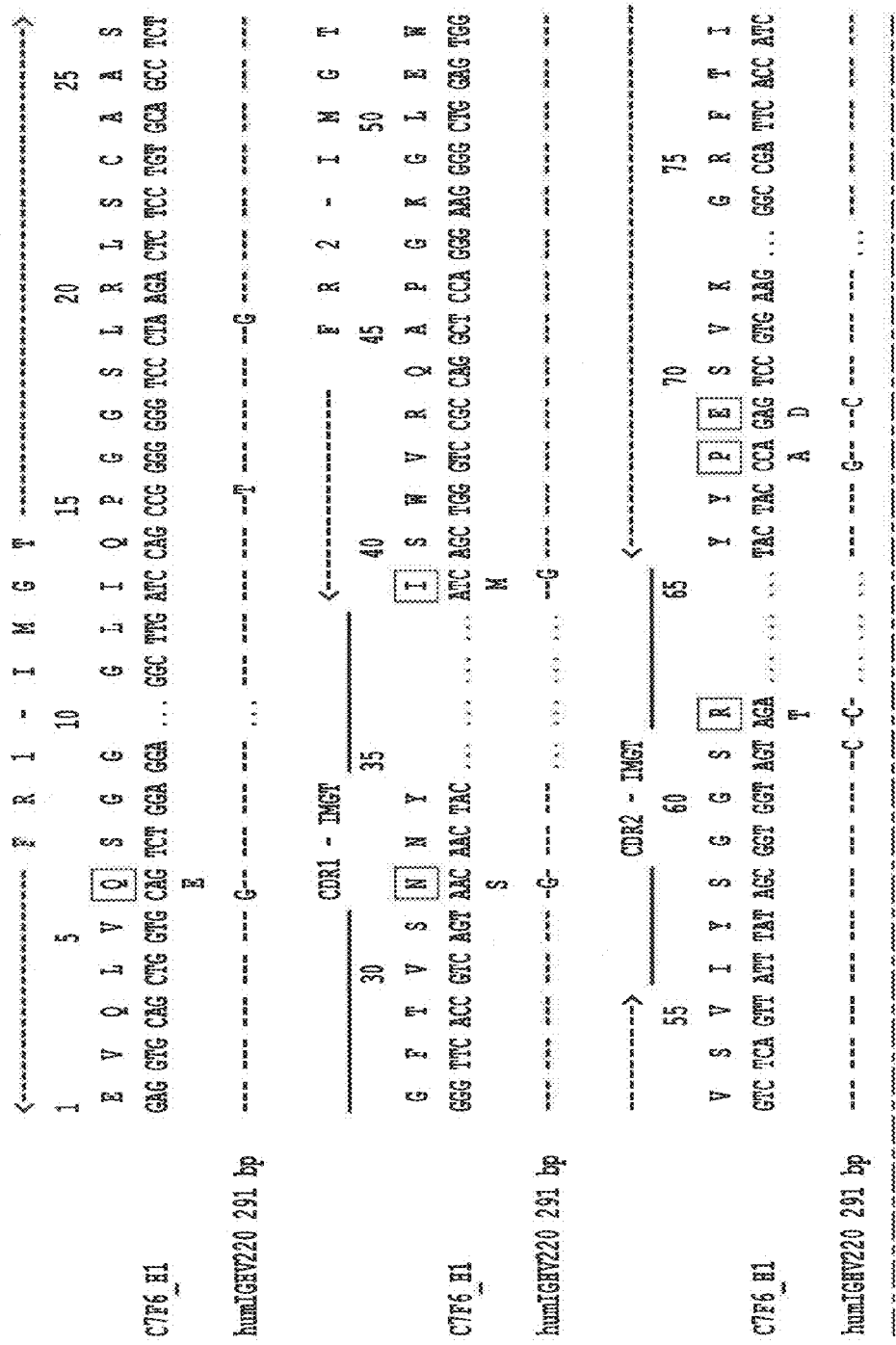
FIG. 35D1

Light chain complementarity determining regions

```
         ----CDR1---->   <--CDR2-->    <----CDR3-----
E3A5 L1  SSNIGSNT....___SNN........___AAWDDSLNGPV

C7F6 L1  SSNIGAGYD...___GNS........___QSYDSSLNGYYV
```

Heavy chain complementarity determining regions

```
         ----CDR1---->   <--CDR2-->    <-----CDR3-------
E3A5 H3  RFTFSRYA....___ITGSGGRT..___AKPPTVTTGDPFDIW
                                            *
C7F6 H1  GFTVSNNY....___IYSGGSR...___ARVSCNSTSCHPVYVRTTVWTSGAKGPQSPSPQ
```

Amino Acid Side Chain Code: small (G,A); nucleophilic (S, T, C); hydrophobic (V, L, I); amide (N,Q); bulky aromatic (F, Y, W); acidic (D,E); basic (H,L,R); proline(P)

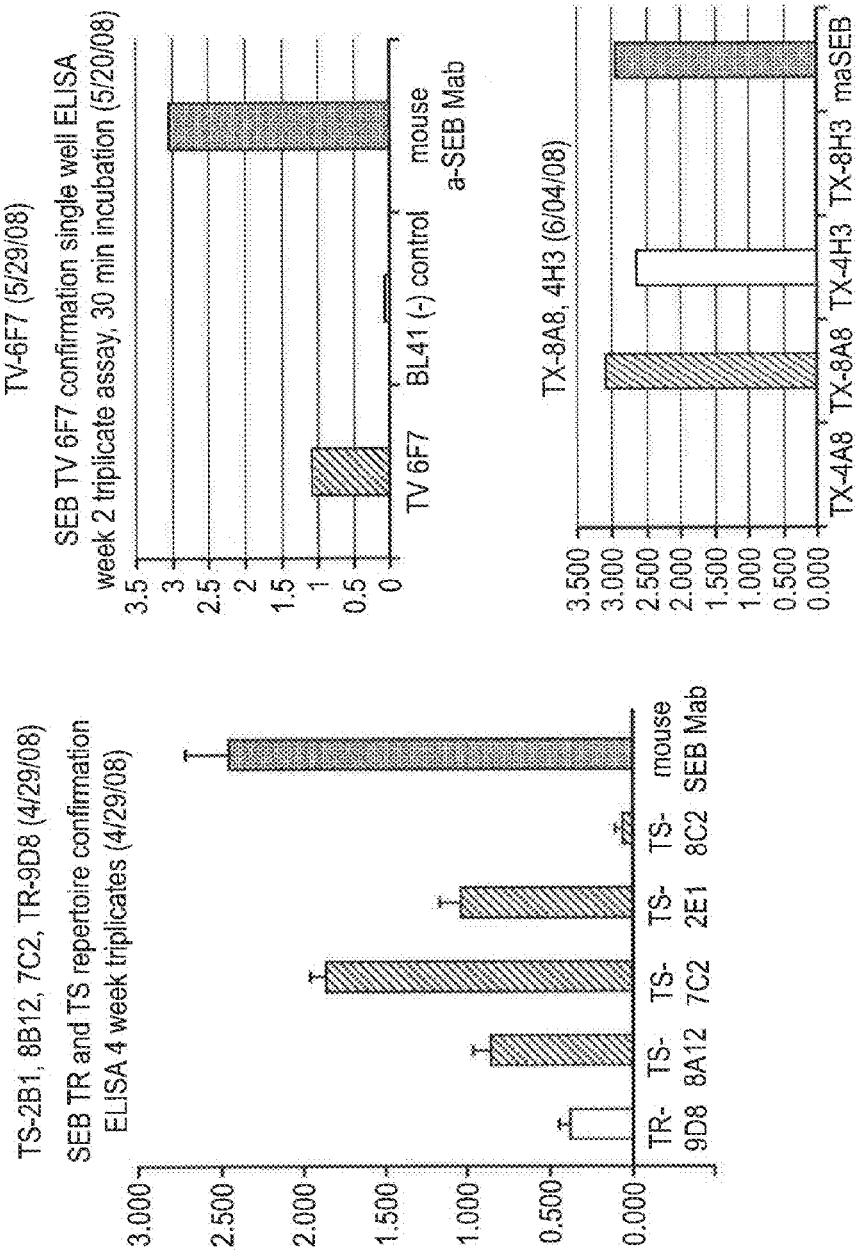

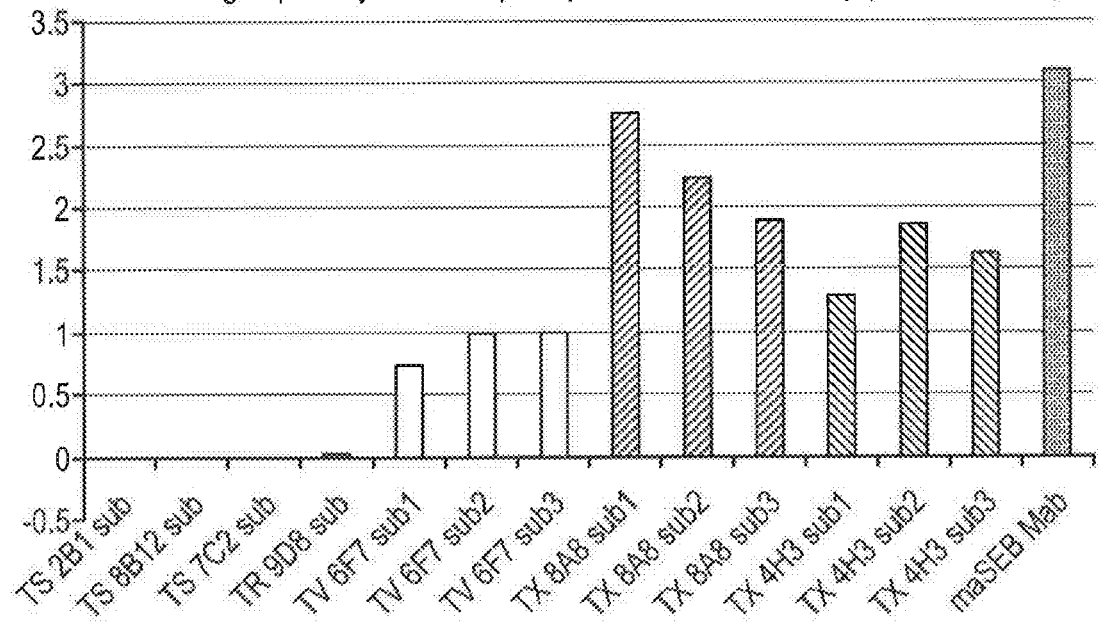

FIG. 39

SEB TV-6F7 screening of wells on primary subclone plates 1-3 (6/17/08)

SEB primary subclone TV-6F7 plates 1-3

ELISA 2 week assay, 2 hour incubation (6/17/08)

SEB TV 6F7 Plate 1 (net results - plate average)

| Value | 1 | 2 | 3 | 4 | 5 | 6 | 7 | 8 | 9 | 10 | 11 | 12 |
|---|---|---|---|---|---|---|---|---|---|---|---|---|
| A | -0.018 | -0.012 | -0.017 | -0.023 | -0.016 | -0.023 | -0.014 | -0.016 | -0.014 | -0.016 | -0.009 | -0.012 |
| B | -0.015 | -0.022 | -0.020 | -0.022 | -0.017 | -0.011 | -0.015 | -0.016 | -0.017 | -0.017 | -0.010 | -0.012 |
| C | -0.020 | -0.016 | -0.014 | -0.021 | -0.019 | -0.019 | -0.010 | -0.014 | -0.012 | -0.018 | -0.017 | -0.022 |
| D | -0.019 | -0.022 | -0.005 | -0.022 | -0.020 | 0.401 | 0.223 | 0.036 | -0.015 | -0.011 | -0.020 | -0.018 |
| E | -0.004 | -0.023 | -0.016 | -0.017 | -0.017 | -0.015 | -0.014 | -0.016 | -0.016 | -0.018 | -0.022 | -0.021 |
| F | 0.339 | 0.022 | -0.021 | -0.014 | -0.013 | -0.005 | -0.013 | -0.012 | -0.009 | -0.011 | 0.018 | -0.016 |
| G | -0.020 | -0.019 | -0.021 | -0.020 | -0.016 | 0.113 | -0.008 | -0.017 | -0.009 | -0.015 | -0.015 | -0.020 |
| H | -0.009 | -0.017 | 0.011 | -0.022 | -0.016 | 0.245 | -0.017 | -0.016 | -0.008 | -0.016 | -0.021 | -0.018 |

SEB TV 6F7 Plate 2 (net results - plate average) well for secondary subcloning: 2H6

| Value | 1 | 2 | 3 | 4 | 5 | 6 | 7 | 8 | 9 | 10 | 11 | 12 | |
|---|---|---|---|---|---|---|---|---|---|---|---|---|---|
| A | -0.032 | -0.033 | -0.033 | -0.035 | -0.028 | -0.032 | -0.036 | -0.032 | -0.031 | -0.012 | -0.033 | -0.031 | |
| B | -0.034 | -0.031 | -0.035 | -0.030 | -0.030 | -0.032 | -0.032 | -0.031 | -0.021 | -0.030 | -0.027 | -0.035 | |
| C | -0.023 | -0.037 | -0.036 | -0.011 | -0.029 | -0.034 | 0.202 | -0.034 | -0.032 | -0.032 | 0.090 | -0.038 | |
| D | -0.036 | -0.039 | -0.037 | -0.035 | -0.012 | -0.033 | -0.032 | -0.031 | -0.035 | -0.030 | -0.033 | -0.032 | |
| E | -0.029 | -0.035 | -0.035 | -0.036 | -0.033 | -0.029 | -0.030 | -0.033 | -0.034 | -0.034 | -0.034 | -0.036 | |
| F | -0.015 | -0.033 | -0.036 | -0.023 | -0.019 | -0.026 | 0.725 | -0.027 | -0.027 | -0.027 | -0.031 | -0.033 | |
| G | -0.037 | -0.038 | -0.037 | -0.036 | -0.033 | -0.033 | -0.035 | -0.035 | -0.036 | -0.036 | -0.036 | -0.037 | |
| H | -0.033 | -0.033 | -0.033 | -0.035 | -0.029 | [1.768] | 0.022 | -0.030 | -0.024 | -0.029 | 0.028 | -0.033 | ◄-- * |

SEB TV 6F7 Plate 3 (net results - plate average) secondary subcloning: 3E2, 3E4

| Value | 1 | 2 | 3 | 4 | 5 | 6 | 7 | 8 | 9 | 10 | 11 | 12 | |
|---|---|---|---|---|---|---|---|---|---|---|---|---|---|
| A | -0.035 | -0.028 | -0.033 | -0.027 | -0.037 | -0.023 | -0.035 | -0.035 | -0.031 | -0.030 | -0.033 | -0.033 | |
| B | -0.020 | -0.025 | -0.027 | 0.012 | -0.008 | -0.034 | -0.026 | -0.029 | -0.031 | -0.028 | -0.026 | 0.611 | |
| C | -0.035 | -0.038 | -0.033 | -0.036 | -0.035 | -0.035 | -0.036 | -0.035 | -0.033 | -0.037 | -0.034 | -0.036 | |
| D | -0.029 | -0.037 | -0.033 | -0.038 | -0.030 | -0.031 | -0.026 | -0.029 | -0.032 | -0.028 | -0.035 | -0.035 | |
| E | -0.033 | [1.089] | -0.036 | [1.246] | -0.034 | -0.036 | -0.034 | -0.034 | -0.038 | -0.035 | -0.037 | -0.030 | ◄-- * |
| F | -0.036 | -0.033 | -0.032 | -0.032 | -0.033 | -0.029 | -0.025 | -0.032 | -0.032 | -0.031 | -0.030 | -0.029 | |
| G | -0.035 | -0.033 | -0.033 | -0.037 | -0.031 | -0.034 | -0.053 | -0.034 | -0.036 | -0.039 | -0.034 | -0.041 | |
| H | -0.026 | -0.030 | -0.025 | -0.033 | -0.031 | -0.031 | -0.035 | -0.028 | -0.032 | -0.030 | -0.033 | -0.022 | | note: no background plate used. Values are subtracted against the plate reading average.

◄-- SEB positive responding well

[ ]◄-- SEB positive responding well used to establish secondary subclone

* TV-6F7 2H6, 3E2, 3E4 chosen for secondary subcloning

FIG. 40

SEB TX-4H3 primary subclone plates 1-3, 6/17/08 ELIZAs (2h)

SEB TX4H3 primary subclone plates 1-3
ELISA 2 week assay, 2 hour incubation (6/17/08)

SEB TX 4H3 Plate 1 (net results - BKG)    well for secondary subcloning: 1E7

| Value | 1 | 2 | 3 | 4 | 5 | 6 | 7 | 8 | 9 | 10 | 11 | 12 |
|---|---|---|---|---|---|---|---|---|---|---|---|---|
| A | 2.867 | 0.003 | -0.006 | 0.002 | 0.004 | 0.008 | 0.006 | 0.002 | -0.004 | -0.002 | 0.026 | 0.035 |
| B | 0.002 | 0.083 | 0.033 | 0.030 | 0.033 | 0.047 | 0.213 | 0.058 | 0.074 | 0.085 | 0.083 | 0.020 |
| C | -0.002 | 0.059 | 0.146 | 0.038 | 0.026 | 0.077 | 0.090 | 0.063 | 0.159 | 0.039 | 0.066 | 0.025 |
| D | -0.007 | 0.033 | 0.026 | 0.046 | 0.031 | 0.329 | 0.078 | 0.068 | 0.107 | 0.040 | 0.041 | 0.001 |
| E | -0.001 | 0.036 | 0.035 | 0.078 | 0.021 | 0.160 | 0.356 | 0.086 | 0.044 | 0.023 | 0.032 | 0.008 | ← *
| F | 0.000 | 0.034 | 0.036 | 0.063 | 0.039 | 0.121 | 0.106 | 0.040 | 0.097 | 0.036 | 0.035 | 0.012 |
| G | -0.001 | 0.043 | 0.025 | 0.065 | 0.047 | 0.044 | 0.117 | 0.054 | 0.039 | 0.017 | 0.045 | 0.022 |
| H | -0.003 | 0.000 | 0.012 | 0.064 | 0.061 | 0.018 | -0.005 | 0.005 | -0.008 | 0.017 | 0.003 | 0.029 |

SEB TX 4H3 Plate 2 (net results - BKG)

| Value | 1 | 2 | 3 | 4 | 5 | 6 | 7 | 8 | 9 | 10 | 11 | 12 |
|---|---|---|---|---|---|---|---|---|---|---|---|---|
| A | 2.956 | 0.003 | -0.005 | 0.003 | 0.004 | 0.005 | 0.005 | -0.007 | 0.002 | 0.004 | 0.003 | 0.016 |
| B | -0.004 | 0.035 | 0.019 | 0.044 | 0.015 | 0.031 | 0.062 | 0.056 | 0.121 | 0.067 | 0.030 | 0.006 |
| C | -0.001 | 0.147 | 0.309 | 0.026 | 0.018 | 0.045 | 0.031 | 0.099 | 0.026 | 0.022 | 0.021 | 0.005 |
| D | -0.005 | 0.132 | 0.030 | 0.014 | 0.021 | 0.069 | 0.039 | 0.042 | 0.046 | 0.029 | 0.125 | 0.008 |
| E | -0.004 | 0.051 | 0.031 | 0.045 | 0.025 | 0.056 | 0.057 | 0.140 | 0.046 | 0.239 | 0.017 | -0.001 |
| F | 0.037 | 0.019 | 0.186 | 0.026 | 0.176 | 0.039 | 0.211 | 0.114 | 0.072 | 0.033 | 0.039 | 0.002 |
| G | -0.001 | -0.002 | -0.002 | -0.008 | -0.006 | -0.001 | -0.001 | 0.000 | -0.031 | -0.002 | -0.006 | 0.000 |
| H | 0.043 | -0.011 | -0.002 | 0.002 | 0.004 | -0.002 | 0.000 | 0.003 | -0.003 | 0.000 | -0.008 | 0.002 |

SEB TX 4H3 Plate 3 (net results - BKG)    secondary subcloning: 3C6, 3D8

| Value | 1 | 2 | 3 | 4 | 5 | 6 | 7 | 8 | 9 | 10 | 11 | 12 |
|---|---|---|---|---|---|---|---|---|---|---|---|---|
| A | 3.157 | -0.002 | -0.002 | 0.003 | 0.000 | 0.000 | 0.003 | -0.001 | -0.004 | 0.000 | 0.004 | 0.002 |
| B | -0.002 | 0.040 | 0.042 | 0.085 | 0.029 | 0.097 | 0.185 | 0.193 | 0.086 | 0.082 | 0.060 | 0.001 |
| C | -0.003 | 0.041 | 0.176 | 0.033 | 0.101 | 0.351 | 0.077 | 0.131 | 0.069 | 0.066 | 0.079 | 0.002 | ← *
| D | -0.001 | 0.700 | 0.035 | 0.079 | 0.066 | 0.215 | 0.053 | 0.228 | 0.058 | 0.052 | 0.065 | 0.002 | ← *
| E | -0.005 | 0.104 | 0.062 | 0.037 | 0.092 | 0.080 | 0.095 | 0.081 | 0.075 | 0.217 | 0.047 | 0.001 |
| F | 0.000 | 0.099 | 0.490 | 0.035 | 0.053 | 0.082 | 0.062 | 0.194 | 0.122 | 0.037 | 0.027 | 0.005 |
| G | 0.005 | 0.145 | 0.138 | 0.026 | 0.063 | 0.067 | 0.016 | 0.147 | 0.033 | 0.201 | 0.032 | 0.001 |
| H | 0.007 | 0.000 | 0.004 | 0.001 | -0.006 | 0.001 | -0.001 | 0.002 | -0.005 | 0.003 | -0.006 | -0.001 | note: red entries = false positive (bubble, cells or debris present in well)

☐ ← positive control well (mouse α-SEB Mab)
← SEB reactive well
⌐ ¬ ← SEB reactive well used to establish secondary subclone

SEB TX-8A8 primary subclone plates 1-3, 6/17/08 ELISAs
SEB primary subclone TX 8A8 plates 1-3
   ELISA 2 week assay, 2 hour incubation (6/17/08)

SEB TX 8A8 Plate 1 (net result - BKG)     well for secondary subcloning: 1C6

| Value | 1 | 2 | 3 | 4 | 5 | 6 | 7 | 8 | 9 | 10 | 11 | 12 |
|---|---|---|---|---|---|---|---|---|---|---|---|---|
| A | 2.829 | 0.012 | 0.004 | 0.005 | 0.000 | -0.003 | 0.000 | 0.003 | 0.003 | 0.000 | 0.011 | 0.030 |
| B | -0.002 | 0.163 | 0.324 | 0.232 | 0.050 | 0.245 | 0.061 | 0.374 | 0.245 | 0.462 | 0.076 | 0.012 |
| C | -0.001 | 0.246 | 0.173 | 0.126 | 0.245 | 0.670 | 0.065 | 0.289 | 0.069 | 0.300 | 0.108 | 0.015 | ←*
| D | -0.002 | 0.337 | 0.157 | 0.322 | 0.050 | 0.200 | 0.083 | 0.269 | 0.184 | 0.285 | 0.442 | 0.006 |
| E | 0.000 | 0.136 | 0.045 | 0.091 | 0.042 | 0.459 | 0.055 | 0.062 | 0.312 | 0.173 | 0.041 | 0.011 |
| F | 0.001 | 0.106 | 0.056 | 0.158 | 0.263 | 0.041 | 0.105 | 0.222 | 0.144 | 0.209 | 0.075 | 0.010 |
| G | 0.012 | 0.311 | 0.040 | 0.383 | 0.166 | 0.467 | 0.049 | 0.081 | 0.223 | 0.182 | 0.035 | 0.013 |
| H | -0.007 | 0.042 | 0.017 | 0.014 | 0.088 | 0.010 | -0.003 | -0.001 | 0.001 | 0.127 | 0.002 | 0.036 |

SEB TX 8A8 Plate 2 (net result - BKG)

| Value | 1 | 2 | 3 | 4 | 5 | 6 | 7 | 8 | 9 | 10 | 11 | 12 |
|---|---|---|---|---|---|---|---|---|---|---|---|---|
| A | 2.998 | 0.008 | -0.005 | 0.004 | 0.002 | 0.003 | -0.005 | -0.004 | 0.003 | -0.003 | 0.019 | 0.017 |
| B | -0.006 | 0.063 | 0.085 | 0.037 | 0.015 | 0.017 | 0.051 | 0.240 | 0.269 | 0.019 | 0.030 | 0.019 |
| C | -0.006 | 0.121 | 0.017 | 0.034 | 0.074 | 0.056 | 0.122 | 0.073 | 0.037 | 0.033 | 0.012 | -0.006 |
| D | -0.001 | 0.035 | 0.058 | 0.087 | 0.084 | 0.037 | 0.092 | 0.208 | 0.146 | 0.140 | 0.001 | 0.011 |
| E | -0.003 | 0.474 | 0.111 | 0.044 | 0.023 | 0.052 | 0.108 | 0.102 | 0.180 | 0.031 | 0.043 | 0.011 |
| F | 0.000 | 0.172 | 0.021 | 0.014 | 0.116 | 0.074 | 0.052 | 0.064 | 0.070 | 0.086 | 0.028 | 0.012 |
| G | 0.024 | -0.008 | -0.011 | -0.016 | -0.007 | -0.011 | -0.010 | -0.009 | -0.007 | -0.010 | -0.006 | 0.044 |
| H | 0.048 | 0.010 | 0.007 | -0.001 | 0.006 | 0.001 | 0.000 | -0.005 | -0.037 | 0.109 | 0.050 | 0.052 |

SEB TX 8A8 Plate 3 (net result - BKG)     wells for secondary subcloning: 3D7, 3F4

| Value | 1 | 2 | 3 | 4 | 5 | 6 | 7 | 8 | 9 | 10 | 11 | 12 |
|---|---|---|---|---|---|---|---|---|---|---|---|---|
| A | 3.143 | -0.002 | 0.008 | -0.001 | 0.001 | -0.007 | -0.001 | -0.003 | 0.001 | 0.005 | 0.007 | -0.009 |
| B | -0.006 | 0.146 | 0.063 | 0.271 | 0.191 | 0.065 | 0.093 | 0.089 | 0.111 | 0.109 | 0.669 | 0.003 |
| C | -0.001 | 0.198 | 0.427 | 0.086 | 0.065 | 0.013 | 0.246 | 0.272 | 0.179 | 0.310 | 0.225 | -0.004 |
| D | -0.004 | 0.440 | 0.105 | 0.079 | 0.349 | 0.378 | 0.713 | 0.449 | 0.230 | 0.079 | 0.010 | -0.004 | ←*
| E | 0.016 | 0.061 | 0.096 | 0.179 | 0.071 | 0.066 | 0.138 | 0.171 | 0.224 | 0.519 | 0.164 | 0.002 |
| F | -0.001 | 0.058 | 0.043 | 0.610 | 0.056 | 0.133 | 0.161 | 0.031 | 0.112 | 0.065 | 0.126 | 0.005 | ←*
| G | 0.000 | 0.155 | 0.061 | 0.033 | 0.054 | 0.165 | 0.465 | 0.065 | 0.075 | 0.424 | 0.091 | 0.006 |
| H | -0.001 | 0.005 | -0.004 | 0.004 | 0.004 | 0.000 | 0.006 | 0.001 | -0.043 | 0.005 | 0.000 | 0.005 |

☐ ←-- positive control well (mouse α-SEB Mab)

Screening of TV-bB2 primary subclone plate pools for SEC2 reactivity (5/29/08)

FIG. 43B

SEC2 screening of TV-bB2 primary subclone plate 2 (6/19/08)
SEC-2 primary subclone TV bB2 plate2

ELISA 2 wk assay, 6 h incubation (6/19/08)

SEC TV bB2 sub2 + SEC 6h (net results- BKG)    wells for secondary subcloning: 2E1, 2F2

| Value | 1 | 2 | 3 | 4 | 5 | 6 | 7 | 8 | 9 | 10 | 11 | 12 |
|---|---|---|---|---|---|---|---|---|---|---|---|---|
| A | 0.172 | 0.018 | -0.025 | -0.026 | -0.036 | -0.005 | -0.377 | -0.158 | 0.113 | -0.035 | -0.012 | 0.004 |
| B | 0.055 | 0.019 | -0.027 | 0.012 | -0.002 | 0.063 | -0.042 | 0.010 | -0.003 | -0.013 | 0.004 | 0.041 |
| C | 0.020 | -0.040 | -0.044 | 0.001 | -0.014 | -0.011 | -0.027 | -0.018 | -0.035 | -0.046 | -0.086 | -1.818 |
| D | -0.002 | 0.139 | -0.056 | -0.255 | -0.020 | -0.032 | -0.068 | -0.007 | -0.037 | -0.570 | 0.029 | 0.019 |
| E | 0.280 | -0.004 | -0.030 | -0.014 | -0.004 | -0.018 | -0.018 | -0.002 | -0.018 | 0.023 | 0.009 | 0.059 |
| F | 0.005 | 0.359 | -0.045 | 0.010 | 0.011 | 0.007 | 0.043 | -0.017 | 0.001 | 0.014 | 0.011 | -0.001 |
| G | -0.075 | -0.060 | -0.060 | -0.029 | 0.008 | -0.013 | -0.005 | 0.000 | -0.013 | -0.012 | 0.020 | 0.002 * |
| H | -0.143 | -0.088 | -0.050 | -0.021 | 0.027 | -0.040 | -0.025 | -0.060 | -0.052 | -0.031 | 0.054 | -0.052 * | note: values subtracted from background plate    Values in red indicated elevated background readings

- - - ▶ SEC reactive well
- - - ▶ SEC reactive well used to establish secondary subclone

* TV-bB2 2E1, 2F2 closen
  for secondary subcloning

[ ] (dashed box indicator)

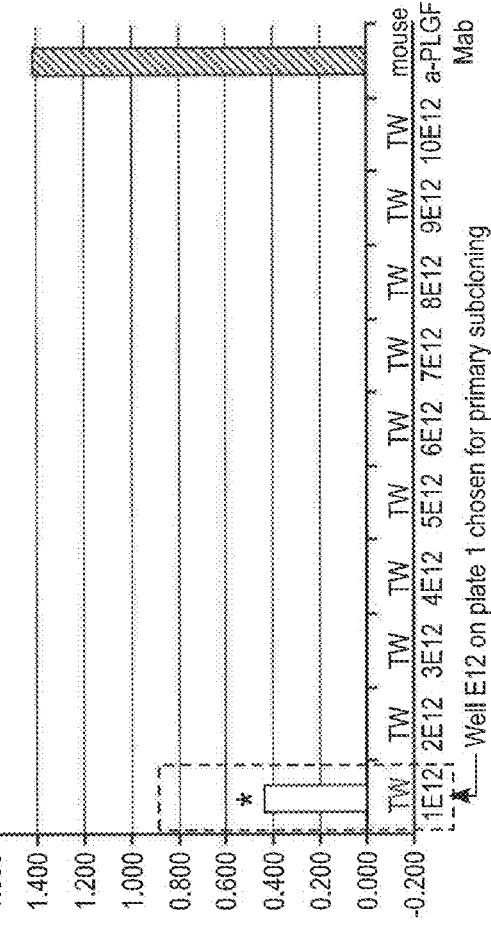

FIG. 45B

PLGF screening of TW primary subclone plates 2 and 5 (6/19/08)
PLGF primary subclone TW 1E12 individual plates 2 and 5
ELISA 2 wk assay, 20h incubation (6/19/08)

PLGF TW 1E12 Plate 2 (net results - BKG)     wells for secondary subcloning: 2E3, 2G9

|   | 1 | 2 | 3 | 4 | 5 | 6 | 7 | 8 | 9 | 10 | 11 | 12 |
|---|---|---|---|---|---|---|---|---|---|----|----|----|
| A | -0.025 | 0.021 | -0.008 | -0.038 | 0.003 | 0.308 | -0.009 | 0.029 | -0.003 | 0.015 | 0.056 | -0.007 |
| B | -0.108 | 0.010 | -0.015 | 0.612 | -0.099 | 0.024 | 0.015 | 0.007 | -0.378 | 0.220 | 0.007 | -0.001 |
| C | -0.065 | 0.538 | 0.391 | 0.145 | 0.319 | 0.058 | -0.006 | -0.024 | 0.382 | 0.237 | 0.101 | 0.026 |
| D | -0.012 | 0.754 | 0.612 | 0.450 | 0.017 | 0.045 | -0.013 | 0.105 | -0.016 | -0.039 | 0.047 | 0.005 |
| E | -0.004 | 0.806 | 1.178 | 0.027 | 0.019 | -0.003 | 0.022 | 0.012 | 0.420 | 0.014 | 0.011 | 0.003 | ◄--*
| F | -0.109 | 0.383 | 0.324 | 0.151 | -0.066 | 0.011 | 0.046 | -0.007 | 0.006 | -0.019 | -0.036 | 0.010 |
| G | -0.113 | 0.633 | 0.747 | 0.592 | 0.003 | -0.002 | 0.005 | -0.010 | 1.938 | 0.008 | 0.006 | 0.007 | ◄--*
| H | -0.090 | -0.129 | 0.281 | -0.021 | -0.036 | 0.015 | 0.111 | 0.012 | -0.003 | 0.015 | 0.041 | 0.006 |

PLGF TW 1E12 Plate 5 (net results - BKG)     wells for secondary subcloning: 5A10

|   | 1 | 2 | 3 | 4 | 5 | 6 | 7 | 8 | 9 | 10 | 11 | 12 |
|---|---|---|---|---|---|---|---|---|---|----|----|----|
| A | 0.021 | 0.025 | 0.019 | 0.020 | 0.055 | 0.007 | 0.115 | 0.025 | 0.029 | 1.201 | 0.032 | 0.084 | ◄--*
| B | 0.317 | 0.070 | 0.153 | 0.206 | -0.057 | 0.029 | 0.386 | 0.045 | -0.365 | 0.337 | 0.033 | 0.058 |
| C | 0.139 | 0.647 | 0.165 | 0.049 | 0.174 | 0.068 | 0.061 | 0.003 | 0.045 | 0.031 | 0.070 | 0.072 |
| D | 0.111 | 0.108 | 0.162 | 0.217 | 0.060 | 0.132 | 0.062 | -0.002 | -0.013 | 0.421 | 0.497 | 0.093 |
| E | 0.101 | -0.007 | 0.092 | 0.093 | 0.171 | 0.048 | 0.140 | 0.081 | 0.054 | 0.067 | 0.205 | 0.017 |
| F | 0.077 | 0.090 | 0.068 | 0.075 | -0.041 | 0.048 | 0.049 | 0.042 | 0.029 | 0.031 | 0.002 | 0.042 |
| G | -0.001 | 0.113 | 0.144 | -0.028 | 0.119 | 0.213 | 0.124 | 0.028 | 0.021 | 0.065 | 0.007 | 0.032 |
| H | 0.290 | 0.069 | 0.140 | 0.122 | 0.116 | 0.065 | 0.011 | 0.017 | 0.028 | 0.013 | 0.020 | -0.005 | note: values subtracted from pooled plate (2 and 5) background plate
values in red indicated elevated background readings ◄-- PLGF reactive well

[ ] ◄-- PLGF reactive well selected for secondary subcloning

\* TW 2E3, 2G9, 5A10 chosen
for secondary subcloning

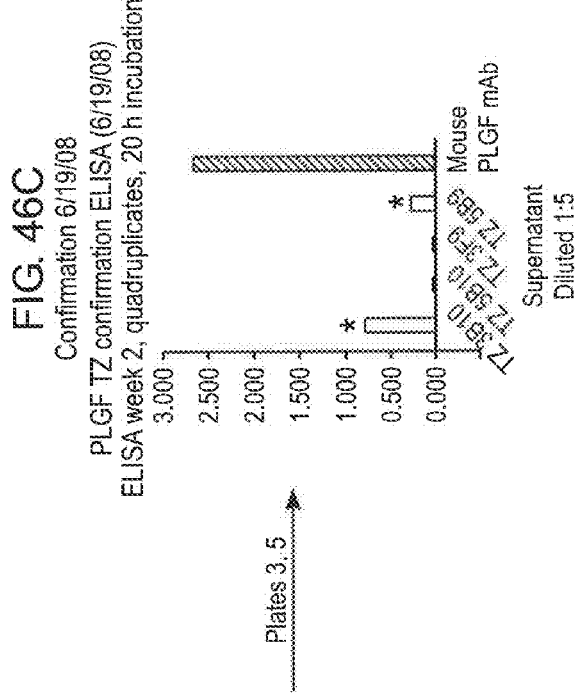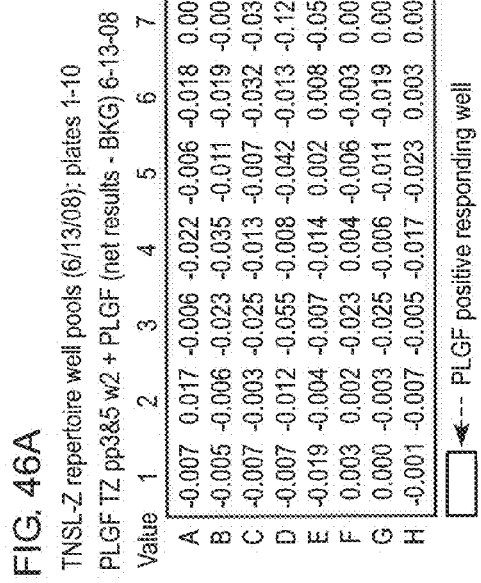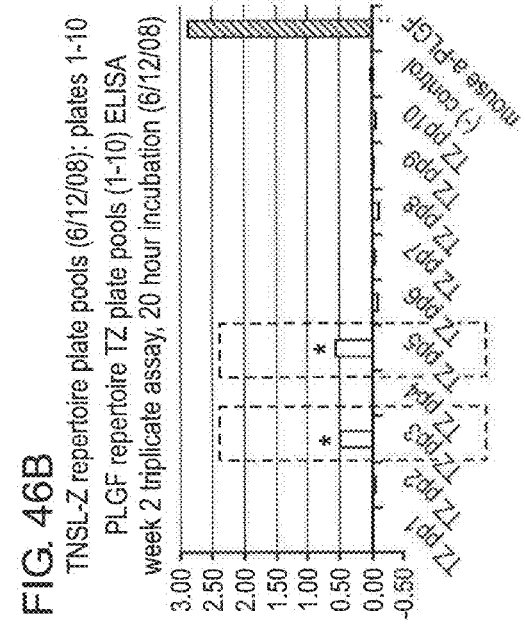

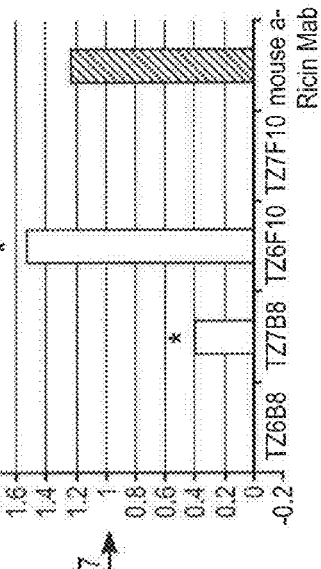
FIG. 47A TNSL-Z repertoire well pools (6/19/08)
Ricin B repertoire TZ well pool (plate 1-10) ELISA
week 2 assay, 20 hour incubation (6/19/08)
ricin TZ wp1-10 w2+ricin 20h (net result-plate average) wells for confirmation testing: xB8, xF10
| Value | 1 | 2 | 3 | 4 | 5 | 6 | 7 | 8 | 9 | 10 | 11 | 12 |
|---|---|---|---|---|---|---|---|---|---|---|---|---|
| A | -0.169 | -0.116 | -0.109 | -0.003 | 0.162 | -0.052 | 0.116 | -0.140 | 0.495 | 0.332 | -0.108 | -0.133 |
| B | -0.055 | -0.200 | -0.114 | 0.059 | 0.020 | 0.104 | -0.131 | 1.248 | -0.163 | 0.011 | 0.336 | -0.155 |
| C | -0.134 | -0.144 | -0.069 | -0.068 | -0.050 | -0.019 | -0.189 | 0.061 | -0.189 | -0.138 | -0.167 | -0.089 |
| D | -0.213 | 0.008 | 0.129 | -0.030 | 0.016 | -0.109 | 0.193 | -0.108 | -0.195 | -0.084 | 0.029 | -0.185 |
| E | 0.007 | -0.174 | 0.029 | -0.050 | 0.027 | 0.151 | -0.180 | -0.096 | -0.171 | -0.087 | 0.710 | -0.117 |
| F | -0.129 | -0.178 | -0.057 | 0.043 | 0.412 | -0.182 | 0.268 | -0.133 | -0.082 | 1.251 | 0.307 | -0.022 |
| G | -0.154 | -0.082 | 0.003 | 0.118 | -0.090 | -0.142 | -0.199 | -0.167 | -0.206 | 0.030 | -0.166 | -0.035 |
| H | -0.105 | 0.077 | -0.011 | -0.147 | -0.130 | -0.146 | -0.207 | -0.067 | 0.628 | -0.159 | 0.485 | -0.144 |
←-- Ricin B reactive well
☐ ←-- Ricin B reactive wells cosen for further testing
Wells B8, F10
FIG. 47B TNSL-Z repertoire plate pools (6/19/08)
Plates 6,7
FIG. 47C Confirmation (6/20/08)

FIG. 48A

Ricin B TZ-7B8 primary subclones plates 1-5
ELISA 3 week assay, background subtracted, 20 hour incubation (7/14/08)

ricin TZ 7B8 Plate 1 20h (net results - BKG)

| Value | 1 | 2 | 3 | 4 | 5 | 6 | 7 | 8 | 9 | 10 | 11 | 12 | |
|---|---|---|---|---|---|---|---|---|---|---|---|---|---|
| A | 0.113 | 0.181 | 0.091 | 0.044 | 0.073 | 0.039 | 0.066 | 0.118 | 0.089 | 0.054 | 0.180 | 0.322 | ◄ * |
| B | 0.098 | 0.055 | 0.146 | 0.139 | 0.228 | 0.135 | 0.064 | 0.037 | 0.066 | 0.064 | 0.071 | -0.020 | |
| C | 0.017 | 0.006 | 0.030 | 0.059 | 0.032 | 0.021 | 0.089 | 0.008 | 0.030 | 0.018 | -0.014 | 0.173 | |
| D | 0.013 | 0.055 | 0.052 | 0.063 | 0.199 | 0.010 | 0.019 | 0.085 | -0.002 | 0.000 | 0.050 | 0.144 | |
| E | 0.044 | 0.049 | 0.407 | 0.121 | 0.040 | 0.013 | 0.004 | 0.243 | 0.010 | 0.049 | 0.013 | 0.009 | ◄ * |
| F | 0.051 | 0.156 | 0.068 | 0.016 | 0.004 | -0.050 | 0.048 | 0.048 | 0.061 | 0.118 | 0.006 | 0.133 | |
| G | 0.099 | 0.059 | 0.085 | 0.059 | 0.164 | 0.090 | 0.057 | 0.074 | 0.016 | 0.036 | 0.133 | 0.013 | |
| H | 0.034 | 0.034 | 0.056 | 0.083 | -0.015 | 0.058 | 0.045 | 0.019 | 0.032 | 0.045 | 0.045 | -0.047 | | ricin TZ 7B8 Plate 2 20h (net results - BKG)

| Value | 1 | 2 | 3 | 4 | 5 | 6 | 7 | 8 | 9 | 10 | 11 | 12 | |
|---|---|---|---|---|---|---|---|---|---|---|---|---|---|
| A | 1.777 | 0.030 | 0.976 | 0.020 | 0.058 | 0.039 | 0.044 | 0.129 | 0.017 | -0.017 | 0.012 | 0.062 | ◄ * |
| B | 0.026 | 0.045 | -0.015 | -0.027 | 0.048 | 0.075 | 0.032 | 0.022 | 0.053 | 0.015 | 0.018 | -0.050 | |
| C | 0.050 | 0.006 | 0.052 | 0.241 | 0.101 | 0.090 | 0.026 | 0.021 | 0.070 | 0.052 | 0.018 | 0.021 | |
| D | -0.021 | 0.031 | 0.051 | 0.025 | 0.083 | 0.009 | 0.028 | 0.035 | 0.008 | 0.140 | 0.013 | 0.101 | |
| E | 0.001 | -0.012 | 0.021 | 0.018 | 0.005 | 0.042 | 0.041 | 0.040 | 0.003 | 0.074 | 0.045 | 0.020 | |
| F | -0.021 | 0.029 | 0.011 | 0.032 | 0.050 | -0.069 | 0.041 | 0.030 | 0.009 | 0.002 | 0.022 | 0.043 | |
| G | 0.008 | 0.055 | 0.104 | 0.097 | 0.077 | 0.066 | 0.073 | 0.022 | 0.009 | 0.003 | -0.016 | -0.037 | |
| H | 0.072 | 0.023 | 0.037 | 0.027 | 0.237 | 0.000 | 0.024 | -0.012 | 0.005 | 0.035 | 0.071 | -0.039 | | ricin TZ 7B8 Plate 3 20h (net results - BKG)

| Value | 1 | 2 | 3 | 4 | 5 | 6 | 7 | 8 | 9 | 10 | 11 | 12 |
|---|---|---|---|---|---|---|---|---|---|---|---|---|
| A | -1.665 | 0.152 | -0.885 | 0.024 | 0.014 | -0.001 | 0.022 | -0.011 | 0.073 | 0.071 | 0.168 | 0.260 |
| B | 0.072 | 0.010 | 0.161 | 0.167 | 0.180 | 0.060 | 0.032 | 0.015 | 0.013 | 0.049 | 0.053 | 0.030 |
| C | -0.033 | -0.001 | -0.022 | -0.182 | -0.069 | -0.069 | 0.063 | -0.013 | -0.040 | -0.034 | -0.032 | 0.151 |
| D | 0.034 | 0.024 | 0.001 | 0.038 | 0.116 | 0.001 | -0.009 | 0.050 | -0.010 | -0.140 | 0.036 | 0.043 |
| E | 0.043 | 0.061 | 0.386 | 0.103 | 0.035 | -0.029 | -0.037 | 0.204 | 0.007 | -0.025 | -0.032 | -0.012 |
| F | 0.072 | 0.127 | 0.058 | -0.016 | -0.046 | 0.019 | 0.007 | 0.017 | 0.052 | 0.116 | -0.016 | 0.090 |
| G | 0.091 | 0.004 | -0.019 | -0.038 | 0.087 | 0.023 | -0.016 | 0.052 | 0.008 | 0.033 | 0.148 | 0.050 |
| H | -0.038 | 0.011 | 0.019 | 0.056 | -0.253 | 0.058 | 0.021 | 0.030 | 0.026 | 0.011 | -0.026 | -0.008 |

◄-- Ricin B moderate reactivity  * TZ-7B8 1A12, 1E3, 2A1, 2A3, 4A1
[____] ◄-- Ricin B high reactivity     chosen for secondary subcloning ricin TZ 7B8 Plate 4 20h (net results - BKG)

| Value | 1 | 2 | 3 | 4 | 5 | 6 | 7 | 8 | 9 | 10 | 11 | 12 | |
|---|---|---|---|---|---|---|---|---|---|---|---|---|---|
| A | 3.442 | -0.122 | 1.861 | -0.005 | 0.044 | 0.040 | 0.022 | 0.140 | -0.056 | 0.088 | -0.156 | -0.199 | ◄-- * |
| B | -0.046 | 0.035 | -0.177 | 0.194 | 0.131 | 0.014 | 0.000 | 0.008 | 0.040 | -0.035 | -0.035 | -0.080 | |
| C | 0.084 | 0.007 | 0.074 | 0.422 | 0.170 | 0.160 | -0.036 | 0.034 | 0.110 | 0.085 | 0.050 | -0.130 | |
| D | -0.055 | 0.007 | 0.050 | -0.012 | -0.033 | 0.008 | 0.037 | -0.015 | 0.018 | 0.280 | -0.023 | 0.059 | |
| E | -0.042 | -0.074 | -0.365 | -0.084 | -0.030 | 0.070 | 0.078 | -0.164 | -0.004 | 0.099 | 0.077 | 0.032 | |
| F | -0.092 | -0.098 | -0.047 | 0.049 | 0.096 | -0.088 | 0.034 | 0.013 | -0.044 | -0.114 | 0.038 | -0.047 | |
| G | -0.083 | 0.051 | 0.123 | 0.135 | -0.010 | 0.043 | 0.089 | -0.029 | 0.001 | -0.029 | -0.164 | -0.087 | |
| H | 0.110 | 0.013 | 0.017 | -0.029 | 0.490 | -0.058 | 0.003 | -0.042 | -0.021 | 0.024 | 0.097 | -0.031 | | ricin TZ 7B8 Plate 5 20h (net results - BKG)

| Value | 1 | 2 | 3 | 4 | 5 | 6 | 7 | 8 | 9 | 10 | 11 | 12 |
|---|---|---|---|---|---|---|---|---|---|---|---|---|
| A | -5.106 | 0.273 | -2.746 | 0.029 | -0.030 | -0.040 | 0.000 | -0.151 | 0.128 | 0.159 | 0.324 | 0.459 |
| B | 0.117 | -0.026 | 0.338 | 0.361 | 0.311 | 0.046 | 0.033 | 0.007 | -0.027 | 0.084 | 0.088 | 0.110 |
| C | -0.117 | -0.007 | -0.096 | -0.604 | -0.240 | -0.229 | 0.099 | -0.047 | -0.150 | -0.119 | -0.082 | 0.282 |
| D | 0.090 | 0.017 | -0.050 | 0.050 | 0.149 | -0.007 | -0.045 | 0.065 | -0.027 | -0.419 | 0.060 | -0.016 |
| E | 0.085 | 0.135 | 0.751 | 0.187 | 0.065 | -0.099 | -0.114 | 0.367 | 0.010 | -0.124 | -0.108 | -0.043 |
| F | 0.164 | 0.224 | 0.105 | -0.065 | -0.141 | 0.107 | -0.027 | 0.004 | 0.096 | 0.230 | -0.055 | 0.137 |
| G | 0.173 | -0.047 | -0.142 | -0.173 | 0.097 | -0.020 | -0.105 | 0.081 | 0.006 | 0.062 | 0.312 | 0.136 |
| H | -0.149 | -0.002 | 0.002 | 0.086 | -0.743 | 0.115 | 0.018 | 0.072 | 0.047 | -0.013 | -0.123 | 0.023 |

◄-- Ricin B moderate reactivity        * TZ-7B8 1A12, 1E3, 2A1, 2A3, 4A1
[   ] ◄-- Ricin B high reactivity        chosen for secondary subcloning

TNSL-N well pools (plates 1-10), H5 HA ELISA, BKG subtracted, 3/3/08

|   | 1 | 2 | 3 | 4 | 5 | 6 | 7 | 8 | 9 | 10 | 11 | 12 |
|---|---|---|---|---|---|---|---|---|---|---|---|---|
| A | 0.01 | 0.00 | -0.01 | 0.00 | 0.02 | -0.01 | 0.03 | 0.00 | 0.05 | 0.04 | 0.07 | 0.00 |
| B | -0.01 | 0.00 | 0.00 | 0.00 | 0.00 | 0.01 | 0.01 | -0.01 | 0.01 | 0.01 | 0.01 | 0.01 |
| C | -0.01 | 0.00 | 0.00 | -0.01 | 0.00 | 0.00 | -0.02 | 0.00 | 0.00 | 0.00 | 0.01 | 0.00 |
| D | -0.01 | 0.00 | 0.00 | -0.91 | 0.00 | 0.00 | -0.01 | 0.00 | 0.00 | 0.00 | 0.00 | 0.00 |
| E | 0.00 | 0.02 | 0.00 | 0.00 | 0.01 | 0.00 | 0.00 | 0.00 | 0.02 | 0.00 | -0.02 | 0.00 |
| F | 0.00 | 0.00 | 0.00 | 0.00 | 0.00 | 0.00 | 0.00 | 0.00 | 0.01 | 0.00 | 0.00 | 0.00 |
| G | -0.01 | 0.00 | 0.00 | 0.00 | -0.04 | -0.01 | 2.66 | 0.01 | 0.00 | 0.00 | 0.01 | 0.00 |
| H | 0.03 | 0.01 | 0.00 | 0.00 | 0.01 | 0.00 | 0.00 | 0.00 | 0.00 | 0.00 | -0.16 | 0.00 |

TNSL-N plate pools in triplicate H5 HA ELISA, 3/3/08

FIG. 51A
TN 6G7 primary subclones well pools (plates 1-10)
H5 HA ELISA (-BKG), 3/19/08
| Value | 1 | 2 | 3 | 4 | 5 | 6 | 7 | 8 | 9 | 10 | 11 | 12 |
|---|---|---|---|---|---|---|---|---|---|---|---|---|
| A | 0.004 | 0.002 | 0.003 | 0.003 | 0.007 | 0.005 | 0.004 | 0.002 | 0.009 | 0.002 | 0.002 | 0.001 |
| B | 0.008 | 0.001 | 0.005 | 1.676 | 1.520 | 0.005 | 0.003 | -0.003 | 0.389 | 1.916 | 0.016 | -0.001 |
| C | 0.009 | 0.006 | 1.822 | 0.412 | 1.924 | 0.007 | 1.846 | 2.017 | 1.579 | 0.719 | 0.003 | 0.002 |
| D | 0.005 | 0.002 | 0.680 | 1.768 | 1.550 | 0.009 | 0.631 | 0.591 | 1.882 | 0.272 | 1.593 | 0.003 |
| E | 0.002 | 0.002 | 1.642 | 0.363 | 0.386 | 1.750 | 0.131 | 0.099 | 0.346 | 1.970 | 0.124 | 0.003 |
| F | 0.009 | 1.870 | 0.384 | 0.180 | 1.701 | 0.526 | 0.061 | 2.068 | 1.512 | 1.944 | 1.464 | 0.003 |
| G | 0.004 | 0.550 | 0.159 | 0.080 | 0.442 | 1.882 | 0.042 | 0.776 | 1.524 | 0.620 | 0.293 | 0.011 |
| H | -0.005 | 0.003 | 0.001 | -0.007 | 0.014 | 0.019 | -0.002 | -0.003 | 0.011 | -0.019 | 0.013 | 0.016 |
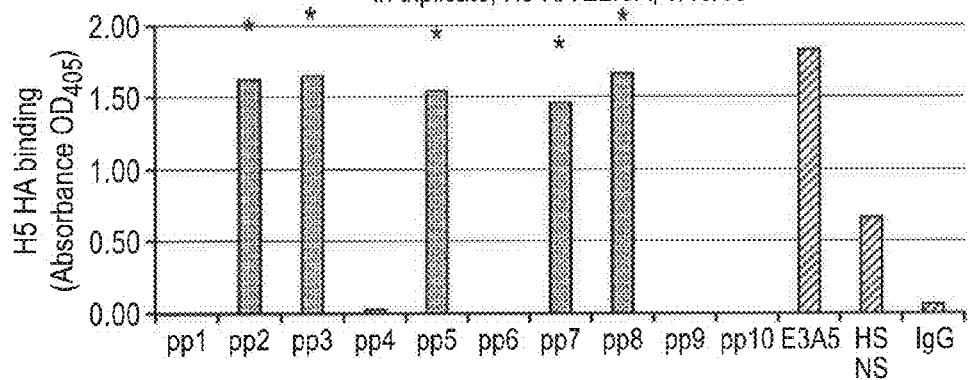
FIG. 51B  TN 6G7 primary subclones plates 1-10 pools, in triplicate, H5 HA ELISA, 3/19/08
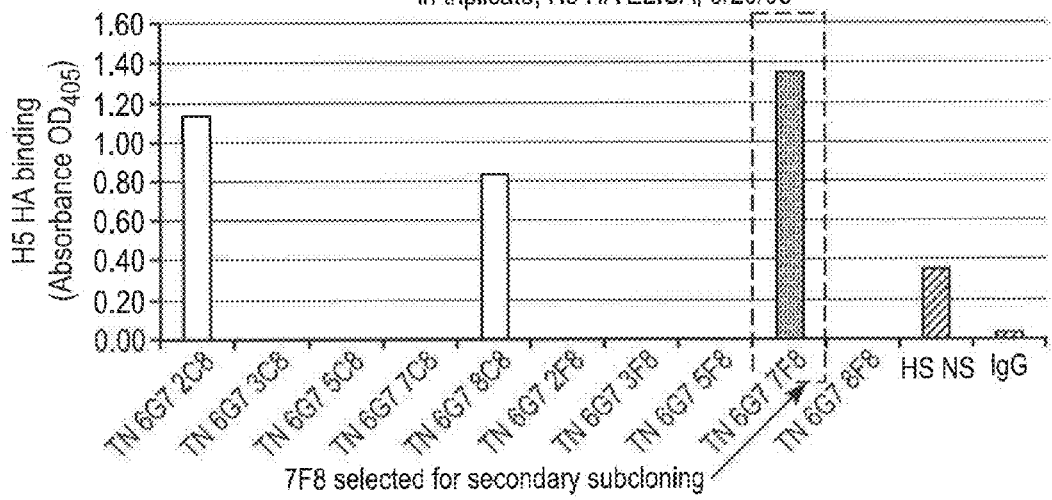
FIG. 51C  TN 6G7 primary subcloning well confirmation, in triplicate, H5 HA ELISA, 3/20/08
7F8 selected for secondary subcloning

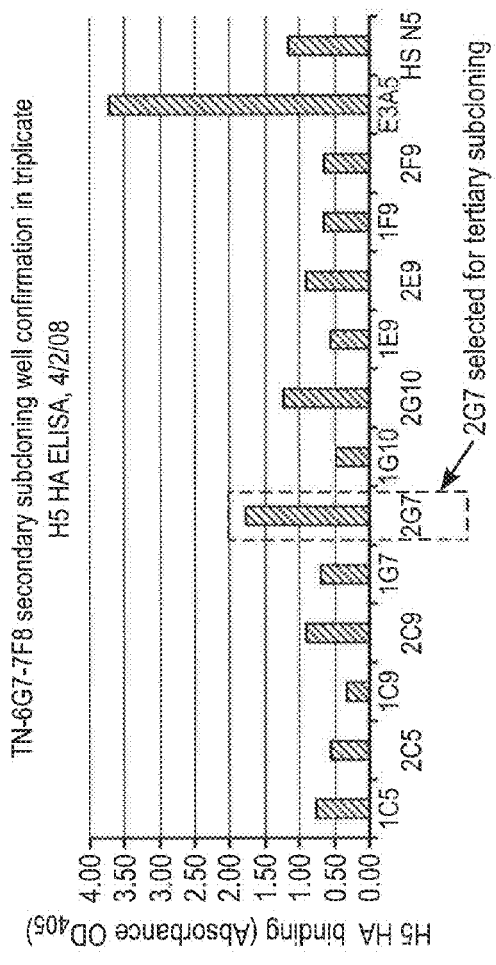
FIG. 52A TN-6G7-7F8 secondary subclone well pools (plates 1&2) BKG subtracted, H5 HA ELISA, 4/1/08
FIG. 52B TN-6G7-7F8 secondary subcloning well confirmation in triplicate H5 HA ELISA, 4/2/08

FIG. 53A

TN-6G7-7F8-2G7 tertiary subcloning results (H5 HA ELISA 6-25-08)

Plate 2:

FIG. 54A

| Primer | Sequence (5' → 3') |
|---|---|
| λ1-xba | TCTAGACAGTCTGTGYTGACKCAGCCGCCCTCA |
| λ2/5-xba | TCTAGACAGTCTGCGCTGACTCARCCGSCCTCT |
| λ3-xba | TCTAGATCCTATGAACTGACTCAGCCACCYT |
| λ4a-xba | TCTAGATCTGAACTGACTCAGCCDSCCTC |
| λ4b-xba | TCTAGATCTGAACTGACTCAGGACCCTGYT |
| λ6-xba | TCTAGARATTTTATGCTGACTCAGCCCCACTCT |
| Clλ-sal | GTCGACAGAGGASGGYGGGAACAGAGTGAC |
| κ1/4-xba | TCTAGAC ATCSRGATGACCCAGTCTCC |
| κ2-xba | TCTAGATATTGTGATGACYCAGWCTCCACTCT |
| κ3-xba | TCTAGAAATTGTRWTGACRCAGTCTCCA |
| Clκ-sal | GTCGACGAAGACAGATGGTGCAGCCACAGT |
| VH1-xba | TCTAGASAGGTGCAGCTGGTGCAGTCT |
| VH2-xba | TCTAGACAGGTRCAGCTGCAGSAGTC |
| VH3-xba | TCTAGAGGTGCAGCTGKTGGAGTCT |
| Chγ1-sal | GTCGACSGATGGGCCCTTGGTGGA |

WOBBLE CODE:
Y = C+T; R = A+G; K = G+T; S = C+G; W = A+T; D = A+G+T

FIG. 54B (RT-PCR, 06-28-08)

Human Ig Variable Regions

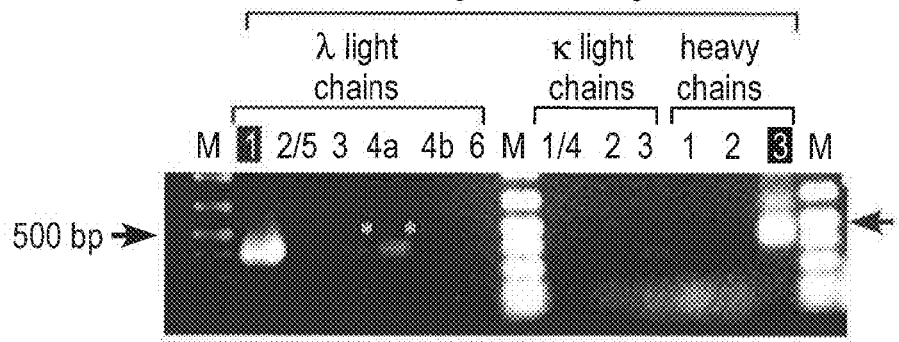

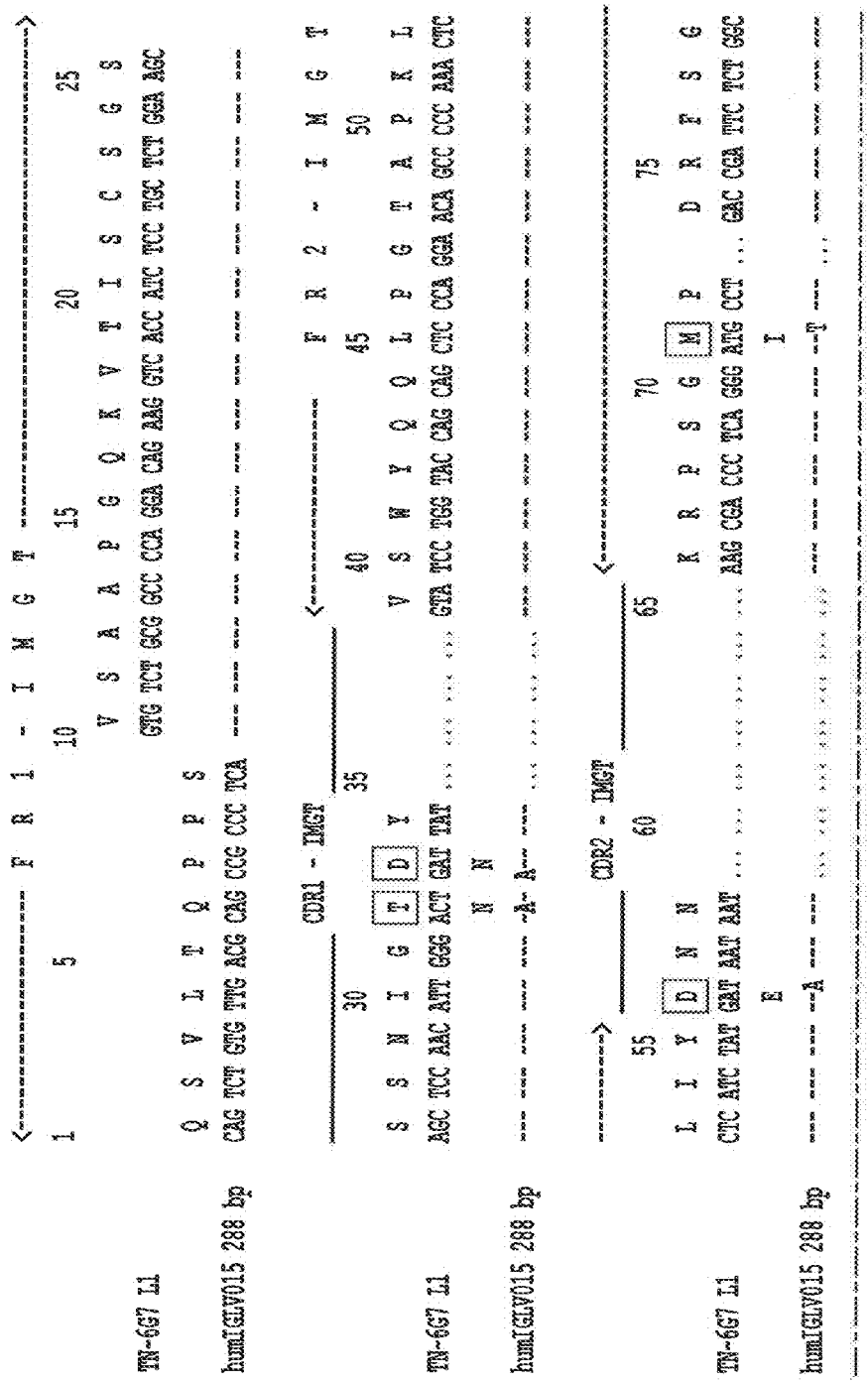
FIG. 55A1

```
                  ---- F R 3 - I M G T ---------------------------------------------------->
                       80              85              90              95             100
                    S  K           S  G  T  S  A  T  L  G  I  T  G  L  Q  T  G  D  E  A  D  Y  Y  C
TN-6G7 L1           TCC AAG ...... TCT GGC ACC TCA GCC ACC CTG GGA ATC ACC GGA CTC CAG ACT GGG GAT GAG GCT GAT TAT TAC TGC humIGLV015 288 bp   ---         ------ --- --- --- --- --- --- --- --- --G --- --- --- --- --- --- --- --- --C --- --- ---
                                        <--------- CDR3 - IMGT ----------><---------- FR4 - IMGT --------->
                         105           110 112             115               120             125            130
                    G  T  W  D     S  S  L  N  G  P  V  V  F  G  G  G  T  K  L  T  V  L  G  H  H  Q
TN-6G7 L1           GGA ACA TGG GAT AGC AGC CTG AAT GGT CCT GTG GTA TTC GGC GGA GGG ACC AAG CTG ACC GTC CTA GGT CAT CAT CAG humIGLV015 288 bp   --- --- --- --- --- --- --- --- --- --- --- --- --- --- --- --- --- --- --- --- --- --- ---
IGLJ2*01                            ---- --- --- --- --- --- --- --- --- --- --- --- --- --- --- --- --- ---

135             140             145             150
                    A  A  A  S  V  T  L  F  P  P  S  S  V  D  V  F  I  K  I  K
TN-6G7 L1           GCT GCC GCC TCC GTC ACT CTG TTT CCG CCA TCC TCT GTT GAC GTC TTT ATT AAA ATT AAA humIGLV015 288 bp
IGLJ2*01            --- --- --- --- --- --- --- --- --- --- --- --- --- ---

TN-6G7 Light Chain            Germline Homology
                                 V_L segment: IGLV015           99%
                                 J_L segment: IGLJ2*01         100%
```

FIG. 55A2

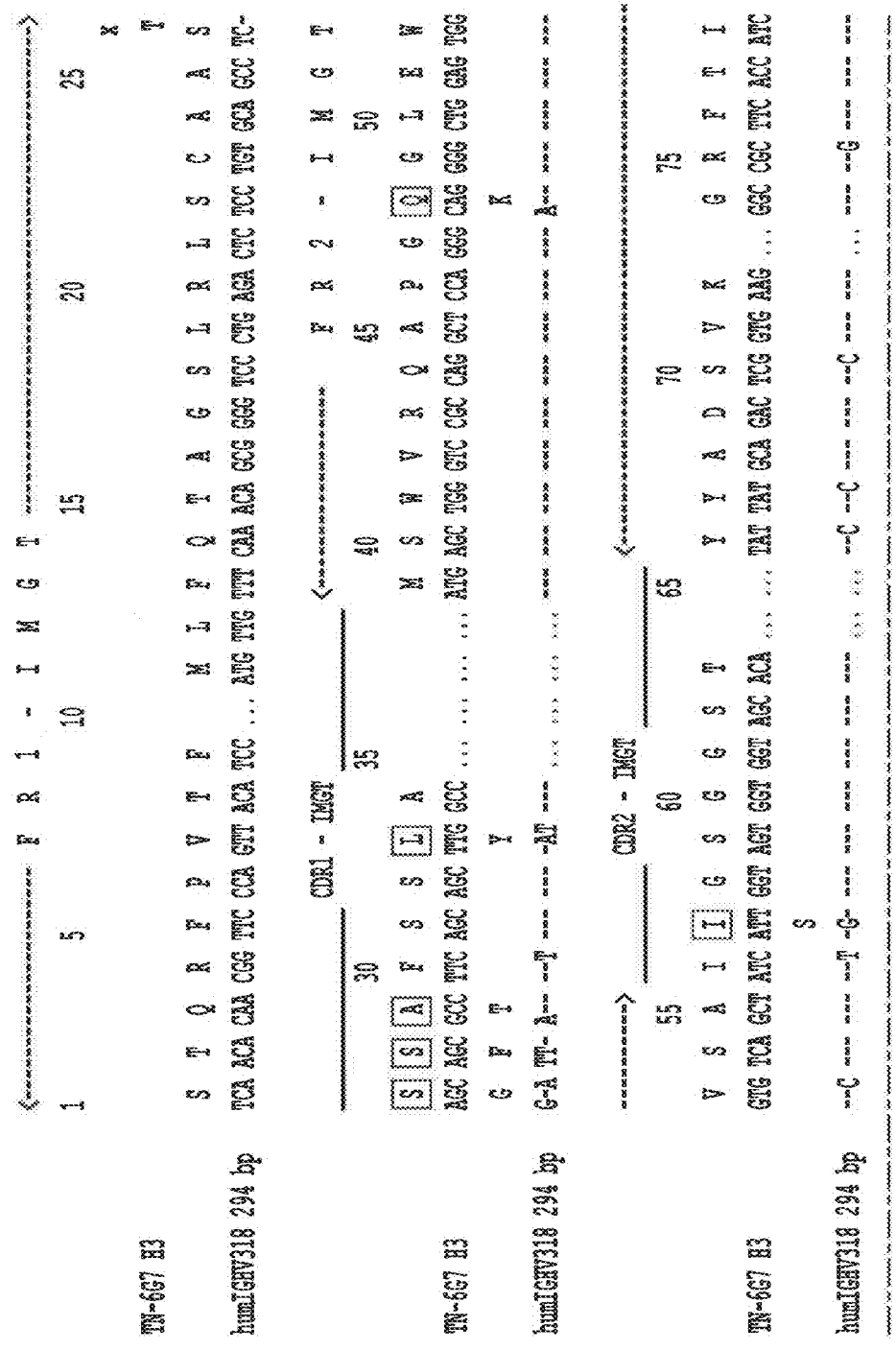
FIG. 55B1

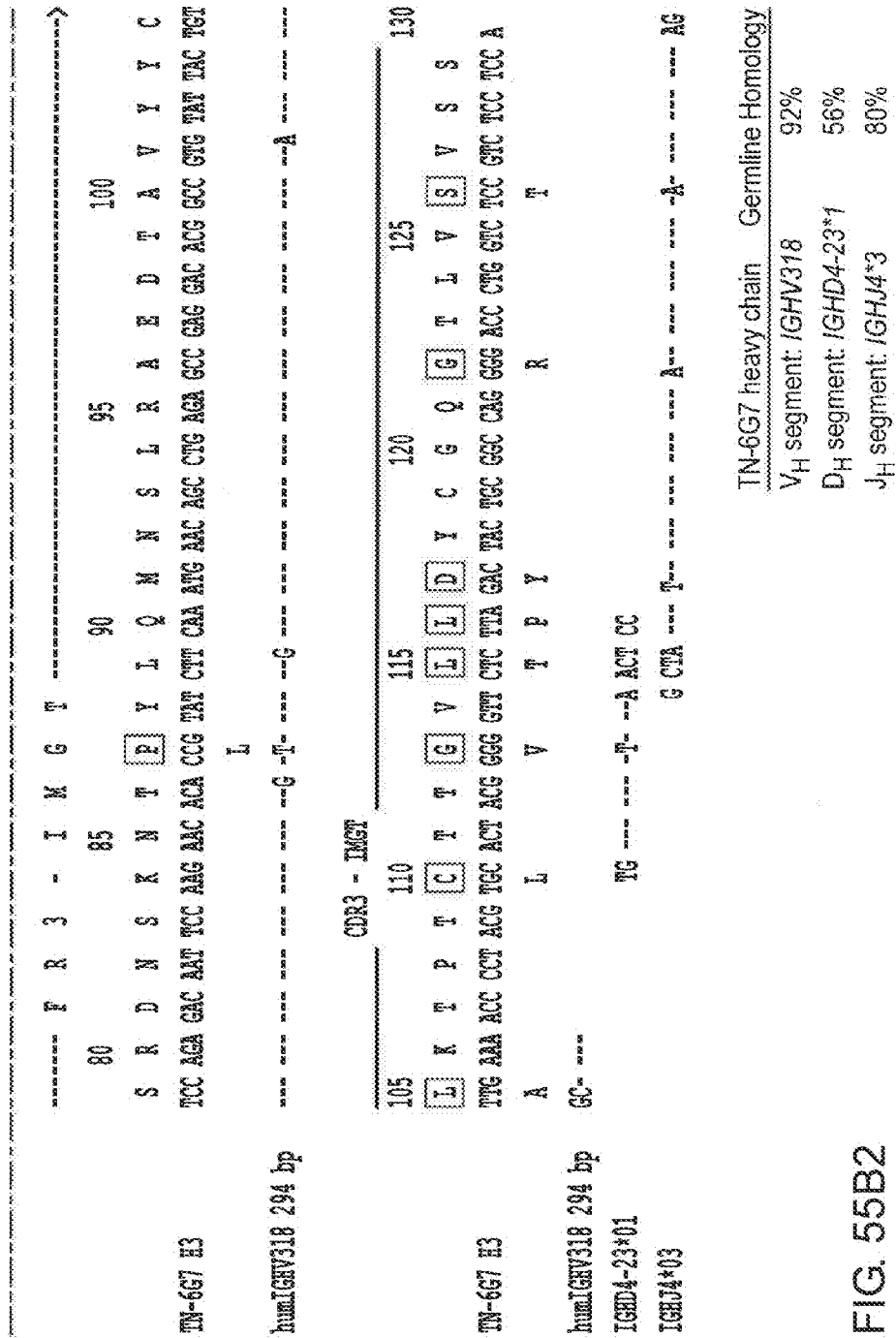
FIG. 55B2

FIG. 55C

TN-6G7 Light chain complementarity determining regions

---CDR1--> <-CDR2-> <--CDR3--

SSNIGTDY....__DNN......___GTWDSSLNGPCV

TN-6G7 Heavy chain complementarity determining regions

---CDR1--> <-CDR2-> <--CDR3---------------

SSAFSSLA....___IIGSGGST..___LKTPTCTTGVLLDYCGQGT

Amino Acid Side Chain Code: (G,A); nucleophilic (S,T,C); hydrophobic (V, L, I); amide (N,Q); bulky aromatic (F,Y,W); acidic (D,E); basic (H,L,R); proline(P)

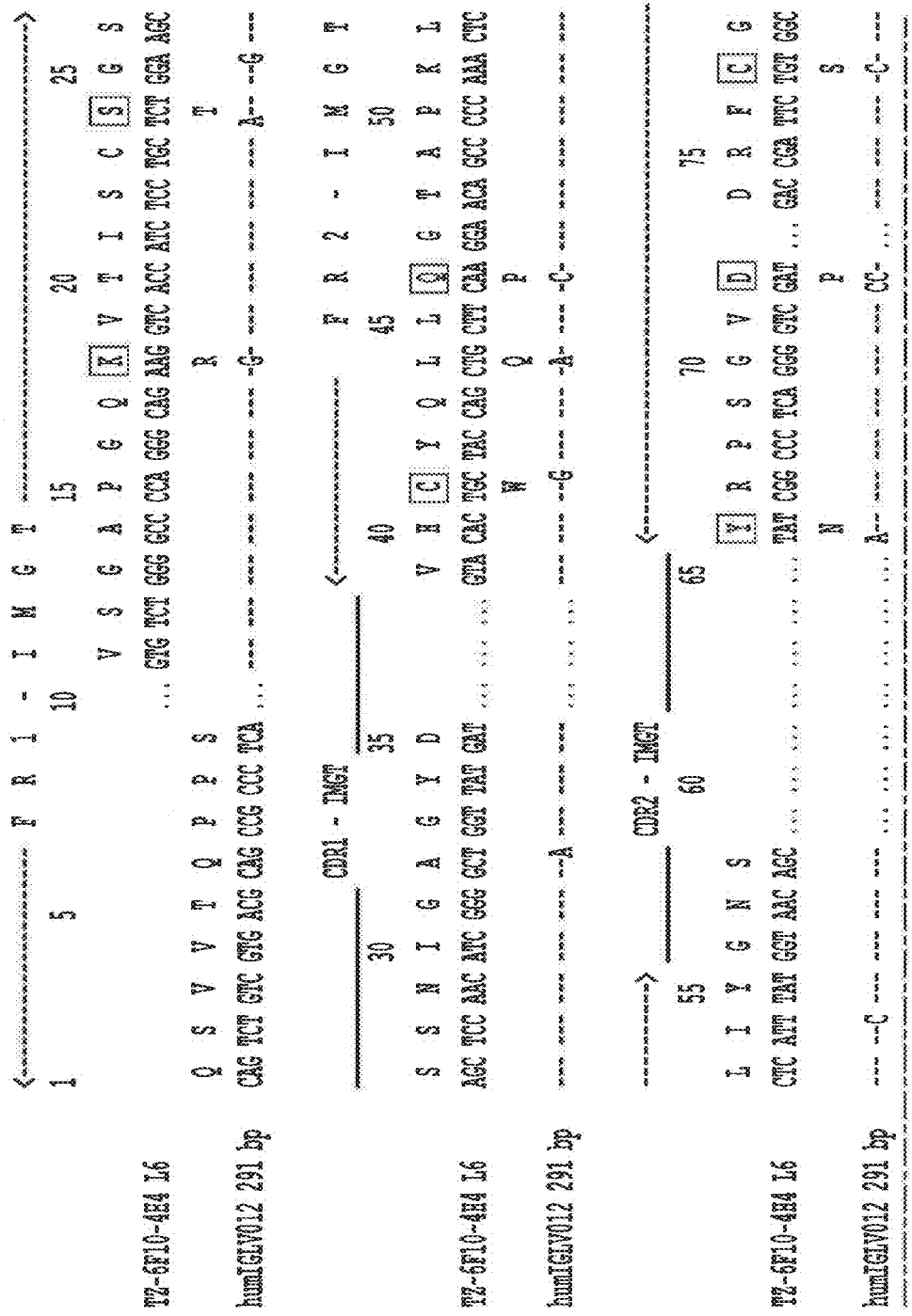
FIG. 59A1

FIG. 59A2

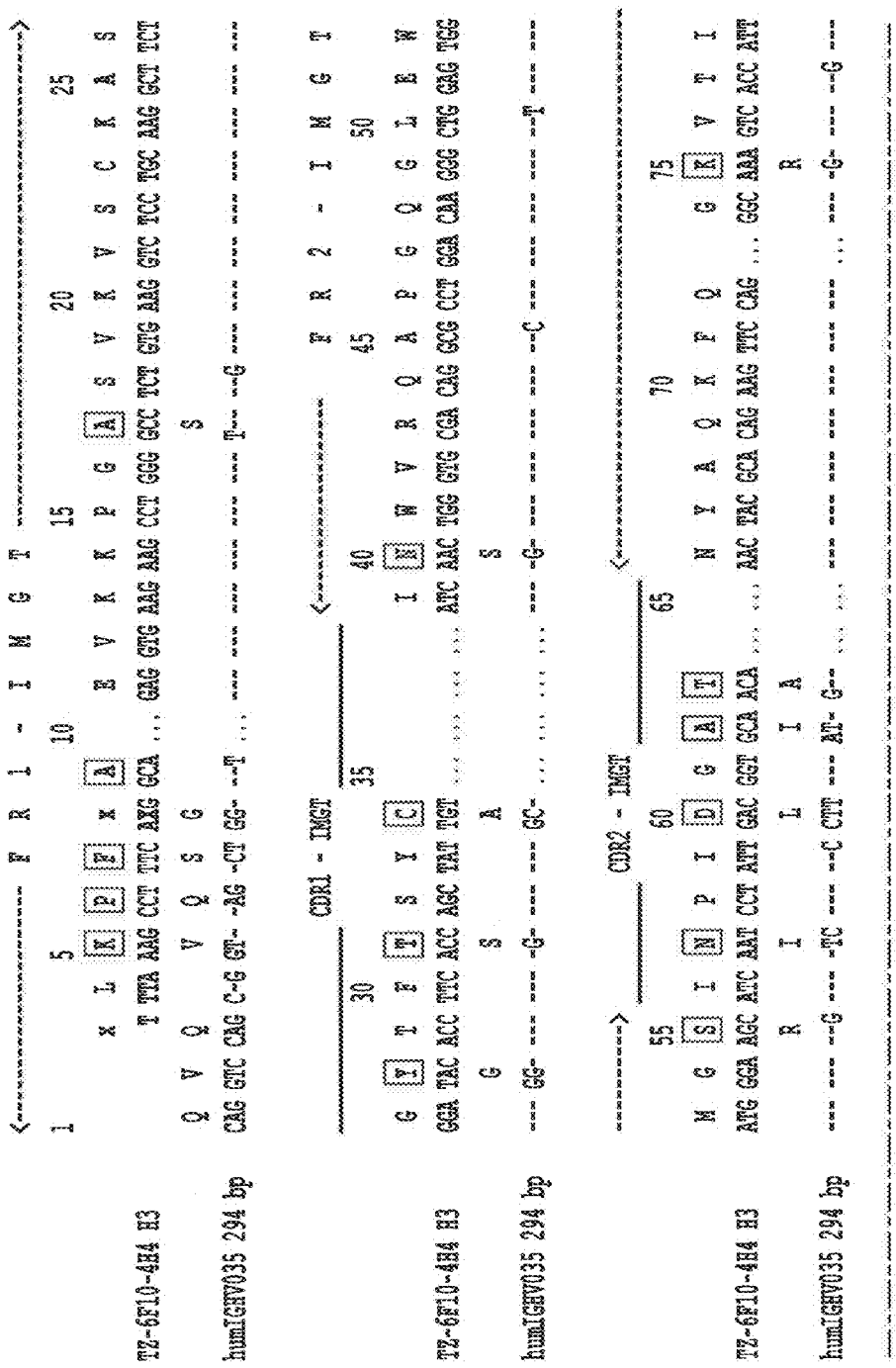
FIG. 59B1

```
           F   R   3   -   I   M   G   T   -------------------------->
           80          S   S   T   A   Y   M   Q   L   S   S   L   K   A   E   D   T   A   V   Y   Y   C
              A   D   K   S   I                        95                      100
TZ-6F10-4H4 H3  TCA GCG GAC AAG TCC ATC AGC ACA GCC TAC ATG CAG TTG AGC AGC CTG AAA GCT GAG GAC ACG GCC GTG TAT TAC TGT
              T               T                       E                    R   S
humIGHV035 294 bp   A-C ---- ---- ---- ---A ---- -CG ---- ---- ---- ---- ---- -G-- C--- ---- -G-- T--- ---- ---- ---- ---- ---- ----

CDR3
           105
           A   R   E
TZ-6F10-4H4 H3  GCG AGA GAG humIGHV035 294 bp   ---- ---- ----

TZ-6F10-4H4 heavy chain    Germline Homology
                                    V_H3 segment: IGHV035           89%
```

FIG. 59B2

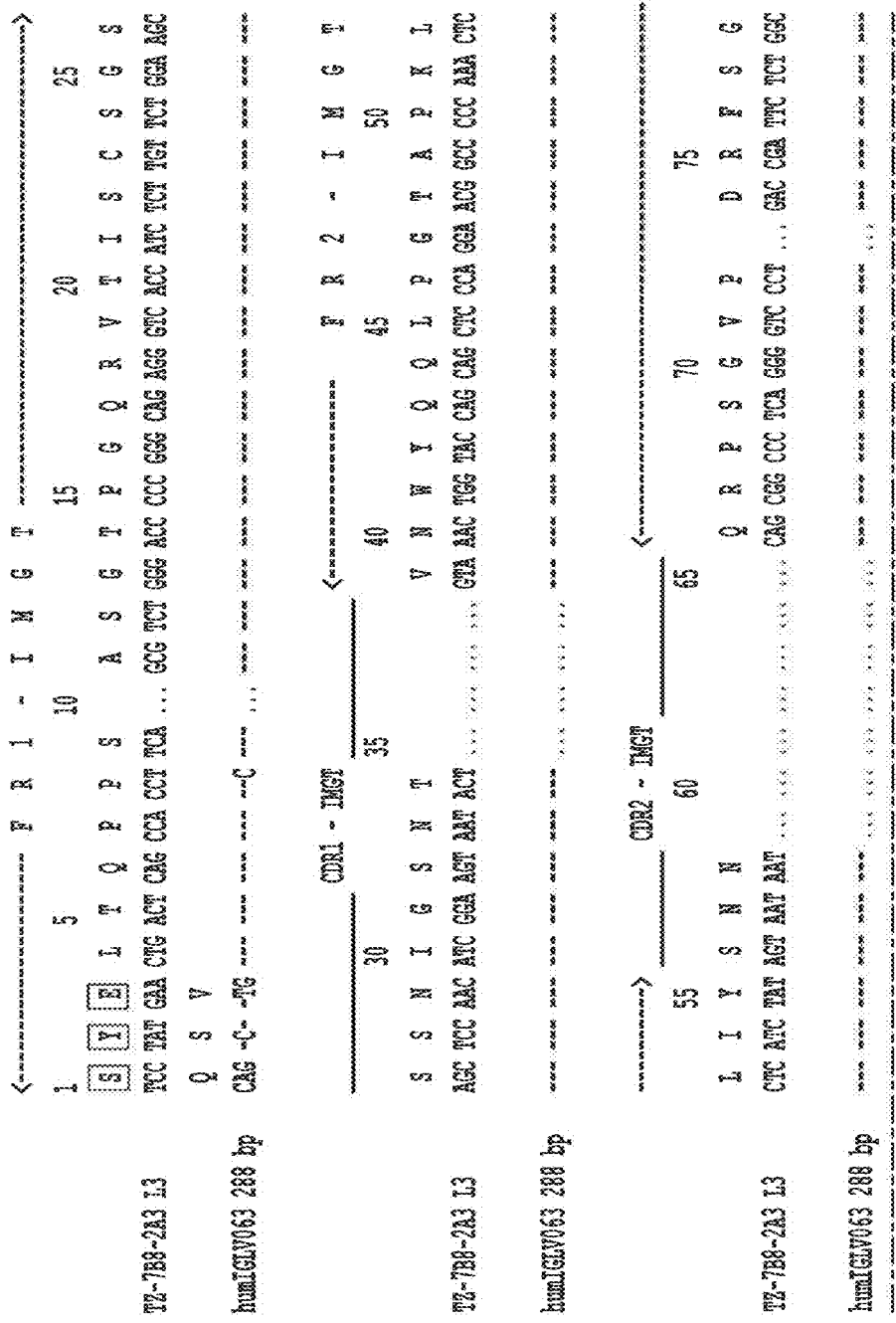
FIG. 59C1

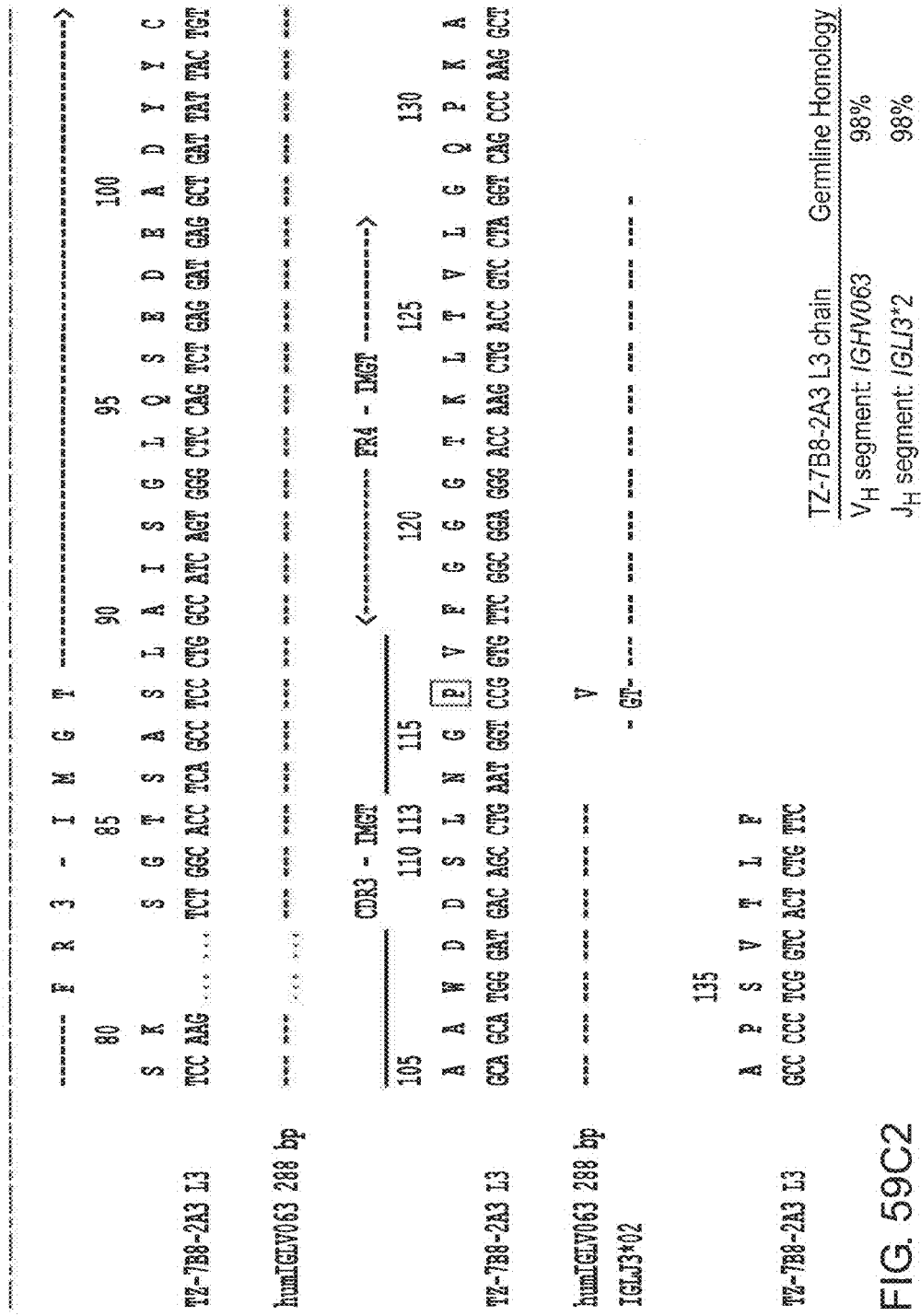
FIG. 59C2

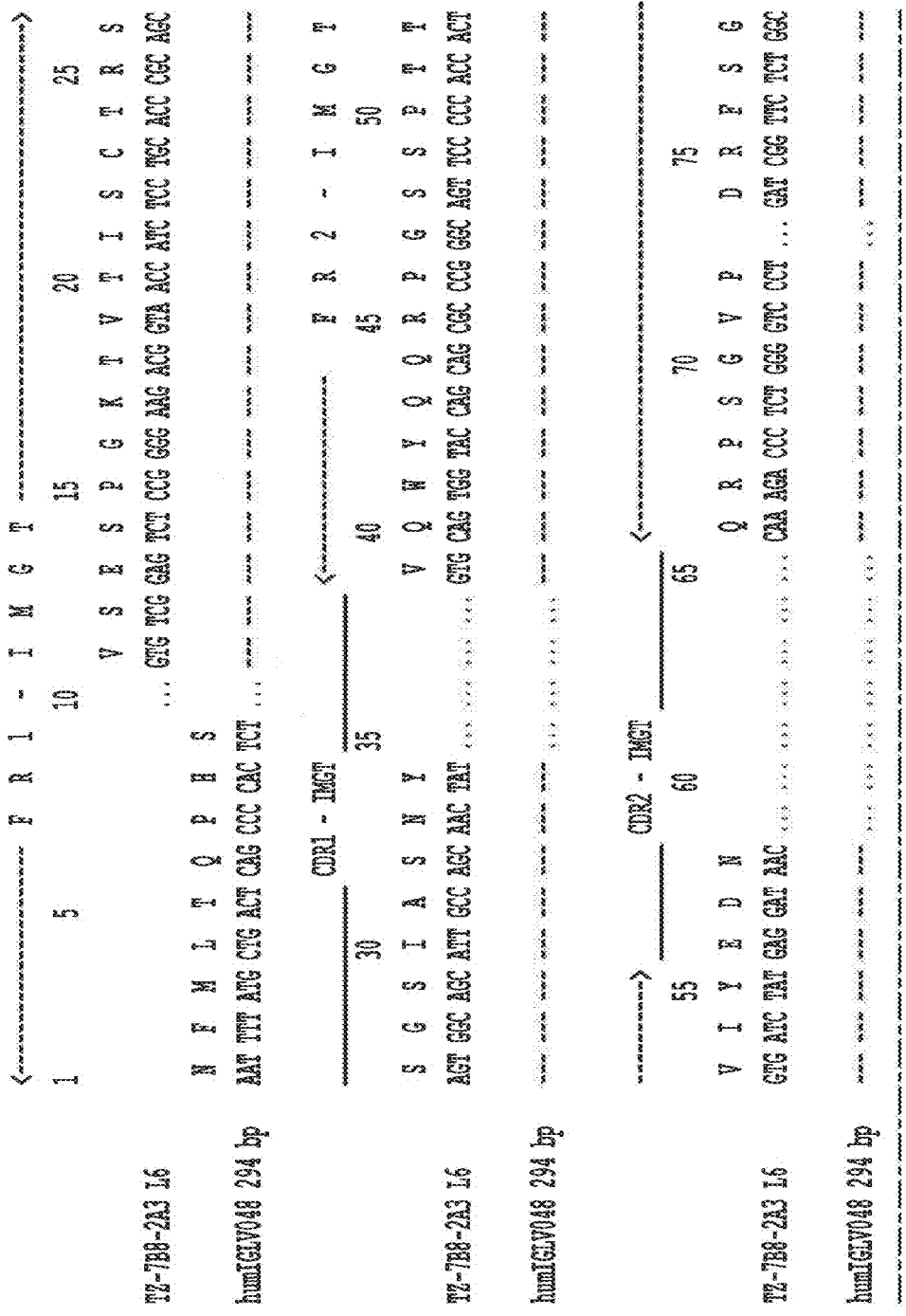
FIG. 59D1

```
                    ------- F R 3 - IMGT -----------------------------------------
                          80              85              90              95              100
                    S  I  D  S  S  S  N  S  A  S  L  T  I  S  G  L  K  T  E  D  E  A  D  Y  Y  C
TZ-7B8-2A3 L6       TCC ATC GAC AGC TCC TCC AAC AGT GCC TCC CTC ACC ATC TCT GGA CTG AAG ACT GAG GAC GAG GCT GAC TAC TAC TGT humIGLV048 294 bp   --- --- --- --- --- --- --- --- --- --- --- --- --- --- --- --- --- --- --- --- --- --- --- --- --- ---

------- CDR3 - IMGT --------       <---------- FR4 - IMGT ---------->
                    105         109 114                        120             125             130
                    Q  S  Y  D  S  S  N  W  V          F  G  G  G  T  K  L  T  V  L  [S]  Q  P  K  A  A  P
TZ-7B8-2A3 L6       CAG TCT TAT GAT AGC AGC AAT TGG GTG TTC GGC GGA GGG ACC AAG CTG ACC GTC CTA AGT CAG CCC AAG GCT GCC CCC humIGLV048 294 bp   --- --- --- --- --- --- --- --- ---                                          G
IGLJ3*02                                            --- --- --- --- --- --- --- --- --- --- --- G
```

| TZ-7B8-2A3 L6 chain | Germline Homology |
|---|---|
| V$_H$ segment: *IGLV048* | 100% |
| J$_H$ segment: *IGLJ3*2* | 99% |

FIG. 59D2

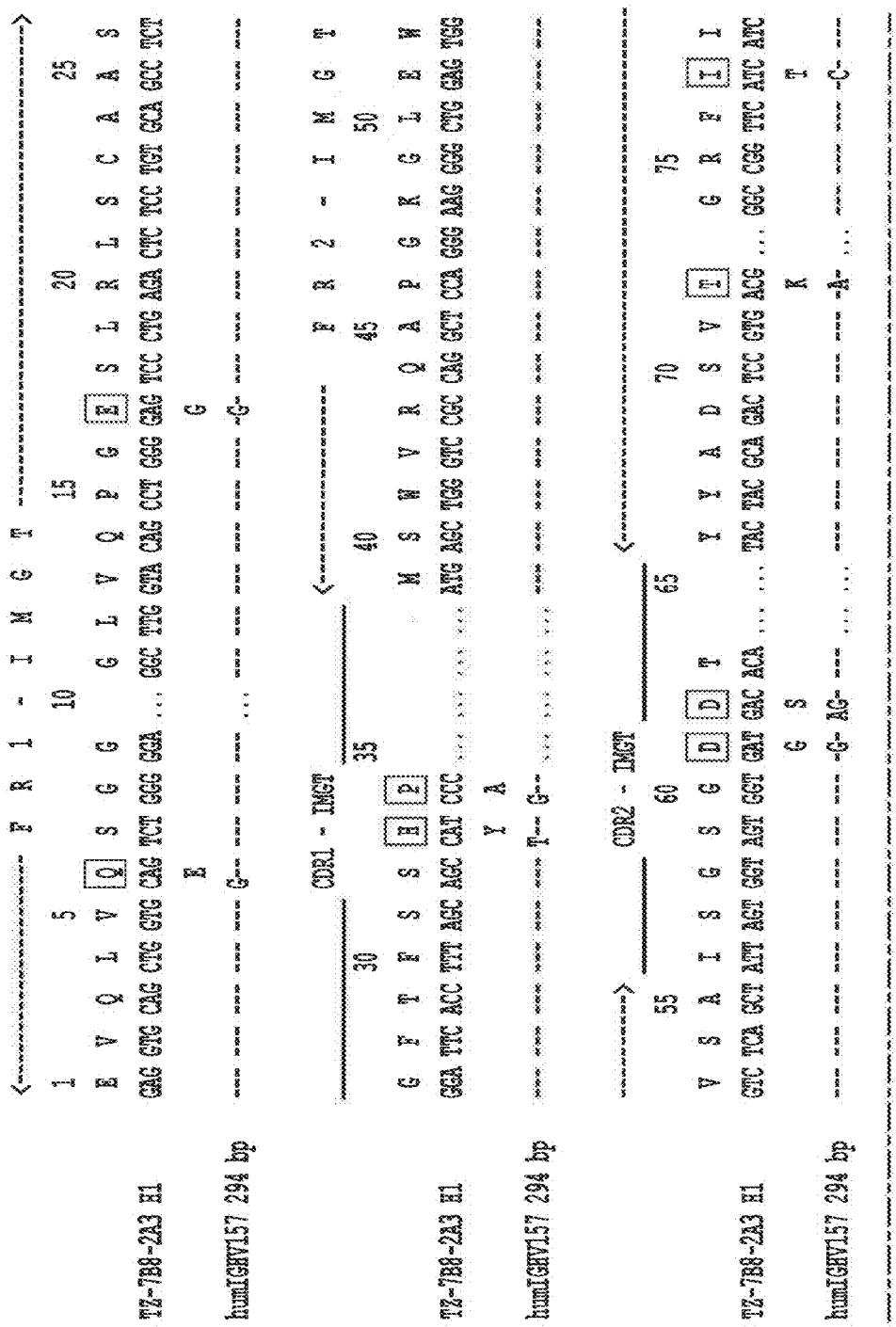
FIG. 59E1

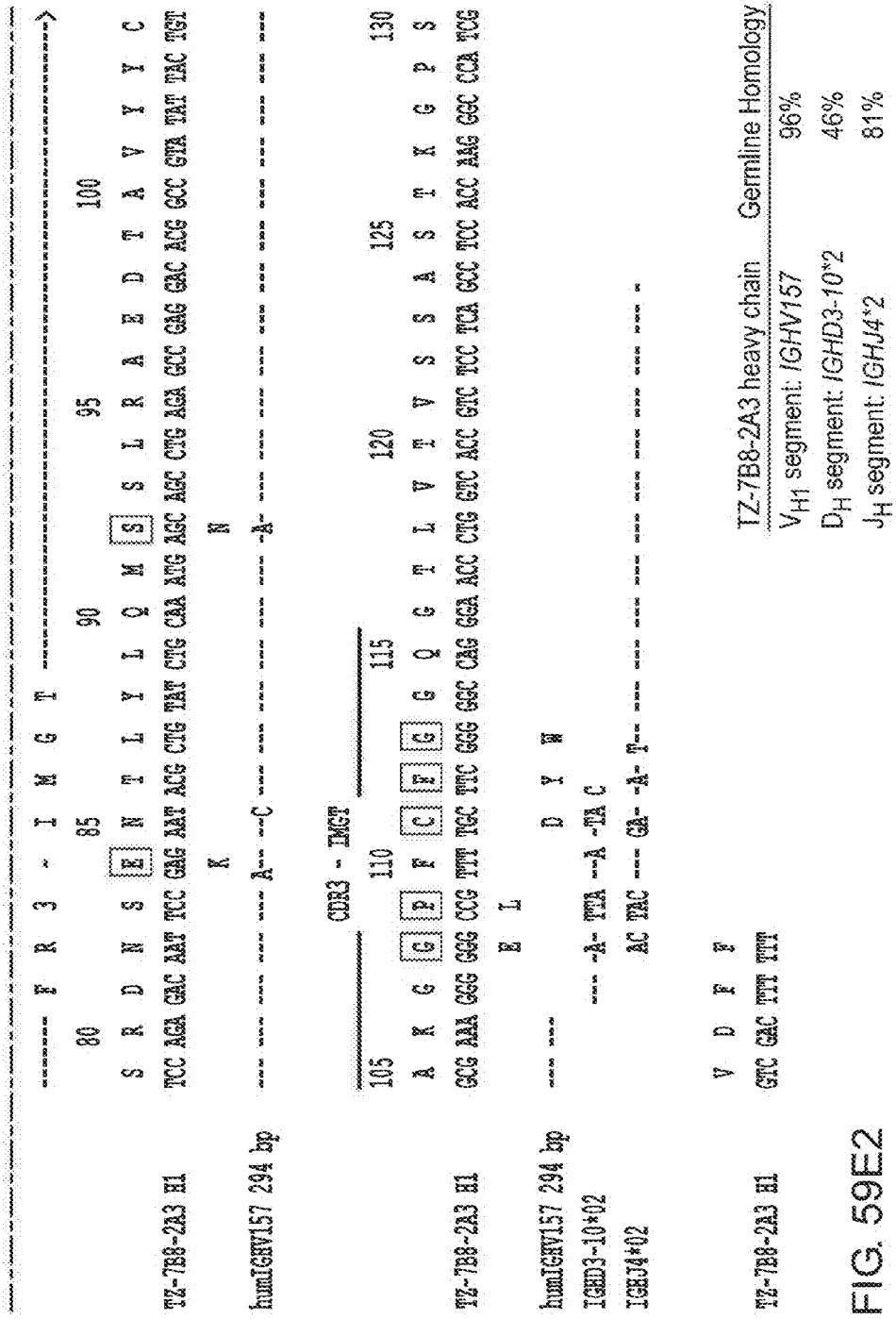
FIG. 59E2

FIG. 59F

Light chain complementarity determining regions

| | --CDR1--> | <-CDR2-> | <----CDR3---- |
|---|---|---|---|
| TZ-6F10-4H4 L6 | SSNIGAGYD... | __GNS....... | __QSYDSILDGYYV |
| TZ-7B8-2A3 L3 | SSNIGSNT.... | __SNN....... | __AAWDDSLNGPV |
| TZ-7B8-2A3 L6 | SGSIASNY.... | __EDN....... | __QSYDSSNWV |

Heavy chain complementarity determining regions

| | --CDR1--> | <-CDR2-> | <----CDR3---- |
|---|---|---|---|
| TZ-6F10-4H4 H3 | GYTFTSYC.... | __INPIDGAT.. | __AR |
| TZ-7B8-2A3 H1 | GFTFSSHP.... | __ISGSGDDT.. | __AKGGPFCFGGQ |

# HUMAN MONOCLONAL ANTIBODIES AND METHODS FOR PRODUCING THE SAME

CROSS-REFERENCE TO RELATED APPLICATIONS

This is a continuation application of prior U.S. application Ser. No. 12/671,936 (now U.S. Pat. No. 8,715,743 issued on May 6, 2014), filed on Aug. 10, 2011, which is a National Stage Application of International Application No. PCT/US2008/072124 filed Aug. 4, 2008, and which claims the priority of U.S. Provisional Patent Application Serial No. 60/953,739, filed Aug. 3, 2007, the entire disclosures of which are specifically incorporated herein by reference.

This invention was made with government support under grant number 5K01CA095443 awarded by the National Cancer Institute, National Institute of Health. The government has certain rights in the invention.

REFERENCE TO A SEQUENCE LISTING

The content of the electronically submitted sequence listing ("205350-0002-01-US-509747SEQLIST.txt", 38,602 bytes, created on Mar. 12, 2014)filed with this application is incorporated herein by reference in its entirety.

BACKGROUND OF THE INVENTION

I. Field of the Invention

The present invention relates generally to the fields of cell biology and immunology. More particularly, it concerns methods and compositions relating to the production of human monoclonal antibodies.

II. Description of Related Art

Current alternatives to vaccination are therapies consisting of antibiotics, antivirals or the passive transfer of antibodies, which are blood derived proteins that bind and neutralize pathogens. The source of antibodies may be a polyclonal supply, such as human or horse serum, or derived from a monoclonal source (single cell clone). With the technologic capability to control and select for specific antigen binding, monoclonal antibodies have yielded dramatic therapeutic benefits in cancer treatment worldwide. While some success in the treatment of infectious agents and toxins has also been observed with monoclonals, the potential for therapeutic and diagnostic agents remains largely untapped.

One particular impediment to the development of monoclonal antibodies for human therapy is the need to "humanize" such antibodies, which are generally made in mice, rats and rabbits. If human patients are administered such antibodies without humanized constant regions, they can suffer from "serum sickness," literally meaning that an antibody is mounted by the recipient against the non-human antibody sequences. While humanizing monoclonal antibodies produced in research animals can avoid this problem, this does not come without a cost—both time and expense for humanization of antibodies are considerable, leading to a bottleneck when it comes to exploiting the use of monoclonal antibodies for therapy and diagnosis in humans.

SUMMARY OF THE INVENTION

Thus, in accordance with the present invention, there is provided a method of producing an immortalized human B-cell secreting an antibody specific for a predetermined antigen comprising (a) obtaining a population of IgM-positive human B-cells; (b) contacting said population with (i) Epstein-Barr virus (EBV) to immortalize said human B-cells, and (ii) a cytokine/growth factor/signaling agent cocktail to induce B-cell differentiation, resulting in IgM-to-IgG immunoglobulin isotype class-switching and immunoglobulin secretion; and (c) culturing cells under conditions supporting said immortalization, differentiation, immunoglobulin isotype class-switching and secretion. The method may further comprise (d) selecting an immortalized human B-cell expressing an antibody for a pre-determined antigen. The selecting step may comprise an immunoassay performed on immortalized B-cell culture medium supernatants. The method may further comprise isolating a nucleic acid encoding an entire heavy and/or light chain from the immortalized human B-cell of step (d), or further comprise isolating a nucleic acid encoding a heavy and/or light chain antigen-binding region from the immortalized human B-cell of step (d), and may even further comprise cloning said nucleic acid into a nucleic acid encoding a framework region of a heavy and/or light chain. Step (d) may occur after thawing stored frozen immortalized B-cells, and/or after thawing stored frozen culture medium supernatants from said immortalized B-cells. The B-cell may be antigen naïve or antigen experienced.

The predetermined antigen may comprise a viral antigen, a bacterial antigen, a fungal antigen, a parasite antigen, a toxin antigen, a cellular receptor antigen for virus entry, a cellular receptor for bacterial entry, a cellular receptor for fungus entry, a cellular receptor mediating parasite entry, a cellular receptor mediating toxin entry, a tumor antigen, a cytokine/chemokine/growth factor antigen, a cytokine/chemokine/growth factor receptor antigen, an antigen on molecules mediating inflammation, an antigen on molecules mediating pain, an antigen on molecules mediating tissue injury/damage, an antigen on activation molecules/ligands/receptors, an antigen on costimulatory molecules/ligands/receptors, an antigen on molecules mediating innate immunity, an antigen on cellular adhesion molecules, an antigen on cellular adhesion molecule receptors, an antigen on over-expressed/under-glycosylated/oxidized/misfolded/mutated cellular proteins ("altered self" antigens) associated with a disease state, an antigen on molecules/ligands/receptors mediating cell apoptosis, or an antigen on growth inhibitory molecules.

The cytokine/signaling agent cocktail may comprise anti-IgM F(ab')$_2$ or other agents that crosslink or activate the B-cell receptor, recombinant human interleukin (IL)-2, IL-4, IL-5, IL-6, IL-9, IL-10, IL-13, interferon-α (IFN)-α, BAFF, and/or other cytokines that cause B-cell differentiation, and/or soluble CD40L, and/or other agents that supply a costimulatory signal to human B-cells. The population may be obtained from peripheral blood, tonsils, bone marrow, spleen, lymph nodes, umbilical cord blood, liver, apheresis procedures, and/or buffy coats.

The method in step (b) may further comprise an EBV concentration step, a centrifugation step during infection, or both. The method may further comprise freezing said population of human B-cells following step (c). Step (b)(ii) may be performed at about 0-96 hours following step (b)(ii), or at about 16-20 hours following step (b)(ii). About 50%-99%, or 90%-99% of said population may be immortalized by EBV infection. Step (d) may occur 1-4 weeks following infection, or 2-3 weeks following infection.

In another embodiment, there is provided an immortalized human B-cell expressing an IgG that binds immunologically to anthrax toxin, an Ebola virus antigen, ricin A chain, an A chain, a *Yersinia pestis* antigen, a Marburg virus antigen, a MDR *Staphylococcus* antigen, cholera toxin, a herpes B virus antigen, a hemorrhagic fever virus antigen.

Other embodiments provide for therapeutic human monoclonal antibodies specific for H5 hemagglutinin of avian influenza, an emerging infectious disease (SEQ ID NOS: 16 and 17). In some embodiments, the monoclonal antibodies have specificity for cancer angiogenic molecule placenta induced growth factor (PLGF), cancer and autoimmunity associated factor interleukin-6 (IL6), and toxins Staphylococcal enterotoxins B and C2 (SEB and SEC2, respectively), and ricin subunit B (the cell binding domain).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." "About" is defined as including amounts varying from those stated by 5-10%.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Effect of TLR ligands and viral preparation. FIG. 1B. Effect of virus stock concentration.

(FIG. 3B) a flow cytometry analysis of infection. Gate indicates that 45% of cells fluoresce above background with a mean fluorescence intensity (MFI) of 15.1 for B95-8 infected cells, and of 61.9 for EBfaV-GFP infected cells.

FIGS. 5A-B. IgM and IgG expression profile after at least 8 weeks in culture of representative samples following treatment with different signaling agent combinations. B cells from three tonsil samples were isolated, inoculated with B95-8 EBV, seeded into 24-well plates, and treated with the indicated combinations of signaling agents as described in Example 1. Cells were treated once a week for the first 3 weeks, and the culture supernatants were collected weekly. Culture supernatants collected on week 8 or week 10 post-infection were analyzed by ELISA for IgG and IgM. levels as described in Example 1, Two representative specimens are shown in (FIG. 5A) that switched from IgM to IgG secretion after continued culture with soluble CD40L, or IL-6 and anti-IgM(Fab')$_2$, but not with IL-4 and anti-IgM (Fab')$_2$ or without addition of cytokines (Media). The IgM and IgG secretion profiles for these same specimens cultured for only one week, at which time mainly IgM was produced, were shown in FIG. 4. (FIG. 5B) depicts representative results from a tonsil specimen that switched from IgM to IgG secretion after culture with BAFF, soluble CD40L and anti-IgM(Fab')2, Again immunoglobulin isotype class switching did not occur after treatment with IL-4 and anti-IgM(Fab')$_2$, or with media only. Means ± SD of samples and controls (n=4) are shown.

FIG. 8. Immortalized peripheral blood B cells obtained from volunteer V-5 (PBMC A1) were stimulated to produce IgG that binds H5N1 hemagglutinin (H5 HA). EBV-immortalized B cells derived from PBMC A1 sample were stimulated to produce IgG by treatment with anti-human IgM (Fab')$_2$, IL-4, IL-6 and BAFF (see Example 1), and cultured in three 96-well plates ($10^4$ cells per well). After week 1 and week 2, culture supernatants from all wells on each plate were collected and pooled, then tested for H5 HA binding as described in Example 1. Mean absorbance at $OD_{405}$ ±SD of samples and controls (n=3) are shown.

FIG. 9. H5 HA specific IgG production in individual rows on plates identified with binding activity, from PBMC A1 sample. Culture supernatants from all wells in each row of reactive plates 1, 2 and 3 were pooled and assayed for H5 HA binding as described in the Example 1. Mean absorbance at $OD_{405}$±SD of samples and controls (n=3) are shown. Rows with significant H5 HA binding (Plate 1 row E, Plate 2, rows C, D and E, Plate 3, row D) were chosen for subsequent analysis.

FIG. 10. H5 HA specific IgG production in adjacent paired wells of rows identified with binding activity, from PBMC A1 sample. Week 3 culture supernatant from pairs of adjacent wells in H5 HA reactive rows (identified in FIG. 9) were pooled and assayed for H5 HA binding as described in Example 1. Mean absorbance at $OD_{405}$±SD of samples and controls (n=3) are shown. Wells 11 and 12 on plate 2 row D were selected for individual analysis.

FIG. 13. Subcloning strategy for isolation of H5 HA specific B cell clones from PBMC A2 sample. EBV-immortalized B cells from PBMC A2 were stimulated to produce IgG by treatment with anti-human IgM(Fab')$_2$, CD40L and BAFF (see Example 1), and cultured in six 96-well plates ($10^4$ cells per well). H5 HA binding was determined as described in Example 1. Culture supernatants from all wells on each plate were collected (150 µl per well), and 50 µl per well were pooled and assayed for H5 HA binding. Plate 4, 5 and 6 were reactive with H5 HA, and culture supernatants from wells in each row on these plates were pooled and assayed (week 2). Supernatants in dual adjacent wells from reactive rows D and G on plate 4, row E on Plate 5 and row C on Plate 6 were collected and analyzed for H5 HA reactivity (week 3). The reactive wells G8 on Plate 4, E1 on Plate 5 and C3 on Plate 6 were subcloned by limiting dilution analysis in 96-well plates containing 1, 10, 100, or 1000 cells per well on week 4. Culture supernatant from all wells on each plate were pooled and tested by ELISA for H5 HA reactivity, identifying potential clonal populations on cells subcloned from Plate 4 and Plate 6 after 8-9 weeks.

FIG. 15. H5 HA specific IgG in culture supernatants from immortalized B cells, from TNSL A sample. EBV-immortalized B cells from TNSL A were stimulated to produce IgG with IL-4, IL-6, BAFF and anti-human IgM (Fab')$_2$ (see Example 1), and cultured in ten 96-well plates ($2\times10^5$ cells per well). H5 HA binding was determined as described in Example 1. Culture supernatants from all wells on each plate (150 µl per well) were collected, and 50 per well were pooled and assayed for H5 HA binding. Week 1 analysis showed no reactivity, while reactivity was detected on Plates 6 and 9 on week 2. Culture supernatants from all wells on individual rows on Plates 6 and 9 were pooled and assayed for H5 HA binding as described in Example 1. Rows C and F on Plate 9 were reactive; however, the sample was lost due to fungal contamination after week 3, and screening was thus discontinued.

FIG. 16. Lack of H5 HA specific IgG in culture supernatants derived from immortalized B cells from TNSL B sample. EBV-immortalized B cells from TNSL B were stimulated to produce IgG with anti-human IgM (Fab')$_2$, CD40L and BAFF (see Example 1), and cultured in ten 96-well plates ($2\times10^5$ cells per well). H5 HA binding was determined as described in Example 1. Culture supernatants from all wells on each plate (150 µl per well) were collected, and 50 µl per well were pooled and assayed for H5 HA binding. Week 1 analysis (Apr. 11, 2007) showed low level reactivity on Plate 3, and culture supernatant from row D on this plate was weakly reactive on week 2; however, after weeks 3 and 4, no H5 HA-reactivity could be detected on any of the plates, and screening was thus discontinued.

FIG. 17. Lack of H5 HA specific IgG in culture supernatants derived from immortalized B cells from TNSL C sample. EBV-immortalized B cells from TNSL C were stimulated to produce IgG with anti-human IgM (Fab')$_2$, CD40L and BAFF (see Example 1), and cultured in ten 96-well plates (>$2\times10^5$ cells per well). H5 HA binding was determined as described in Example 1. Culture supernatants from all wells on each plate (150 µl per well) were collected, and 50 µl per well were pooled and assayed for H5 HA binding. Week 1 analysis showed very low level reactivity on plates 7, 8, 9, and 10; however, after weeks 2 and 3, no H5 HA-reactivity could be detected on any of the plates, and screening was thus discontinued.

Figure 18:
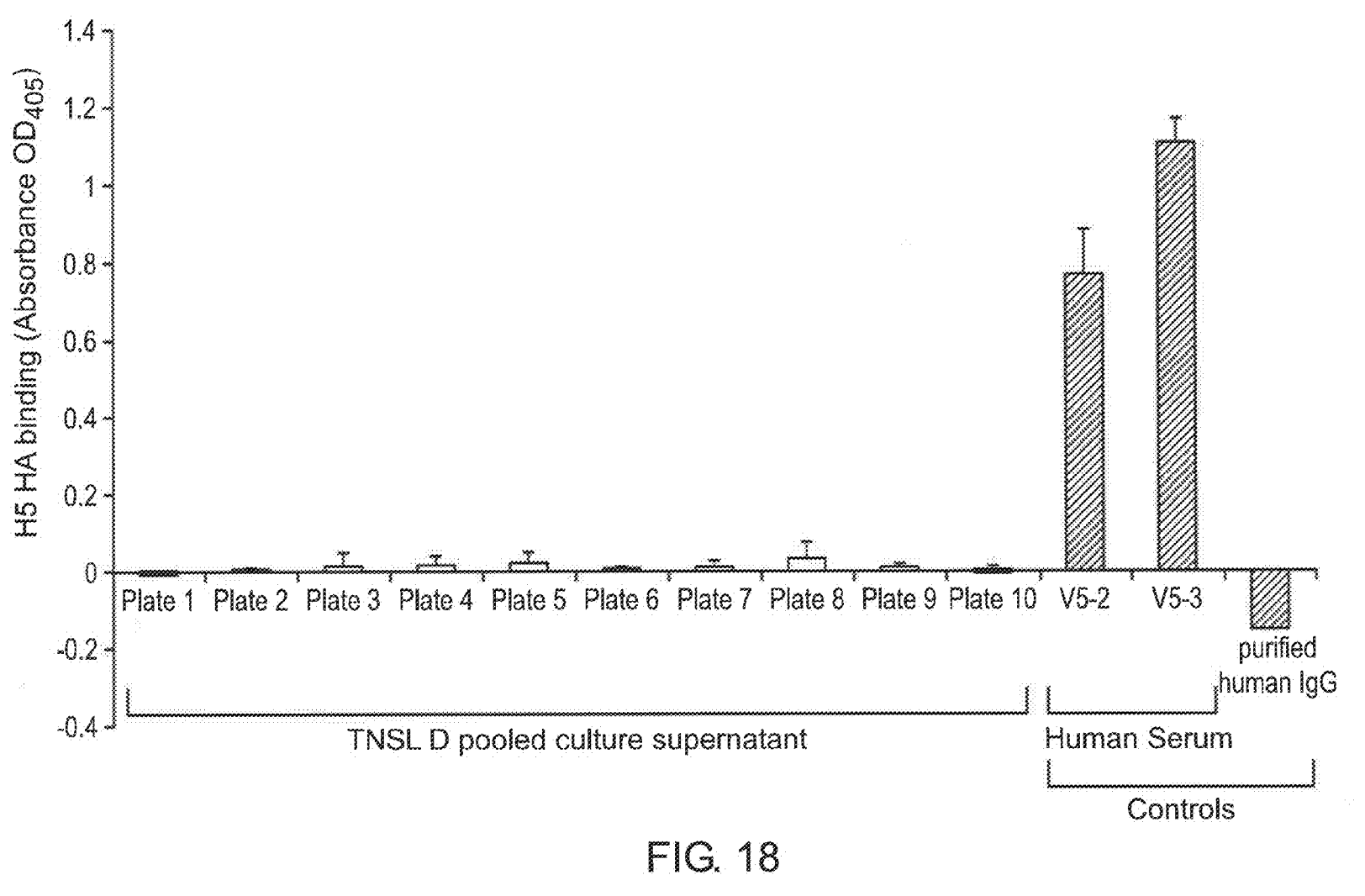

FIG. 18. Immortalized tonsil B cells produced very little or no H5 HA reactive IgG after one week of culture, from TNSL D sample. EBV-immortalized tonsil B cells from TNSL D were stimulated to produce IgG with anti-human IgM (Fab')$_2$, CD40L and BAFF (see Example 1), and were cultured in ten 96-well plates at $1.5 \times 10^5$ cells per well. One week later, culture supernatants from all wells on each plate (150 µl per well) were collected and 50 µl of each was pooled, and then tested for H5 HA binding as described in Example 1. Significant H5 HA specific binding was not detected on any plates. Mean absorbance levels at $OD_{405} \pm SD$ of samples and controls (n=3) are shown.

Figure 19:
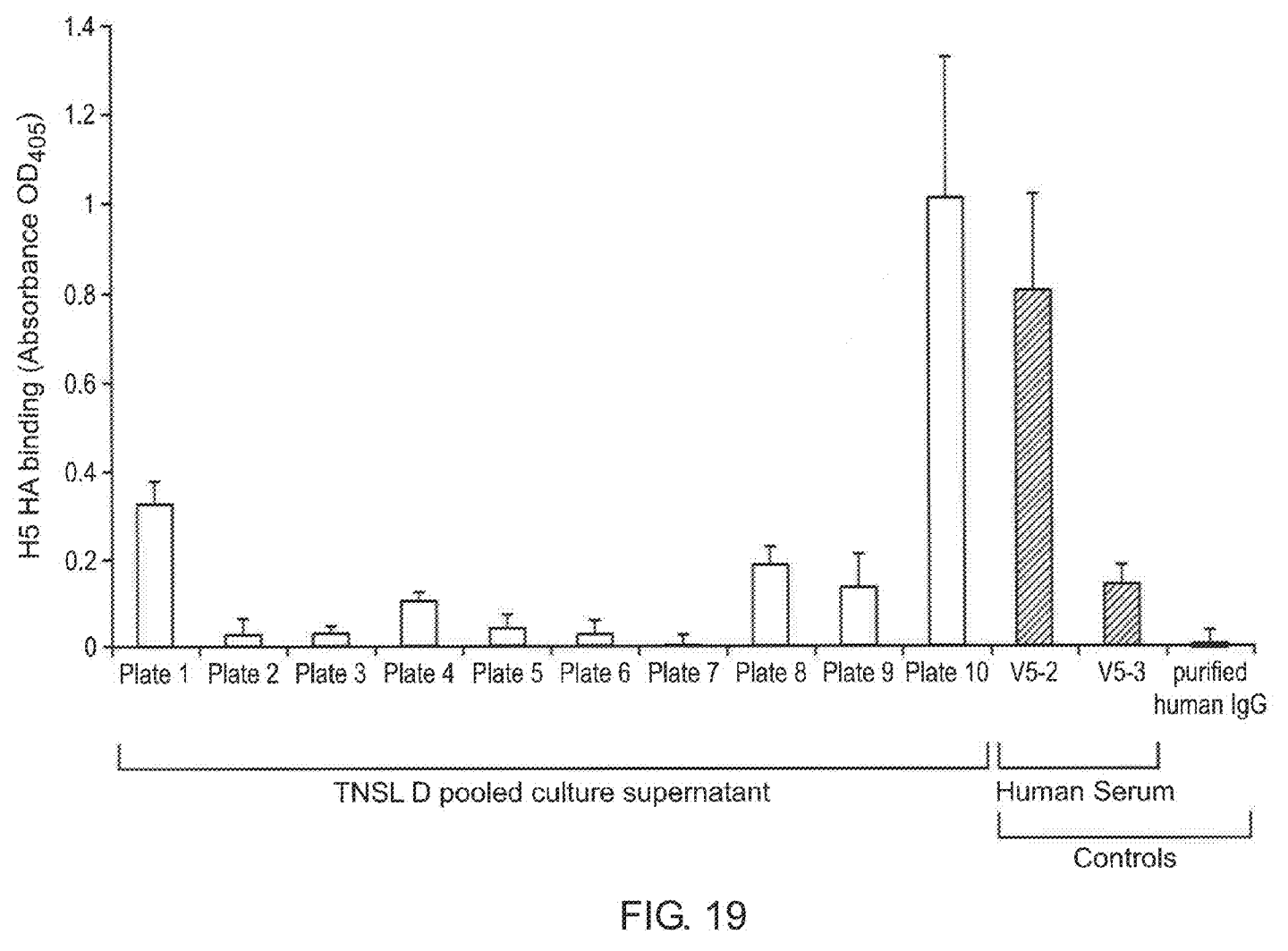

FIG. 19. Immortalized tonsil B cells on Plate 10 produced IgG that specifically binds H5 HA after two weeks of culture, from TNSL D sample. EBV-immortalized tonsil B cells from TNSL D sample were cultured in ten 96-well plates at $1.5 \times 10^5$ cells per well. 2 weeks later, 150 µl of culture supernatants from all wells on each plate were collected and 50 µA were pooled, then tested for H5 HA binding as described in Example 1. H5 HA specific binding was detected on Plates 1, 8, 9 and 10, with highest reactivity on Plate 10. Mean absorbance level at $OD_{405} \pm SD$ of samples and controls (n=3) are shown.

FIG. 22. Subcloning strategy for isolating H5 HA specific B cell clones from TNSL D sample. EBV-immortalized tonsil B cells from TNSL D sample were stimulated to produce IgG with anti-human IgM (Fab')$_2$, CD40L and BAFF (see Example 1), and were cultured in ten 96-well plates at $1.5 \times 10^5$ cells per well. One week later, culture supernatants from all wells on each plate (150 µl per well) were collected and 50 µl of each was pooled, and then tested for H5 HA binding as described in Example 1. After one week, no plates had H5 HA reactive IgG. However, after two weeks plates 1, 8, 9 and 10 were reactive, with Plate 10 exhibiting strong reactivity. Culture supernatants from individual rows on plates 1, 8 and 9 were analyzed on week 3; and supernatant from adjacent paired wells for each row on plate 10 were pooled and assayed simultaneously. Paired wells 3 and 4 in Row G on Plate 10 produced H5 HA reactive IgG, and production was subsequently localized to well G4, which was subcloned by limiting dilution analysis into 96-well plates containing 1, 10, 100, or 1000 cells per well. H5 HA reactive IgG was identified at weeks 7 and 8 in plates containing 100 and 1000 cells per well. Isolation of a single cell clonal population is currently ongoing. H5 HA reactivity could no longer be identified from plates 1, 8 and 9 after three weeks, at which point screening was discontinued.

Figure 24:
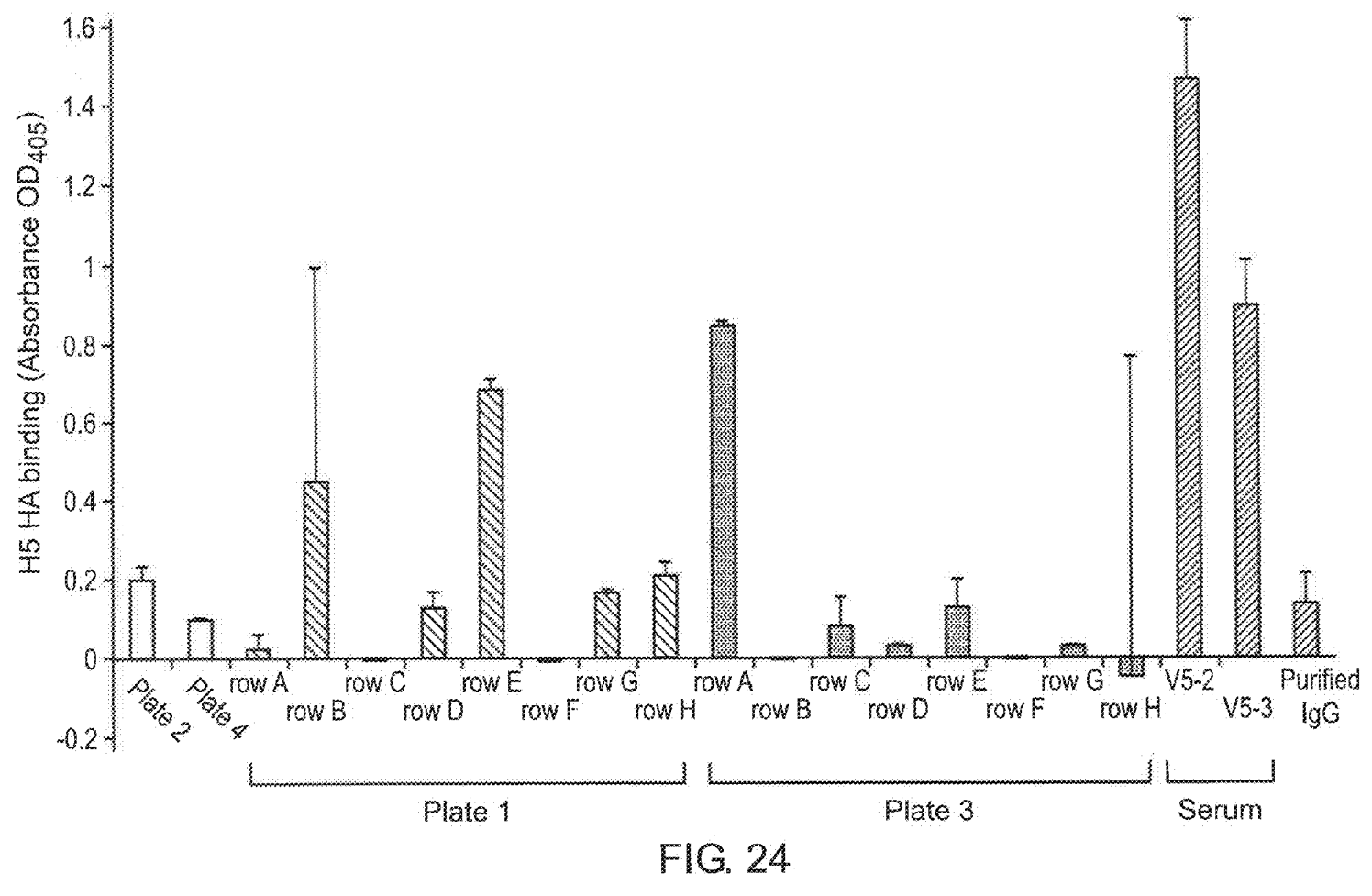

FIG. 24. H5 HA reactive IgG was detected in culture supernatants from individual rows on Plates 1 and 3, from TNSL-E sample. EBV-immortalized tonsil B cells from TNSL E sample were stimulated to produce IgG with anti-human IgM(Fab)$_2$, CD40L and BAFF (see Example 1), and were cultured in four 96-well plates at $10^5$ cells per well. Two weeks later, culture supernatants from all wells on each plate (150 µl per well) were collected and 50 of each was pooled from individual rows on plates 1 and 3, and then tested for H5 HA binding as described in Example 1; supernatants from all wells on plates 2 and 4 were pooled and simultaneously assayed. Row A of plate 3 and rows E and B of plate 1 had significant levels of H5 HA reactive IgG, and were subjected to further analysis. Mean absorbance level at $OD_{405} \pm SD$ of samples and controls (n=3) are shown.

(FIG. 30A) Pooled culture supernatants from individual rows on plate containing TNSL-E subclones (FIG. 29, 1000 cells/well), were assayed for H5 HA binding by ELISA as described in Example 1. Strong H5 HA binding was observed in rows C and E. (FIG. 30B) Culture supernatants from individual wells in rows C and E were next assayed for H5 HA binding by ELISA. Cells in reactive wells C7 and E3 were then subcloned by 2 additional rounds of limiting dilution cloning. (FIG. 30) Culture supernatants from resulting clones C7F6 and E3A5 were tested for H5 HA binding by ELISA. In all cases, controls consisted of reactive human serum from volunteer V5 (1:1000 dilution), and purified human IgG (500 ng, Sigma). Mean absorbance±SD of samples and controls (n=3) are shown.

FIGS. 34A-B Identification of light and heavy chain variable regions comprising the H5 HA reactive IgG1 molecules produced by TE-3A10-E3A5 and -C7F6 clones. Sequences of forward and reverse primers used to amplify light (λ, κ) and heavy chain ($V_H$) immunoglobulin genes are listed in table (FIG. 34A). Primers were optimized to amplify the maximum number of potential variable region sequences (adapted from Welschof et al, 1995, J. Immunol, Methods, 179: 203-214). Restriction enzyme cleavage site sequence for XbaI was added to the forward primers, and SaiI was added to reverse primers for subsequent cloning and sequencing of the amplification products (SEQ ID NOS:1-15). (FIG. 34B) PCR amplification of cDNA from E3A5 and C7F6 H5 HA reactive clones was performed using each primer pair, and all PCR products were sequenced (see appendix). Both clones expressed X1. light chain variant; E3A5 expressed $V_{H3}$ heavy chain gene, and C7F6 expressed $H_{H1}$, indicating that the two clones had unique origins, and were not derived from a common precursor. (*Minor PCR bands resulted from 3' primer homology between 21-xba with 2 3-xba and 2 4a-xba primers as confirmed by sequencing.) Lane M: marker=1 kb Plus ladder from Gibco-BRL; arrow indicates location of 500 bp band.

FIGS. 35A1-E. DNA and amino add sequences of the heavy and light chain variable regions of the H5 HA reactive dunes, TE-3A10-E3A5 and -C7F6. PCR products described in FIG. 34 were sequenced and analyzed. Results of the analysis are shown for light chains (FIGS. 35A1, 35A2, 35B1 and 35B2) (SEQ ID NOS:16, 17, 18, 19, 20 and 21) and heavy chains (SEQ ID NOS: 22, .23, 24, 25, 26, and 27) (FIGS. 35C1, 35C2, 35D1 and 35D2) of E3A5 and C7F6, respectively. The. DNA sequences of the clones are aligned against the germ-line sequences, which have the closest homology, Any changes in the DNA code are depicted below, and changes in the amino acid sequence are shown. Sequences of different segments and the junction region are shown, as follows: variable (V) segments, diversity (D) segments, joining (J) segments, P nucleotides, N nucleotides. Comparison of the complementarity determining regions of both clones is shown in (FIG. 35E). *Mutations in the D-J region of C7F6 heavy chain made exact prediction of the CDR3 terminal location unreliable by VBASE2 software (SEQ ID NOS: 28, 29, 30 and 31).

(FIG. 37A) Two weeks later, culture supernatants from corresponding wells on all of the 10 plates, e.g., all A1 wells, were pooled and tested for SEB binding, on a single 96-well ELISA plate. Wells A8 and H3 were significantly increased above background, indicating that wells A8 and H3 each were positive on one of the 10 plates. (FIG. 37B) Simultaneously, aliquots of the same culture supernatants from all wells on each plate were pooled and assayed for SEB binding by ELISA, which indicated that plates 4 and 8 had reactivity. $OD_{405}$ absorbance values for each well minus the plate average are shown. (FIG. 37C) Combining the wells A8 and H3 reactivity in (FIG. 37A) with plates 4 and 8 reactivity in (FIG. 37B), the inventors confirmed that plate 8 well A8 and plate 4 well H3 (TX4A8 and TX8H3) were SEB reactive by testing their culture supernatants. Controls consisted of mouse anti-SEB monoclonal antibody diluted 1:5000.

FIGS. 38A-B Confirmation of repertoire SEB reactivity and screening of primary subclone plate pools. (FIG. 38A) Tonsil repertoires TR, TS, TV, and TX were screened for SEB reactivity as in FIG. 2. Wells with confirmed reactivity were chosen for primary subcloning. (FIG. 38B) All wells on each primary subclone plate were pooled and screened for SEB reactivity. TR and TS subclones lost reactivity, while Reactivity was detected at varying levels on TV and TX pooled subclones on each plate.

FIG. 39 Screening of TV-6F7 primary subclone plates for SEB reactivity. Plates were screened by ELISA ~2 weeks after primary subcloning. TV-6F7-2H6, -3E2 and -3E4 were chosen for secondary subcloning at 50 cells per well, 3 plates each.

FIG. 40 Screening of TX-4H3 primary subclone plates for SEB reactivity. Plates were screened by ELISA ~2 weeks after primary subcloning. TX-4H3-1E7, 3C6 and 3D8 were chosen for secondary subcloning at 50 cells per well, 3 plates each.

FIG. 41 Screening of TX-8A8 primary subclone plates for SEB reactivity. Plates were screened by ELISA ~2 weeks after primary subcloning. TX-8A8-1C6, 3D7 and 3F4 were chosen for secondary subcloning at 50 cells per well, 3 plates each.

(FIG. 42A) Tonsil repertoires TR and TS were screened for SEC2 reactivity using the strategy from FIG. 2. Wells with confirmed reactivity (TR-10A4, -10E12, TS-6C5) were chosen for primary subcloning. (FIG. 42B) All wells on each primary subclone plate were pooled and screened for SEC2 reactivity. Tonsil repertoire TV was also screened, resulting in identification of well TV-bB2 with SEC2 reactivity. TR and TS subclones lost reactivity. Well TV-bB2 was selected for primary subcloning, 3 plates.

FIGS. 43A-B Screening of TX-bB2 primary subclone plates for SEC2 reactivity. Plates were screened by ELISA ~2 weeks after primary subcloning. (FIG. 43A) All wells on each primary subclone plate were pooled and screened for SEC2 reactivity, which was detected on plate 2. (FIG. 43B) TV-bB2-2E1 and 2F2 were chosen for secondary subcloning at 50 cells per well, 2 plates each.

FIGS. 44A-B Screening of tonsil repertoire TW and confirmation of PLGF reactivity. (FIG. 44A) Culture supernatants from corresponding wells on all of the 10 plates, e.g., all A1 wells, were pooled and tested for PLGF binding, on a single 96-well ELISA plate. Well E12 was significantly increased above background, indicating that well E12 was positive on one of the 10 plates. (FIG. 44B) Culture supernatants from E12 wells on each of the 10 TW repertoire plates were individually screened for PLGF reactivity by ELISA, Plate 1 well E12 had significant reactivity, and was chosen for subcloning, 5 plates, 1000 cells/well.

FIGS. 45A-B Screening of TW-1E12 primary subclone plates for PLGF reactivity. Plates were screened by ELISA ~2 weeks after primary subcloning. (FIG. 45A) All wells on each primary subclone plate were pooled and screened for SEC2 reactivity, which was detected on plates 2 and 5. (FIG. 45B) Individual wells on plates 2 and 5 were screened for PLGF reactivity. TW-2E3, 2G9; 5A10 were chosen for secondary subcloning at 50 cells per well, 3 plates each.

FIGS. 46A-C Screening of tonsil repertoire TZ and confirmation of PLGF reactivity. (FIG. 46A) Culture supernatants from corresponding wells on all of the 10 plates, e.g., all A1 wells, were pooled and tested for PLGF binding, on a single 96-well ELISA plate. Wells B10, F9 were significantly increased above background, indicating that wells B10, F9 were positive on one of the 10 plates. (FIG. 46B) Pooled supernatants from all wells on each of the 10 TZ repertoire plates were screened, indicating, that plates 3 and 5 had PLGF reactivity. (FIG. 46C) Combining reactivity in wells B10 and F9 with plates 3 and 5, this confirmed that TZ 3B10 and TZ-5F9 had significant reactivity, and were thus chosen for primary subcloning, 3 plates each, 1000 cells/well.

FIGS. 47A-C Screening of tonsil repertoire TZ and confirmation of ricin B reactivity. (FIG. 47A) Culture supernatants from 6F10 corresponding wells on all of the 10 plates, e. g. , all A1 wells, were pooled and tested for ricin B binding, on a single 96-well ELISA plate. Wells B8, F10 were significantly increased above background, indicating that wells B8, F10 were positive on one of the 10 plates. (FIG. 47B) Pooled supernatants from all wells on each of the 10 TZ repertoire plates were screened, indicating that plates 6 and 7 had ricin B reactivity. (FIG. 47C) Combining reactivity in wells B8 and F10 with plates 6 and 7 confirmed that TZ-6F10 and TZ-7B8 had significant reactivity, and were thus chosen for primary subcloning, 5 plates each, 100 cells/well.

FIG. 48A B. Screening of TZ-7B8 primary subclone plates for ricin B reactivity. Plates were screened by ELISA ~3 weeks after primary subcloning. TZ-7B8 1A12, 1 E3, 2A1, 2A3, 4A1 were chosen for secondary subcloning.

FIG. 49 Screening of TZ-6F10 primary subclone plates for ricin B reactivity. Plates were screened by ELISA ~3 weeks after primary subcloning. TZ-6F10 1C3, 1D6, 1F11, 2F2, 2G2, 3E1, 4H4, 4G6, 5D7 were chosen for secondary subcloning.

Figures 50A, 50B:
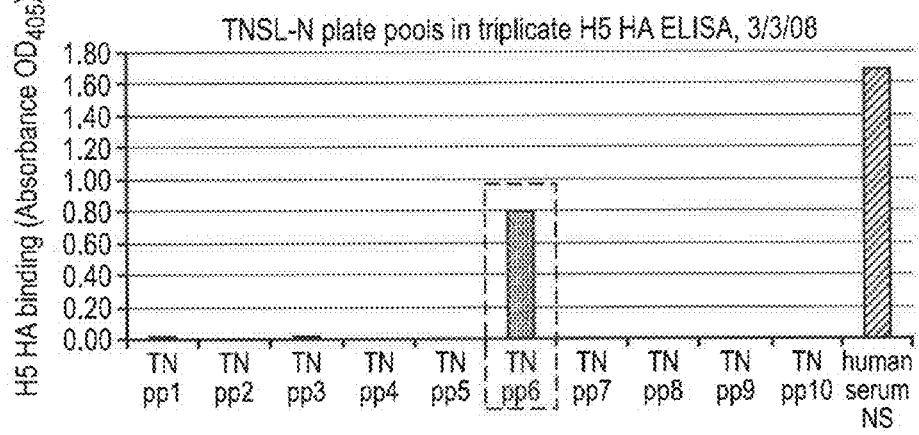

FIGS. 50A-C Rapid screening strategy for H5 HA reactivity in tonsil N repertoire. Tonsil repertoire N (TNSL-N) was immortalized with Epstein-Barr virus, induced to differentiate with recombinant human Baff, soluble CD40L and anti-human IgM (Fab')$_2$ and cultured in ten 96-well plates (Feb. 5, 2008) as summarized in Table 16. (FIG. 50A) Three weeks later, culture supernatants from corresponding wells on all of the 10 plates, e.g. all A1 wells, were pooled and tested for H5 HA binding on a single 96-well ELISA plate. Well G7 was significantly increased above background, indicating that well G7 was positive on one of the 10 plates. (FIG. 50B) Simultaneously, aliquots of the same culture supernatants from all wells on each plate were pooled and assayed for H5 HA binding by ELISA on Mar. 3, 2008, which indicated that plate 6 had reactivity. OD405 absorbance values for each well minus the antigen free background are shown. (FIG. 50C) Combining the well G7 reactivity shown in (FIG. 50A) with plate 6 reactivity shown in (FIG. 50B), it was confirmed that plate 6 well G7 (TN 6G7) was H5 HA reactive by testing the culture supernatant by ELISA on Mar. 4, 2008. Controls consisted of H5 HA-reactive clone E3A5 supernatant, H5 HA-reactive human serum (diluted 1:500) and non-reactive human IgG (diluted 1:300).

FIGS. 51A-C Screening of TN-6G7 primary subclones for H5 HA reactivity and selection of wells for secondary subcloning. (FIG. 51A) Cells from well TN-6G7 were subcloned into ten 96 well plates (500 cells/well; primary subcloning). Two weeks later, culture supernatants from corresponding wells on all of the 10 plates were pooled and tested for H5 HA binding on a single 96-well ELISA plate. Several wells showed reactivity with wells C8 and F8 having significant reactivity above background, indicating that wells C8 and F8 were positive on at least one of the 10 plates. (FIG. 51B) Simultaneously, aliquots of these same culture supernatants were pooled from all wells on each plate and assayed for H5 HA binding by ELISA on Mar. 19, 2008, which indicated that plates 2, 3, 5, 7, and 8 had reactivity. OD$_{405}$ absorbance values for each well minus background (wells containing no antigen) are shown, (FIG. 51C) Combining the wells C8 and F8 reactivity in (FIG. 51A) with plates 2, 3, 5, 7, and 8 reactivity in (FIG. 51B), it was found that plate 7 well F8 (TN-6G7-7F8) had the highest H5 HA reactivity by ELISA testing of culture supernatants; cells from that well were selected for secondary subcloning. Controls consisted of H5 HA-reactive clone E3A5 supernatant, H5 HA-reactive human serum (diluted 1:500) and non-reactive human IgG (diluted 1:300).

FIGS. 52A-B Screening of TN-6G7-7F8 secondary subclones for H5 HA reactivity and selection of wells for tertiary subcloning. (FIG. 52A) Cells from well TN-6G7-7F8 were subcloned into two 96-well plates (500 cells/well; secondary subcloning). Three weeks later, culture supernatants from corresponding wells on both plates were pooled and tested for H5 HA binding on a single 96-well ELISA plate. Several wells showed reactivity with well G7 showing the highest reactivity. (FIG. 52B) The wells with highest reactivity were identified by testing the culture supernatant on both plates from individual wells that gave positive results in (FIG. 52A), Plate 2 well G7 (TN-6G7-7F8-2G7) had the highest H5 HA reactivity by ELISA testing. Controls consisted of H5 HA-reactive clone E3A5 supernatant, and, H5 HA-reactive human serum (diluted 1:500).

Figure 53A:
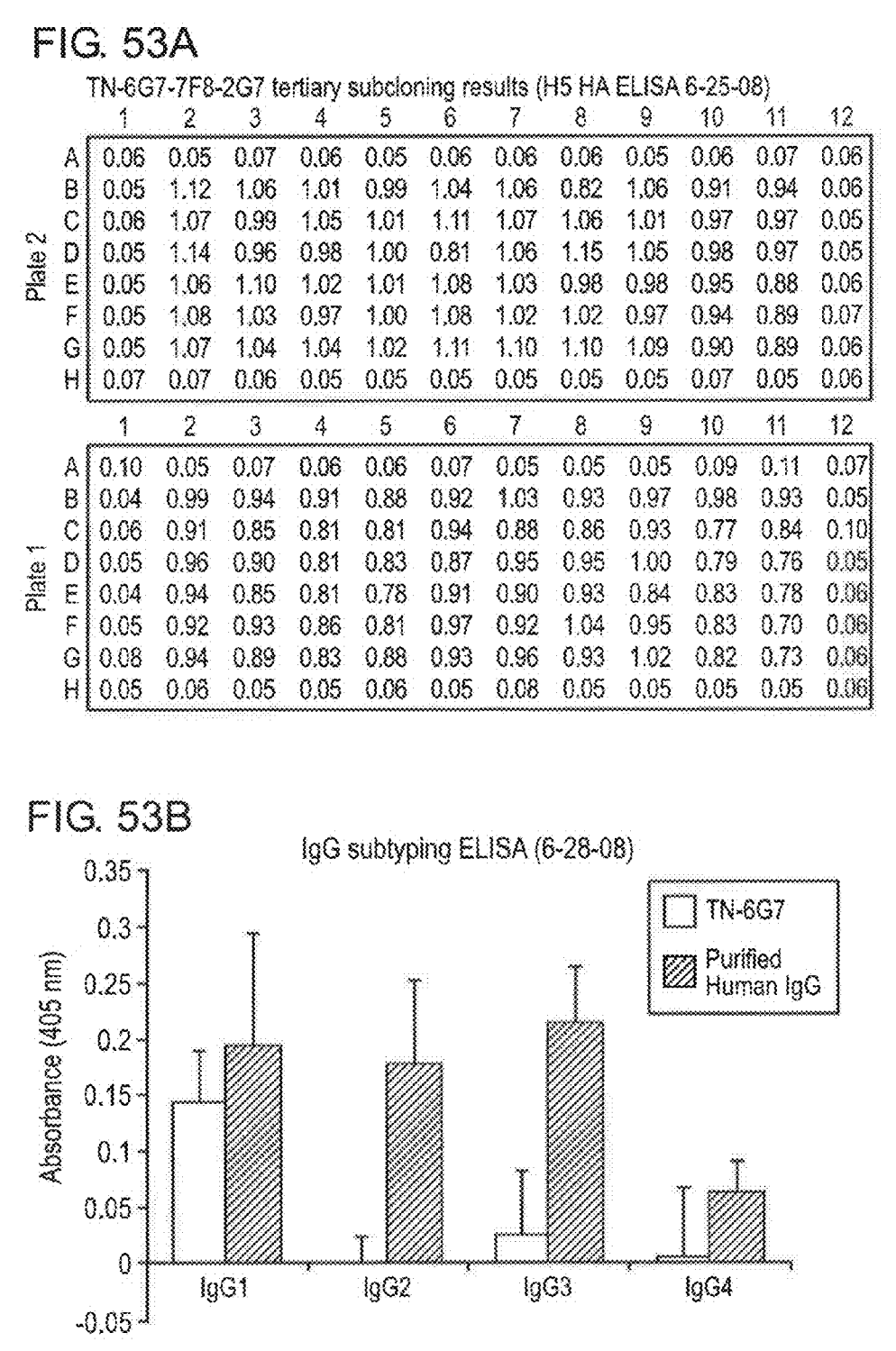

FIGS. 53A-B Initial characterization of clone TN-6G7-7F8-2G7. (FIG. 53A) Cells in well TN-6G7-7F8-2G7 were subcloned into 2 plates (50 cells/well); however, 4 weeks later, both plates had fungal contamination and were discarded. Following this, a frozen aliquot of TN 6G7-7F8-2G7 cells was thawed, briefly cultured and plated into two 96-well plates (50 cells/well, 60 wells/plate, tertiary subcloning). 4 weeks later, culture supernatants from both plates were tested for H5 HA binding on two 96-well ELISA plates. All wells demonstrated H5 HA reactivity, indicative of clonality. (FIG. 53B) IgG in the TN-6G7-7F8-2G7 supernatant was tested by a capture ELISA for IgG$_{1-4}$ subtypes. The results indicated that TN-6G7-7F8-2G7 cells secrete IgG$_1$. Purified human IgG (2 μg/ml, Sigma) was used as a positive control for detection of each IgG subtype.

FIGS. 54A-B identification of light and heavy chain variable regions comprising the TN-6G7-7F8-2G7 H5 HA reactive IgG$_1$ molecule. TN-6G7-7F8-2G7 cells were collected and 2.5×10$^6$ cells were incubated with H5 HA conjugated magnetic beads (bound through a HIS-tag on the H5 HA to anti-HIS mAb on the beads, THE™ MagBeads). Cells bound to the magnetic beads were lysed for RNA extraction. Sequences of forward and reverse primers used to amplify light (λ, κ) and heavy chain (VH) immunoglobulin genes are listed in table (FIG. 54A) (SEQ ID NOS: 1-15). Primers were optimized to amplify the maximum number of potential variable region sequences (adapted from Welschof et al, 1995, J. Immunol. Methods, 179: 203-214). Restriction enzyme cleavage site sequence for XbaI was added to the forward primers, and SalI was added to reverse primers for subsequent cloning and sequencing of the amplification products. (FIG. 54B) PCR amplification of cDNA obtained from 27,000 TN-6G7-7F8-2G7 cells recovered from magnetic beads conjugated to H5 HA (described in FIG. 53), indicated that TN-6G7-7F8-2G7 cells express λ1 light chain and VH3 heavy chain. (*Minor PCR bands resulted front 3' primer homology between λ1-xba with λ3-xba and λ4a-kba primers). Lane M. marker=1 kb Plus ladder from Gibco-BRL; arrow indicates location of 500 bp band.

FIGS. 55A1-C. DNA and amino acid sequences of the heavy and light chain variable regions of the H5 HA reactive clone, TN-6G7. PCR products obtained as described in FIG. 54 were sequenced, and results of the analysis are shown for light chain (FIGS. 55A1-2) (SEQ ID NOS: 32, 33, 34 and 35) and heavy chain (SEQ ID NOS:36, 37, and 38) (FIGS. 55B1-2). The DNA sequences of the clones were aligned against the germ-line sequences, which have the closest homology. Amino acid numbering and CDR positioning were performed according to Kabat et al. (1991) as described in Sequences of Proteins of Immunological Interest. Any changes in the DNA code are depicted below, and changes in the amino acid sequence are shown. Sequences of different segments and the junction region are shown, as follows: variable (V) segments, diversity (D) segments, joining (J) segments, P nucleotides, N nucleotides. Triple dots (. . . ) indicate gaps in DNA and amino acid sequences that correspond to sequences present in some germline genes (but not in TN-6G7-7F8-2G7). Gaps were inserted to maintain amino acid alignments with Kabat convention, Dashes (-) indicate germline DNA sequences that are identical to the TN-6G7 sequence. (FIG. 55C) Complementarity determining regions of TN-6G7 light Chain and heavy chain genes are depicted. Single dots (.) indicate gaps that have been inserted for CDR alignment purposes (see above).

Figure 56:
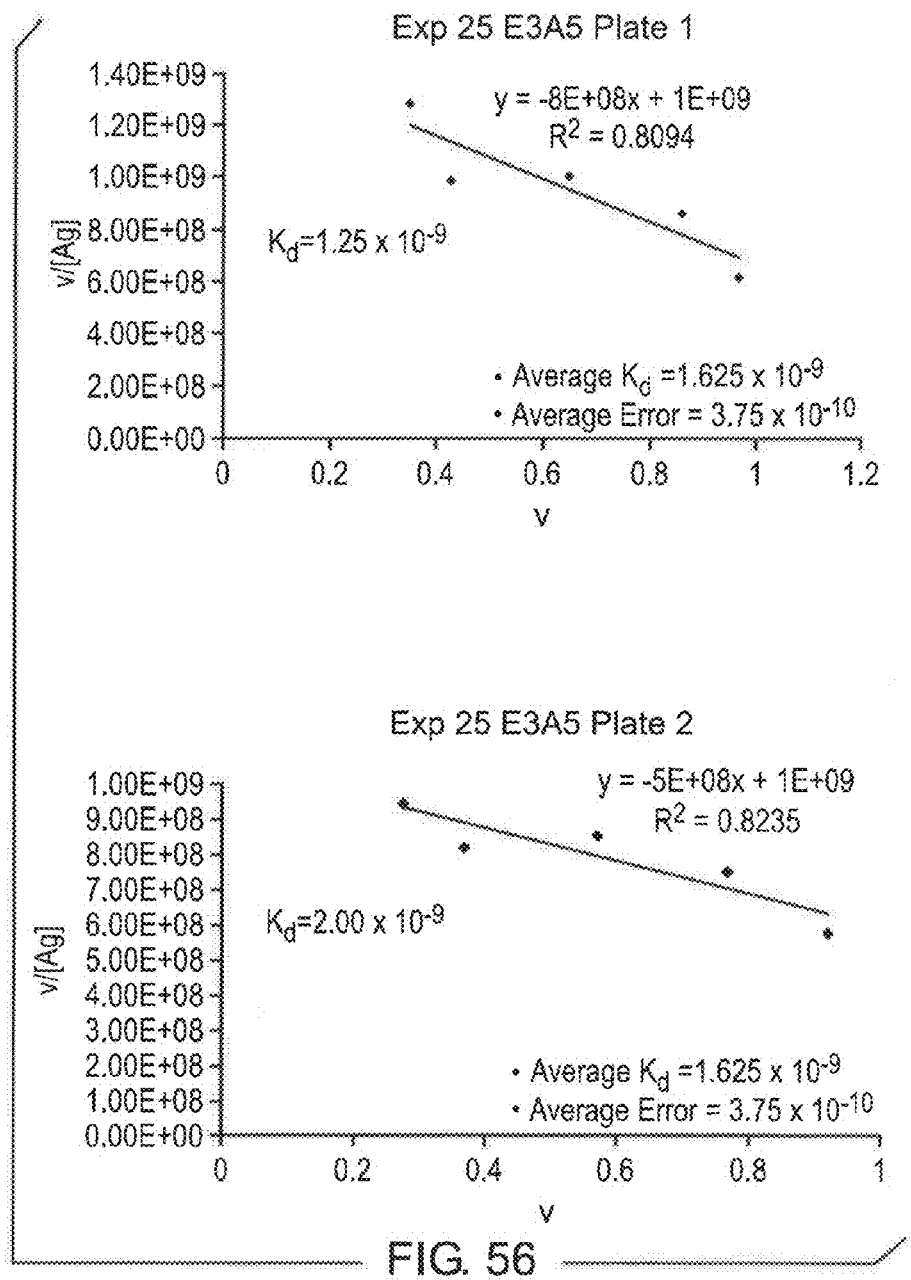

FIG. 56 Determination of dissociation constants (Kd) for E3A5 human mAbs. Competitive ELISA methods were used to calculate Kd. First, transfer experiments were used to determine conditions under which less than 10% of total antibody bound to the ligand coating the wells. Titration of a constant antibody concentration equilibrated with different concentrations of his-H5 HA was used to calculate Kd for E3A5. υ, bound antibody fraction; [Ag], concentration of free antigen.

Figures 57A, 57B:
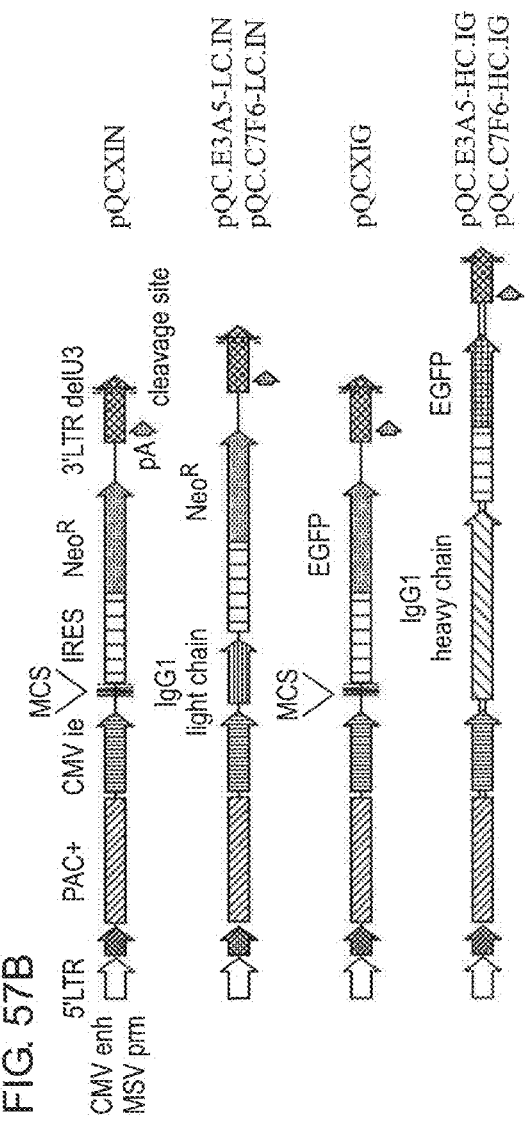

FIGS. 57A-B Generation of recombinant expression vectors for large scale production of E3A5 and C7F6 human mAbs. (FIG. 57A) full length light and heavy IgG1 chains for both E3A5 and C7F6 have been generated by PCR using primers to leader and C-terminal sequences. (FIG. 57B) Construction of retrovirus vectors expressing E3A5 and C7F6 light chains in combination with NeoR selection marker, and heavy chains in combination with EGFP fluorescent marker.

Figure 58A:
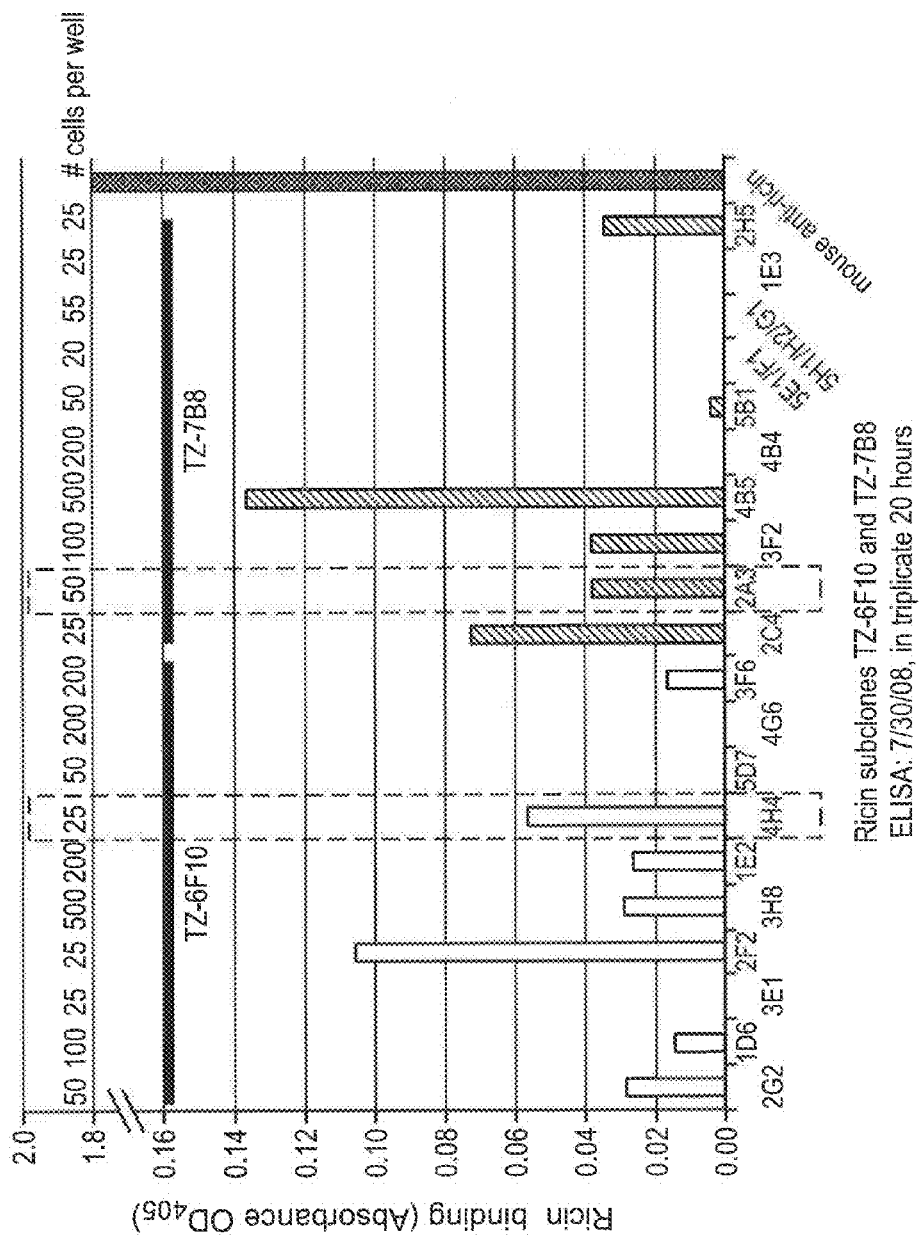
Figure 58B:
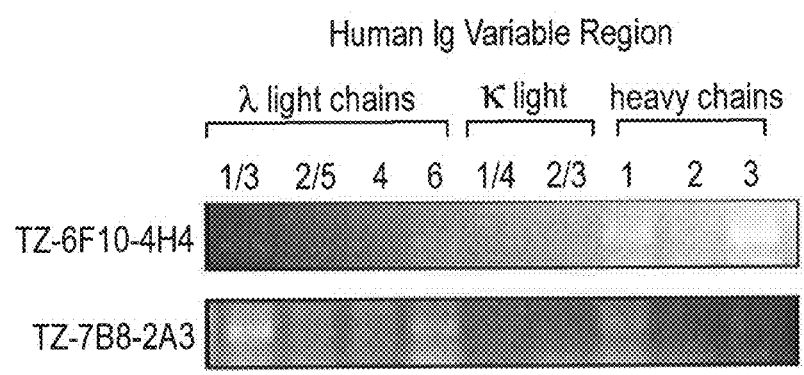

FIGS. 58A-B ELISA analysis and human immunoglobulin (Ig) variable region identification in Ricin B subcloned cells TZ-6F10-4H4 and TZ-7B8-2A3. (FIG. 58A) TZ-6F10 and TZ-7B8 subclones were tested by ELISA for ricin subunit B binding 2 weeks after secondary subcloning at 25-500 cells per well (# cells per well listed at top of graph). TZ-6F10-4H4 and T7-7B8-2A3 subclones were chosen for Ig gene analysis since both had significant activity, arising from 25 or 50 cells per well. (FIG. 58B) RT-PCR was performed on cells in wells TZ-6F10-4H4 and TZ-7B8-2A3 using primer sequences listed in FIGS. 34A and 54A, using same PCR conditions. Each well contained 11/3 and 16 sequences, and VH1 and VH3 sequences. All amplified sequences were subsequently sequenced.

FIGS. 59A1-F DNA and amino acid sequences of the heavy and light chain variable regions of ricin B reactive subcloned cells TZ-6F10-4H4 and TZ-7B8-2A3. PCR products were sequenced and analyzed as described in Methods. Results of the analyses are shown for light chains: TZ-6F10 (FIG. 59A1-2) (SEQ ID NOS:47, 48, 49 and 50) TZ-7F8 (FIGS. 59C1-2, D1-2) (SEQ ID NOS:55, 56, 57, 58, 59, 60, 61 and 62) and heavy chains TZ-6F10 (FIG. 59B1-2) (SEQ ID NOS:51, 52, 53 and 54), TZ-7B8 (FIG. 59E1-2) (SEQ ID NOS:63, 64, 65 and 66). The DNA sequences of the clones were aligned against the germ-line sequences, which have the closest homology. Amino acid numbering and CDR positioning were done according to Kabat et al. (1991) as described in Sequences of Proteins of Immunological Interest. Any changes in the DNA code are depicted below, and changes in the amino acid sequence are shown. Sequences of different segments and the junction region. are shown, as follows: variable (V) segments, diversity (D) segments, joining (J) segments, P nucleotides, N nucleotides. Triple dots (. . . ) indicate gaps in DNA and amino acid sequences that correspond to sequences present in some (but not in our) germline genes. Gaps are inserted to maintain amino acid alignments with Kabat convention. Dashes (-)indicate germline DNA sequences that are identical to our sequences. (FIG. 59F) (SEQ ID NOS:67, 68, 69, 70 and 71) Complementarity determining regions of each of the sequences. Dots (.) indicate gaps that have been inserted for CDR alignment purposes (see above).

DESCRIPTION OF ILLUSTRATIVE EMBODIMENTS

A variety of prior efforts have been directed at the production of human monoclonal antibodies, including EP 0 218 158, EP 0 161 941, U.S. Pat. No. 5,024,946, U.S. Patent Publication No. 2006/0252124, Traggia et al. (2004) and Lanzavecchia et al. (2006). However, to date there remains a need for improved methods of human antibody selection.

The present invention provides a solution to various problems limiting the prior work on human monoclonals. In particular, by targeting B-cells that have not undergone immunoglobulin isotype class switching, i.e., are still IgM+, and transforming these cells with a high efficiency EBV transformation protocol, the inventors have been able to select rare B-cells that secrete human monoclonal antibodies. In addition, they have optimized a cocktail of cytokines/growth factors/signaling agents that efficiently induce immunoglobulin isotype class switching from IgM to IgG in the EBV-immortalized B-cells.

I. Target Antigens

Virtually any antigen may be utilized to select a B-cell in accordance with the present invention. These include toxins, cellular receptors (e.g., for virus entry, bacterial entry, fungus entry, parasite entry, toxin entry), tumor antigens, cytokine/chemokine/growth factors, cytokine/chemokine/growth factor receptors, an inflammation mediator, pain mediator, tissue injury/damage mediator, an antigen on activation molecules/ligands/receptors, an antigen on costimulatory molecules/ligands/receptors, a molecule mediating innate immunity, a cellular adhesion molecule, a cellular adhesion receptor, an over-expressed/under-glycosylated/oxidized/misfolded/mutated cellular proteins ("altered self" antigens), a molecule/ligand/receptor mediating cell apoptosis, or a growth inhibitory molecule. This list is not exhaustive and is provided for exemplification only.

A. Infectious Agents

A variety of infectious agents have antigens that can serve as targets in the present invention. For example, bacteria, molds & fungi, parasites and viruses all present antigens that are suitable targets for antibodies.

1. Influenza

The influenza virus is an RNA virus of the family Orthomyxoviridae, which comprises the influenzaviruses, Isavirus and Thogotovirus. There are three types of influenza virus: Influenzavirus A, Influenzavirus B or Influenzavirus C. Influenza A and C infect multiple species, while influenza B almost exclusively infects humans. The type A viruses are the most virulent human pathogens among the three influenza types, and cause the most severe disease. The Influenza A virus can be subdivided into different serotypes based on the antibody response to these viruses. The serotypes that have been confirmed in humans, ordered by the number of known human pandemic deaths, are:

H1N1 caused "Spanish Flu"
H2N2 caused "Asian Flu"
H3N2 caused "Hong Kong Flu"
H5N1 is a pandemic threat in 2006-7 flu season
H7N7 has unusual zoonotic potential
H1N2 is endemic in humans and pigs
H9N2, H7N2, H7N3, H10N7

Influenza B virus is almost exclusively a human pathogen, and is less common than influenza A. The only other animal known to be susceptible to influenza B infection is the seal. This type of influenza mutates at a rate 2-3 times lower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur. The influenza C virus infects humans and pigs, and can cause severe illness and local epidemics. However, influenza C is less common than the other types and usually seems to cause mild disease in children. The three strains with substantial enough pathology every year to be included as components of the trivalent vaccine are the influenza A strains H1N1 and H2N3, and influenza B.

The following applies for all influenza viruses, although other strains are very similar in structure: the influenza A virus particle or virion is 80-120 nm in diameter and usually roughly spherical, although filamentous forms can occur. Unusually for a virus, the influenza A genome is not a single piece of nucleic acid; instead, it contains eight pieces of segmented negative-sense RNA (13.5 kB total), which encode 11 proteins (HA, NA, NP, M1, M2, NS1, NEP, PA, PB1, PB1-F2, PB2). The best-characterised of these viral proteins are hemagglutinin and neuraminidase, two large glycoproteins found on the outside of the viral particles. Neuraminidase is an enzyme involved in the release of progeny virus from infected cells, by cleaving sugars that bind the mature viral particles. By contrast, hemagglutinin is a lectin that mediates binding of the virus to target cells and entry of the viral genome into the target cell. The hemagglutinin (HA or H) and neuraminidase (NA or N) proteins are targets for antiviral drugs. These proteins are also recognised by antibodies, i.e., they are antigens. The responses of antibodies to these proteins are used to classify the different serotypes of influenza A viruses, hence the H and N in H5N1.

Influenza viruses bind through hemagglutinin onto sialic acid sugars on the surfaces of epithelial cells; typically in the nose, throat and lungs of mammals and intestines of birds. The cell imports the virus by endocytosis. In the acidic endosome, part of the haemagglutinin protein fuses the viral envelope with the vacuole's membrane, releasing the viral RNA (vRNA) molecules, accessory proteins and RNA-dependent RNA transcriptase into the cytoplasm. These proteins and vRNA form a complex that is transported into the cell nucleus, where the RNA-dependent RNA transcriptase begins transcribing complementary positive-sense vRNA. The vRNA is either exported into the cytoplasm and translated, or remains in the nucleus. Newly-synthesised viral proteins are either secreted through the Golgi apparatus onto the cell surface or transported back into the nucleus to bind vRNA and form new viral genome particles. Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA transcriptase, and other viral proteins are assembled into a virion. Hemagglutinin and neuraminidase molecules cluster into a bulge in the cell membrane. The vRNA and viral core proteins leave the nucleus and enter this membrane protrusion. The mature virus buds off from the cell in a sphere of host phospholipid membrane, acquiring hemagglutinin and neuraminidase with this membrane coat. As before, the viruses adhere to the cell through hemagglutinin; the mature viruses detach once their neuraminidase has cleaved sialic acid residues from the host cell. After the release of new influenza virus, the host cell dies.

Because of the absence of RNA proofreading enzymes, the RNA-dependent RNA transcriptase makes a single nucleotide insertion error roughly every 10 thousand nucleotides, which is the approximate length of the influenza vRNA. Hence, nearly every newly-manufactured influenza virus is a mutant. The separation of the genome into eight separate segments of vRNA allows mixing or reassortment of vRNAs if more than one viral line has infected a single cell. The resulting rapid change in viral genetics produces antigenic shifts and allow the virus to infect new host species and quickly overcome protective immunity. This is important in the emergence of pandemics, as discussed in Epidemiology.

i. Vaccination

Vaccination against influenza with an active flu vaccine is strongly recommended for high-risk groups, such as children and the elderly. These vaccines can be produced in several ways; the most common method is to grow the virus in fertilised hen eggs. After purification, the virus is inactivated (for example, by treatment with detergent) to produce an inactivated-virus vaccine. Alternatively, the virus can be grown in eggs until it loses virulence and the avirulent virus given as a live vaccine. The effectiveness of these flu vaccines is variable. As discussed above, due to the high mutation rate of the virus, a particular flu vaccine usually confers protection for no more than a few years. Every year, the World Health Organization predicts which strains of the virus are most likely to be circulating in the next year, allowing pharmaceutical companies to develop vaccines that will provide the best immunity against these strains. Vaccines have also been developed to protect poultry from avian influenza. These vaccines can be effective against multiple strains and are used either as part of a preventative strategy, or combined with culling in attempts to eradicate outbreaks.

ii. Therapy

The two classes of anti-virals are neuraminidase inhibitors and M2 inhibitors (adamantane derivatives). Neuramimidase inhibitors are currently preferred for flu virus infections. The CDC recommended against using M2 inhibitors during the 2005-06 influenza season.

Antiviral drugs such as oseltamivir (trade name Tamiflu) and zanamivir (trade name Relenza) are neuraminidase inhibitors that are designed to halt the spread of the virus in the body. These drugs are often effective against both influenza A and B. The Cochrane Collaboration reviewed these drugs and concluded that they reduce symptoms and complications. Resistance has not yet been a problem with neuraminidase inhibitors. Resistant viruses have been identified but, unlike the situation with amantadine, in which the resistant viruses are fully virulent and able to transmit, that does not appear to be the case with neuraminidase. Different strains of influenza virus have differing degrees of resistance against these antivirals and it is impossible to predict what degree of resistance a future pandemic strain might have.

The antiviral drugs amantadine and rimantadine are designed to block a viral ion channel and prevent the virus from infecting cells. These drugs are sometimes effective against influenza A if given early in the infection, but are always ineffective against influenza B. In fact, measured resistance to amantadine and rimantadine in American isolates of H3N2 has increased to 91% in 2005. Monoclonal antibodies can inhibit neuminaidase activity, M2, or hemagglutin binding to sialic acids. This one of the features of the technology described herein.

2. Other Viruses

In addition to influenza, a variety of other viruses may be used to generate antibodies, and subsequently be diagnosed or treated, by antibodies. Table 1 lists a variety of other virus targets for

TABLE 1

VIRUSES

Abelson murine leukemia virus, Retroviridae
Adelaide River virus, Rhabdoviridae
Adeno-associated virus 1, Parvoviridae
Adeno-associated virus 2, Parvoviridae
Adeno-associated virus 3, Parvoviridae
Adeno-associated virus 4, Parvoviridae
Adeno-associated virus 5, Parvoviridae
African green monkey cytomegalovirus, Herpesviridae
African green monkey HHV-like virus, Herpesviridae
African green monkey polyomavirus, Papovaviridae
African horse sickness viruses 1 to 10, Reoviridae
African swine fever virus, African swine fever-like viruses
Aleutian disease virus, Parvoviridae
Aleutian mink disease virus, Parvoviridae
American ground squirrel herpesvirus, Herpesviridae
Baboon herpesvirus, Herpesviridae
Baboon polyomavirus 2, Papovaviridae
Bovine adeno-associated virus, Parvoviridae
Bovine adenoviruses 1 to 9, Adenoviridae
Bovine astrovirus 1, Astroviridae
Bovine astrovirus 2, Astroviridae
Bovine coronavirus, Coronaviridae
Bovine diarrhea virus, Flaviviridae
Bovine encephalitis herpesvirus, Herpesviridae
Bovine enteric calicivirus, Caliciviridae
Bovine enterovirus 1, Picornaviridae
Bovine enterovirus 2, Picornaviridae
Bovine ephemeral fever virus, Rhabdoviridae
Bovine herpesvirus 1, Herpesviridae
Bovine herpesvirus 2, Herpesviridae
Bovine herpesvirus 4, Herpesviridae
Bovine herpesvirus 5, Herpesviridae
Bovine immunodeficiency virus, Retroviridae
Bovine leukemia virus, Retroviridae
Bovine mamillitis virus, Herpesviridae
Bovine papillomavirus 1, Papovaviridae
Bovine papillomavirus 2, Papovaviridae
Bovine papillomavirus 4, Papovaviridae
Bovine papular stomatitis virus, Poxviridae
Bovine parainfluenza virus 3, Paramyxoviridae
Bovine parvovirus, Parvoviridae
Bovine polyomavirus, Papovaviridae
Bovine respiratory syncytial virus, Paramyxoviridae
Bovine rhinovirus 1, Picornaviridae
Bovine rhinovirus 2, Picornaviridae
Bovine rhinovirus 3, Picornaviridae
Bovine syncytial virus, Retroviridae
California encephalitis virus, Bunyaviridae
California harbor sealpox virus, Poxviridae
Canine adeno-associated virus, Parvoviridae
Canine adenovirus 1, Adenoviridae
Canine adenovirus 2, Adenoviridae
Canine calicivirus, Caliciviridae
Canine coronavirus, Coronaviridae
Canine distemper virus, Paramyxoviridae
Canine herpesvirus, Herpesviridae
Canine minute virus, Paruoviridae
Canine oral papillomavirus, Papovaviridae
Canine parvovirus, Parvoviridae
Chicken anemia virus, Circoviridae
Chicken parvovirus, Paruoviridae
Chimpanzee herpesvirus, Herpesviridae
Cottontail herpesvirus, Herpesviridae
Cottontail rabbit papillomavirus, Papovaviridae
Cowpox virus, Poxviridae
Deer fibroma virus, Papovaviridae
Deer papillomavirus, Papovaviridae
Elephant loxondontal herpesvirus, Herpesviridae
Elephant papillomavirus, Papovaviridae
Elephantid herpesvirus, Herpesviridae
Epstein-Barr virus, Herpesviridae
Equid herpesvirus 1, Herpesviridae
Equid herpesvirus 2, Herpesviridae
Equid herpesvirus 3, Nerpesviridae
Equid herpesvirus 4, Herpesviridae
Equid herpesvirus 5, Herpesviridae
Equid herpesvirus 6, Herpesviridae
Equid herpesvirus 7, Herpesviridae

TABLE 1-continued

VIRUSES

Equid herpesvirus 8, Herpesviridae
Equine abortion herpesvirus, Herpesviridae
Equine adeno-associated virus, Parvoviridae
Equine adenovirus 1, Adenoviridae
Equine arteritis virus, Arterivirus
Equine cytomegalovirus, Herpesviridae
Equine encephalosis viruses 1 to 7, Reoviridae
Equine herpesvirus 1, Herpesviridae
Equine herpesvirus 3, Herpesviridae
Equine herpesvirus 4, Herpesviridae
Equine herpesvirus 5, Herpesviridae
Equine infectious anemia virus, Retroviridae
Equine papillomavirus, Papovaviridae
Equine rhinopneumonitis virus, Herpesviridae
Equine rhinovirus 1, Picornaviridae
Equine rhinovirus 2, Picornaviridae
Equine rhinovirus 3, Picornaviridae
European bat virus 1, Rhabdoviridae
European bat virus 2, Rhabdoviridae
European brown hare syndrome virus, Caliciviridae
European elk papillomavirus, Papovaviridae
European ground squirrel cytomegalovirus, Herpesviridae
European hedgehog herpesvirus, Herpesviridae
Feline calicivirus, Caliciviridae
Feline herpesvirus 1, Herpesviridae
Feline immunodeficiency virus, Retroviridae
Feline infectious peritonitis virus, Coronaviridae
Feline leukemia virus, Retroviridae
Feline parlleukopenia virus, Parvoviridae
Feline parvovirus, Parvoviridae
Feline syncytial virus, Retroviridae
Feline viral rhinotracheitis virus, Herpesviridae
Field mouse herpesvirus, Herpesviridae
Foot-and-mouth disease virus A, Picornaviridae
Foot-and-mouth disease virus ASIA 1, Picornaviridae
Foot-and-mouth disease virus C, Picornaviridae
Foot-and-mouth disease virus O, Picornaviridae
Foot-and-mouth disease virus SAT 1, Picornaviridae
Foot-and-mouth disease virus SAT 2, Picornaviridae
Foot-and-mouth disease virus SAT 3, Picornaviridae
Goat herpesvirus, Herpesviridae
Goatpox virus, Poxviridae
Ground squirrel hepatitis B virus, Hepadnaviridae
GroupA rotaviruses, Reoviridae
Group B rotaviruses, Reoviridae
Group C rotaviruses, Reoviridae
Group D rotaviruses, Reoviridae
Group E rotaviruses, Reoviridae
Group F rotaviruses, Reoviridae
Guinea pig cytomegalovirus, Herpesviridae
Guinea pig herpesvirus 1, Herpesviridae
Guinea pig herpesvirus 3, Herpesviridae
Guinea pig t, vpe C oncovirus, Retroviridae
Hamster herpesvirus, Herpesviridae
Hamster polyomavirus, Papovaviridae
Hantaan virus, Bunyaviridae
Harbor seal herpesvirus, Herpesviridae
Hare fibroma virus, Poxviridae
Hepatitis A virus, Picornaviridae
Hepatitis B virus, Hepadnaviridae
Hepatitis C virus, Flaviviridae
Herpesvirus M, Herpesviridae
Herpesvirus papio, Herpesviridae
Herpesvirus platyrrhinae type, Herpesviridae
Herpesvirus pottos, Herpesviridae
Herpesvirus saimiri 2, Herpesviridae
Herpesvirus salmonis, Herpesviridae
Herpesvirus sanguinus, Herpesviridae
Herpesvirus scophthalmus, Herpesviridae
Herpesvirus sylvilagus, Herpesviridae
Herpesvirus T, Herpesviridae
Herpesvirus tarnarinus, Herpesviridae
Hog cholera virus, Flaviviridae
Herpes simiae virus, Herpesviridae
Herpes simplex virus 1, Herpesviridae
Herpes simplex virus 2, Herpesviridae
Herpes virus B, Herpesviridae
Herpesvirus aotus 1, Herpesviridae

TABLE 1-continued

VIRUSES

Herpesvirus aotus 3, Herpesviridae
Herpesvirus ateles strain 73, Herpesviridae
Herpesvirus cuniculi, Herpesviridae
Herpesvirus cyclopsis, Herpesviridae
Human adenoviruses 1 to 47, Adenoviridae
Human astrovirus 1, Astroviridae
Human astrovirus 2, Astroviridae
Human astrovirus 3, Astroviridae
Human astrovirus 4, Astroviridae
Human astrovirus 5, Astroviridae
Human calicivirus, Caliciviridae
Human caliciviruses, Caliciviridae
Human coronavirus 229E, Coronaviridae
Human coronavirus OC43, Coronaviridae
Human coxsackievirusA 1 to 22, Picornaviridae
Human coxsackievirus A 24, Picornaviridae
Human coxsackievirus B 1 to 6, Picornaviridae
Human cytomegalovirus, Herpesviridae
Human echovirus 1 to 7, Picornaviridae
Human echovirus 11 to 27, Picornaviridae
Human echovirus 29 to 33, Picornaviridae
Human echovirus 9, Picornaviridae
Human enterovirus 68 to 71, Picornaviridae
Human foamy virus, Retroviridae
Human herpesvirus 1, Herpesviridae
Human herpesvirus 2, Herpesviridae
Human herpesvirus 3, Herpesviridae
Human herpesvirus 3, Nerpesviridae
Human herpesvirus 5, Herpesviridae
Human herpesvirus 6, Herpesviridae
Human herpesvirus 7, Herpesviridae
Human immunodeficiency virus 1, Retroviridae
Human immunodeficiency virus 2, Retroviridae
Human papillomavirus 11, Papovaviridae
Human papillomavirus 16, Papovaviridae
Humanpapillomavirus 18, Papovaviridae
Human papillomavirus 31, Papovaviridae
Human papillomavirus 33, Papovaviridae
Human papillomavirus 5, Papovaviridae
Human papillomavirus 6b, Papovaviridae
Human papillomavirus 8, Papovaviridae
Human papillomavirus 1a, Papovaviridae
Human parainfluenza virus 1, Paramyxoviridae
Human parainfluenza virus 2, Paramyxoviridae
Human parainfluenza virus 3, Paramyxoviridae
Human parainfluenza virus 4a, Paramyxoviridae
Human parainfluenza virus 4b, Paramyxoviridae
Human poliovirus 1, Picornaviridae
Human poliovirus 2, Picornaviridae
Human poliovirus 3, Picornaviridae
Human respiratory syncytial virus, Paramyxoviridae
Human rhinovirus 1 to 100, Picornaviridae
Human rhinovirus 1A, Picornaviridae
Human spumavirus, Retroviridae
Human T-lymphotropic virus 1, Retroviridae
Human T-lymphotropic virus 2, Retroviridae
Jaagsiekte virus, Retroviridae
Japanese encephalitis virus, Flaviviridae
JC virus, Papovaviridae
Kirsten murine sarcoma virus, Retroviridae
Lagos bat virus, Rhabdoviridae
Lymphocytic choriomeningitis virus, Arenaviridae
Mice minute virus, Parvoviridae
Mice pneumotropic virus, Papovaviridae
Moloney murine sarcoma virus, Retroviridae
Moloney virus, Retroviridae
Monkeypox virus, Poxviridae
Mouse cytomegalovirus 1, Herpesviridae
Mouse Elberfield virus, Picornaviridae
Mouse herpesvirus strain 68, Herpesviridae
Mouse mammary tumor virus, Retroviridae
Mouse thymic herpesvirus, Herpesviridae
Mule deerpox virus, Poxviridae
Murine adenovirus 2, Adenoviridae
Z murine adenovirus 1, Adenoviridae
Murine hepatitis virus, Coronaviridae
Murine herpesvirus, Herpesviridae
Murine leukemia virus, Retroviridae
Murine parainfluenza virus 1, Paramyxoviridae
Murine poliovirus, Picornaviridae
Murine polyomavirus, Papovaviridae
Murray Valley encephalitis virus, Flaviviridae
Nairobi sheep disease virus, Bunyaviridae
Ovine adeno-associated virus, Parvoviridae
Ovine adenoviruses 1 to 6, Adenoviridae
Ovine astrovirus 1, Astroviridae
Ovine herpesvirus 1, Herpesviridae
Ovine herpesvirus 2, Herpesviridae
Ovine pulmonary adenocarcinoma virus, Retroviridae
Patas monkey herpesvirus pH delta, Herpesviridae
Penguinpox virus, Poxviridae
Pneumonia virus of mice, Paramyxoviridae
Porcine adenoviruses 1 to 6, Adenoviridae
Porcine astrovirus 1, Astroviridae
Porcine circovirus, Circoviridae
Porcine enteric calicivirus, Caliciviridae
Porcine enterovirus 1 to 11, Picornaviridae
Porcine epidemic diarrhea virus, Coronaviridae
Porcine hemagglutinating encephalomyelitis virus, Coronaviridae
Porcine parvovirus, Parvoviridae
Porcine respiratory and reproductive syndrome, Arterivirus
Porcine rubulavirus, Paramyxoviridae
Porcine transmissible gastroenteritis virus, Coronaviridae
Porcine type C oncovirus, Retroviridae
Porpoise distemper virus, Paramyxoviridae
Primate calicivirus, Caliciviridae
Rabbit coronavirus, Coronaviridae
Rabbit fibroma virus, Poxviridae
Rabbit hemorrhagic disease virus, Caliciviridae
Rabbit kidney vacuolating virus, Papovaviridae
Rabbit oral papillomavirus, Papovaviridae
Rabbitpox virus, Poxviridae
Rabies virus, Rhabdoviridae
Raccoon parvovirus, Parvoviridae
Raccoonpox virus, Poxviridae
Red deer herpesvirus, Herpesviridae
Red kangaroopox virus, Poxviridae
Reindeer herpesvirus, Herpesviridae
Reindeer papillomavirus, Papovaviridae
Reovirus 1, Reoviridae
Reovirus 2, Reoviridae
Reovirus 3, Reoviridae
Reticuloendotheliosis virus, Retroviridae
Rhesus HHV-4-like virus, Herpesviridae
Rhesus leukocyte associated herpesvirus strain 1, Herpesviridae
Rhesus monkey cytomegalovirus, Herpesviridae
Rhesus monkey papillomavirus, Papovaviridae
Rubella virus, Togaviridae
Sealpox virus, Poxviridae
Sendai virus, Paramyxoviridae
Sheep associated malignant catarrhal fever of, Herpesviridae
Sheep papillomavirus, Papovaviridae
Sheep pulmonary adenomatosis associated herpesvirus, Herpesviridae
Sheeppox virus, Poxviridae
Simian adenoviruses 1 to 27, Adenoviridae
Simian agent virus 12, Papovaviridae
Simian enterovirus 1 to 18, Picornaviridae
Simian foamy virus, Retroviridae
Simian hemorrhagic fever virus, Arterivirus
Simian hepatitis A virus, Picornaviridae
Simian immunodeficiency virus, Retroviridae
Simian parainfluenza virus 10, Paramyxoviridae
Simian parainfluenza virus 41, Paramyxoviridae
Simian parainfluenza virus 5, Paramyxoviridae
Simian rotavirus SA11, Reoviridae
Simian sarcoma virus, Retroviridae
Simian T-lymphotropic virus, Retroviridae
Simian type D virus 1, Retroviridae
Simian vancella herpesvirus, Herpesviridae
Simian virus 40, Papovaviridae
Sindbis virus, Togaviridae
Skunkpox virus, Poxviridae
Spider monkey herpesvirus, Herpesviridae
Squirrel fibroma virus, Poxviridae
Squirrel monkey herpesvirus, Herpesviridae

TABLE 1-continued

VIRUSES

Squirrel monkey retrovirus, Retroviridae
Swine cytomegalovirus, Herpesviridae
Swine infertility and respiratory syndrome virus, Arterivirus
Swinepox virus, Poxviridae
Tree shrew adenovirus 1, Adenoviridae
Tree shrew herpesvirus, Herpesviridae
Vaccinia subspecies, Poxviridae
Vaccinia virus, Poxviridae
Varicella-zoster virus 1, Herpesviridae
Vesicular stomatitisAlagoas virus, Rkabdoviridae
Vesicular stomatitis Indiana virus, Rhabdoviridae
Vesicular stomatitis New Jersey virus, Rhabdoviridae
West Nile virus, Flaviviridae
Western equine encephalitis virus, Togaviridae
Woodchuck hepatitis B virus, Hepadnaviridae
Woodchuck herpesvirus marmota 1, Herpesviridae
Woolly monkey sarcoma virus, Retroviridae
Yaba monkey tumor virus, Poxviridae
Yellow fever virus, Flaviviridae

3. Other Infectious Agents

In addition to viruses, other infectious agents may also be targeted according to the present invention. These include bacteria, set forth in Table 2, as well as molds, fungi and parasites.

TABLE 2

BACTERIA

*Bacillus* spp.
*Bacteroides fragilis*
*Bordetella bronchiseptica*
*Bordetella parapertussis*
*Bordetella pertussis*
*Bordetella pertussis*
*Borrelia burgdorferi*
*Branhamella (Moraxella) catarrhalis*
*Branhamella (Moraxella) catarrhalis*
*Branhamella (Moraxella) catarrhalis* (non β-lactamase producer)
*Branhamella (Moraxella) catarrhalis* (non β-lactamase producer)
*Branhamella (Moraxella) catarrhalis* (non β-lactamase producer)
*Branhamella (Moraxella) catarrhalis* (non β-lactamase producer)
*Branhamella (Moraxella) catarrhalis* (β-lactamase producer)
*Branhamella (Moraxella) catarrhalis* (β-lactamase producer)
*Branhamella (Moraxella) catarrhalis* (β-lactamase producer)
*Branhamella (Moraxella) catarrhalis* (β-lactamase producer)
*Campylobacter jejuni*
*Campylobacter jejuni*
*Campylobacter pylori*
*Campylobacter pylori*
*Corynebacterium* JK
*Corynebacterium* JK
*Enterococcus faecalis*
*Enterococcus faecalis*
*Enterococcus faecalis*
*Enterococcus faecalis*
*Enterococcus faecium*
*Enterococcus* spp.
*Haemophilus ducreyi*
*Haemophilus influenzae*
*Haemophilus influenzae*
*Haemophilus influenzae* (non β-lactamase producer)
*Haemophilus influenzae* (non β-lactamase producer)
*Haemophilus influenzae* (β-lactamase producer)
*Haemophilus influenzae* (β-lactamase producer)
*Haemophilus influenzae* (penicillin susceptible)
*Haemophilus influenzae* (penicillin resistant)
*Haemophilus parainfluenzae*
*Legionella* spp.
*Legionella pneumophila*
*Legionella pneumophila*
*Legionella pneumophila*
*Listeria monocytogenes*
*Listeria monocytogenes*

TABLE 2-continued

BACTERIA

*Listeria monocytogenes*
*Mycoplasma hominis*
*Mycoplasma hominis*
*Mycoplasma pneumoniae*
*Mycoplasma pneumoniae*
*Neisseria gonorrhoeae*
*Neisseria gonorrhoeae* (non β-lactamase producer)
*Neisseria gonorrhoeae* (non β-lactamase producer)
*Neisseria gonorrhoeae* (β-lactamase producer)
*Neisseria gonorrhoeae* (β-lactamase producer)
*Neisseria meningitidis*
*Nocardia asteroides*
*Staphylococcus aureus*
*Staphylococcus aureus*
*Staphylococcus aureus* (penicillin susceptible)
*Staphylococcus aureus* (penicillin susceptible)
*Staphylococcus aureus* (penicillin resistant)
*Staphylococcus aureus* (methicillin susceptible)
*Staphylococcus aureus* (methicillin susceptible)
*Staphylococcus aureus* (methicillin susceptible)
*Staphylococcus aureus* (methicillin resistant)
*Staphylococcus aureus* (methicillin resistant)
*Staphylococcus aureus* (methicillin resistant)
*Staphylococcus aureus* (methicillin resistant)
*Staphylococcus* coagulase f
*Staphylococcus* coagulase f
*Staphylococcus* coagulase f (non β-lactamase producer)
*Staphylococcus* coagulase f (β-lactamase producer)
*Staphylococcus epidermidis*
*Staphylococcus haemolyticus*
*Staphylococcus hominis*
*Streptococcus agalactiae*
*Streptococcus agalactiae*
*Streptococcus pneumoniae*
*Streptococcus pneumoniae*
*Streptococcus pneumoniae*
*Streptococcus pneumoniae*
*Streptococcus pneumoniae*
*Streptococcus pneumoniae*
*Streptococcus pyogenes*
*Streptococcus pyogenes*
*Streptococcus pyogenes*
*Streptococcus pyogenes*
*Streptococcus* spp.
*Streptococcus* spp.
*Ureaplasma urealyticum*
*Ureaplasma urealyticum*
*Mycoplasma hominis*
*Mycoplasma pneumoniae*
*Staphylococcus aureus*
*Ureaplasma urealyticum*

B. Other Antigens (Non-Infectious Agents)

A variety of other antigens are contemplated for use in accordance with the present invention. For example, an autoantigen is usually a normal protein or complex of proteins (and sometimes DNA or RNA) that is recognized by the immune system of patients suffering from a specific autoimmune disease. These antigens should under normal conditions not be the target of the immune system, but due to mainly genetic and environmental factors the normal immunological tolerance for such an antigen has been lost in these patients. The following autoantigens are contemplated as targets for antibodies of the present invention: acetylcholine receptor, adenine nucleotide translocator (ANT), aromatic L-amino acid decarboxylase, asialoglycoprotein receptor, bactericidal/permeability-increasing protein (Bpi), calcium-sensing receptor, cholesterol side-chain cleavage enzyme (CYP11α), collagen type IV α$_3$ chain, cytochrome P450 2D6 (CYP2D6), desmin, desmoglein 1, desmoglein 3, f-actin, GM gangliosides, glutamate decarboxylase (GAD65), glutamate receptor (GLUR), H/K ATPase, 17-α-Hydroxylase (CYP17), 21-hydroxylase (CYP21), IA-2

(ICA512), insulin, insulin receptor, intrinsic factor type 1, leukocyte function-associated antigen (LFA-1), myelin-associated glycoprotein (MAG), myelin basic protein, myelin oligodendrocyte glycoprotein (MOG), myosin, p-80-coilin, pyruvate dehydrogenase complex-E2 (PDC-E2), sodium iodide symporter (NIS), SOX-10, thyroid and eye muscle shared protein, thyroglobulin, thyroid peroxidase, thyrotropin receptor, tissue transglutaminase, transcription coactivator p75, tryptophan hydroxylase, tyrosinase, tyrosine hydroxylase, ACTH, aminoacyl-tRNA histidyl synthetase, aminoacyl-tRNA synthetase (several), cardiolipin, carbonic anhydrase II, collagen (multiple types), centromere-associated proteins, DNA-dependent nucleosome-stimulated ATPase, fibrillarin, fibronectin, glucose-6-phosphate isomerase, β2-glycoprotein I (β2-GPI), golgin (95, 97, 160, 180), heat shock protein, hemidesmosomal protein 180, histone H2A-H2B-DNA, IgE receptor, keratin, myeloperoxidase, proteinase 3 (PR3), RNA polymerase I-III (RNP), signal recognition protein (SRP54), topoisomerase-I (Scl-70), tubulin, vimentin, C1 inhibitor, Clq, factor H, factor V, factor VII, factor VIII, factor IX, factor X, factor XI, factor XII, thrombin, vWF, 60-kDa Ro protein, glycoprotein IIb/IIIg and Ib/IX, oxidized LDL, amphiphysin, cyclin B1, DNA topoisomerase II, desmoplakin, gephyrin, Hu proteins, neuronal nicotinic acetylcholine receptor, p53, p62 (IGF-II mRNA-binding protein), recoverin, Ri protein, βIV spectrin, synaptotagmin, voltage-gated calcium channels, and yo protein.

Another antigen that can be used is a tumor antigen. Tumor antigens are those antigens that are presented by MHC I or MHC II molecules on the surface of tumor cells. These antigens can sometimes be presented only by tumor cells and never by the normal ones. In this case, they are called tumor-specific antigens (TSAs) and typically result from a tumor specific mutation. More common are antigens that are presented by tumor cells and normal cells, and they are called tumor-associated antigens (TAAs). Cytotoxic T lymphocytes that recognized these antigens may be able to destroy the tumor cells before they proliferate or metastasize. Tumor antigens can also be on the surface of the tumor in the form of, for example, a mutated receptor, in which case they will be recognized by B-cells. Tumor antigens include the MAGE (1-10) and BAGE proteins, MUC-1, CEA, 17-1A, TRP-2, M-urinary antigen, M-fetal antigen, UTAA, GM2 ganglioside, GD2 ganglioside, hTRT, cytokeratin 19, SCCA-1 and -2, Orf73, PSA, CA 19-9, CA 72-4, CA 195, CA 55.1, NOVA2, CA 125, ART1, CASA, and CO-029.

Another group of antigen targets involve signaling proteins found in humans and other animals. These include cytokine receptors and the corresponding cytokines, growth factors and their corresponding receptors, and chemokines and their corresponding receptors. Included are interferons α, β and γ, interleukins (IL-1α, -1β, -2, -3, -4, -5, -6, -7, -8, -9, -10, -11, -12, -13, -14, -15, -16, -17, -18, -19, -20, -21, -22, -23, LIF), GM-CSF, G-CSF, TGF-α, IGF-I, IGF-II, TGF-β, BMP, VEGF, EPO, NGF, BDNF, PDGF, neutrophins, TPO, GDF-8, GDF-9, bFGF, EGF, HGF, CCL1, CCL2, CCL3, CCL4, CCL5, CCL6, CCL7, CCL8, CCL9/10, CCL11, CCL12, CCL13, CCL14, CCL15, CCL16, CCL17, CCL18, CCL19, CCL20, CCL21, CCL22, CCL23, CCL24, CCL25, CCL26, CCL27, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, CX3CL1, and receptors for each of the foregoing ligands.

II. Preparing Human Monoclonal Antibodies From IgM$^+$ B-Cells

The following are descriptions of the general procedures by which one can obtain human monoclonal antibodies. These procedures are exemplary and may be modified while retaining the essential aspects of the invention.

A. Obtaining IgM B-Cell Populations

To prepare B-cells from tonsils, tonsil tissue is mixed with antibiotic, chopped and minced to approximately 1 mm$^3$ pieces, followed by gentle grinding of tonsil pieces and straining through a nylon strainer. The suspension is then centrifuged on a Ficoll cushion. The boundary layer containing mononuclear cells is extracted, washed and re-suspended in DPBS. Further enrichment (>95%) can be achieved by negative selection using antibodies and magnetic beads.

To prepare B-cells from peripheral blood, venous blood is drawn into syringes containing heparin sodium to which prevent coagulation, diluted, centrifuged on a Ficoll cushion, collected and stored in aliquots. The boundary layer containing mononuclear cells is extracted, washed and re-suspended in DPBS. Further enrichment can be achieved as stated above.

B. EBV Immortalization

For infection by inoculation with EBV supernatant, B-cells are resuspended at 10$^6$ to 10$^7$ cells per ml in complete RPMI media, and mixed with an equal volume of filtered EBV supernatant, then incubated for 4 hours at 37° C. and 5% CO$_2$. The culture volume may be adjusted by the addition of complete RPMI media, such that infected cells were resuspended for cell culture at a desired concentration (generally 10$^5$ to 10$^6$ cells per ml). Cells are then dispensed into multi-well plates and transferred to a tissue culture incubator at 37° C. and 5% CO$_2$.

For spinfection, B-cells are resuspended at 10$^6$ to 10$^7$ cells per ml in complete RPMI media, and mixed with an equal volume of 10-fold ultrafiltration concentrated EBV and placed in a well of a 6-well tissue culture plate. The plate is then centrifuged at 900 g for 1 hr at ambient temperature, at which time infected cells are re-suspended in complete RPMI media at a desired concentration (generally 10$^5$ to 10$^6$ cells per ml), dispensed into multi-well plates and transferred to a tissue culture incubator at 37° C. and 5% CO$_2$.

Optionally, B-cells may be contacted with Toll Like Receptor (TLR) ligands at the time of or subsequent to the infection. The ligands may be added at the following final concentrations: Pam3CSK4 (0.5 µg/ml), Zymoson (1 µg/ml), poly I:C (25 µg/ml), LPS (5 µg/ml), Imiquinoid (1 µg/ml), and CpG (1 µg/ml).

Infectivity varies based upon route of infection. Infection of tonsil B cells by inoculation with EBV supernatant results in immortalization of approximately 1-5% of B cells. Addition of TLR ligands approximately doubles infection efficiency. Infection of tonsil B cells by spinfection with concentrated virus increases infection efficiency to virtually 100% after 24 hours.

C. Culturing to Induce Immunoglobulin Isotype Class Switching

To induce B-cell differentiation and immunoglobulin isotype class switching, cytokines and other signaling agents are added to EBV infected B-cells immediately after infection, 16 to 20 hr after infection, and/or sequentially at weekly intervals (2, 3, 4 or 5 times). Agents may be diluted in media and added to cells at the following final concentrations: recombinant human interleukins (IL) IL-4, 0.2 ng/ml; IL-5, 0.2 ng/ml; IL-6, 0.1 ng/ml; IL-9, 0.2 ng/ml; IL-10, 0.24 ng/ml; IL-13, 1 ng/ml; recombinant human interferon-α2a (IFN-α2a), 2,000 IU/ml; recombinant human BAFF, 1 ng/ml; recombinant human soluble CD40L, 5 ng/ml; goat anti-human IgM F(ab')$_2$, 1.4 µg/ml (amounts are approximate). Particular combinations comprise anti-IgM F(ab')$_2$, CD40L+/−BAFF; anti-IgM F(ab')$_2$ and BAFF; CD40L+/−BAFF; anti-IgM F(ab')$_2$ and IL-6+/−IL4; and anti-IgM F(ab')$_2$ and IL-9+/−IL-13.

The initiation of immunoglobulin isotype class switching begins from about 7 to about 10 days following exposure to the cytokine/growth factor/signaling agent cocktail, and the process continues for the following 10 days.

D. Selection of Immortalized B-Cells

Following collection, culture supernatants are collected once a week from tonsil and blood B-cell cultures, pooled, and tested using an ELISA or other screening format, such as dot blot, or flow cytometry. Antigen may be layered on the wells of a polystyrene (e.g., 96-well) plate and allowed to bind, e.g., overnight. Plates are then washed, blocked, and contacted with immortalized B cell culture supernatant samples or controls in triplicate or other replicates. Subsequently, the plate is washed extensively, and then e.g., alkaline phosphatase (AP)-coupled goat anti-human IgG or other antibody is added for detection of bound IgG by AP conversion of colorimetric substrate p-nitrophenyl phosphate disodium salt.

Based upon the discussion above, immunoglobulin isotype class switching starts at about 7 days following exposure to the cytokine/growth factor/signaling agent cocktail. Thus, from about 7-21 days, about 10-21, about 7-10 days or about 10-14 days, or at 7, 8, 9, 10, 11, 12, 13, 14, 15, 16, 17, 18, 19, 20 or 21 days, one will select B-cells that have undergone immunoglobulin isotype class switching and thus predominantly secrete IgG.

III. Cloning And Expression Of Human Immunoglobulin Light And Heavy Chains

Various methods may be employed for the cloning and expression of human immunoglobulin light and heavy chain sequences. Weltschof et al. (1995), incorporated herein by reference, describes in detail the methods used by the inventors. The variable regions, or variable+constant regions, may be cloned.

Other techniques, such as those described by Takekoshi et al. (2001), are also useful. In that reference, total cellular RNA was isolated from pelleted cells using a commercial kit (RNeasy mini kit, Qiagen). Using random 9-mers, nucleotides and reverse transcriptase (Takara, RNA-PCR kit, Ohtsu), cDNAs were synthesized and were amplified by the polymerase chain reaction (PCR), with heavy and light chain primers specific for human immunoglobulins (Ig). A "touchdown" PCR protocol was employed, i.e., three cycles each of denaturation at 95° C. for 1 min, annealing for 1 min, and elongation at 72° C. for 2 min, for a total of 11 cycles. The annealing temperature was varied from 65-55° C. in steps of 1° C. The touchdown cycles were followed by 25 cycles using an annealing temperature of 55° C. The resultant PCR product was gel-purified in agarose and extracted using Qiaquick spin-columns (Qiagen). The light chain and heavy chain Fc genes were then cloned into the NheI/AscI and the SfiI/NotI sites of the expression vector pFab1-His2. The ligated pFab1-His2 vectors with the light chain (κ and λ) and Fc heavy chain genes (γ and µ) were introduced into competent E. coli JM109 cells (Toyobo, Osaka). After transformation, the E. coli cells were plated onto Luria-Bertani (LB)/ampicillin (50 µg/ml) plates. Isolated bacterial colonies were incubated at 30° C. in 2 ml of Super Broth (SB) with ampicillin (50 µg/ml) and MgCl$_2$ (1.5 mM). Isopropyl-β-D-thiogalactopyranoside (IPTG) was used to induce production of the Fab protein. Cells from the bacterial cultures were pelleted, resuspended in 0.3 ml of B-PER (Pierce) with a protease inhibitor cocktail (Complete, Boehringer Mannheim), and shaken for 5 min at room temperature. Cell lysates were centrifuged at 15,000 G for 10 min, and the resultant supernatant containing the Fab antibody portion was collected.

The foregoing is purely exemplary and other methods may be employed.

IV. Antibody Production

Once cloned, the nucleic acids for the human light and heavy chains will be inserted into appropriate expression vectors and transferred into host cells (e.g., antibody-producing cells) that will support production of antibodies. Particular cell lines contemplated for production are 293 cells, CHO cells, COS cells or various forms of myeloma cells, some lacking IgG. These cells may be exploited for human MAb production in two basic ways. First, myelomas or immortalized cells can be injected (often into the peritoneal cavity) into a histocompatible animal of the type that was used to provide the somatic and myeloma cells for the original fusion (e.g., a syngeneic mouse), or into an immunodeficient animal for injection of noncompatible cells. Optionally, the animals are primed with a hydrocarbon, especially oils such as pristane (tetramethylpentadecane) prior to injection. The injected animal develops tumors secreting the specific monoclonal antibody produced by the transfected myeloma. The body fluids of the animal, such as serum or ascites fluid, can then be tapped to provide human MAbs in high concentration. Second, the individual cell lines could be cultured in vitro, where the human MAbs are naturally secreted into the culture medium from which they can be readily obtained in high concentrations.

Human MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction.

V. Diagnostics

The present invention contemplates the use of human monoclonal antibodies in in vivo diagnostic procedures. Cancers, for example, are advantageously detected using antibodies that, if human in origin, can be administered systemically. "Detectable labels" are compounds and/or elements that permit detection of bound antibody. Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

VI. Passive Immunization

A. Administration

A major advantage of passive antibody immunization is that it immediately provides a state of immediate immunity that can last for weeks and possibly months. Some human IgG isotypes have serum half-lives in excess of 30 days, which would confer long-lived protection to passively immunized persons. Antibodies are natural products with minimal toxicity, provided that they contain no aggregates and have no reactivity with host tissues. Also, since active vaccines are available, simultaneous administration of vaccine and antibody may be possible to provide both immediate and long-lasting protection (e.g., for rabies in post-exposure prophylaxis).

Administration of MAbs produced as described above will follow the general protocols for passive immunization. Although passive antibodies are generally given systemically, oral administration can be useful against certain gastrointestinal agents. While many antibody preparations in clinical use are given intravenously, novel monoclonal antibodies used therapeutically for autoimmune disease are often administered subcutaneously, and injection of gamma-globulin for hepatitis prophylaxis was traditionally administered intra-muscularly. The need for intravenous administration is a severe constraint for mass passive immunization and would likely limit this practice to a few recipients. However, this disadvantage may potentially be circumvented because Ig preparations can theoretically be administered intramuscular, subcutaneous, intralesional, or even intraperitoneal routes. Hence, generating antibody preparations suitable for delivery into one of the large muscles of the arm, leg or buttock, or into the subcutaneous fat in the stomach or thigh, may be possible without the need for logistically complicated intravenous infusions. The present invention is ideally suited to provide this option, as antibody preparations for these routes of administration would require high specificity, permitting administration in a relatively small volume.

B. Pharmaceutical Compositions

It is envisioned that, for administration to a host, MAbs will be suspended in a formulation suitable for administration to a host. Aqueous compositions of the present invention comprise an effective amount of an antibody dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Antibodies will generally be formulated for parenteral administration, e.g., formulated for injection via the intravenous, intramuscular, subcutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration.

Generally, dispersions are prepared by incorporating the various soluble receptors, antibodies, inhibitory factors, or viable cells into a sterile vehicle which contains the basic dispersion medium and the required other ingredients for maintaining cell viability as well as potentially additional components to effect proliferation or differentiation in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods for B-Cells Reactive to H5 HA

Isolation and culture of tonsil B cells. To prepare B cells from tonsils, tonsil tissue was placed inside a sterile Petri dish (VWR International, cat. #25384-088) containing 20-30 ml Dulbecco's phosphate buffered saline (DPBS, without $CaCl_2$ or $MgCl_2$; Gibco/Invitrogen, Grand Island, N.Y. cat. #14190144) supplemented with 1×Antibiotic-Antimycotic (Gibco/Invitrogen cat. #15240-062). The tissue was chopped and minced with scalpels to approximately 1 $mm^3$ pieces. Additional lymphocytes were released by gentle grinding of tonsil pieces between the frosted glass surfaces of two sterile microscope slides (VWR cat. #12-550-34), and single cell preparation was made by straining through 70 μm nylon strainer (BD Falcon, cat. #352350, BD Biosciences, Two Oak Park, Bedford, Mass.). This suspension was layered onto a Ficoll (Amersham Biosciences cat. #17-1440-03, Uppsala, Sweden) cushion (35 ml sample over 15 ml Ficoll) and resolved at 1500G for 20 min. The boundary layer containing mononuclear cells was extracted, washed 2× with DPBS (1300G for 7 min), counted, and re-suspended in DPBS at $10^8$ cells/ml. A highly enriched (>95%) B-cell population was obtained with the use of StemSep Negative Selection Human B-cell Enrichment Kit antibody cocktail (cat. #14064A) and magnetic beads (cat. #19150) from StemCell Technologies Inc., Vancouver, Canada, according to manufacturer's instructions, with the following modifications for use on a "The Big Easy" EasySep magnet (StemCell Tech. cat. #18001). All steps were performed in a laminar flow biohazard hood at ambient temperature. The cell suspension was placed in a sterile round bottom 14 ml polypropylene tube (VWR cat. #60818-689), mixed with an equal volume of the StemSep Negative Selection Human B-cell Enrichment Kit antibody cocktail, and incubated for 10 minutes. Then, a volume of magnetic bead suspension equal to the antibody cocktail volume was added, followed by 10 minute incubation. The volume inside the tube was brought to 10 ml with DPBS and the tube (minus the cap) was placed inside the magnet for 10 minutes, at which time the contents of the tube (still inside the magnet) were gently decanted in a single pour into a second sterile 14 ml tube. The original tube with non-B cells adhering to its walls was removed from the magnet, and the second tube was inserted for 10 minute clean-up incubation. The enriched B-cell suspension obtained after the first and second negative selection steps was poured into a 15 ml Falcon tube, counted, washed with DPBS (1300G for 7 min) and resuspended in an appropriate volume of complete RPMI media for in vitro culture (generally $10^5$ to $10^6$ cells/ml) in a 37° C., 5% $CO_2$ tissue culture incubator. Complete RPMI media contains RPMI 1640 (Gibco/Invitrogen cat. #11875-093) supplemented with 10% fetal bovine serum (FBS, HyClone cat. #SH30088.03, lot. #AQC23460, Logan, Utah), and 100 U/ml Penicillin, 100 μg/ml Streptomycin (cat. #15140-122), 2 mM L-Glutamine (cat. #25030-081), 1 mM Sodium Pyruvate (cat. #11360-070), 10 mM HEPES (cat. #15630-080), 0.1% 2-mercaptoethanol (cat. #21985.023), and 0.1% Falk's Cloning Cocktail, which consists of 50 mM α-thioglycerol (Sigma, cat.# M6145), 20 μM bathocuproinedisulfonic acid (Sigma, cat. #B1125), 100 mM Na pyruvate (cat. #11360-070), 1M HEPES pH 7.4 (cat. #15630-080). L-glutamine, Sodium Pyruvate, Penicillin/Streptomycin and HEPES were obtained from Gibco/Invitrogen.

Isolation and Culture of peripheral blood B cells. To prepare B cells from peripheral blood, venous blood (up to 180 ml) was drawn into 60 ml syringes containing 1-5 ml citric acid or heparin sulfate, which prevent coagulation, diluted with equal volume of DPBS, layered onto a Ficoll cushion (35 ml of diluted sample over 15 ml Ficoll) and resolved at 2000 rpm for 20 min. Serum (from upper layer) was collected and stored in aliquots. The boundary layer containing mononuclear cells was extracted, washed 2× with DPBS (1300G for 7 min), counted, and re-suspended in DPBS at $10^8$ cells/ml. Highly pure populations of B-cells were obtained with the use of StemSep Negative Human B-cell Enrichment Kit (StemCell Technologies Inc.) as described above for isolation of peripheral blood B-cells. Isolated B-cells were washed (1300G for 7 min) and re-suspended at $10^5$-$10^6$ cells per ml of complete RPMI media (described above), and cultured in a 37° C., 5% $CO_2$ tissue culture incubator.

EBV stock preparation. To prepare infectious Epstein-Barr virus (EBV) stocks, B95-8 cells, a marmoset lymphoblastoid cell line (LCL) chronically infected with B95-8 strain EBV (Miller & Lipman, 1973), or EBfaV-GFP cells (Speck et al., 1999; described below), were cultured in complete RPMI media (described above) at a cell density of approximately $10^5$ cells/ml, in a 37° C., 5% $CO_2$ tissue culture incubator. EBfaV-GFP cells were derived from B95-8 cells, where the EBV genome was modified by homologous recombination, deleting the LMP2a gene and replacing it with enhanced green fluorescence protein (EGFP) (under control of the CMV immediate/early promoter) as well as neomycin resistance ($neo^R$) genes (Speck et al., 1999). These cells contain a mixture of EBfaV-GFP ($LMP2a^-EGFP^+$) genomes and wild-type B95-8 genomes.

Approximately 140 ml of cell culture (containing either B95-8 EBV or recombinant EBfaV-GFP) was induced to enter lytic virus production phase by treatment with phorbol myristate acetate (PMA, 10 ng/ml, Calbiochem, cat. #524400). After a four hour incubation with PMA, the PMA was removed from the culture supernatant and replaced with complete RPMI media. The cells were cultured for 3 to 4 days until highly confluent, at which point cells were removed by centrifugation (1300G for 7 min), and culture supernatant was filtered through 150 ml Nalgene 0.45 µm vacuum filter (Corning cat. #430320). Filtered supernatant was either flash-frozen in liquid nitrogen in 1.4 ml aliquots for storage at −80° C. in 1.5 ml Eppendorf tubes, or concentrated by ultrafiltration as described below.

EBV concentration. Viral concentration was performed by loading the filtered supernatant into two Centricon Plus-70 (100K MW cut-off) units (Millipore, Billerica, Mass.) and concentrated according to manufacturer's instructions. The filter units were centrifuged (2000G) for between 15 and 45 minutes (monitored each 15 minutes), until the minimal retentate volume (approximately 0.5 ml per filtration unit) was achieved. The filtrate was discarded, and virus-containing concentrates were re-suspended with complete RPMI media up to a total volume of 14 ml (or ¹/₁₀ of the original culture supernatant volume). One ml aliquots were transferred into cryovials, flash-frozen in liquid nitrogen, and transferred to −80° C. freezer for storage.

B cell infection by inoculation. B cells were resuspended at $10^6$ to $10^7$ cells/ml in complete RPMI media, and were mixed with an equal volume of filtered EBV supernatant, then placed in a T-25 flask and incubated for 4 hours in a tissue culture incubator at 37° C. and 5% $CO_2$. The culture volume was then adjusted by the addition of complete RPMI media, such that infected cells were resuspended for cell culture at the desired concentration (generally $10^5$ to $10^6$ cells per ml), dispensed into multi-well plates and transferred to a tissue culture incubator at 37° C. and 5% $CO_2$.

B cell infection by spinfection with concentrated EBV stocks. B cells were resuspended at $10^6$ to $10^7$ cells/ml in complete RPMI media, and were mixed with an equal volume of concentrated EBV and placed in a well of a 6-well tissue culture plate (Greiner bio-one, cat. #65760). The plate was then centrifuged at 900G for 1 hour at ambient temperature, at which time infected cells were re-suspended in complete RPMI media at a desired concentration (generally $10^5$ to $10^6$ cells per ml), dispensed into multi-well plates and transferred to a tissue culture incubator at 37° C. and 5% $CO_2$.

Infection in the presence of TLR ligands. B cells were infected with B95-8 strain EBV as described above, with the addition of Toll-Like Receptor (TLR) ligands at the time of the infection. The ligands were added at the following final concentrations: lipoprotein Pam3-CSK4 (0.5 µg/ml), zymosan (Zymoson) (1 µg/ml), polyinosine, polycitadylic acid (poly I:C) (25 µg/ml), lipopolysaccharide (LPS) (5 µg/ml), Imiquimod (1 µg/ml), unmethylated CpG DNA (1 µg/ml). All TLR ligands (from InVivogen Inc) were generously donated by Dr. Mohamed Salem (MUSC).

Evaluation of B cell immortalization efficiency by lymphoblastoid cell outgrowth. At 12 hours post-infection, B cells were counted and dispensed into wells of 96-well round bottom plates (Greiner cat#650180) as a 2-fold dilution series, with each consecutive row of wells containing half the number of cells found in the previous row. The initial rows contained 50,000 cells per well, and final rows in the dilution series contained 24 cells per well. Cells were incubated for 9 days in a tissue culture incubator at 37° C. and 5% $CO_2$, at which point lymphoblastoid cell outgrowth was visible by microscopy. Immortalization efficiency was estimated based upon the assumption that lymphoblastoid cell proliferation resulted from EBV immortalization of at least one B cell in the well. Thus, the efficiency was calculated from rows containing wells with the lowest number of cells per well in which lymphoblastoid cell proliferation was consistently observed by microscopy, and expressed as 1 immortalization event per number of cells originally dispensed into the well.

Evaluation of EBV-GFP infection efficiency of 293 cells. Because recombinant EBV-GFP virus contains the EGFP gene encoding enhanced green fluorescence protein in place of the latent membrane protein-2 (LMP2) gene, infection with the virus can be measured by fluorescence microscopy or by flow cytometry as early as 24 hours post-infection. 293 cells were infected by inoculation or by spinfection as follows. Cells were trypsinized, washed and resuspended in complete DMEM media, containing DMEM (Mediatech cat. #10-013-CM), 10% Cosmic Calf serum (CCS, HyClone cat. #HS0087.03, lot. #APE21241), Penicillin, 100 U/ml, Streptomycin, 100 µg/ml (Gibco/Invitrogen, cat. #15140-122), at $1\times10^6$ cells/1 ml per well into 6-well plates. 1 ml of EBfaV-GFP virus stock, concentrated or unconcentrated, was added to the cells. Plates were either incubated overnight for inoculation or centrifuged for 1 hour at 900G for spinfection. Infection efficiency was determined 48 hours post-infection by visual inspection using fluorescence microscopy.

Evaluation of EBfaV-GFP infection efficiency of B cells. To quantitatively evaluate B cell infection efficiency, tonsil B cells were dispensed into wells of a 96-well plate at $2\times10^5$ cells/100 µl per well. TLR ligands were added to some of the wells at the concentrations previously described above, and cells were incubated for 4 hours at 37° C., 5% $CO_2$. Concentrated EBfaV-GFP virus stock (100 µl/well) was then added to all wells and the cells were infected by spinfection as previously described. Infection efficiency was analyzed by flow cytometry for $EGFP^+$ cells 24 hours later.

Flow Cytometry analysis was performed using a Becton Dickinson FACSCalibur instrument at the MUSC Flow Cytometry Facility, according, to established methods. Antibodies are listed in Table 3.

TABLE 3

Antibodies for B-Cell Characterization

| NAME | FUNCTION | EXPRESSION |
|---|---|---|
| CD19 | Assembles with the BCR in order to decrease the threshold for antigen-specific receptor-dependent stimulation | Pantropic B cell marker |
| CD20 | B-cell surface molecule with a role in the differentiation and development of B-cells into plasma cells | Present on all B lymphocytes, except plasma cells |
| CD27 | Member of the NGF/TNF receptor superfamily; present on germinal center B-cells. Soluble CD27 is produced by plasma B-cells | Marker for human somatically mutated, B-cells; found on both B and T lymphocytes upon cell activation; upregulated on post-germinal B cells |
| CD30 | Transmembrane cytokine receptor belonging to the TNF receptor superfamily; has a role in regulating the function, differentiation and/or proliferation of normal lymphoid cells | Upregulated on post-germinal center cells; present on Hodgkin's and Reed-Sternberg cells and on tumor cells of anaplastic large cell lymphomas |
| CD38 | Functions in cell adhesion, signal transduction and calcium signaling | Expressed at multiple stages; first appears on bone marrow precursor cells, but is lost on mature lymphocytes; it protects germinal center cells from apoptosis, but memory cells exiting the germinal center lack CD38; present on terminally differentiated cells. |
| IgD | Immunoglobulin molecule with unknown function | Present on the mature B-lymphocytes that have not initiated immunoglobulin isotype class switching and somatic hypermutation |

Induction of B cell differentiation. To determine their effect on B cell differentiation during the immortalization process, cytokines and other signaling agents were added to EBV infected B cells either immediately after infection, or 16 to 20 hours after infection, and twice more at weekly intervals. All agents were diluted in complete RPMI media and added to cells at the following final concentrations: recombinant human interleukins (IL) IL-4, 0.2 ng/ml; IL-5, 0.2 ng/ml; IL-6, 0.1 ng/ml; IL-9, 0.2 ng/ml; IL-10, 2.4 ng/ml; IL-13, 1 ng/ml; recombinant human interferon-α (IFN-α2a), 2,000 IU/ml; recombinant human BAFF, 1 ng/ml; recombinant human soluble CD40L, 5 ng/ml; goat anti-human IgM (Fab')$_2$, 1.4 μg/ml. IL-4 (cat. #200-04), IL-5 (cat. #200-05), IL-6 (cat. #200-06), IL-9 (cat. #200-09), IL-10 (cat. #200-10), IL-13 (cat. #200-13), CD40L (cat. #310-02) and BAFF (cat. #310-13) were obtained from PeproTech (Rocky Hill, N.J.). IFN-α2a (Roferon$^R$-A) was from Roche Pharmaceuticals, and goat anti-human IgM (Fab')$_2$ (cat. #109-006-129) was from Jackson Immune Research Laboratories Inc.

Creation of immortalized B cell repertoires used in H5 hemagglutinin binding studies. Tonsil or peripheral blood B cells were infected by spinfection with concentrated B95-8 virus as described above. Immediately following spinfection, cells were resuspended in complete RPMI media to which IL-4 (0.2 ng/ml), IL-6 (0.1 ng/ml), BAFF (10 ng/ml), and goat anti-human IgM (Fab')$_2$ (1.62 μg/ml) (for three samples) or CD40L (5 ng/mL), BAFF (10 ng/ml), and goat anti-human IgM (Fab')$_2$ (1.62 μg/ml) (for five samples) were added.

Measurement of human immunoglobulin IgM and IgG production by ELISA. Culture supernatants (1 ml from each well of 24 well plates) were collected at various time points beginning 1 week after infection and stored frozen at −20° C. until assay. Thawed supernatants, 10 μl per sample, or 10 μl of standards consisting of purified human IgG (Sigma-Aldrich cat. #12511) or IgM (cat. #18260), were mixed with 90 μl of binding buffer consisting of 100 mM Na$_2$HPO$_4$, pH 9. Samples were then bound directly to quadruplicate wells of Nunc 96-well EasyWash plates (Costar cat. #3369). All samples were added to duplicate plates, one for detection of IgG, the other for detection of IgM. Plates were incubated at room temperature for 1 hour, washed 4 times with wash buffer consisting of PBST (80.0 g NaCl, 11.6 g Na$_2$HPO$_4$, 2.0 g KCl, 5 ml Tween-20, pH 7.0 in 10 L), and blocked with 2% BSA in wash buffer for 1 hour. Plate bound IgG and IgM were detected using alkaline phosphatase (AP) coupled goat anti-human IgG or IgM (Southern Biotech cat #2040-04 or 2020-04 respectively), 100 μl per well diluted 1:1,000 was added for 1 hour. After washing, AP conversion of colorimetric substrate p-nitrophenyl phosphate disodium salt (PNPP, Peirce cat #37620) was detected by measuring absorbance at OD$_{405}$ using a Multiskan Spectrum plate reader (ThermoLabsystems). Levels of human immunoglobulin in culture supernatant samples were calculated following standard curve calibration of purified human IgG and IgM standards using MultiSkan software.

Sample collection for H5 HA ELISA analysis. Culture supernatants were collected once a week from tonsil and peripheral blood immortalized B cell cultures (150 μl from each well, replaced with fresh RPMI plus CD40L, BAFF and anti-human IgM). After weeks 1 and 2, the supernatants were pooled by combining 25 μl of sample from each well on a plate. For week 3, pooled supernatants were generated from individual rows on each plate by combining 50 μl from each well in a specified row (A, B, C, etc.). Supernatant from the entire well was used for analysis when testing individual or pooled dual wells. Once an individual well secreting anti-H5 HA IgG had been identified, cells from that well were counted, and subcloned into at least four 96-well plates, each containing 1000, 100, 10 or 1 cell/well. After 2 weeks, sample collection and analysis of supernatants from plates, then rows, then wells were repeated. The goal of the subcloning strategy was to obtain H5 HA-reactive IgG from the wells initially plated with no more than 1 cell per well.

H5 HA ELISA. Purified recombinant H5 hemagglutinin (HA) from H5N1 avian influenza strain A/Vietnam/1203/2004 (Protein Sciences Corp) was diluted to 2 µg/ml in a high pH 100 mM sodium phosphate binding buffer (pH 9.0), dispensed at 50 µl per well into 96-well EasyWash plates (Costar cat. #3369), and allowed to bind overnight. To help control for non-specific plate binding in each sample, an equal number of wells received binding buffer only. Plates were then washed, and blocked with a neutral pH 100 mM sodium phosphate buffer (pH 7.2) containing 2% BSA. Culture supernatant from samples or controls 100 µl per well was added in triplicate. Controls included serum from healthy human volunteers, diluted 1:500 with complete RPMI media; purified human IgG (Sigma) and Rituxan$^R$ (a humanized anti-CD20 IgG$_1$ monoclonal antibody, Genentech, San Francisco, Calif. 94080, cat. #50242-051-21, lot #M70267) diluted to 5 µg/ml in complete RPMI media. Subsequently, the plate was washed extensively. Next, alkaline phosphatase (AP)-coupled goat anti-human IgG diluted 1:1000 (Southern Biotech cat. #2040-04) was added 100 µl per well, and incubated for 1 hour at ambient temperature, followed by detection with AP conversion of colorimetric substrate consisting of p-nitrophenyl phosphate disodium salt (PNPP, Peirce cat. #37620). Absorbance was measured at 405 nm. Results were expressed as average OD$_{405}$ values±standard deviations (n=3). Background values resulting from non-specific sample binding to uncoated wells (binding buffer only) was subtracted from the values obtained from binding to H5 HA coated wells.

Example 2

Results for B Cells Reactive to H5 HA

Figure 1A:
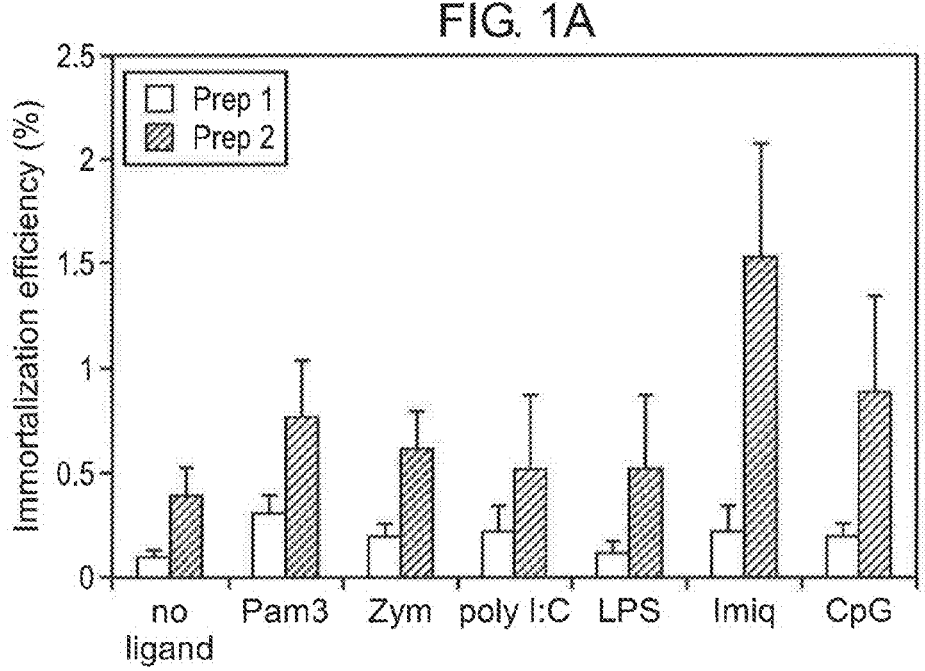
FIGS. 1A-B. Effect of TLR ligands and viral stock concentration on EBV infection efficiency. Primary tonsil B cells ($10^6$ cells/ml/well were seeded in 24-well plate and infected with 1 ml of concentrated or un-concentrated B95-8 viral stocks from several different preparations, with the addition of various TLR ligands as indicated (see Example 1). After a 4 hr incubation, cells were dispensed into a 96-well plate using a 2-fold serial dilutions, starting at $5 \times 10^4$ cells/well and ending with 24 cells/well. LCLs were scored visually by phase contrast microscopy 9 days post-infection. % immortalization efficiency was calculated as described in Example 1. Means±SD are shown (n=3).

Toll-Like Receptor (TLR) ligands and EBV concentration did not significantly improve EBV infectivity. Traggiai et al. (2004) reported that addition of at least one TLR ligand (CpG) to cultured memory B cells could enhance EBV infection efficiency. Since naïve B cells express several TLR (Bourke et al., 2003) it was reasonable to assess the effect of several TLR ligands on EBV infection of naïve B cells. Primary B cells were incubated overnight with either Pam3 (Pam$_3$Cys-Ser-(Lys)$_4$) (0.5 µg/mL), zymosan (1 µg/mL), Poly I:C (polyinosinic-polycytidylic acid) (25 µg/mL), LPS (lipopolysaccharide) (5 µg/mL), Imiquimod (1 µg/mL), CpG (10 µg/mL), or no ligand. These are synthetic proteins that mimic common pathogenic antigens. Each of these activates different innate immune pathways in B-cells. Lipopeptide Pam3 (Hamilton-Williams et al., 2005) binds TLR 2 and 1, zymosan (a yeast cell wall component prepared from *Saccharomyces cerevisiae*) binds TLR 2 and 6, Poly I:C (a viral double stranded DNA mimic) binds TLR 3, LPS (a microbial cell wall component) binds TLR 4 (Hamilton-Williams et al., 2005), Imiquimod (a small-molecule compound in the imidazoquinoline family, which displays both antiviral and antitumor effects) binds TLR 7, and hypomethylated CpG DNA binds TLR 9 (Hamilton-Williams et al., 2005). The inventors chose these TLR ligands because they bind to a wide range of TLR and would give a good range of activities. Following overnight incubation, the cells were infected with two different preparations of unconcentrated B95-8 EBV (prep 1, prep 2). As shown in FIG. 1A, Imiquimod, Pam3 and CpG addition improved infection efficiency to nearly 1.5% in some cases, but the overall infectivity was very low. In addition, variation between viral stock preparations significantly affected viral infectivity (FIG. 1A).

Figure 1B:
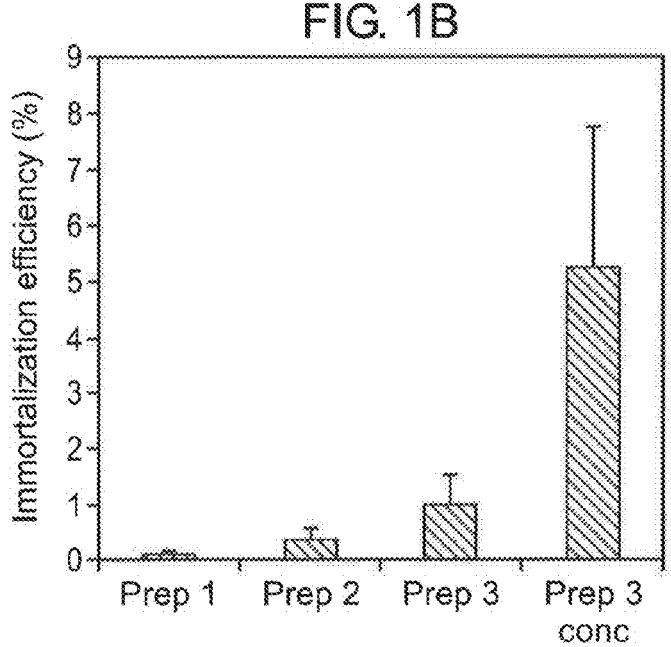

Since the addition of TLR ligands did not increase infection efficiency sufficiently for the inventors needs, viral concentration was pursued because of success with increasing retrovirus infection (Kanbe & Zhang, 2004). Viral concentration has been used to achieve higher virus titer and greater infectivity; concentration can be achieved through several techniques. For these studies; the inventors used ultrafiltration centrifugation to concentrate the EBV 10-fold. Concentrated or unconcentrated EBV was applied to primary B cells, and infectivity was determined using phase microscopy to assess lymphoblast formation. These findings indicated that concentration of EBV improved infection efficiency to nearly 5%, as compared to unconcentrated virus from the same preparation which reached only 1% infectivity (FIG. 1B). While viral concentration significantly increased infectivity, it was still not sufficient to immortalize a large portion of the naïve B cell repertoire.

Figure 2A:
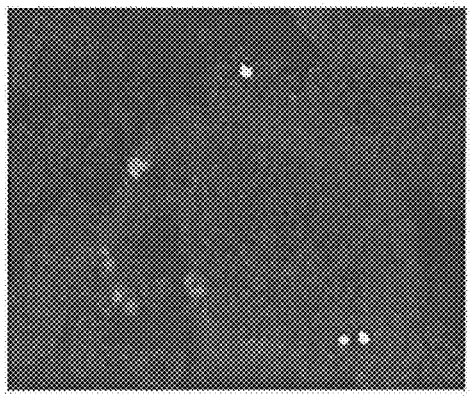
FIGS. 2A-C. Effect of EBV concentration and spinfection on Q293A infection efficiency. Q293A cells were trypsinized, counted and seeded at $1 \times 10^6$ cells/1 ml/well into 6-well plates, and 1 ml of EBfaV-GFP stock, concentrated or un-concentrated, was added to the cells. Plates were (FIG. 2A) incubated overnight with un-concentrated EBfaV-GFP, (FIG. 2B) incubated overnight with concentrated EBfaV-GFP for inoculation or (FIG. 2C) centrifuged for 1 hour at 900G for spinfection. EGFP fluorescence was detected with inverted microscope 48 hr post-infection.
Figure 2B:
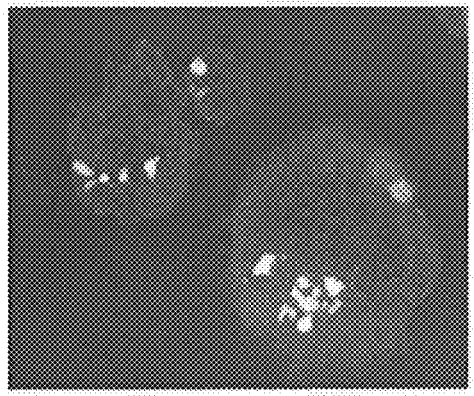
Figure 2C:
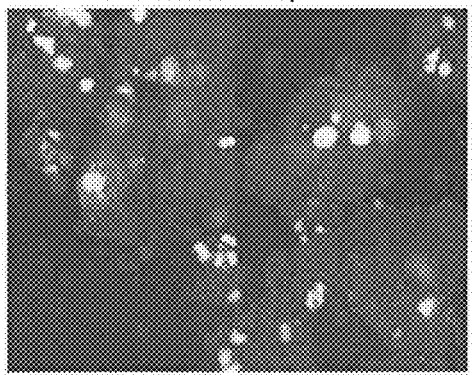

The combination of viral concentration and "spinfection" increased EBV infectivity. "Spinfection" or "spinoculation" has been reported to enhance the infectivity of other enveloped viruses such as HIV (Audige et al., 2006; O'Doherty et al., 2000). This technique involves combining cells and viral stock, then centrifuging this combination at low speeds for one hour. To evaluate concentration and "spinfection" techniques, the adherent cell line Q293A was infected with recombinant EBfaV-GFP virus, in which EBV latent gene LMP2a was replaced with the enhanced green fluorescent protein EGFP gene (Speck et al, 1999). Q293A cells were inoculated for 24 hours with concentrated or unconcentrated preparations of EBfaV-GFP virus stocks, or were "spinfected" for 1 hour at 900G with concentrated virus. FIG. 2A demonstrated the low infection efficiency of unconcentrated virus. A marked increase of infectivity over unconcentrated virus was observed with a 10-fold concentration of EBfaV-GFP (FIG. 2B). In FIG. 2C, Q293A cells were "spinfected" with concentrated virus; the combination increased infection efficiency over inoculation with either unconcentrated or concentrated virus (FIGS. 2A-C).

Figure 3A:
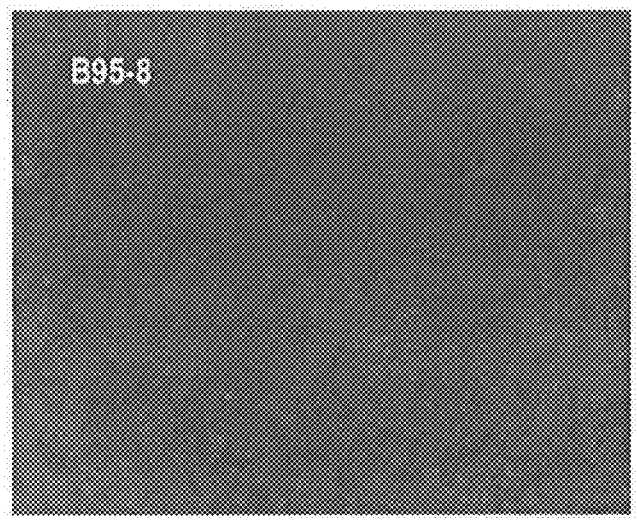
FIGS. 3A-B. Efficient infection of primary tonsil B cells with EBfaV-GFP. B cells ($2 \times 10^5$ cells/0.1 ml/well) were seeded into wells of 96-well plate, mixed with 0.1 ml of 10-fold concentrated EBfaV-GFP and "spinfected" "spinoculated" at 900 G for 1 hour, Similar number of cells was infected with B95-8 as a negative fluorescence control. Infection was evaluated 24 hours later, either as (FIG. 3A) visual evaluation of infection efficiency with fluorescent microscope.
Figure 3B:
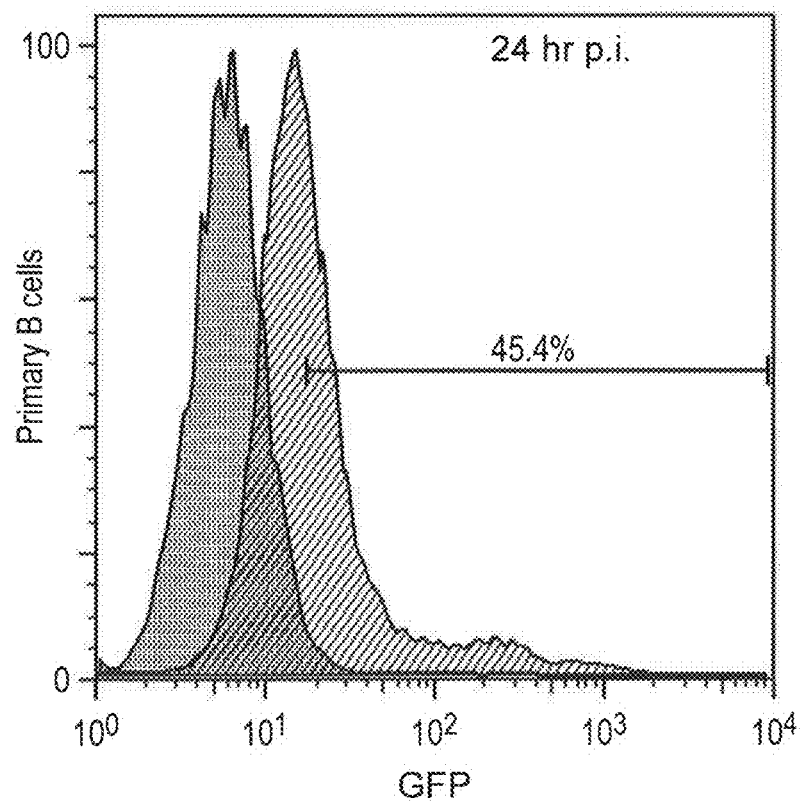

While "spinfection" and EBV concentration increased infection efficiency of an established cell line, these techniques still needed to be evaluated on primary human B cells, and infection efficiency needed to be quantified. Primary tonsil B cells were "spinfected" with concentrated non-fluorescent B95-8 EBV or with fluorescent EBfaV-GFP and analyzed for EGFP expression 24 hours post-infection. Visual inspection of the infection efficiency using a fluorescent microscope revealed that the combination of virus concentration and "spinfection" was effective on tonsil B cells (FIG. 3A). The infection efficiency was quantified by flow cytometry for EGFP expression 24 hours after infection. The combination of "spinfection" and concentration significantly increased EBV infection of primary B cells, such that 45% of EBfaV-GFP infected cells had higher fluorescence than B95-8 infected cells, with a mean fluorescence intensity (MFI) value of 61.9 compared with 15.1 (FIG. 3B). A shift of the entire peak in FIG. 3B indicated that nearly 100% of B cells were infected with EBfaV-GFP using this method, which was a great improvement over inoculation with unconcentrated virus and would be sufficient for immortalizing a large portion of the tonsil B cell repertoire.

Overall, these results on the optimization of EBV infection of B cells indicated that TLR ligand stimulation and viral concentration did not increase infection efficiency adequately for the inventors' needs. However, the combination of viral concentration and "spinfection" dramatically increased infection of primary B cells.

T cell derived cytokines had varying effects on IgM and IgG secretion from different samples. Naïve B cells are activated through interactions between the B cell receptor (BCR) and specific antigen; activation is helped by co-stimulatory signals from T cells. B cell differentiation in vivo is dependent upon T cell help. Therefore, the inventors postulated that if one could supply both T cell derived growth and differentiation factors, while cross-linking the BCR to mimic antigen, EBV immortalized LCLs could be forced to differentiate in vitro.

Figure 4:
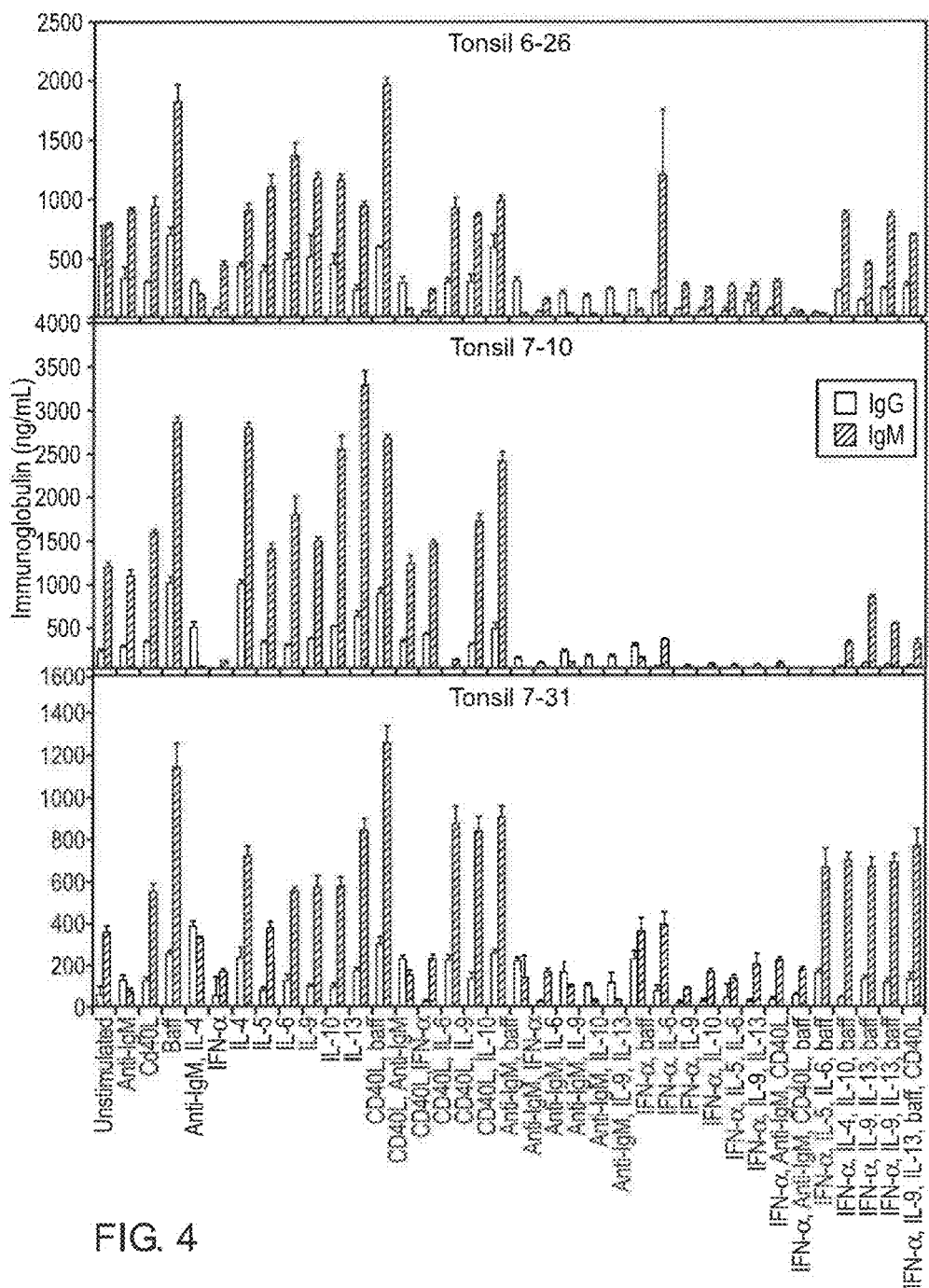
FIG. 4. IgG and IgM secretion profiles of B-cells from three tonsil samples treated for 1 week with different signaling agents. Tonsil B cells from 3 separate samples were prepared, inoculated with B95-8, seeded into 24-well plates, and treated with indicated signaling agents and cytokine combinations as described in Example 1. Culture supernatants were collected one week post-infection, and analyzed by ELISA for IgG and IgM levels as described in Example 1. Means±SD of samples and controls (n=4) are shown.

To test this postulate, the inventors examined the effect that different cytokine and/or signaling molecule combinations had on differentiation, specifically, as determined by IgG secretion. To examine the effects that these agents had on IgM and IgG secretion, primary tonsil B cells were infected with B95-8 EBV, treated with cytokines or other agents listed in Table 4 or the combinations of these as outlined in FIG. 4, and one week later, culture supernatant was analyzed for IgM or IgG by ELISA. FIG. 4 shows the secretion patterns of IgM and IgG in three different samples, one week after infection and treatment. IgM was primarily secreted at higher levels than IgG by all of the samples after most cytokine treatments (FIG. 4). Specifically, BAFF treatment or the combination of BAFF and CD40L increased IgM secretion over untreated cells (FIG. 4), while B cells treated with cytokine combinations containing anti-IgM (Fab')$_2$ in general decreased total immunoglobulin secretion after one week, when compared to untreated controls (FIG. 4). Since similar patterns of immunoglobulin secretion were obtained from three different donor samples, the signaling agents had reproducible effects. Also, since the majority of immunoglobulin secretion was IgM, this indicated that a large portion of the tonsil B cells had not undergone immunoglobulin isotype class switching or affinity maturation.

TABLE 4

Cytokines and Factors For Ig Class Switching Cocktail

| Name | Function | Working Concentration |
|---|---|---|
| Anti-IgM F(ab')$_2$ | Goat anti-human IgM F(ab')$_2$; cross-links IgM, thus mimicking specific antigen binding; activates differentiation and Ig switching pathways | 1.62 ng/ml |
| IL-4 | Cytokine produced by activated T cells and other immune cells; participates in several B-cell activation processes, including enhanced secretion and surface expression of IgE an IgG | 0.2 ng/ml |
| IL-5 | Cytokine secreted by Th2 cells; acts as a growth and differentiation factor for both B-cells and eosinophils; promotes production of Ig | 0.22 ng/ml |
| IL-6 | Cytokine plays a role in B-cell growth and differentiation of multiple stages including the final differentiation of B-cells into Ig-secreting plasma cells | 0.1 ng/ml |
| IL-9 | Cytokine secreted by Th2 cells; stimulates cell proliferation and growth and prevents apoptosis | 2 ng/ml |
| IL-10 | Cytokine produced primarily by monocytes and lymphocytes; enhances B-cell survival, proliferation and antibody production | 2.4 ng/ml |
| IL-13 | Cytokine produced by activated Th2 cells; involved in B-cell maturation and differentiation; up-regulates CD23 and MHC II class II expression and promotes IgE isotype switching | 10 ng/ml |
| IFNα | Cytokine produced by stimulated T lymphocytes and many other cell types; enhances MHC I and II expression; activates a subset of antiviral genes | 12.5 ng/ml |
| BAFF | B lymphocyte activating factor; expressed by monocytes, macrophages and dendritic cells; plays a role in B lymphocyte development, selection and homeostasis | 10 ng/ml |
| CD40L | Ligand for CD40; CD40 signaling induces B-cell differentiation and Ig hypermutation | 5 ng/ml |

Anti-IgM(Fab')$_2$, CD40L and/or Cytokines Induced Immunoglobulin Isotype Class Switching after Several Weeks in Culture. Tonsil B cells were treated with cytokines and signaling agents for three weeks; culture supernatant was analyzed by ELISA after each week for up to 10 weeks. The tonsil B cells from two of the donor samples represented in FIG. 4 were treated with a limited panel of signaling agent combinations for three weeks. While these samples initially secreted primarily IgM after one week (FIG. 4), the expression pattern of IgM and IgG changed with time in vitro. Starting as soon as 10 days after culture, immunoglobulin isotype class switching occurred after treatment with particular combinations of cytokines. As can be seen in FIG. 5, for cells cultured for more than 8 weeks, the immunoglobulin expression pattern was clearly different (FIGS. 5A and 5B). Continued cytokine treatments with CD40L alone, or anti-IgM(Fab')$_2$ in combination with IL-6, resulted in high levels of IgG secretion (FIG. 5A). This increase in IgG was accompanied by a drop in IgM secretion (FIG. 5A). In contrast, B cells treated with anti-IgM (Fab')$_2$ and IL-4 secreted higher levels of IgM than IgG (FIGS. 5A and 5B). FIG. 5B showed that cells cultured with CD40L, anti-IgM (Fab')$_2$ and BAFF also resulted in preferential IgG secretion. In all cases, the B cells continued to secrete immunoglobulin at high levels for many weeks. These results suggested that the LCLs had undergone immunoglobulin isotype class switching from IgM to IgG after treatment with the signaling agents.

Figure 6:
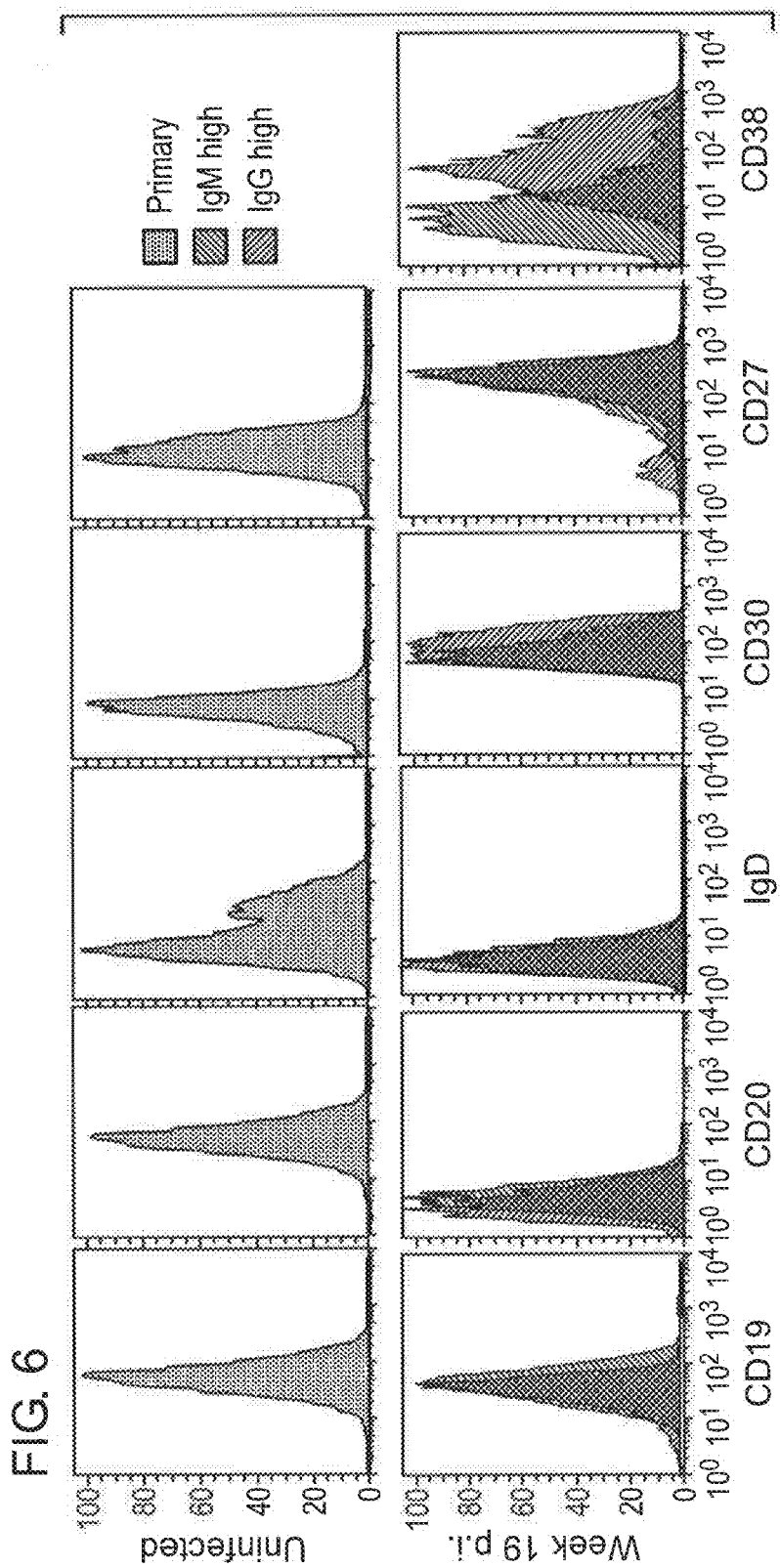
FIG. 6. Immortalized B cells cultured with anti-IgM (Fab')$_2$ and IL4 or IL6 differentiated into early plasma-like stage in vitro. Expression of indicated B-cell surface markers (role of which is summarized in Table 5) was evaluated by flow cytometry (see Example 1) on primary tonsil B cells and immortalized B cells cultured for 19 weeks with either anti-IgM(Fab')$_2$ and IL4, which secrete high IgM levels, or anti-IgM(Fab')$_2$ and IL6, which secrete high IgG levels.
Figure 7:
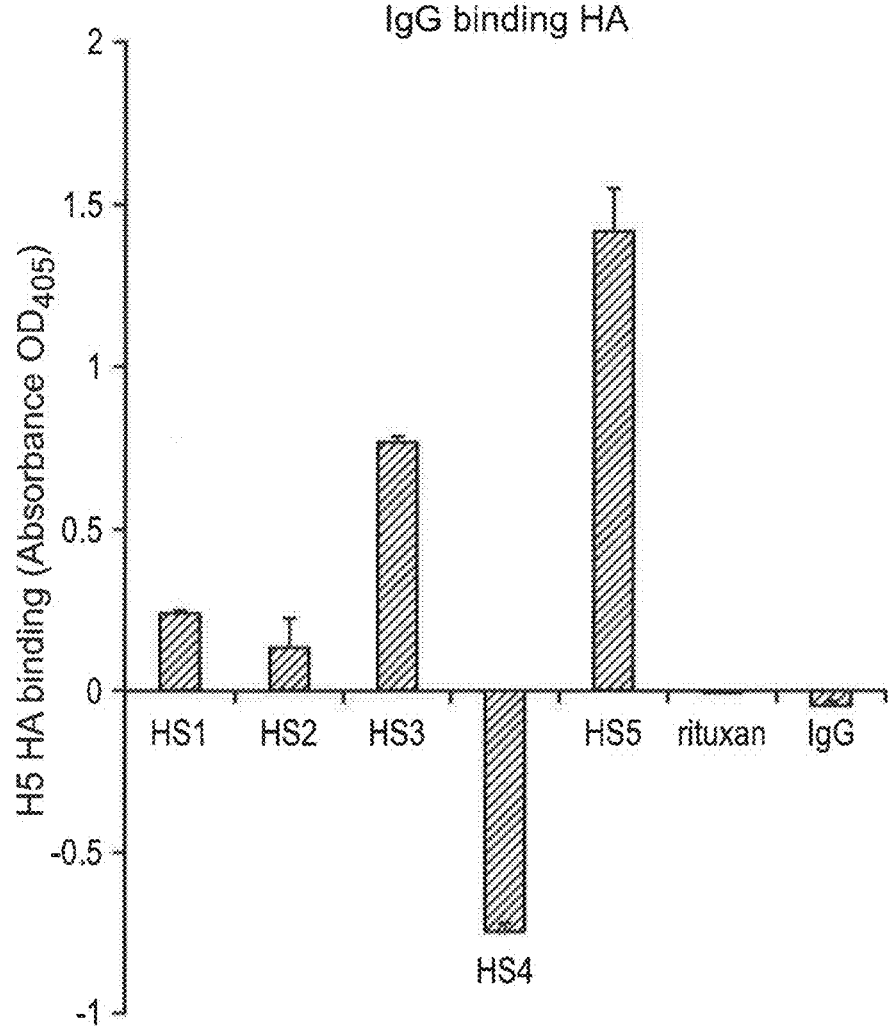
FIG. 7. H5 HA-reactive antibodies are present in human sera from individuals never exposed to H5N1 avian influenza. Rituxan and purified human IgG were diluted to 5 mg/ml, while human sera were diluted 1:1000 in complete RPMI media. Samples or controls 0.1 ml per well were added in triplicate to ELISA plates previously coated with recombinant. H5 HA, or to uncoated control wells. Plates were washed, blocked and probed with anti-human IgG as described in the methods (see Example 1), H5 HA coated plates were prepared by overnight incubation with recombinant protein diluted to 2 µg/ml in binding buffer, 0.1 ml per well. To help control for background non-specific binding, each sample was added to an equal number of control uncoated wells, receiving binding buffer only. Specific IgG binding to H5 HA was calculated by subtracting out the values obtained from background binding to the control uncoated wells; mean absorbance at $OD_{405}$ ±SD of samples and controls are shown.

Treatment with signaling agents induced differentiation of EBV immortalized B cells to early plasma B cell stage. FIGS. 5A and 5B demonstrated that EBV immortalized cells treated with anti-IgM (Fab')$_2$ and IL-6, soluble CD40L alone, or anti-IgM (Fab')$_2$, BAFF and soluble CD40L, preferentially increased IgG secretion, while EBV immortalized cells treated with anti-IgM (Fab')$_2$ and IL-4, or cultured in the absence of cytokines and signaling agents with media only, mainly secreted IgM. Immortalized cells secreted high amounts of immunoglobulin for more than 20 weeks (data not shown). These observations, when taken together, indicated B cell differentiation had occurred. In order to investigate whether immortalized B cells differentiated into plasma-like cells in vitro, EBV immortalized B cells treated with anti-IgM(Fab')$_2$ and IL-4 or IL-6, and secreting primarily IgM or IgG, respectively, were stained for common B cell surface markers (see Table 5 for description) and compared with primary tonsil B cells prior to immortalization. FIG. 6A showed that uninfected primary tonsil B cells (top panel) were mostly naïve or had not undergone immunoglobulin isotype class switching. Primary tonsil B cells stained positive for the pantropic B cell surface markers CD19 and CD20, and a large portion of the cells stained positive for surface immunoglobulin IgD, which is a marker of naïve B cells and mature B cells that have not undergone immunoglobulin isotype class switching or somatic hypermutation. In addition, the primary cells had low level expression of activation markers CD27 and CD30 (FIG. 6A). In contrast, immortalized cells that secreted primarily. IgM or IgG (FIG. 6B, bottom panel) phenotypically resembled early plasma cells; as would be expected, both populations were positive for the pan B cell marker CD19, but they had decreased expression of CD20, which is commonly lost on plasma B-cells, and IgD, which is a marker of naïve and early stage mature B cells, while they had increased expression of the activation markers CD30 and CD27 (FIG. 6B). Immortalized B cells secreting primarily IgG or IgM differed only in the expression of CD38, which is a terminal differentiation marker that was up-regulated on the IgG secreting cells (FIG. 6B). These results confirmed that the immortalized cells treated with signaling agents had indeed differentiated in vitro.

TABLE 5

CELL DETERMINANTS USED TO CHARACTERIZE B-CELL POPULATIONS BY FLOW CYTOMETRY

| Marker | Function | Expression |
| --- | --- | --- |
| CD19 | Assembles with the BCR and modulates the threshold for antigen-specific receptor-dependent stimulation | Pantropic B-cell marker |
| CD20 | B cell surface molecule with a role in B cell differentiation and calcium conductance | Present on all mature B lymphocytes, except plasma cells |
| CD27 | Member of the NGF/TNF receptor superfamily. Soluble CD27 is produced by terminally differentiated cells, e.g. plasma B cells | Marker for human somatically mutated cells. Found on both B and T lymphocytes upon cell activation |
| CD30 | Transmembrane cytokine receptor belonging to the TNF superfamily, has a role in regulating the function, differentiation an/or proliferation of normal lymphoid cells | Present on B lymphocytes after activation |
| CD38 | Functions in cell adhesion, signal transduction and calcium signaling; co-receptor for superantigens of viral or bacterial origin | Appears on bone marrow precursor cells, is also present on terminally differentiated B cells |
| IgD | Immunoglobulin molecule with unknown function | Present on mature naïve B lymphocytes |

Summary: To date, Epstein-Barr virus infection of primary B cells with recombinant EGFP expressing virus has been optimized to achieve an overnight population of fluorescent cells with significantly increased mean fluorescent activity (MFI), for example, 61.9 compared with a background MFI of 15.1, through viral concentration using centrifugal ultrafiltration and "spinfection" technique. Combinations of signaling agents (CD40L alone or in combination with anti-IgM (Fab')$_2$ and BAFF; or anti-IgM (Fab')$_2$ in combination with IL-6, with or without IL4) were identified that consistently increased B-cell activation and differentiation, resulting in preferential secretion of IgG. Other combinations of cytokines inconsistently induced IgG secretion, e.g., IL-9 and IL-13. Flow cytometric staining with antibodies specific for different B cell surface markers, indicated that EBV immortalized B LCLs that had been induced to differentiate in vitro, resembled plasma B cells, and not the early stage primary tonsil B cells from which they derived.

H5N1 hemagglutinin (HA) specific antibodies were found in sera of healthy humans. The creation of plasma cells in vitro, suggested that the process might be exploited for the creation of human monoclonal antibodies specific for targets of interest, like avian influenza. While most people have not been exposed to avian influenza, they have been exposed to other closely related flu strains. Therefore it is reasonable to assume that healthy individuals may have memory B cells that were stimulated by human influenza viruses and which cross-react with the H5 HA protein of avian influenza. To confirm if H5 HA reactive IgG antibodies were present in the blood of healthy individuals, serum was collected from five healthy volunteers that had never been exposed to H5N1 avian influenza (HS 1-5), and then assayed by ELISA for antibodies that bind to commercially obtained recombinant H5 HA. To detect these antibodies in the serum, an ELISA using recombinant H5 HA was created. H5 HA specific binding was calculated by subtracting out background from total binding (described in methods). Four donors (HS 1, 2; 3, 5) had varying amounts of H5 HA-specific IgG in the serum (FIG. 7) with donors HS 3 and 5 having the highest reactivity. In contrast, donor HS 4 had lower reactivity than the negative controls, which consisted of the humanized monoclonal antibody rituximab, specific for CD20 antigen (Rituxan$^R$), or purified total human IgG, indicating that this volunteer lacked H5 HA cross-reactive IgG antibodies (FIG. 7). The detection of H5 HA-specific IgG in the serum of healthy volunteers indicated that the H5 HA reactive IgG antibodies could be detected by ELISA screening. However, the inventors could not use the ELISA to detect IgM antibody binding because background binding was too high to yield meaningful results (data not shown). These results bolstered the hypothesis that IgG antibodies specific for H5 hemagglutinin of avian influenza could be created by exploiting the B cell differentiation pathway in EBV immortalized cells, since they indicated that healthy humans never exposed to H5N1, have the ability to make an antibody response against the virus.

Immortalized B cell repertoires from PBMC secreted IgG antibodies specific for H5 HA. The ELISA results suggested that B cell clones of a given specificity could be isolated from individuals that have not been exposed to H5N1 avian influenza. To test the immortalization and differentiation techniques, PBMC were extracted from Volunteer 5 (HS5=V5). B cells were cultured using two different cytokine/signaling agent combinations: (1) anti-IgM (Fab')$_2$, IL-4 and IL-6 (see PBMC A1 results); (2) anti-IgM (Fab')$_2$, CD40L and BAFF (see PBMC A2 results).

Figure 8:
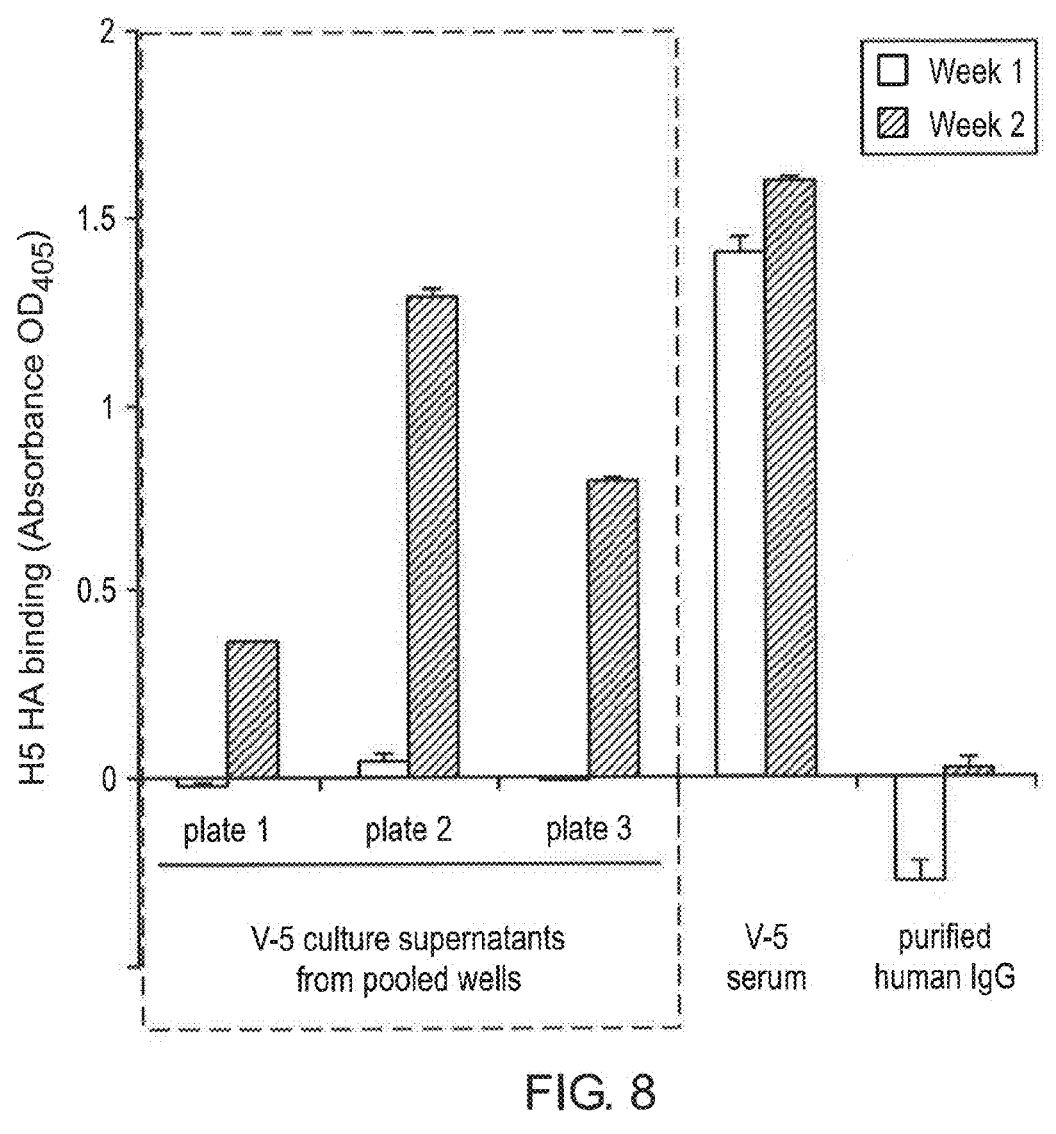
Figure 9:
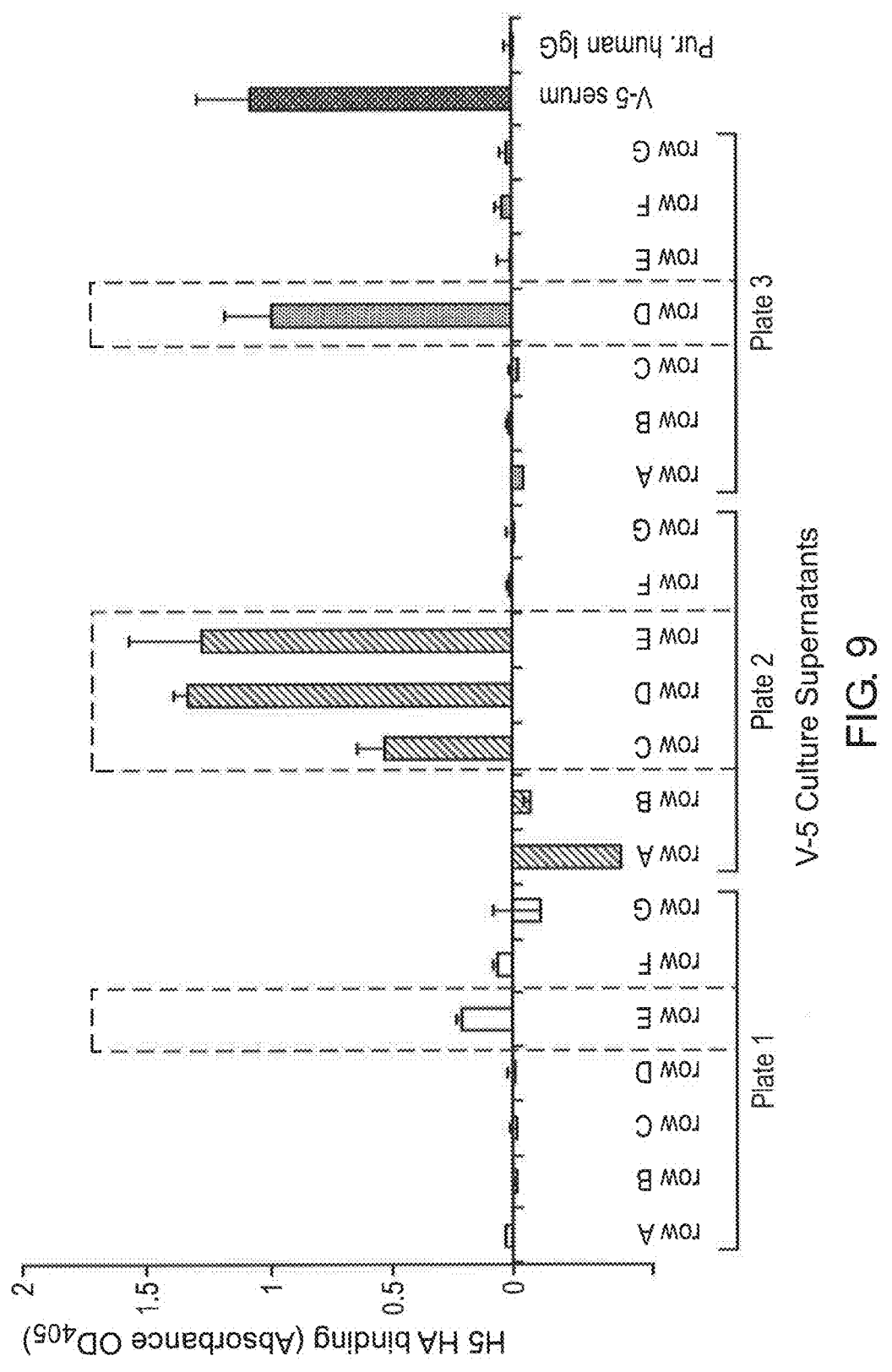
Figure 10:
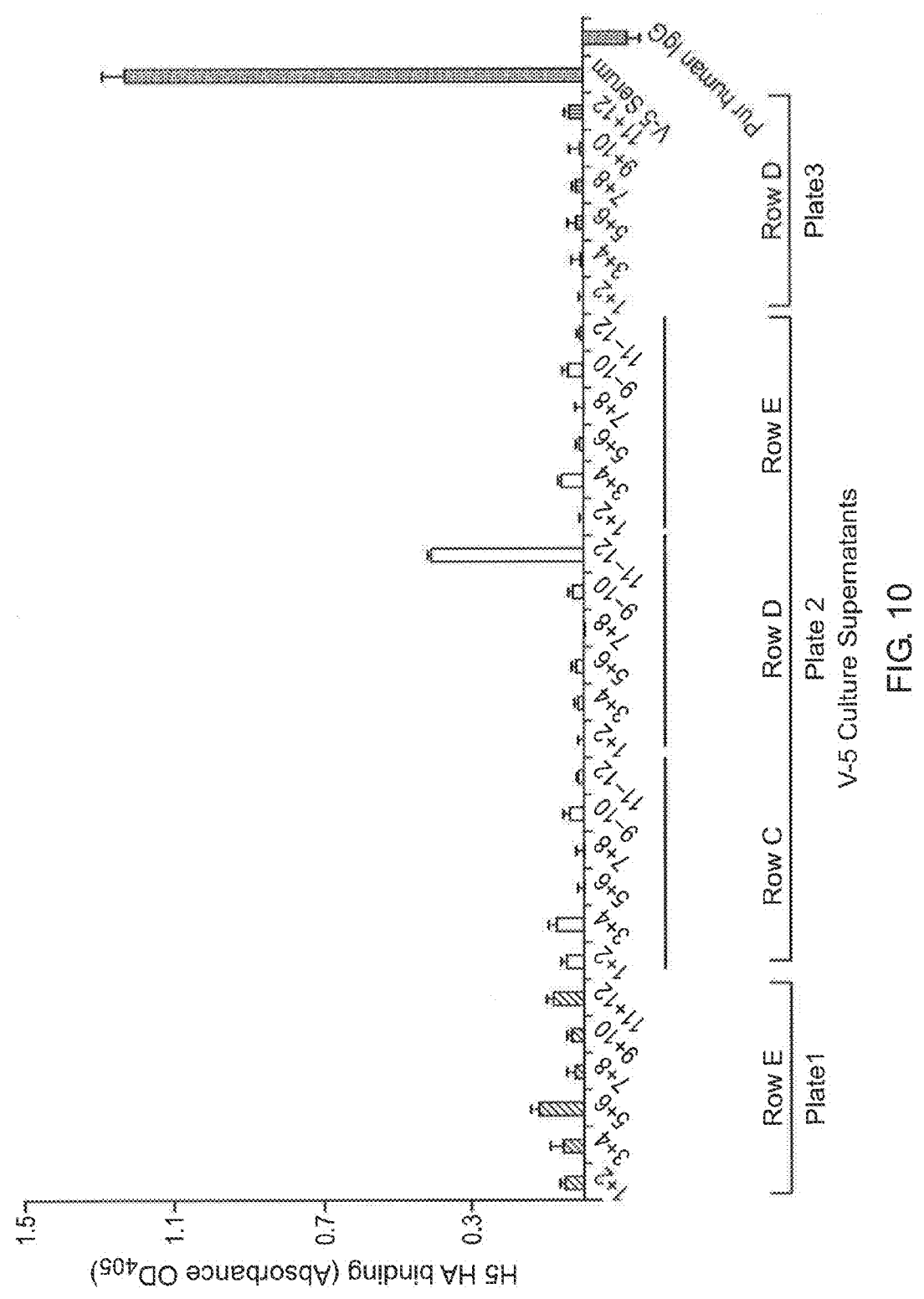
Figure 11:
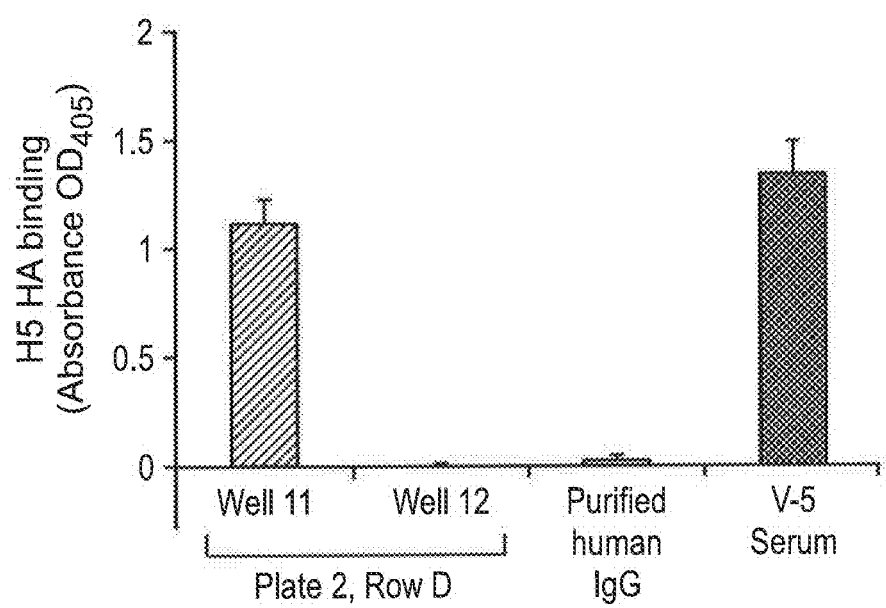
FIG. 11. H5 HA specific IgG production localized to plate 2 well D11, from PBMC A1 sample. Culture supernatants from individual wells on plate 2, D11 and D12, were assayed for H5 HA binding as described in Example 1. Mean absorbance±SD of samples and controls (n=3) are shown. H5 HA reactivity at a level similar to that found in human serum controls was observed in well D11; cells from this well were chosen for subcloning.

PBMC A1: B cells were isolated from PBMC of volunteer HS 5 and immortalized with EBV as described in methods and as summarized in Table 6. Cells were treated with anti-IgM(Fab')$_2$, IL-4 and IL-6 to induce B cell differentiation and immunoglobulin production, and were then plated in three 96-well plates. After one week, culture supernatants from all wells on each plate were collected and pooled; there was little or no H5 HA-specific IgG binding detected in the pooled supernatant samples from any of the three plates, compared with the human serum control (FIG. 8). However, after two weeks of treatment, H5 HA-specific IgG was detected in pooled culture supernatants from all three plates of B cells (FIG. 8, Plate 1, Plate 2 and Plate 3). To determine the location of the reactive B cell clones secreting the H5 HA reactive IgG, all wells in each row on reactive plates were pooled and assayed. Several rows from each of the three plates contained H5 HA-reactive B cells (plate 1, row E; plate 2, rows C, D and E; and plate 3, row D) (FIG. 9). FIG. 10 indicated that the most reactive B cells were located on plate 2, in pooled supernatant from adjacent wells 11 and 12 on row D. With further analysis of the supernatants, the reactive B cells were found to be on plate 2, in row D, well 11 (FIG. 11); these cells were secreting H5 HA-reactive IgG at a level similar to the positive serum control (FIG. 11). This well was subcloned; however, the H5 HA-reactive B cells died before they could be isolated after 12 weeks of culture. A summary of the clonal isolation scheme and findings are summarized in FIG. 12 and Table 6.

TABLE 6

Summary of data on screening and production of immortalized human B cells secreting antibodies reactive with H5 HA

| Sample | Date received | # of B cells (×10⁷) | # of plates | # of sub-cloned wells | # of possible clones | Treatment for inducing B cell differentiation | H5 HA specific IgG | Status |
|---|---|---|---|---|---|---|---|---|
| PBMC A1 | Jan. 16, 2007 | 0.2 | 3 | 1 | 0 | Anti-IgM (Fab')2, IL-4, IL6 | Positive originally | Subcloned 1 well: PA1-2D11 lost reactivity |
| PBMC B | Feb. 16, 2007 | 0.2 | 3 | 0 | 0 | Anti-IgM (Fab')2, IL-4, IL6 | Negative | Screening discontinued: negative at week 3 |
| PBMC A2 | Mar. 14, 2007 | 0.6 | 6 | 3 | 0 | Anti-IgM (Fab')2, CD40L, BAFF | Positive originally | Subcloned 3 wells; lost reactivity |
| PBMC C | Sep. 22, 2007 | 3 | 10 | 1 | 1 | Anti-IgM (Fab')2, CD40L, BAFF | Positive originally | Subcloned 1 well (PC-9F9) lost reactivity |
| PBMC A3 | Jan. 28, 2008 | 4 | 10 | 2 | 2 | Anti-IgM (Fab')2, CD40L, BAFF | Positive originally | Subcloned 2 wells: (PA3-4F5, PA3-3F2) lost reactivity |
| TNSL A | Jan. 22, 2007 | 20 | 10 | 2 | 0 | Anti-IgM (Fab')2, IL-4, IL6 | Positive lost | Screening discontinued: week 3 fungal contamination |
| TNSL B | Mar. 26, 2007 | 20 | 10 | 0 | 0 | Anti-IgM (Fab')2, CD40L, BAFF | Negative | Screening discontinued: negative at week 4 |
| TNSL C | Apr. 16, 2007 | 22 | 10 | 0 | 0 | Anti-IgM (Fab')2, CD40L, BAFF | Negative | Screening discontinued: negative at week 3 |
| TNSL D | Apr. 23, 2007 | 15 | 10 | 1 | 0 | Anti-IgM (Fab')2, CD40L, BAFF | Positive originally | Subcloned 1 well; lost reactivity |
| TNSL E | May 14, 2007 | 4 | 4 | 1 | 2 | Anti-IgM (Fab')2, CD40L, BAFF | Positive | Subcloned 1 well, 2 clones isolated: (TE-3A10-E3A5, TE-3A10-C7F6) |
| TNSL F | Sep. 24, 2007 | 20 | 10 | 0 | 0 | Anti-IgM (Fab')2, CD40L, BAFF | Negative | Screening discontinued: negative at week 3 |
| TNSL G | Nov. 19, 2007 | 13 | 10 | 0 | 0 | Anti-IgM (Fab')2, CD40L, BAFF | Negative | Screening discontinued: negative at week 3 |
| TNSL H | Nov. 19, 2007 | 12.5 | 10 | 0 | 0 | Anti-IgM (Fab')2, CD40L, BAFF | Negative | Screening discontinued: negative at week 3 |
| TNSL I | Dec. 10, 2007 | 10 | 10 | 0 | 0 | Anti-IgM (Fab')2, CD40L, BAFF | Negative | Screening discontinued: negative at week 4 |

TABLE 6-continued

Summary of data on screening and production of immortalized human B cells secreting antibodies reactive with H5 HA

| Sample | Date received | # of B cells (×10⁷) | # of plates | # of sub-cloned wells | # of possible clones | Treatment for inducing B cell differentiation | H5 HA specific IgG | Status |
|---|---|---|---|---|---|---|---|---|
| TNSL J | Jan. 07, 2008 | 11 | 10 | 2 | 2 | Anti-IgM (Fab')2, CD40L, BAFF | Positive | Subcloned 2 wells: (TJ-1G6, TJ-1C8); both at tertiary subcloning stage |
| TNSL K | Jan. 14, 2008 | 13.5 | 10 | 0 | 0 | Anti-IgM (Fab')2, CD40L, BAFF | Negative | Screening discontinued: negative at week 3 |
| TNSL L | Feb. 01, 2008 | 8 | 10 | 0 | 0 | Anti-IgM (Fab')2, CD40L, BAFF | Negative | Screening discontinued: negative at week 3 |
| TNSL M | Feb. 05, 2008 | 17 | 10 | 2 | 2 | Anti-IgM (Fab')2, CD40L, BAFF | Positive originally | Subcloned 2 wells: (TM-7C2, TM-7F8) reactivity lost |
| TNSL N | Feb. 05, 2008 | 5 | 10 | 1 | 1 | Anti-IgM (Fab')2, CD40L, BAFF | Positive | Subcloned 1 well: (TN-6G7); isolated clone TN-6G7-7F8-2G7 |
| TNSL O | Feb. 06, 2008 | 23 | 10 | 0 | 0 | Anti-IgM (Fab')2, CD40L, BAFF | Negative | Screening discontinued: negative at week 2 |
| TNSL P | Mar. 11, 2008 | 27 | 10 | 1 | 1 | Anti-IgM (Fab')2, CD40L, BAFF | Positive | Subcloned 1 well: (TP-2C2) secondary subcloning stage |
| TNSL Q | Mar. 18, 2008 | 18.8 | 10 | 0 | 0 | Anti-IgM (Fab')2, CD40L, BAFF | Negative | Screening discontinued: negative at week 2 |
| TNSL R | Mar. 31, 2008 | 21 | 10 | 1 | 1 | Anti-IgM (Fab')2, CD40L, BAFF | Positive originally | Subcloned 1 well; (TR-8E9) lost reactivity |
| TNSL S | Mar. 31, 2008 | 17 | 10 | 2 | 2 | Anti-IgM (Fab')2, CD40L, BAFF | Positive originally | Subcloned 2 wells (TS-8G1, TS-1A8); lost reactivity |
| TNSL V | May 2, 2008 | 8 | 10 | 0 | 0 | Anti-IgM (Fab')2, CD40L, BAFF | Negative | Bead assay used; Screening discontinued: negative at week 3 |
| TNSL W | May 14, 2008 | 14 | 10 | 0 | 0 | Anti-IgM (Fab')2, CD40L, BAFF | Negative | Screening discontinued: negative at week 2 |
| TNSL X | May 19, 2008 | 11 | 10 | 0 | 0 | Anti-IgM (Fab')2, CD40L, BAFF | Negative | Screening discontinued: negative at week 2 |
| TNSL Z | Jun. 2, 2008 | 12.5 | 10 | 3 | 3 | Anti-IgM (Fab')2, CD40L, BAFF | Positive | Subcloned 3 wells: (TZ-4F12, TZ-10G1, TZ-10G9) |
| TNSL α | Jun. 6, 2008 | 7 | 10 | 1 | 1 | Anti-IgM (Fab')2, CD40L, BAFF | Positive | Subcloned 1 well: (Ta-6G8) |
| TNSL β | Jun. 11, 2008 | 11 | 10 | 0 | 0 | Anti-IgM (Fab')2, CD40L, BAFF | Negative | Screening discontinued: negative at week 2 |
| TNSL γ | Jun. 18, 2008 | 12 | 10 | 0 | 0 | Anti-IgM (Fab')2, CD40L, BAFF | Negative | Screening discontinued: negative at week 2 |

PBMC A2: B cells were isolated a second time from PBMC of Volunteer HS 5 and infected with EBV as described in the methods and as summarized in Table 6. Cells were then induced to differentiate by treatment with anti-IgM (Fab')$_2$, CD40L, and BAFF as described in the methods. (This combination of agents improved levels of IgG antibody production over the combination used on PBMC A1 and B.) Culture supernatants from all wells on each of six 96-well plates were collected weekly after infection, pooled and assayed for H5 HA reactive IgG antibodies. After 4 weeks, three wells on different plates (Plate 4 G8, Plate 5 E1 and Plate 6 C2) contained H5 HA reactive IgG. The three reactive wells were subcloned, and possible clones were subsequently identified from two of the wells as outlined in FIG. 13, and summarized in Table 6. H5 HA-reactive B cells died after 10 weeks in culture prior to their isolation.

Figure 14:
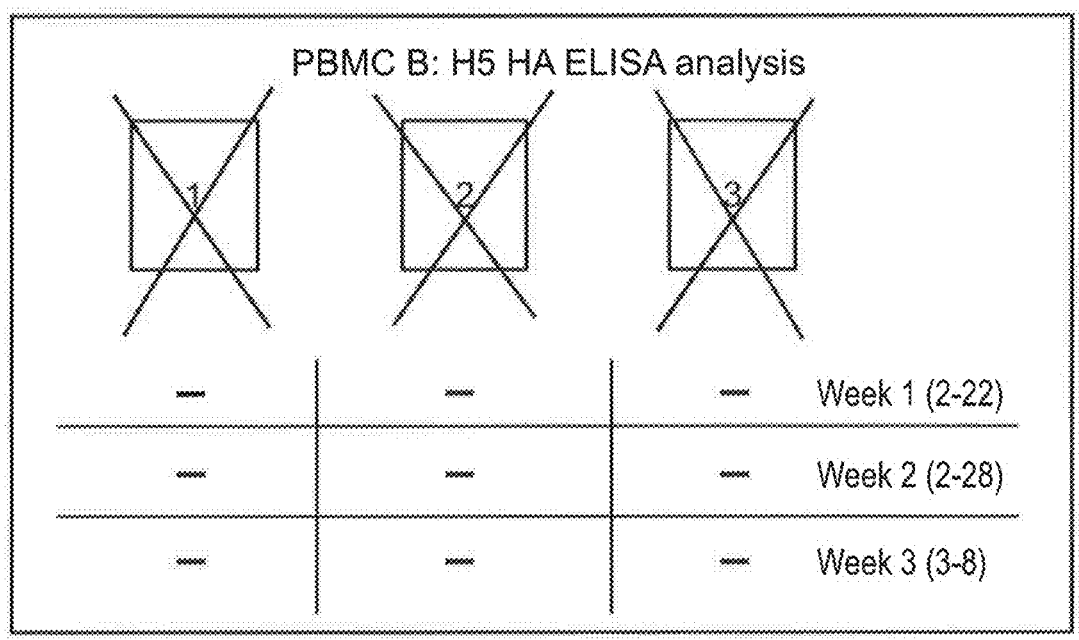
FIG. 14. Lack of H5 HA specific IgG in culture supernatants derived from immortalized B cells from PBMC B sample. EBV-immortalized B cells from PBMC B were stimulated to produce IgG with IL-4, IL-6, BAFF and anti-human IgM (Fab')$_2$ (see Example 1), and cultured in three 96-well plates (<$10^4$ cells per well). H5 HA binding was determined as described in Example 1. Culture supernatants from all wells on each plate (150 µl per well) were collected, and 50 µl per well were pooled and assayed for H5 HA binding. This was repeated for three consecutive weeks without significant detection of H5 HA reactivity, at which point screening was discontinued.
Figure 20:
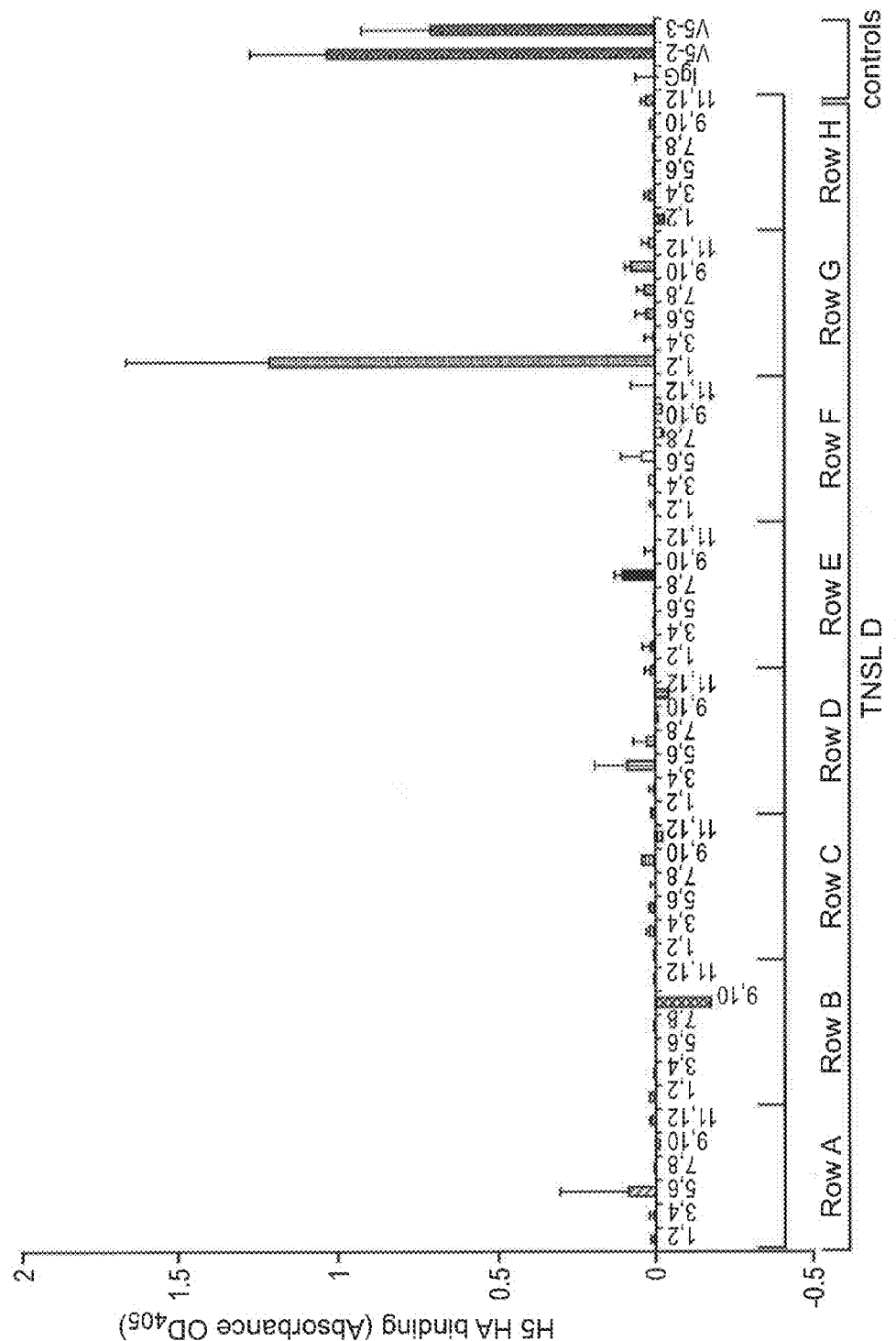
FIG. 20. H5 HA specific. IgG production identified in culture supernatant from paired adjacent wells on row G of Plate 10, from TNSL sample. Culture supernatants from EBV immortalized B-cells from TNSL D sample (150 µl per well) were collected from each well after 3 weeks of culture, and 50 µl per sample from paired adjacent wells on reactive plates 1, 8, 9, and 10 were pooled and assayed for H5 HA binding as described in Example 1. Row G, wells 3 and 4 had the highest H5 HA binding, similar to human serum controls, Mean absorbance levels at $OD_{405} \pm SD$ of samples and controls (n=3) are shown.
Figure 21:
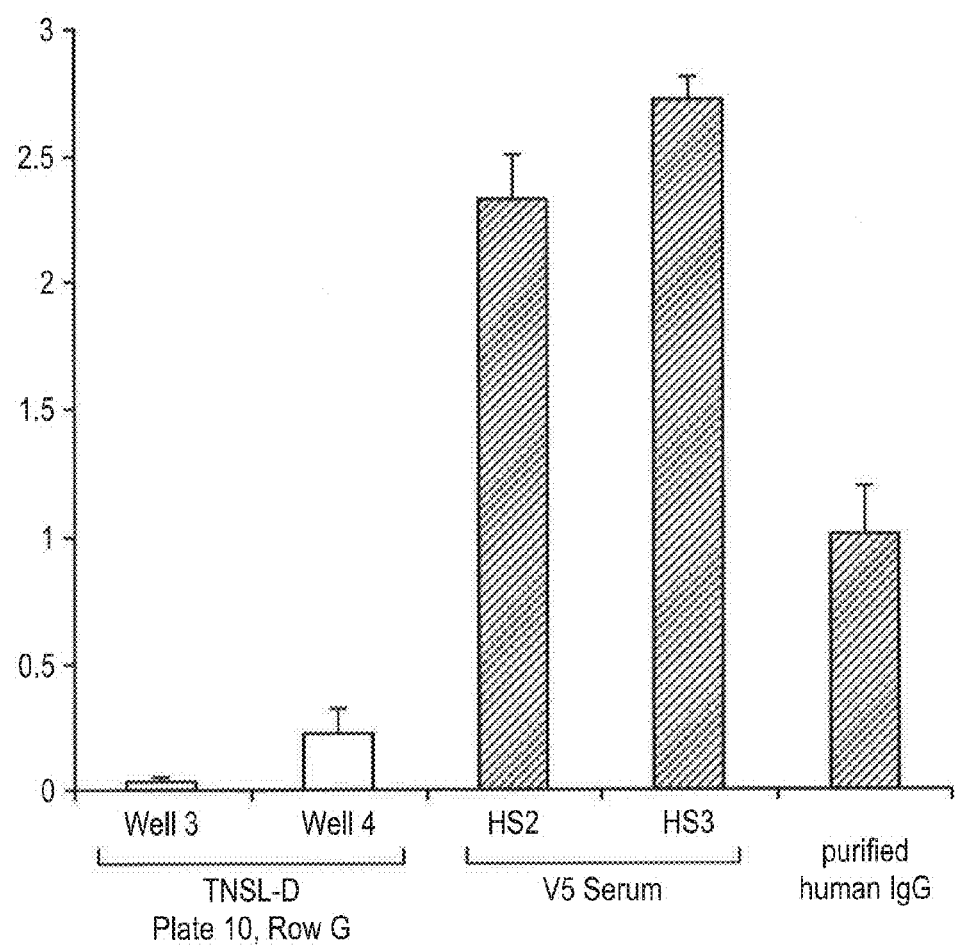
FIG. 21. Identification of H5 HA reactive IgG in well G4 on Plate 10, from TNSL D sample. Culture supernatants from EBV immortalized B-cells from TNSL D sample (50 µl per well) on plate 10, Row G, wells 3 and 4 were tested for H5 HA binding as described in Example 1. Row G, well 4 (green) had the highest H5 HA binding, and cells from this well were selected for continued sub-cloning. Mean absorbance levels at $OD_{405} \pm SD$ of samples and controls (n=3) are shown.
Figure 23:
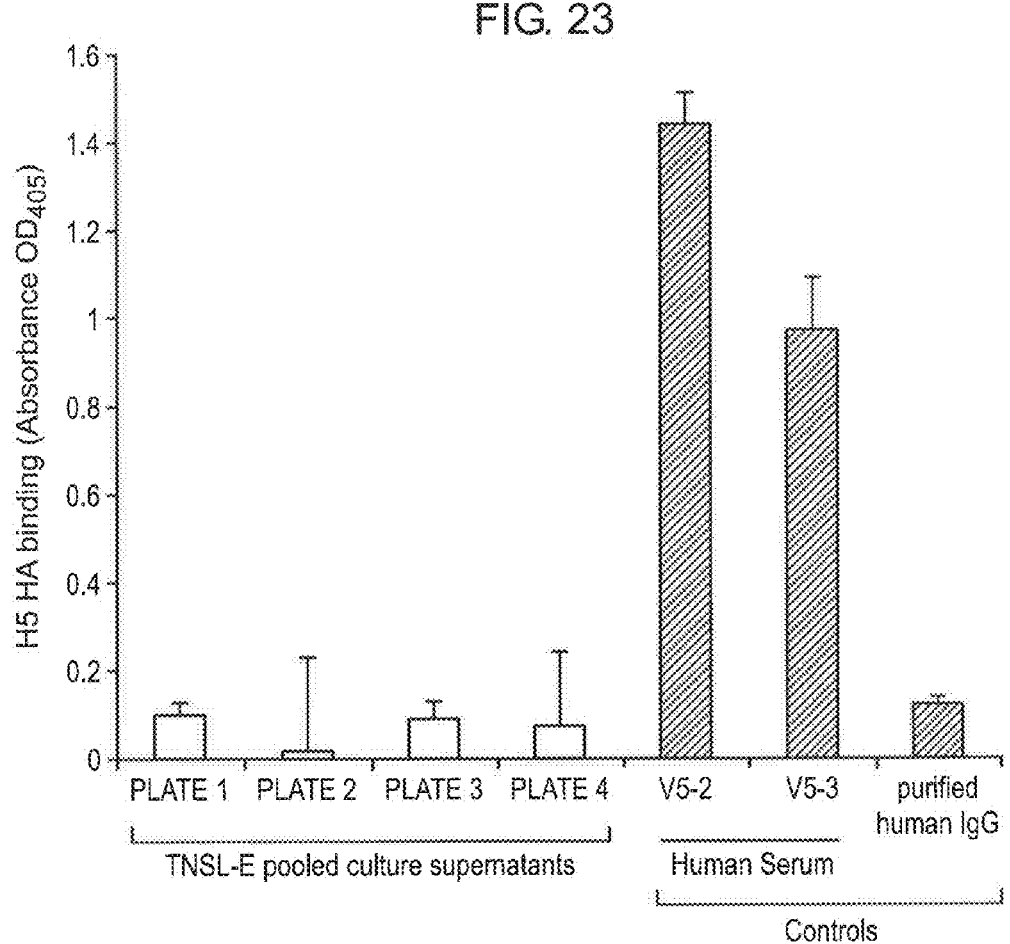
FIG. 23. Immortalized tonsil B cells produced very little or no H5 HA reactive IgG after one week of culture, from TNSL E sample. EBV-immortalized tonsil B cells from TNSL E sample were stimulated to produce IgG with anti-human IgM (Fab')$_2$, CD40L and BAFF (see Example 1), and were cultured in four 96-well plates at $10^5$ cells per well. One week later, culture supernatants from all wells on each plate (150 µl per well) were collected and 50 µl of each was pooled, and then tested for H5 HA binding as described in Example 1. Significant H5 HA specific binding was not detected on any plate above negative control purified human IgG. Mean absorbance level at $OD_{405} \pm SD$ of samples and controls (n=3) are shown.
Figure 25:
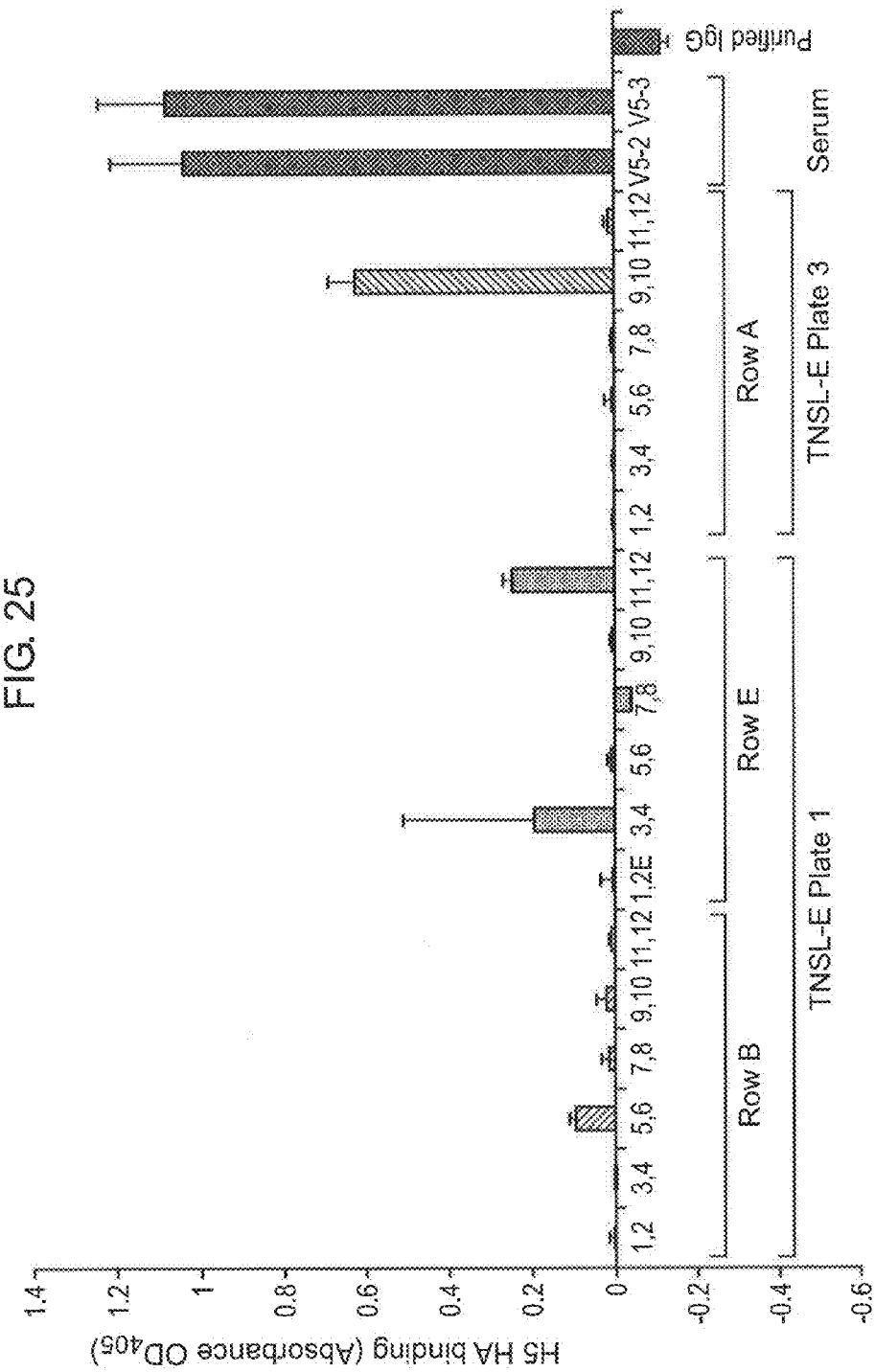
FIG. 25. H5 HA specific IgG production identified in culture supernatant from pooled adjacent wells on Plates 3, 5, and 6, from TNSL E sample. Week 3 TNSL-E culture supernatants from pairs of adjacent wells in plate 1, rows B and E, and plate 3, row A were pooled and assayed for H5 HA binding activity as described in Example 1. Plate 1 row B, wells 5 and 6; Plate 1 row E, wells 11 and 12, 3 and 4; and Plate 3, row A, wells 9 and 10 exhibited H5 HA reactive IgG production and were selected for individual analysis. Mean absorbance level at $OD_{405} \pm SD$ of samples and controls (n=3) are shown.
Figure 26:
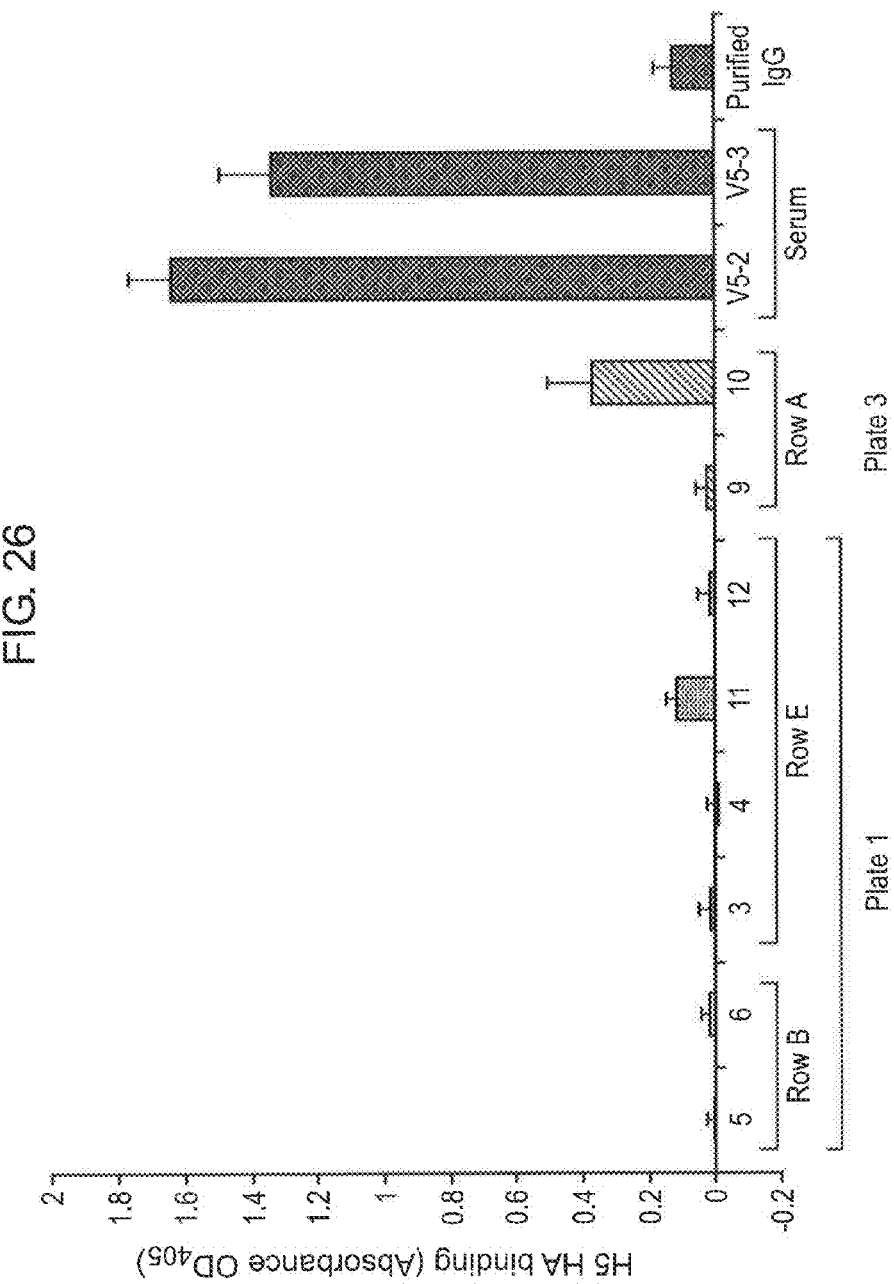
FIG. 26. Identification of H5 HA reactive IgG production in culture supernatant from individual wells on reactive plates, from TNSL E sample. Week 4 culture supernatants from individual wells B5 and B6, E3 and E4, E11 and E12 on Plate 1, and wells A9 and A10 on Plate 3, were assayed for H5 HA binding as described in Example 1. Strong H5 HA binding was observed from well A10 on plate 3, which and was selected for subcloning. Mean absorbance level at $OD_{405} \pm SD$ of samples and controls (n=3) are shown.
Figure 27:
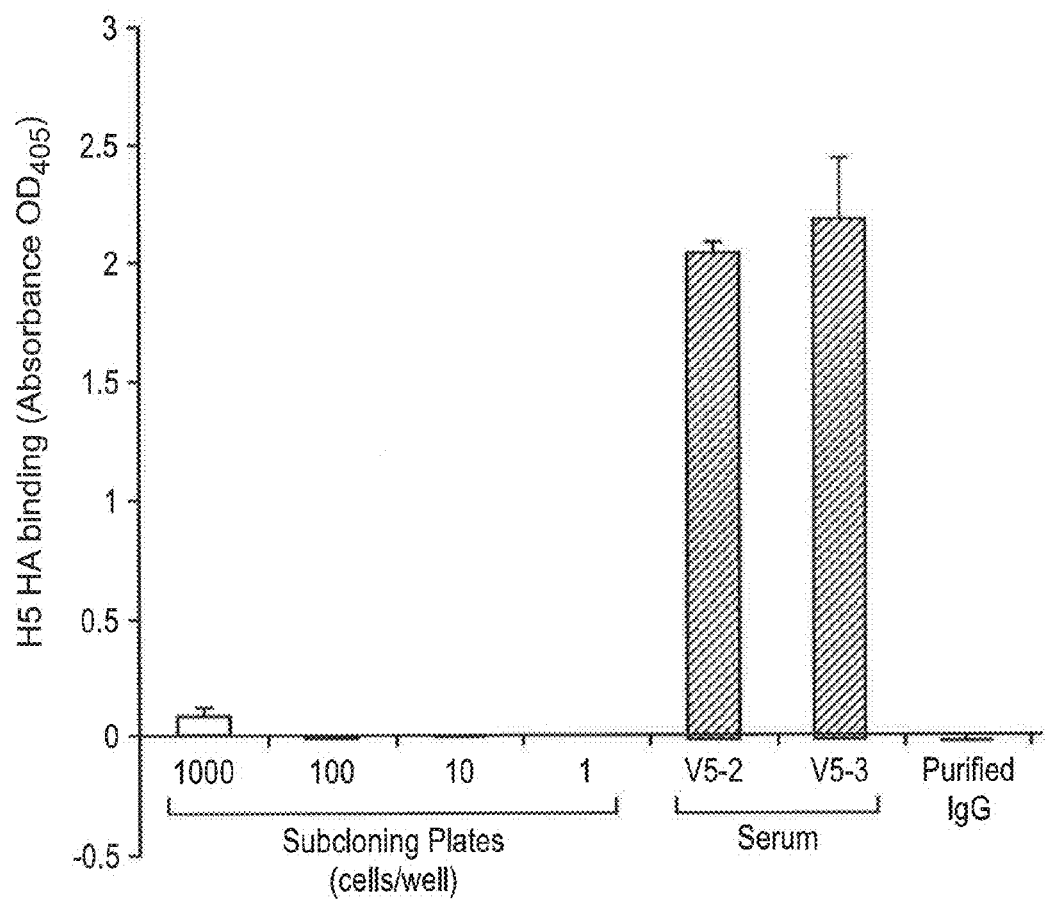
FIG. 27. H5 HA specific IgG production was identified in culture supernatant two weeks after subcloning on plates containing 1000 cells per well, from TNSL E sample. Two weeks after subcloning immortalized B cells by limiting dilution analysis, culture supernatants from each of the plates were pooled and assayed for H5 HA binding as described in Example 1. H5 HA binding was only observed in supernatants from the 1000 cells/well plate. Further subcloning analysis is ongoing. Mean absorbance level at $OD_{405} \pm SD$ of samples and controls (n=3) are shown.
Figure 28:
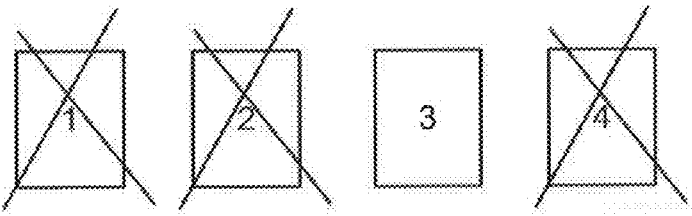
FIG. 28. Subcloning strategy for isolating H5 HA reactive B cells from TNSL E sample. EBV-immortalized tonsil B cells from TNSL E sample were stimulated to produce IgG with anti-human IgM(Fab')$_2$, CD40L and BAFF (see Example 1), and were cultured in four 96-well plates at $10^5$ cells per well. Culture supernatants from all wells on each plate (150 µl per well) were collected after one week, and 50 µl from each well was pooled and assayed by ELISA as described in Example 1, but significant binding was not detected above controls. After two weeks, 150 µl of supernatant was collected from all wells, then 50 µl from each well was pooled from individual rows on plates 1 and 3, and from all wells on plates 2 and 4, and were simultaneously assayed for H5 HA binding. Plate 1 rows B and E and Plate 3 row A were reactive after two weeks. The following week, supernatants from paired adjacent wells in the reactive rows were pooled and analyzed for H5 HA reactivity. B cells from reactive well A10 on Plate 3 were subsequently subcloned by limiting dilution analysis into 96-well plates containing 1, 10, 100, or 1000 cells per well. Starting one week later, the culture supernatants from each well were collected weekly and pooled from these plates; reactivity was seen in the 1000 cell per well plate, and isolation of H5 HA reactive IgG producing single cell clones is ongoing.
Figure 29:
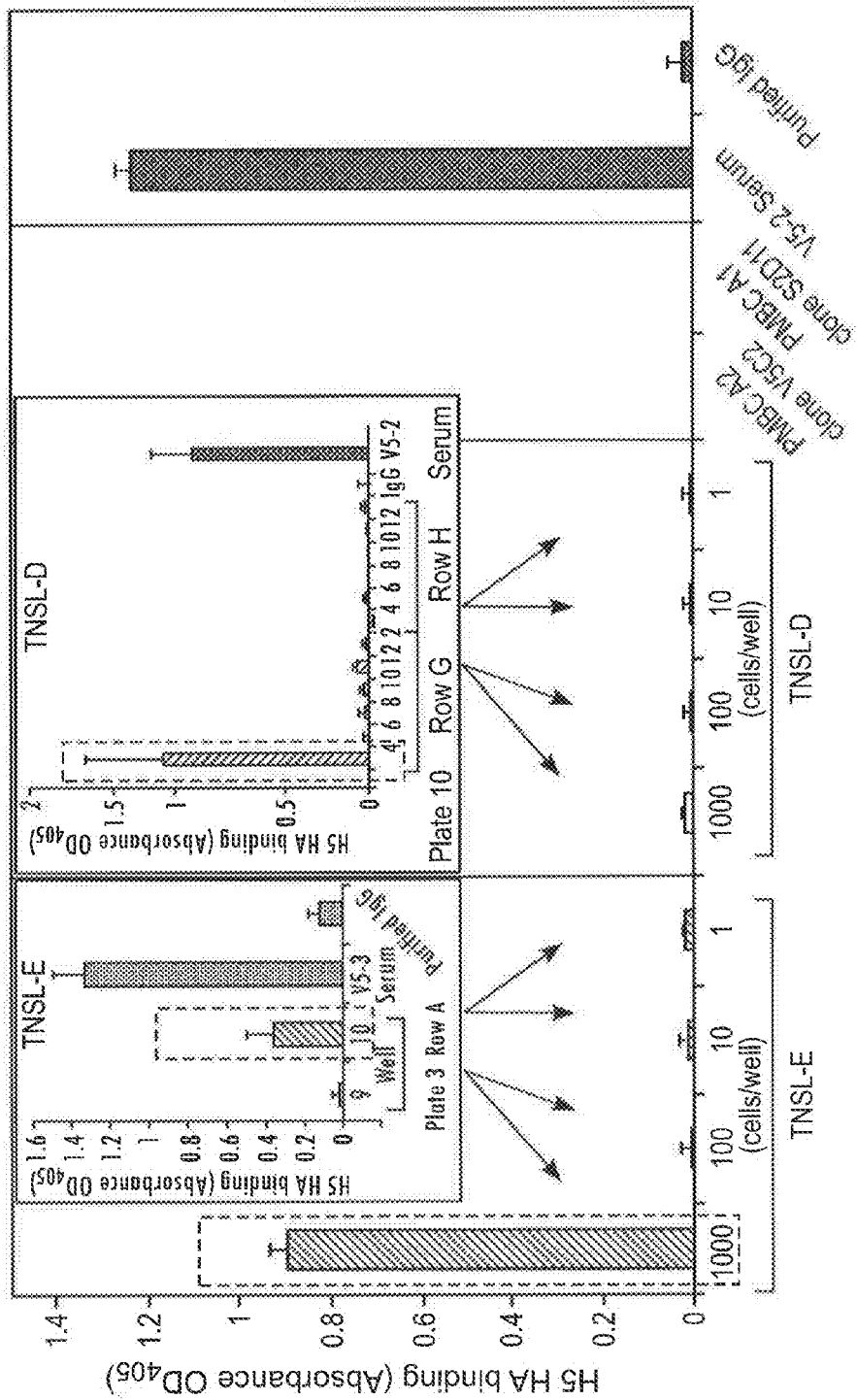
FIG. 29 Identification of H5 HA reactive IgG in pooled wells from TNSL-E subclones but loss of activity in TNSL-D, PBMC-A1 and A2 subclones. H5 HA reactive IgG was previously identified in TNSL D repertoire on plate 10 well G4, and in TNSL E repertoire on plate 3 well A10 (shaded insets). The cells in these wells were subcloned into 96-well plates at 1000, 100, 10 or 1 cell per well. 3 weeks after subcloning, culture supernatants from each plate were pooled and assayed for H5 HA binding by ELISA as described in Example 1. Culture supernatant from clones previously isolated from PBMC-A1 and A2 repertoires were simultaneously tested. Controls consisted of human serum from volunteer (V5), previously found to be H5 HA reactive (diluted 1:1000), and nonreactive purified human IgG (500 ng, Sigma). Mean absorbance±SD of samples and controls (n=3) are shown.
Figure 30A:
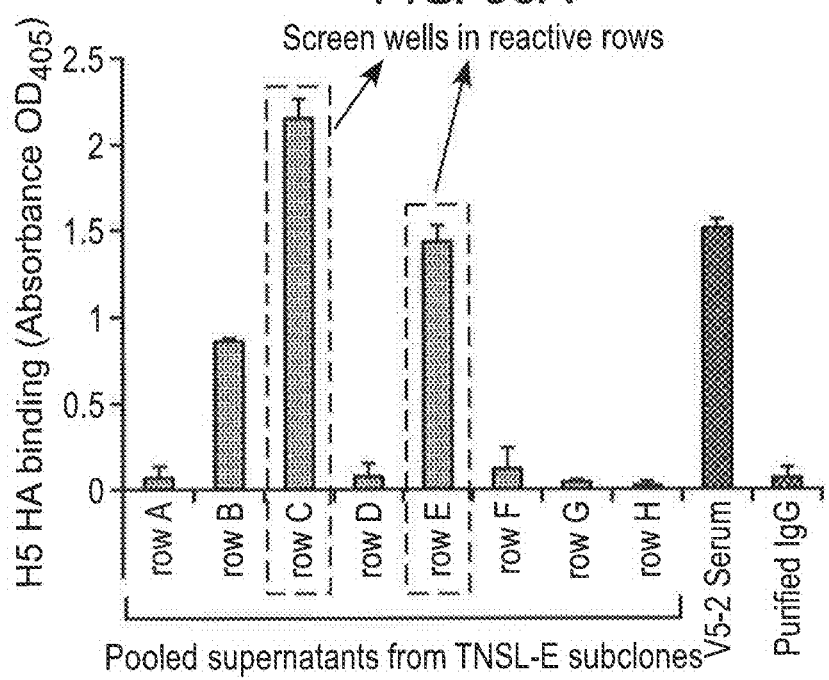
FIGS. 30A-C Isolation of H5 HA reactive clones from TNSL E repertoire.
Figure 30B:
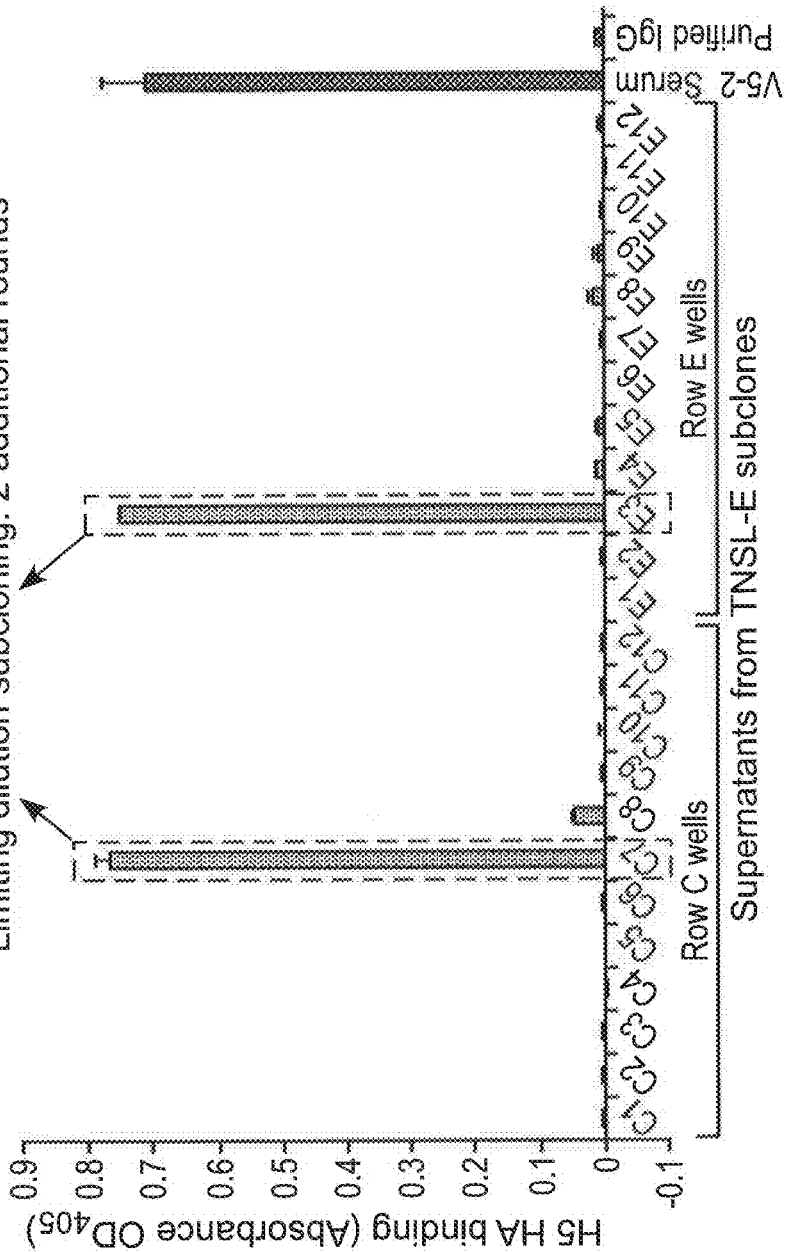
Figure 30C:
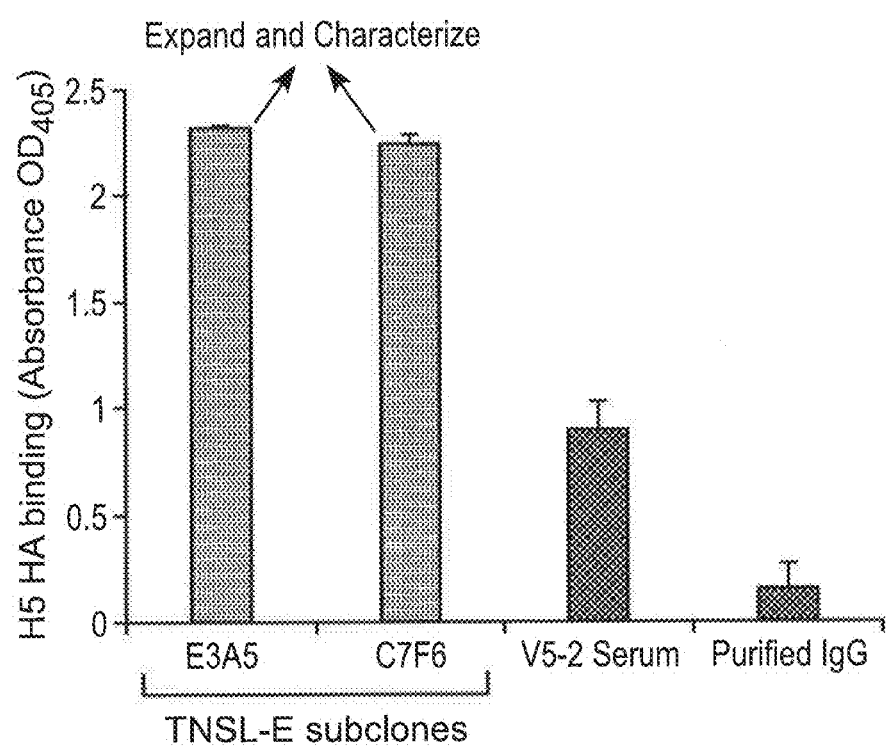

PBMC B: B cells were isolated from peripheral blood of Volunteer 6 and immortalized with EBV as described in the methods, and as summarized in Table 6. The immortalized cells were treated with anti-IgM (Fab')$_2$, IL-4 and IL-6 and plated into three 96-well plates. After three weeks of cytokine treatments no H5 HA-specific IgG antibodies were detected in the supernatant or serum of Volunteer 6 (FIG. 14). Analysis of this sample was discontinued due to the repeated lack of H5 HA reactivity in either the serum or the supernatant of immortalized cells.

Figure 31:
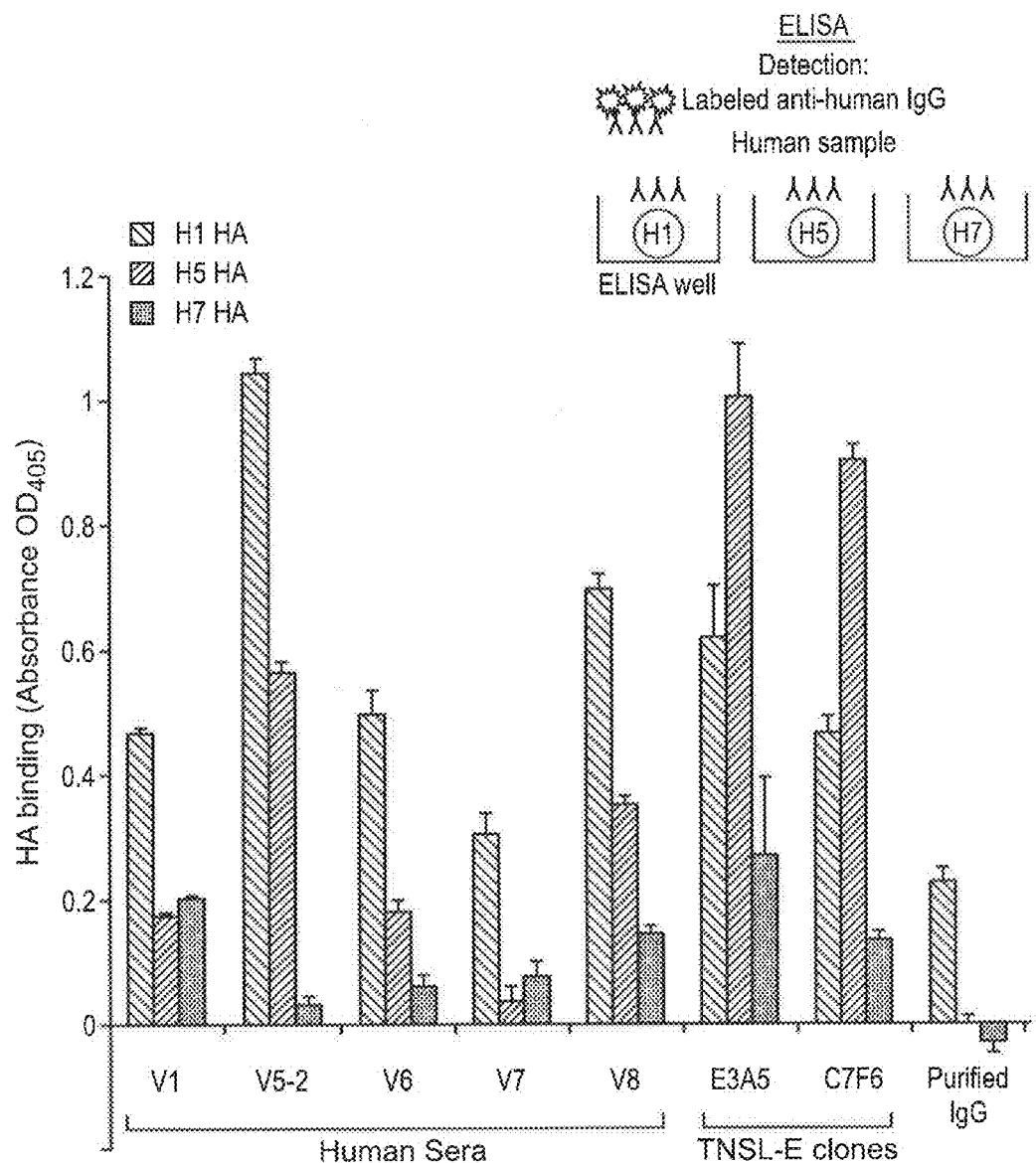
FIG. 31 TNSL-e clones E3A5 and C7F6 secrete IgG that binds H5 HA with higher affinity than H1 or H7 HA, while human sera from healthy volunteers bind H1 HA with higher affinity. Sera from 5 healthy adult volunteers (diluted 1:1000), and culture supernatants from TNSL-E clones E3A5 and C7F6, were assayed for IgG binding to H1, H5 and H7 HA by ELISA, as described in Example 1. H1 strain is currently responsible for most human influenza virus infections and is targeted by flu vaccines, while H5 and H7 are avian influenza virus strains. Mean absorbance±SD of samples and controls (n=3) are shown.

Summary: Peripheral blood derived B cells from two volunteers were isolated and immortalized with EBV, then induced to differentiate with either anti-IgM (Fab')$_2$, IL-4 and IL-6; or anti-IgM (Fab')$_2$, CD40L, and BAFF. B cells that secrete H5 HA reactive IgG antibodies were isolated from one of the volunteers, on two separate occasions (PBMC A1 and A2), and induced to differentiate using either method. The Different cytokine combinations were tested with the aim of optimizing the efficiency of inducing immunoglobulin isotype class switching, in order to obtain more H5 HA reactive IgG secreting B cell cells in these samples. While this change yielded more reactive cells from PBMC A2 repertoire than from PBMC A1 repertoire, the difference was not significant. The samples were isolated from the same volunteer a little over a month apart. In contrast, B cells isolated from Volunteer 6 did not yield any reactive clones. These results are summarized in Table 6.

Immortalized B cell repertoires from tonsils secreted IgG antibodies specific for H5 HA. While immortalized B cells that produced H5 HA-reactive IgG were successfully isolated from peripheral blood (PBMC), in order to prove that they were inducing differentiation of naïve B cells, a naïve population of cells for creation of the repertoire was obtained from tonsil B cells from otherwise healthy children undergoing tonsillectomy for medical reasons. As demonstrated in FIG. 6A, tonsil B cells are mainly naïve or have not undergone immunoglobulin isotype class switching. The inventors repeated the experiments performed on the peripheral blood samples on 26 tonsil samples (summarized in Table 6). The treatment for inducing differentiation was changed from anti-IgM (Fab')$_2$, IL-4 and IL-6 after the first tonsil (TNSL A) to anti-IgM (Fab')$_2$, CD40L and BAFF for all of the rest (TNSL B-E), because the second combination selectively increased IgG secretion (data not shown). Representative results from several of the tonsil repertoires are shown in FIG. 15-32.

TNSL A: B cells were isolated from tonsil, immortalized with EBV, treated with anti-IgM (Fab')$_2$, IL-4 and IL-6, and then cultured in ten 96-well plates, as described in the methods and as summarized in Table 6. After one week, no H5HA reactive IgG was detected. However, after two weeks of cytokine treatments, H5 HA binding activity was detected on two (plates 6 and 9) out of ten plates (FIG. 15). After three weeks, two rows (C and F on plate 9) were identified as having cross-reactive IgG; unfortunately, this sample was lost due to fungal contamination and analysis was discontinued (FIG. 15). Despite the loss, this sample demonstrated that obtaining IgG reactivity to the antigen of interest was possible from tonsil B cells.

TNSL B: B cells were isolated from tonsil, immortalized with EBV, treated with anti-IgM (Fab')$_2$, CD40L and BAFF, to increase IgG antibody production and plated in ten 96-well plates, as described in methods and as summarized in Table 6. Low levels of H5 HA reactive IgG was detected on Plate 3 row D after two weeks of analysis, but no reactivity was recovered subsequently; therefore, sample analysis was discontinued (FIG. 16).

TNSL C: B cells were isolated from tonsil, immortalized with EBV, stimulated with anti-IgM (Fab')$_2$, CD40L and BAFF and plated in ten 96-well plates, as described in the methods and as summarized in Table 6. After the first week, H5 HA reactive IgG was detected on plates 7, 8, 9 and 10 (FIG. 17) at very low levels. However, after two weeks no H5 HA reactive IgG antibodies were detected on any of the plates and no reactivity was subsequently recovered. Therefore, sample analysis was discontinued after four weeks (FIG. 17).

TNSL D: B cells were isolated from tonsil, immortalized with EBV, stimulated with anti-IgM (Fab')$_2$, CD40L and BAFF and plated in ten 96-well plates, as described in the methods and as summarized in Table 6. After one week, there was no detectable H5 HA reactive IgG in the culture supernatant (FIG. 18). However, after 2 weeks, H5 HA reactive IgG was identified on plates 1, 8, 9 and 10 (FIG. 19). Plate 10 exhibited robust H5 HA reactivity, similar to human serum from volunteer HS 5; therefore, culture supernatants from individual wells were analyzed immediately. The other plates lost binding strength after the second week and were not pursued for subcloning. The reactive B cells were found on plate 10, row G, in pooled samples from adjacent wells 3 and 4, which exhibited binding levels similar to human serum controls (FIG. 20). The reactive well was identified as G4 (FIG. 21); however, reactivity was reduced, indicating that the cells producing the antibody might have begun to die. B cells from this well were subsequently subcloned, but as was shown in FIG. 29, the cells producing H5 HA-reactive IgG did not survive, and could not be isolated. The isolation scheme is summarized in FIG. 22.

TNSL E: B cells were isolated from tonsil, immortalized with EBV, stimulated with anti-IgM (Fab')$_2$, CD40L and BAFF and plated in four 96-well plates, as described in the methods and as summarized in Table 6. After one week, plates 1 and 3 were weakly reactive to H5 HA (FIG. 23). After two weeks, plate 1, rows B and E and Plate 3, row A were identified as containing B cells that secreted IgG reactive with H5 HA (FIG. 24). Analysis of culture supernatants from pooled adjacent wells determined that plate 1, row B wells 5 and 6, row E, wells 3 and 4, 11 and 12; and plate 3 row A, wells 9 and 10 contained IgG reactive with H5 HA (FIG. 25). Of these paired wells, plate 1 row E well 11 and plate 3, row A, well 10 contained H5 HA reactive IgG (FIG. 26). Plate 3 well A10 was subcloned because it had the strongest H5 HA binding. Reactivity was detected in wells containing only 1000 cells after five weeks (FIG. 27). The isolation scheme for the primary round of subcloning was summarized and outlined in FIG. 28. H5 HA reactivity was identified during the primary round of subcloning on a plate containing 1000 cells per well (FIG. 29). The reactive cells were identified in wells C7 and E3 (FIGS. 30A and 30B). Cells from these wells were subjected to two additional rounds of limiting dilution cloning, resulting in identification of two H5 HA-reactive clones, TE-3A10-E3A5 and TE-3A10-C7F6, (FIG. 30C), sometimes referred to as E3A5 and C7F6, respectively.

Characterization of TNSL-E derived H5 HA reactive clones, TE-3A10-C7F6 and TE-3A10-E3A5. To evaluate specificity of binding to H5 HA, the relative affinity for TE-3A10-C7F6 and TE-3A10-E3A5 (C7F6 and E3A5) binding to H5 HA compared with their affinities for H1 HA and H7 HA was studied. ELISA assays specific for H1 and H7 HA were developed. Culture supernatants from clones C7F6 and E3A5 were assayed for relative binding, in comparison with human sera from 5 healthy adult volunteers (FIG. 31). Most healthy adults would be expected to have an antibody response against H1 HA, because most human influenza virus infections are caused by H1 strain viruses, and H1 HA is a component of the yearly flu vaccine. As can be seen in FIG. 31, all volunteers had H1 HA reactive IgG in serum, but had much lower serum reactivity to H5 HA and H7 HA, as would be expected because H5 and H7 are avian influenza strains. In contrast, both clones C7F6 and E3A5 secreted IgG that bound to H5 HA with significantly more reactivity than bound to H1 or to H7 HA (FIG. 31), indicating that both C7F6 and E3A5 were relatively specific for H5 HA. Interestingly, the H5 HA reactive clones had some cross-reactivity to the human strain H1 HA, but had low level reactivity with the other avian H7 strain. Purified human IgG was used as control, and as can be seen in FIG. 31, H1 HA reactivity was also present in this sample, consistent with the strong reactivity with H1 HA found in all donors.

Figures 32A, 32B:
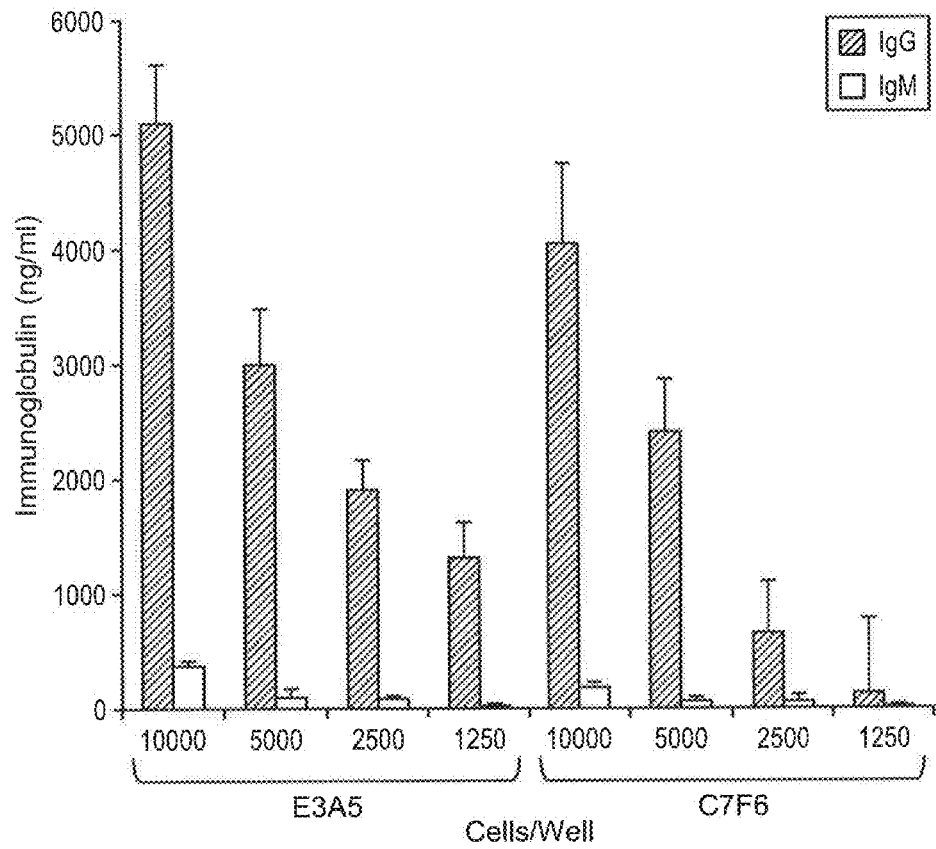
FIGS. 32A-B Tonsil Sample E isolates E3A5 and C7F6 secrete significant amounts of IgG. E3A5 and C7F6 cells were washed once with DPBS, and seeded at the indicated numbers in 0.2 ml of media into wells of a 96-well plate. Supernatants (0.1 ml) were collected 72 hr later and (A) assayed for human IgG and IgM levels, as described in Example 1. Both isolates secreted IgG in a cell number dependent pattern, with no significant amounts of IgM being produced. Mean values±SD of samples (n=3) are shown. (B) The table shows production of IgG for each isolate, calculated as picograms of IgG secreted by 1 cell over the period of 24 hours. Each value represents means±SD of 12 samples.

A dose response type experiment indicated that the C7F6 and E3A5 clones produced approximately 20-50 pg of IgG per cell per day. E3A5 and C7F6 cells were washed with DPBS and seeded into wells of a 96-well plate at 10,000, 5,000, 2,500 and 1,250 cells per well, in the same volume of culture media (200 µl per well). Culture supernatants were collected 72 hours later and evaluated for IgG and IgM levels. Calculation of the levels of IgG and IgM produced by the clones in each test sample was performed by comparing the experimental values with those derived from a standard curve, established by serially diluting purified IgG and IgM of known concentration. As can be seen in FIG. 32, both C7F6 and E3A5 cells produced only IgG in a dose-dependent manner. As expected, IgM was not produced (FIG. 32), (residual background levels of IgM seen at the highest cell number resulted from cross-reactivity of the goat anti-human IgM ELISA detection antibodies with human IgG). At the highest cell density (10,000 cells per 200 µl), the clones produced 4-5 micrograms per ml of media in 72 h. Combining the data from each sample at all cell densities, the average IgG production per cell per 24 hours was calculated. E3A5 cells produced on average 49±16 picograms of IgG per cell per 24 hours, while C7F6 cells produced 21±11 pg of IgG per cell per 24 hr (FIG. 32). Because E3A5 cells grew faster than C7F6 cells at lower cell density (data not shown), these differences might not be significant.

Figure 33:
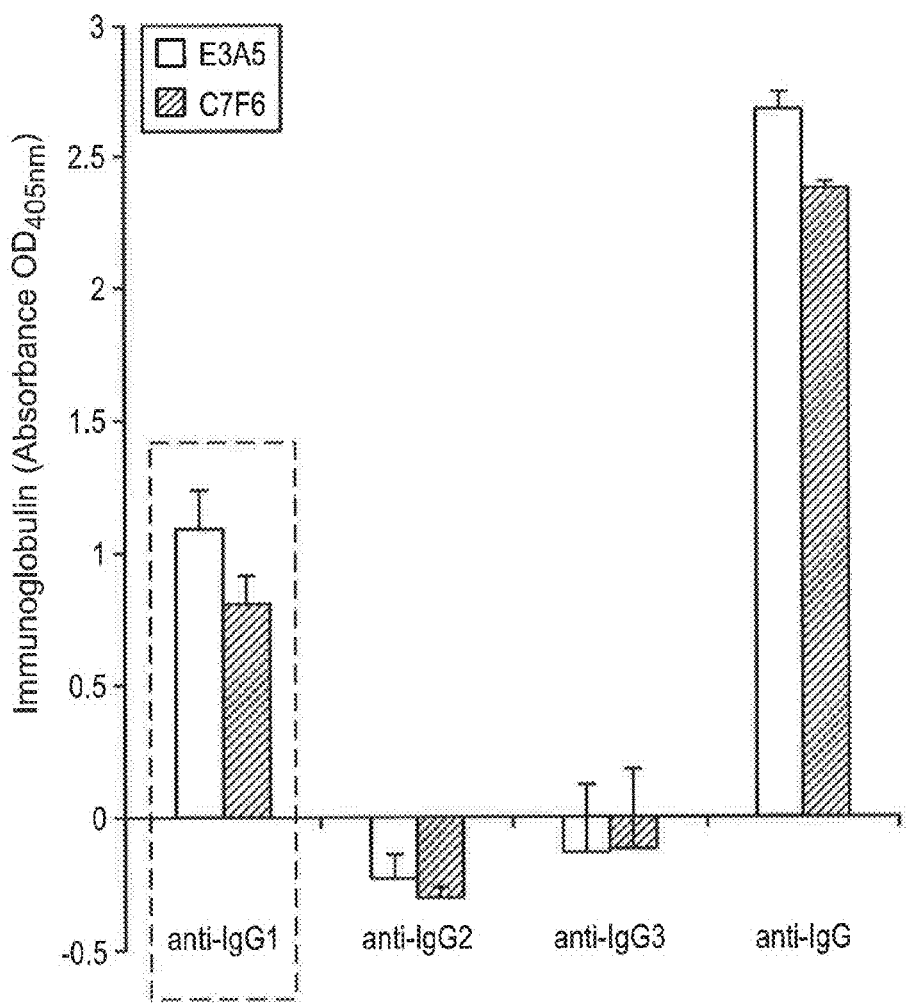
FIG. 33 Tonsil Sample E isolates E3A5 and C7F6 secrete IgG1. E3A5 and C7F6 cells were washed once with DPBS, and seeded into T25 flasks at $10^6$ cells/flask and 10 ml culture media. Supernatants (5 ml) were collected 96 hr later and assayed for the presence of human IgG isotypes, using mouse-derived monoclonal antibodies against human IgG1, IgG2 and IgG3, as described in Example 1. The standard goat anti-human IgG-AP was used as a positive control. Both isolates secreted IgG1, with no detectable amounts of IgG2 or IgG3 being produced. Mean values±SD of samples (n=3) are shown.

Next the IgG subtype(s) produced by the C7F6 and E3A5 isolates were identified. Human IgG has 4 subtypes, $IgG_1$, $IgG_2$, $IgG_3$ and $IgG_4$, with $IgG_1$ and $IgG_4$ being the most and least common, respectively. To identify the subtype of each clone, culture supernatants from both isolates were tested by ELISA, using as detection antibodies murine monoclonal antibodies that specifically recognized human $IgG_1$, $IgG_2$ and $IgG_3$, the three most common subtypes, each coupled to alkaline phosphatase (AP). As can be seen in (FIG. 33), both C7F6 and E3A5 secreted $IgG_1$. As positive control, AP-labeled polyclonal goat anti-human IgG was used, which binds all IgG subtypes better than the IgG1 specific monoclonal antibody, leading to higher $OD_{405}$ values (FIG. 33).

Figure 35D2:
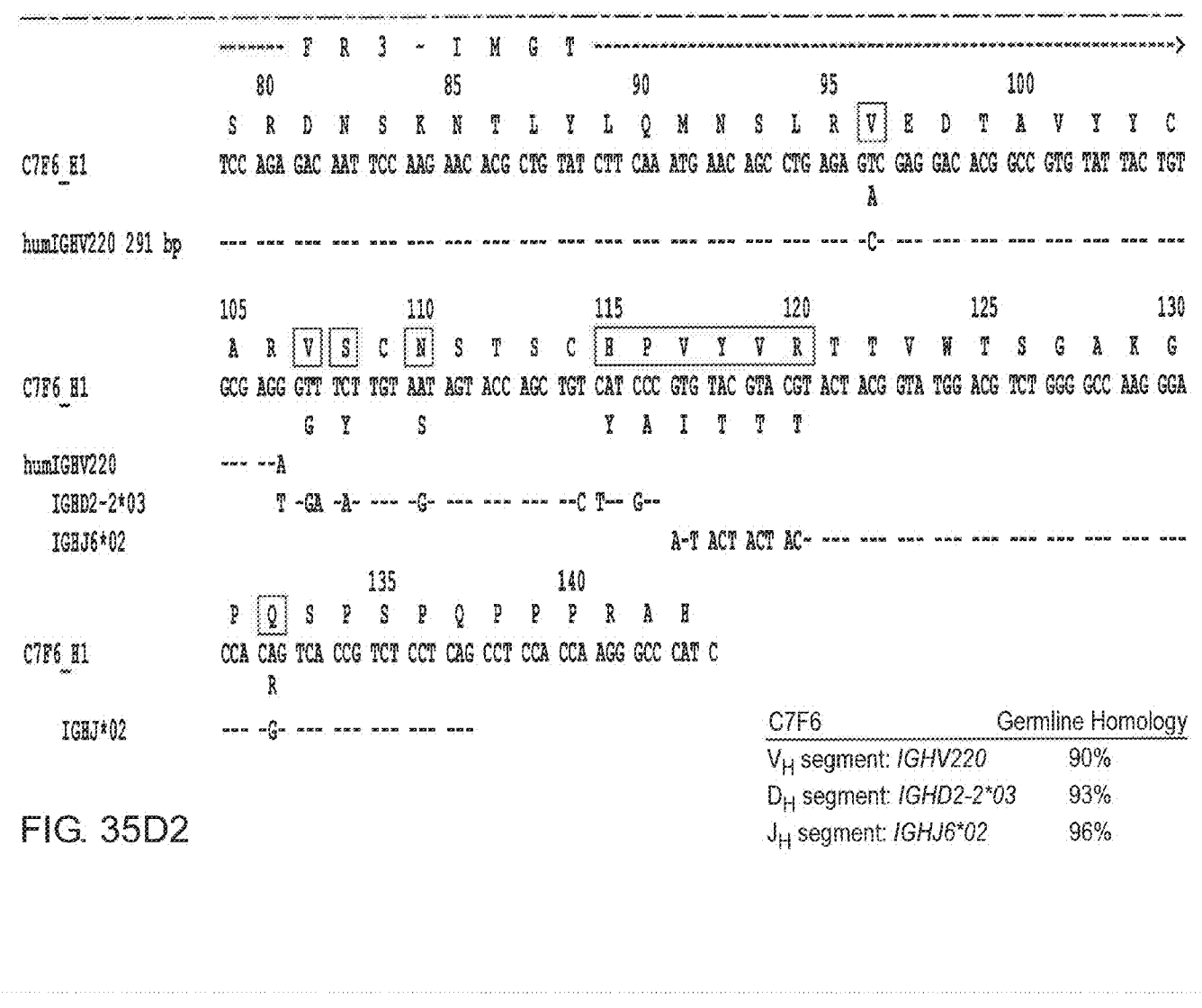

Analysis of the heavy and light chain variable region sequences of the H5 HA binding immunoglobulins produced by the TE-3A10-E3A5 and TE-3A10-C7F6 clones. Total RNA was extracted from approximately $10^6$ cells of each clone using RNEasy protocol (Qiagen, #74104) with QIAshredder columns (Qiagen, #79654). RNA was converted to cDNA with the High Capacity cDNA Reverse Transcription Kit according to manufacturer's instructions (Applied Biosystems, #4368813) and analyzed by PCR for light and heavy chain type content using a set of primers adapted from Welschof et al. (1995) (FIG. 34A). All forward primers incorporated an XbaI restriction site, while the reverse primers incorporated a SalI restriction site. PCR products were analyzed on 1% agarose gel (FIG. 34B), indicating that both E3A5 and C7F6 had λ1 light chain, and E3A5 had $V_{H3}$ heavy chain, while C7F6 had $V_{H1}$ heavy chain. Reactions that resulted in detectable product were scaled up using the proofreading Accuzyme™ Mix kit (Bioline, # BIO-25027). PCR products were gel-purified using QIAquick Gel Extraction Kit (Qiagen, #28704), and a portion of each was submitted for sequencing to the MUSC DNA Core Facility with the original forward and reverse PCR primers. The remainder of each product was digested with XbaI and SalI (New England Biolabs), and cloned into XbaI/SalI digested pSP73 plasmid (Promega, # P2221) for subsequent subcloning into mammalian expression vectors. Forward and reverse DNA sequences were aligned using Vector NTI (Invitrogen) ALIGN function, and combined corrected sequences were generated. These were analyzed using VBASE2 online software (Retter et al., 2005). Results of this analysis are shown in FIG. 35A-35E. Sequence numbering and motif alignments were performed according to Kabat standards (Johnson and Wu, 2000). E3A5 (SEQ ID NOS:16 and 17) had $V_L$ gene segment IGLV063 and $J_L$ segment IGLJ3*02, with homology to germline sequences at 99% and 100%, respectively (FIG. 35A). C7F6 (SEQ ID NOS:19 and 20) had $V_L$ gene segment IGLV067 and $J_L$ segment IGLJ1*01, with homology to germline sequences at 99% and 100%, respectively (FIG. 35B). E3A5 (SEQ ID NOS:22 and 23) had $V_H$ gene segment IGHV157, $D_H$ segment IGHD4-17*1, and $J_H$ segment IGHJ3*02, with homology to germline sequences at 90%, 93% and 96%, respectively (FIG. 35C). C7F6 (SEQ ID NOS:25 and 26) had $V_H$ gene segment IGHV220, $D_H$ segment IGHD2-2*03, and $J_H$ segment IGHJ6*02, with homology to germline sequences at 90%, 93% and 96%, respectively (FIG. 35D). The light and heavy chain complementarity determining regions for both C7F6 and E3A5 are depicted in FIG. 35E (SEQ ID NOS:28, 29, 30, and 31).

Example 3

Materials & Methods for Producing Human B-Cells Secreting Monoclonal Antibodies Reactive with SEB, SEC-2, PLGF, and Ricin B Chain Creation of immortalized tonsil repertoires. Generation of concentrated EBV stocks and preparation of B cells from tonsil tissue have been described in Examples 1 and 2. No changes have been made to these methods. For induction of differentiation of EBV immortalized B cells, the inventors used complete RPMI medium (Gibco) supplemented with 10% FBS (Hyclone) containing soluble CD40 ligand (5 ng/ml), BAFF (10 ng/ml), and goat anti-human IgM F(ab')2 (1.62 ng/ml), as previously described.

Sample Collection for ELISA Analysis. Collection and screening of sample culture supernatants for antigen reactivity by ELISA have been modified as follows. Culture supernatants were collected into corresponding wells on a 96-well plate on day 10-14 post-transduction at 100 µl from each well, and aliquots were pooled (30 µl of supernatant from all wells on each plate) and screened by the specific ELISA for antigen reactivity. The culture supernatant was replaced with 100 µl fresh RPMI medium containing CD40L, BAFF and anti-human IgM(Fab')2. If antigen reactivity was detected in pooled wells, each of the individual wells contributing to the pool was split into 5 new wells to preserve the viability of the culture while the identity of the positive well was confirmed by additional ELISA experiments. Once individual wells containing specific antigen reactive IgG had been identified in tonsil repertoires, using the rapid screening strategy, cells from that well were counted, and 50-80% of them were subcloned into 96-well plates (~500-1000 cells per well, depending upon the count), while the remainder were frozen. After 7 to 10 days, supernatants were collected as outlined above and rapid screening analysis was repeated. This was followed by 2 additional rounds of limiting dilution subcloning and screening. Clonality was assumed when at the lowest dilution, clones were obtained in fewer than 30% of wells on the 96-well plate, and all clones on the plate were producing specific antigen reactive IgG.

SEB ELISA

Binding of test antigen to assay plate. The day before, add to 1× binding buffer (20 mM Tris-Cl pH 8.5) the SEB antigen (BT202red and biotinylated BT202 B, Toxin Technologies, Inc.) at 5 ug/mL. The amount of buffer to use is 5 mL per 96-well plate at 50 uL buffer/well. Note: SEB antigen kept in locked 80° C. freezer in SEB/SEC2 box. Each aliquot of 0.5 μg/μL SEB is individually labeled. Use aliquots in increasing order. Upon thawing and usage of an aliquot, record usage in the IBC notebook with the SEB toxin log. Using a multichannel-pipettor, add 50 uL/well of the antigen-binding buffer mix to the test wells of a non-sterile, flat-bottomed 96-well plate (use CoStar EIA/RIA plate, no lid 96-well Easy Wash, prod #3369). For the control background wells, add 50 μL of 1× binding buffer (without antigen). Cover plate(s) with adhesive plate film and place at 4° C. overnight.

ELISA assay. Remove from the 20° C. freezer any supernatant samples needing for the assay and leave at room temperature to thaw. Prepare the plate washer (Wellwash 4 Mk2) as follows: Insert control card into right side of machine and turn machine on. Make sure parameters on the card are set as follows: Dials: Soak×0.5 min=0, Pause=0, Washes=3, Volume×50 μL=4; Toggles: single, 12way, plate, stepoff, wash H1, dry, F1 off, F2 off, F dry. Empty waste reservoir if waste present. Replace $dH_2O$ reservoir with 1×TBST reservoir. Make certain at least 500 mL/plate of TBST is in reservoir before starting. Press the <PRIME> button to flush the $dH_2O$ from the system. With the "Wash Plate" in place, wash system by pressing <4> row button then <START> button. Plate washer should wash the first half of the plate 3 times then aspirate the plate leaving it dry.

Blocking. Remove adhesive plate film from plate to be washed and place on washer. Wash plate 3 times (press <8> then <START>). After washing, shake out any remaining TBST from plate with a sharp swing (do this after each wash from here on). Pipet 100 μL of blocking solution into each well using multichannel pipetter. Cover plate with adhesive plate film and leave at room temperature 1 hour.

Sample binding. If using samples of supernatant from a 96-well plate, briefly spin thawed sample plate in centrifuge at 2K rpm/2 mins/RT. Dilute any supernatant samples as needed. Use blocking solution to dilute so that 100 uL of diluted sample can be added per well. For duplicate assays with background controls, at least 400 uL of diluted sample will be needed. Wash blocked plate 3 times. Pipette samples onto plate according to plate diagram using 100 uL of sample/well. If needed, add (+) and (−) controls on plate (ex. 1:5000 dilution of mouse α-SEB monoclonal antibody in blocking buffer for SEB assay). Blank wells should have 100 uL of blocking solution added. Cover plate with adhesive plate film and place on plate shaker set for 1 hour at 450 rpm. To shake multiple plates, wrap a narrow strip of parafilm around plate stack before loading.

2° antibody binding. Make secondary antibody dilution. Use blocking solution and the appropriate antibody at the appropriate dilution. 100 μL, is needed per well so 10 mL will be needed per plate. [For α-human IgG 2° Ab, use goat α-human IgG antibody at a dilution of 1:10,000 (1 μL 2o Ab/10 mL blocking solution). For the positive control mouse α-SEB monoclonal antibody, use 1:10,000 dilution of goat anti-mouse IgG-AP 2° Ab]. Post sample binding, remove from shaker and remove adhesive films. Change wash dial on control card from 3 to 4 and wash plate 4 times. Pipet 100 uL of secondary antibody into each well. Seal plate with new adhesive film and put on plate shaker for 1 hour at 450 rpm.

Substrate addition. 5 minutes before 2° Ab binding is completed, prepare reactant. For 1 plate, mix 2 mL of 5× substrate buffer with 8 mL diH2O and 2 reactant tablets in a 15 mL culture tube. Mix by inverting until tablets are fully dissolved. Remove plate from mixer and remove adhesive films. All procedures to be conducted in the fume hood to contain toxin. All waste products and consumables to be disposed of in biohazardous waste containers and autoclaved. Liquid waste to be treated with bleach at 10% prior to disposal. Use appropriate protective gear (gloves and safety goggles) during assay. Refer to SEB-specific IBC regulations prior to usage. Time to completion: Plate coating (the day before assay) 30 minutes ELISA assay 4-8 hours plus development time (30 min-24 h)

SEC2 ELISA

Binding of test antigen to assay plate. The day before, add to 1× binding buffer (20 mM Tris-Cl pH 8.5) the SEC-2 antigen at 5 μg/mL. The amount of buffer to use is 5 mL per 96-well plate at 50 μL buffer/well. Note: SEC-2 antigen kept in locked 80° C. freezer in SEB/SEC2 box. Each aliquot of 0.5 ug/uL SEC-2 is individually labeled. Use aliquots in increasing order. Upon thawing and usage of an aliquot, record usage in the IBC notebook with the SEC-2 toxin log. Using a multichannel pipetter, add 50 μL/well of the antigen-binding buffer mix to the test wells of a non-sterile, flat-bottomed 96-well plate (use CoStar EIA/RIA plate, no lid 96-well Easy Wash, prod #3369). For the control background wells, add 50 μL of 1× binding buffer (without antigen). Cover plate(s) with adhesive plate film and place at 4° C. overnight.

ELISA assay. Remove from the 20° C. freezer any supernatant samples needing for the assay and leave at room temperature to thaw. Prepare the plate washer (Wellwash 4 Mk2) as follows: Insert control card into right side of machine and turn machine on. Make sure parameters on the card are set as follows: Dials: Soak×0.5 min=0, Pause=0, Washes=3, Volume×50 μL=4; Toggles: single, 12way, plate, stepoff, wash HI, dry, F 1 off, F2 off, F dry. Empty waste reservoir if waste present. Replace $dH_2O$ reservoir with 1×TBST reservoir. Make certain at least 500 mL/plate of TBST is in reservoir before starting. Press the <PRIME> button to flush the $dH_2O$ from the system. With the "Wash Plate" in place, wash system by pressing <4> row button then <START> button. Plate washer should wash the first half of the plate 3 times then aspirate the plate leaving it dry.

Blocking. Remove adhesive plate film from plate to be washed and place on washer. Wash plate 3 times (press <8> then <START>). After washing, shake out any remaining TBST from plate with a sharp swing (do this after each wash from here on). Pipet 100 μL of blocking solution into each well using multichannel pipetter. Cover plate with adhesive plate film and leave at room temperature 1 hour.

Sample binding. If using samples of supernatant from a 96] well plate, briefly spin thawed sample plate in centrifuge at 2K rpm/2 mins/RT. Dilute any supernatant samples as needed. Use blocking solution to dilute so that 100 μL of diluted sample can be added per well. For duplicate assays with background controls, at least 400 μL of diluted sample will be needed. Wash blocked plate 3 times. Pipette samples onto plate according to plate diagram using 100 μL of sample/well. If needed, add (+) and (−) controls on plate (ex. 1:5000 dilution of mouse α-SEC-2 monoclonal antibody in blocking buffer for SEC-2 assay). Blank wells should have 100 μL of blocking solution added. Cover plate with adhesive plate film and place on plate shaker set for 1 hour at 450 rpm. To shake multiple plates, wrap a narrow strip of parafilm around plate stack before loading.

2° antibody binding. Make secondary antibody dilution. Use blocking solution and the appropriate antibody at the appropriate dilution. 100 μL is needed per well so 10 mL will be needed per plate. [For α-human IgG 2° Ab, use goat α-human IgG antibody at a dilution of 1:10,000 (1 μL 2° Ab/10 mL blocking solution). For the positive control mouse α-SEC-2 monoclonal antibody, use 1:10000 dilution of goat α-mouse IgG-AP 2° Ab]. Post sample binding, remove from shaker and remove adhesive films. Change wash dial on control card from 3 to 4 and wash plate 4 times. Pipet 100 μL of secondary antibody into each well. Seal plate with new adhesive film and put on plate shaker for 1 hour at 450 rpm.

Substrate addition. 5 minutes before 2° Ab binding is completed, prepare reactant. For 1 plate, mix 2 mL of 5× substrate buffer with 8 mL diH2O and 2 reactant tablets in a 15 mL culture tube. Mix by inverting until tablets are fully dissolved. Remove plate from mixer and remove adhesive films. Change wash dial on control card from 4 to 6 and wash plate 6 times. Add 100 μL of prepared reactant to each well of plate. Place fresh adhesive film on plate and place plate in drawer of desk beneath plate reader. Leave plate in drawer and monitor for color change from clear to yellow. The time for development may be from 30 minutes for an extremely strong reaction to 6 hours for a very weak reaction. It is ideal to read the plates when color is evident in some wells and before the solution becomes saturated.

Plate reading. When plates are ready for quantitation, make sure plate reader is turned on and the Scanit RE for MSS2.2 software is open. Open the appropriate plate reading program and setup run if desired. Remove cover film from plate to be loaded. Load plate into machine and scan. Observe the results of the scan (Photometric and Statistics) to determine if additional scans are needed. If scanning is completed, remove plate, replace cover film, and place in drawer to reserve overnight. After all scans have been completed, turn off plate reader.

Reagents and Buffers:

Antigen: *Staph* Entertoxin C-2 Toxin Technologies, Inc. (CT222red)

Positive control antibody: anti-SEC g1 murine Mab: Toxin Technologies, Inc. (MC 165)

Binding buffer (1×) 20 mM Tris-Cl, pH 8.5

TBST buffer (1×) 50 mM Tris, 0.9% NaCl (w:v), 0.1% Tween-20 (v:v), pH. to 7.5 with HCl. Dilute from 5×TBS stock using di$H_2O$, add Tween-20 and mix using stir bar for several minutes. It can be mixed in a glass bottle or the TBST Wellwash reservoir. A stirbar is left in the reservoir.

Blocking solution (1×) Pierce SuperBlock dry blend, TBS blocking buffer (prod #0037545). Add 1 packet of buffer powder to 200 mL of diH2O. Mix until dissolved. Store at 4° C. All procedures to be conducted in the fume hood to contain toxin. All waste products and consumables to be disposed of in biohazardous waste containers and autoclaved. Liquid waste to be treated with bleach at 10% prior to disposal. Use appropriate protective gear (gloves and safety goggles) during assay. Refer to SEC-specific IBC regulations prior to usage.

Time to completion: Plate coating (the day before assay) 30 minutes ELISA assay 4-8 hours plus development time (30 min-24 h)

PLGF ELISA

Binding of test antigen to assay plate. The day before, add to 1× binding buffer (1×DPBS, Gibco 14190) the PLGF antigen at 2 ug/mL. The amount of buffer to use is 5 mL per 96-well plate at 50 μL buffer/well. Using a multichannel pipetter, add 50 μL/well of the antigen-binding buffer mix to the test wells of a non-sterile, flat-bottomed 96-well plate (use CoStar EIA/RIA plate, no lid 96-well Easy Wash, prod #3369). For the control background wells, add 50 μL of 1× binding buffer (without antigen). Cover plate(s) with adhesive plate film and place at 4° C. overnight.

ELISA assay. Remove from the 20° C. freezer any supernatant samples needing for the assay and leave at room temperature to thaw. Prepare the plate washer (Wellwash 4 Mk2) as follows: Insert control card into right side of machine and turn machine on. Make sure parameters on the card are set as follows: Dials: Soak×0.5 min=0, Pause=0, Washes=3, Volume×50 μL=4; Toggles: single, 12way, plate, stepoff, wash HI, dry, F1 off, F2 off, F dry. Empty waste reservoir if waste present. Replace dH2O reservoir with 1×TBST reservoir. Make certain at least 500 mL/plate of TBST is in reservoir before starting. Press the <PRIME> button to flush the d$H_2O$ from the system. With the "Wash Plate" in place, wash system by pressing <4> row button then <START> button. Plate washer should wash the first half of the plate 3 times then aspirate the plate leaving it dry.

Blocking. Remove adhesive plate film from plate to be washed and place on washer. Wash plate 3 times (press <8> then <START>). After washing, shake out any remaining TBST from plate with a sharp swing (do this after each wash from here on). Pipet 100 μL of blocking solution into each well using multichannel pipetter. Cover plate with adhesive plate film and leave at room temperature 1 hour.

Sample binding. If using samples of supernatant from a 96-well plate, briefly spin thawed sample plate in centrifuge at 2K rpm/2 mins/RT. Dilute any supernatant samples as needed. Use blocking solution to dilute so that 100 μL of diluted sample can be added per well. For duplicate assays with background controls, at least 400 μL of diluted sample will be needed. Wash blocked plate 3 times. Pipette samples onto plate according to plate diagram using 100 μL of sample/well. If needed, add (+) and (−) controls on plate (ex. 1:2000 dilution of mouse α-human PLGF monoclonal antibody in blocking buffer for PLGF assay). Blank wells should have 100 μL of blocking solution added. Cover plate with adhesive plate film and place on plate shaker set for 1 hour at 450 rpm. To shake multiple plates, wrap a narrow strip of parafilm around plate stack before loading.

2° antibody binding. Make secondary antibody dilution. Use blocking solution and the appropriate antibody at the appropriate dilution. 100 μL is needed per well so 10 mL will be needed per plate. For α-human IgG 2° Ab, use goat α-human IgG antibody at a dilution of 1:10,000 (1 μL 2° Ab/10 mL blocking solution). For the positive control mouse α-human PLGF monoclonal antibody, use 1:10000 dilution of goat α-mouse IgG-AP 2° Ab]. Post sample binding, remove from shaker and remove adhesive films. Change wash dial on control card from 3 to 4 and wash plate 4 times. Pipet 100 μL of secondary antibody into each well. Seal plate with new adhesive film and put on plate shaker for 1 hour at 450 rpm.

Substrate addition. 5 minutes before 2° Ab binding is completed, prepare reactant. For 1 plate, mix 2 mL of 5× substrate buffer with 8 mL di$H_2O$ and 2 reactant tablets in a 15 mL culture tube. Mix by inverting until tablets are fully dissolved. Remove plate from mixer and remove adhesive films. Change wash dial on control card from 4 to 6 and wash plate 6 times. Add 100 μL of prepared reactant to each well of plate. Place fresh adhesive film on plate and place plate in drawer of desk beneath plate reader. Leave plate in drawer and monitor for color change from clear to yellow. The time for development may be from 30 minutes for an extremely strong reaction to 6 hours for a very weak reaction. It is ideal to read the plates when color is evident in some wells and before the solution becomes saturated.

Plate reading. When plates are ready for quantitation, make sure plate reader is turned on and the Scanit RE for MSS2.2 software is open. Open the appropriate plate reading program and setup run if desired. Remove cover film from plate to be loaded. Load plate into machine and scan. Observe the results of the scan (Photometric and Statistics) to determine if additional scans are needed. If scanning is completed, remove plate, replace cover film, and place in drawer to reserve overnight. After all scans have been completed, turn off plate reader.

Reagents and Buffers:
Antigen: recombinant human PLGF PeproTech (100-06)
Positive control antibody: mouse anti-human PLGF Mab: R&D Systems (MAB264)
Binding buffer (1×) 1× Dulbecco's Phosphate Buffered Saline, Gibco (14190)
TBST buffer (1×) 50 mM Tris, 0.9% NaCl (w:v), 0.1% Tween-20 (v:v), pH. to 7.5 with HCl. Dilute from 5×TBS stock using diH$_2$O, add Tween-20 and mix using stir bar for several minutes. It can be mixed in a glass bottle or the TBST Wellwash reservoir. A stirbar is left in the reservoir.
Blocking solution (1×) Pierce SuperBlock dry blend, TBS blocking buffer (prod #0037545). Add 1 packet of buffer powder to 200 mL of diH$_2$O. Mix until dissolved. Store at 4° C. For long term storage (>1 week) add 100 mg sodium azide/200 mL.
Substrate (1×) Pierce phosphatase substrate kit (prod #37620). For 1 plate, make 10 mL as follows in a 15 mL culture tube: 2 mL 5×DEA substrate buffer, 8 mL diH2O, 2 PNPP tablets. Mix by inverting until tablets are fully dissolved.
Time to completion: Plate coating (the day before assay) 30 minutes ELISA assay 4-8 hours plus development time (30 min-24 h)

Ricin B ELISA

Binding of test antigen to assay plate. The day before, add to 1× binding buffer (1×DPBS, Gibco 14190) the ricin B chain antigen at 5 ug/mL. The amount of buffer to use is 5 mL per 96-well plate at 50 μL buffer/well. Using a multichannel pipettor, add 50 μL/well of the antigen-binding buffer mix to the test wells of a non-sterile, flat-bottomed 96-well plate (use CoStar EIA/RIA plate, no lid 96-well Easy Wash, prod #3369). For the control background wells, add 50 μL of 1× binding buffer (without antigen). Cover plate(s) with adhesive plate film and place at 4° C. overnight.

ELISA assay. Remove from the 20° C. freezer any supernatant samples needing for the assay and leave at room temperature to thaw. Prepare the plate washer (Wellwash 4 Mk2) as follows: Insert control card into right side of machine and turn machine on. Make sure parameters on the card are set as follows: Dials: Soak×0.5 min=0, Pause=0, Washes=3, Volume×50 μL=4; Toggles: single, 12 way, plate, stepoff, wash HI, dry, F1 off, F2 off, F dry. Empty waste reservoir if waste present. Replace dH$_2$O reservoir with 1×TBST reservoir. Make certain at least 500 mL/plate of TBST is in reservoir before starting. Press the <PRIME> button to flush the dH2O from the system. With the "Wash Plate" in place, wash system by pressing <4> row button then <START> button. Plate washer should wash the first half of the plate 3 times then aspirate the plate leaving it dry.

Blocking. Remove adhesive plate film from plate to be washed and place on washer. Wash plate 3 times (press <8> then <START>). After washing, shake out any remaining TBST from plate with a sharp swing (do this after each wash from here on). Pipet 100 μL of blocking solution into each well using multichannel pipetter. Cover plate with adhesive plate film and leave at room temperature 1 hour.

Sample binding. If using samples of supernatant from a 96-well plate, briefly spin thawed sample plate in centrifuge at 2K rpm/2 mins/RT. Dilute any supernatant samples as needed. Use blocking solution to dilute so that 100 μL of diluted sample can be added per well. For duplicate assays with background controls, at least 400 μL of diluted sample will be needed. Wash blocked plate 3 times. Pipette samples onto plate according to plate diagram using 100 μL of sample/well. If needed, add (+) and (−) controls on plate (ex. 1:5000 dilution of mouse α-ricinB monoclonal antibody in blocking buffer for ricin assay). Blank wells should have 100 μL of blocking solution added. Cover plate with adhesive plate film and place on plate shaker set for 1 hour at 450 rpm. To shake multiple plates, wrap a narrow strip of parafilm around plate stack before loading.

2° antibody binding. Make secondary antibody dilution. Use blocking solution and the appropriate antibody at the appropriate dilution. 100 μL is needed per well so 10 mL will be needed per plate. [For α-human IgG 2° Ab, use goat α-human IgG antibody at a dilution of 1:10,000 (1 μL 2° Ab/10 mL blocking solution). For the positive control mouse α-ricinB monoclonal antibody, use 1:10000 dilution of goat α-mouse IgG-AP 2° Ab]. Post sample binding, remove from shaker and remove adhesive films. Change wash dial on control card from 3 to 4 and wash plate 4 times. Pipet 100 μL of secondary antibody into each well. Seal plate with new adhesive film and put on plate shaker for 1 hour at 450 rpm.

Substrate addition. 5 minutes before 2° Ab binding is completed, prepare reactant. For 1 plate, mix 2 mL of 5× substrate buffer with 8 mL diH$_2$O and 2 reactant tablets in a 15 mL culture tube. Mix by inverting until tablets are fully dissolved. Remove plate from mixer and remove adhesive films. Change wash dial on control card from 4 to 6 and wash plate 6 times. Add 100 μL of prepared reactant to each well of plate. Place fresh adhesive film on plate and place plate in drawer of desk beneath plate reader. Leave plate in drawer and monitor for color change from clear to yellow. The time for development may be from 30 minutes for an extremely strong reaction to 6 hours for a very weak reaction. It is ideal to read the plates when color is evident in some wells and before the solution becomes saturated.

Plate reading. When plates are ready for quantitation, make sure plate reader is turned on and the Scanit RE for MSS2.2 software is open. Open the appropriate plate reading program and setup run if desired. Remove cover film from plate to be loaded. Load plate into machine and scan. Observe the results of the scan (Photometric and Statistics) to determine if additional scans are needed. If scanning is completed, remove plate, replace cover film, and place in drawer to reserve overnight. After all scans have been completed, turn off plate reader.

Reagents and Buffers:
Antigen: ricin B chain Vector Laboratories (L-1290)
Positive control antibody: mouse anti-ricinB Mab: Santa Cruz Biotechnologies (sc-52197)
Binding buffer (1×) 1× Dulbecco's Phosphate Buffered Saline, Gibco (14190)

TBST buffer (1×) 50 mM Tris, 0.9% NaCl (w:v), 0.1% Tween-20 (v:v), pH. to 7.5 with HCl. Dilute from 5×TBS stock using diH2O, add Tween☐]20 and mix using stir bar for several minutes. It can be mixed in a glass bottle or the TBST Wellwash reservoir. A stirbar is left in the reservoir.

Blocking solution (1×) Pierce SuperBlock dry blend, TBS blocking buffer (prod #0037545). Add 1 packet of buffer powder to 200 mL of diH$_2$O. Mix until dissolved. Store at 4° C. For long term storage (>1 week) add 100 mg sodium azide/200 mL.

Substrate (1×) Pierce phosphatase substrate kit (prod #37620). For 1 plate, make 10 mL as follows in a 15 mL culture tube: 2 mL 5×DEA substrate buffer, 8 mL diH$_2$O, 2 PNPP tablets. Mix by inverting until tablets are fully dissolved.

Time to completion: Plate coating (the day before assay) 30 minutes ELISA assay 4-8 hours plus development time (30 min-24 h)

IL6 ELISA

Binding of test antigen to assay plate. The day before, add to 1× binding buffer (1×DPBS, Gibco 14190) the IL-6 antigen at 5 ug/mL. The amount of buffer to use is 5 mL per 96-well plate at 50 µL buffer/well. Using a multichannel pipetter, add 50 µL/well of the antigen-binding buffer mix to the test wells of a non-sterile, flat-bottomed 96-well plate (use CoStar EIA/RIA plate, no lid 96-well Easy Wash, prod #3369). For the control background wells, add 50 µL of 1× binding buffer (without antigen). Cover plate(s) with adhesive plate film and place at 4° C. overnight.

ELISA assay. Remove from the 20° C. freezer any supernatant samples needing for the assay and leave at room temperature to thaw. Prepare the plate washer (Wellwash 4 Mk2) as follows: Insert control card into right side of machine and turn machine on. Make sure parameters on the card are set as follows: Dials: Soak×0.5 min=0, Pause=0, Washes=3, Volume×50 uL=4; Toggles: single, 12 way, plate, stepoff, wash HI, dry, F1 off, F2 off, F dry. Empty waste reservoir if waste present. Replace dH2O reservoir with 1×TBST reservoir. Make certain at least 500 mL/plate of TBST is in reservoir before starting. Press the <PRIME> button to flush the dH2O from the system. With the "Wash Plate" in place, wash system by pressing <4> row button then <START> button. Plate washer should wash the first half of the plate 3 times then aspirate the plate leaving it dry.

Blocking. Remove adhesive plate film from plate to be washed and place on washer. Wash plate 3 times (press <8> then <START>). After washing, shake out any remaining TBST from plate with a sharp swing (do this after each wash from here on). Pipet 100 µL of blocking solution into each well using multichannel pipetter. Cover plate with adhesive plate film and leave at room temperature 1 hour.

Sample binding. If using samples of supernatant from a 96-well plate, briefly spin thawed sample plate in centrifuge at 2K rpm/2 mins/RT. Dilute any supernatant samples as needed. Use blocking solution to dilute so that 100 µL of diluted sample can be added per well. For duplicate assays with background controls, at least 400 µL of diluted sample will be needed. Wash blocked plate 3 times. Pipette samples onto plate according to plate diagram using 100 µL of sample/well. If needed, add (+) and (−) controls on plate (ex. 1:5000 dilution of mouse α-human IL-6 monoclonal antibody in blocking buffer for IL-6 assay). Blank wells should have 100 µL of blocking solution added. Cover plate with adhesive plate film and place on plate shaker set for 1 hour at 450 rpm. To shake multiple plates, wrap a narrow strip of parafilm around plate stack before loading.

2° antibody binding. Make secondary antibody dilution. Use blocking solution and the appropriate antibody at the appropriate dilution. 100 µL is needed per well so 10 mL will be needed per plate. [For α-human IgG 2°Ab, use goat α-human IgG antibody at a dilution of 1:10,000 (1 µL 2° Ab/10 mL blocking solution). For the positive control mouse α-human IL-6 monoclonal antibody, use 1:10000 dilution of goat α-mouse IgG-AP 2°Ab]. Post sample binding, remove from shaker and remove adhesive films. Change wash dial on control card from 3 to 4 and wash plate 4 times. Pipet 100 µL of secondary antibody into each well. Seal plate with new adhesive film and put on plate shaker for 1 hour at 450 rpm.

Substrate addition. 5 minutes before 2° Ab binding is completed, prepare reactant. For 1 plate, mix 2 mL of 5× substrate buffer with 8 mL diH2O and 2 reactant tablets in a 15 mL culture tube. Mix by inverting until tablets are fully dissolved. Remove plate from mixer and remove adhesive films. Change wash dial on control card from 4 to 6 and wash plate 6 times. Add 100 µL of prepared reactant to each well of plate. Place fresh adhesive film on plate and place plate in drawer of desk beneath plate reader. Leave plate in drawer and monitor for color change from clear to yellow. The time for development may be from 30 minutes for an extremely strong reaction to 6 hours for a very weak reaction. It is ideal to read the plates when color is evident in some wells and before the solution becomes saturated.

Plate reading. When plates are ready for quantitation, make sure plate reader is turned on and the ScanIt RE for MSS2.2 software is open. Open the appropriate plate reading program and setup run if desired. Remove cover film from plate to be loaded. Load plate into machine and scan. Observe the results of the scan (Photometric and Statistics) to determine if additional scans are needed. If scanning is completed, remove plate, replace cover film, and place in drawer to reserve overnight. After all scans have been completed, turn off plate reader.

Reagents and Buffers:

Antigen: recombinant human IL-6 GenScript (Z00372-1 mg)

Positive control antibody: mouse anti-human IL-6 Mab: PeproTech (500-M06)

Binding buffer (1×) 1× Dulbecco's Phosphate Buffered Saline, Gibco (14190)

TBST buffer (1×) 50 mM Tris, 0.9% NaCl (w:v), 0.1% Tween-20 (v:v), pH. to 7.5 with HCl. Dilute from 5×TBS stock using diH2O, add Tween☐] ]20 and mix using stir bar for several minutes. It can be mixed in a glass bottle or the TBST Wellwash reservoir. A stirbar is left in the reservoir.

Blocking solution (1×) Pierce SuperBlock dry blend, TBS blocking buffer (prod #0037545). Add 1 packet of buffer powder to 200 mL of diH2O. Mix until dissolved. Store at 4° C. For long term storage (>1 week) add 100 mg sodium azide/200m L.

Substrate (1×) Pierce phosphatase substrate kit (prod #37620). For 1 plate, make 10 mL as follows in a 15 mL culture tube: 2 mL 5×DEA substrate buffer, 8 mL diH$_2$O, 2 PNPP tablets. Mix by inverting until tablets are fully dissolved.

Time to Completion: Plate coating (the day before assay) 30 minutes ELISA assay 4-8 hours plus development time (30 min-24 h)

Example 4

Figure 36:
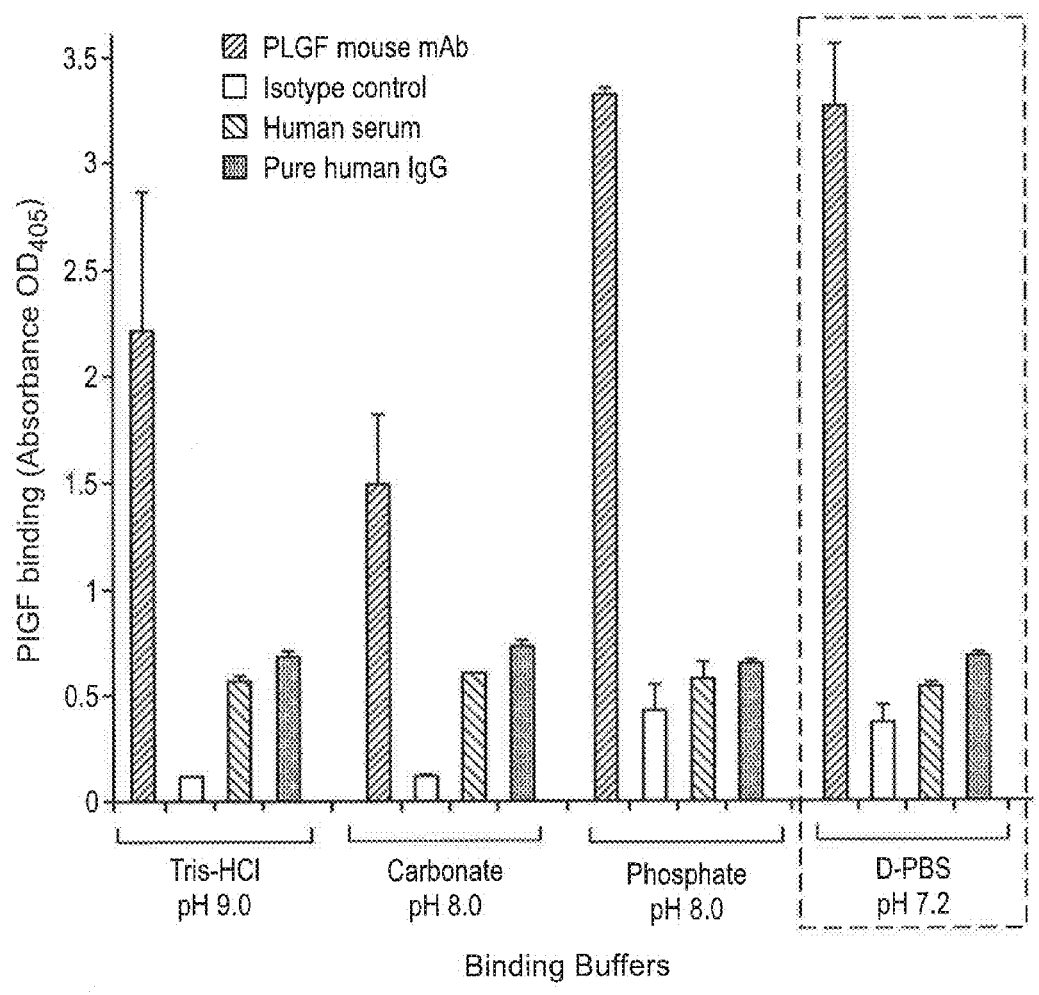
FIG. 36. Determination of optimal ELISA conditions for PLGF binding: binding buffers. Purified PLGF was brought to 4 µg/ml in the indicated binding buffers and bound to ELISA plates overnight at 4° C. 100 µl of 100 ng/ml PLGF mAb (mouse IgG1) was added to each well and incubated for 1 hr at RT. PLGF and PLGF mAb concentrations were determined in previous optimization experiments. Isotype control: purified mouse IgG at 1000 ng/ml; human serum from healthy volunteer (V-2) diluted 1:1000; purified human IgG(Sigma) at 5000 ng/ml. Isotype control and PLGF mAb binding were detected with goat anti-mouse IgG-AP; human serum and purified human IgG binding were detected with goat anti-human IgG-AP (both secondaries diluted 1:10, 000). Neutral Dulbecco's phosphate buffered saline solution (D-PBS) was chosen. Similar assays were developed for SEB, SEC2, ricin subunit B, and IL6.

Results for Human B-Cells Secreting Monoclonal Antibodies Reactive with SEB, SEC-2, PLGF, and Ricin B Chain Development of ELISAs that detect human IgG that is reactive with specific antigens. In order to screen immortalized tonsil repertoires for antibodies that are reactive with SEB, SEC2, PLGF, ricin subunit B, or IL6, the inventors developed enzyme linked immunosorbent assays (ELISAs). For each ELISA, the specific antigen was first bound to the plate, and then cell supernatants from the immortalized repertoires containing human IgG were applied to the wells. Nonspecific IgG was washed away, while antigen specific IgG bound to the antigen coated wells. The bound IgG was then detected with labeled anti-human IgG in the presence of a chromogenic substrate, which increased absorbance at OD405 nm, and was detected by spectrophotometry. Each ELISA required: 1) optimization of amount of antigen bound to plates; 2) optimization of detection antibodies; 3) optimization of buffer; 4) comparison with mouse-monoclonal antibody binding, used as positive control. As an example, steps 3 and 4, optimization of buffers and comparison with mouse monoclonal antibody binding, used for the PLGF ELISA is shown in FIG. 36. Similar results were obtained for each ELISA. The optimized conditions for each were described in detail in the Materials and Methods section.

Creation of immortalized tonsil repertoires. Eleven tonsil repertoires were created and screened for reactivity with different antigens: TNSL-R, -S, -T, -V, -W, -X, -Y, -Z, -α, β, γ. Each repertoire contained 7-21×10$^7$ EBV immortalized cells that were plated into ten 96-well round-bottom plates, and induced to differentiate with soluble CD40 ligand (5 ng/ml), BAFF (10 ng/ml), and goat anti-human IgM F(ab')$_2$ (1.62 ng/ml), as described in Materials and Methods. A summary of the characteristics of each repertoire can be found in Tables 7 and 9. In addition 3 immortalized tonsil repertoires that had previously been created and then stored frozen in liquid nitrogen, were thawed and cultured in two 24-well plates: TNSL-G, -H, -I (Tables 7 and 9).

TABLE 7

Summary of data on isolation of immortalized human B cells secreting monoclonal antibodies reactive with SEB.

| Sample | Date received | # of B cells (×107) | # of plates | # of sub-cloned wells | # of possible clones | Treatment for inducing B cell differentiation | SEB specific IgG | Status |
|

TABLE 9

Summary of data on isolation of immortalized human B cells secreting monoclonal antibodies reactive with SEC-2

| Sample | Date received | # of B cells (×10⁷) | # of plates | # of sub-cloned wells | # of possible clones | Treatment for inducing B cell differentiation | SEC-2 specific IgG | Status |
|---|---|---|---|---|---|---|---|---|
| TNSL R | Mar. 31, 2008 | 21 | 10 | 2 | 2 | Anti-IgM (Fab')2, CD4OL, BAFF | Positive but lost | 2 subclones, 1 plate each: (TR 10A4, TR 10E12) Reactivity lost in 2/2 subclones |
| TNSL S | Mar. 31, 2008 | 17 | 10 | 1 | 1 | Anti-IgM (Fab')2, CD4OL, BAFF | Positive but lost | 1 subclone, 1 plate: (TS 6C5) Reactivity lost in 4/4 subclones |
| TNSL T | Apr. 28, 2008 | 7.2 | 9 | 0 | 0 | Anti-IgM (Fab')2, CD4OL, BAFF | Negative | Screening discontinued: negative at week 2 |
| TNSL V | May 2, 2008 | 8 | 9 | 2 | 2 | Anti-IgM (Fab')2, CD4OL, BAFF | Positive | 1 subcloned, 3 plates (TV bB2) Weak reactivity in 1/3 plates |
| TNSL W | May 14, 2008 | 14 | 10 | 0 | 0 | Anti-IgM (Fab')2, CD4OL, BAFF | Negative | Screening discontinued: negative at week 2 |
| TNSL X | May 19, 2008 | 11 | 10 | 0 | 0 | Anti-IgM (Fab')2, CD4OL, BAFF | Negative | Screening discontinued: negative at week 2 |
| TNSL Y | Jun. 2, 2008 | 7 | 10 | 0 | 0 | Anti-IgM (Fab')2, CD4OL, BAFF | Negative | Screening discontinued: negative at day 10 |
| TNSL Z | Jun. 2, 2008 | 12.5 | 10 | 0 | 0 | Anti-IgM (Fab')2, CD4OL, BAFF | Negative | Screening discontinued: negative at day 10 |
| TNSL α | Jun. 6, 2008 | 7 | 10 | 0 | 0 | Anti-IgM (Fab')2, CD4OL, BAFF | Negative | Screening discontinued: negative at week 2 |
| TNSL β | Jun. 11, 2008 | 11 | 10 | 0 | 0 | Anti-IgM (Fab')2, CD4OL, BAFF | Negative | Screening discontinued: negative at week 2 |
| TNSL y | Jun. 18, 2008 | 12 | 10 | 0 | 0 | Anti-IgM (Fab')2, CD4OL, BAFF | Negative | Screening discontinued: negative at week 2 |
| TNSL G | Nov. 19, 2007 | 6.5 | 2 × 24-well | 0 | 0 | Anti-IgM (Fab')2, CD4OL, BAFF | Negative | Screening discontinued: negative at week 2 |
| TNSL H | Nov. 19, 2007 | 5.2 | 2 × 24-well | 0 | 0 | Anti-IgM (Fab')2, CD4OL, BAFF | Negative | Screening discontinued: negative at week 2 |
| TNSL I | Dec. 10, 2007 | 5.0 | 2 × 24-well | 0 | 0 | Anti-IgM (Fab')2, CD4OL, BAFF | Negative | Screening discontinued: negative at week 2 |

Screening of immortalized tonsil repertoires. Eleven tonsil repertoires, and 3 thawed repertoires were screened for binding to SEB (Table 7), and SEC2 (Table 9). Ten of the new repertoires (TNSL-R, -S, -V, -W, -X, -Y, -Z, -α, -β, -γ), and 3 thawed repertoires were screened for PLGF binding (Table 11). Nine of the new repertoires (TNSL-R, -S, -V, -W, -X, -Z, -α, -γ), and 3 thawed repertoires were screened for ricin subunit B binding (Table 13). Four of the new repertoires (TNSL-R, -S, -β, -γ) were screened for IL6 binding (Table 15). Fewer repertoires were screened for IL6 because it took longer to optimize that ELISA.

TABLE 11

Summary of data on isolation of immortalized human B cells secreting monoclonal antibodies reactive with PLGF

| Sample | Date received | # of B cells (×10⁷) | # of plates | # of sub-cloned wells | # of possible clones | Treatment for inducing B cell differentiation | PLGF specific IgG | Status |
|---|---|---|---|---|---|---|---|---|
| TNSL R | Mar. 31, 2008 | 21 | 10 | 0 | 0 | Anti-IgM (Fab')2, CD4OL, BAFF | Negative | Screening discontinued: negative at week 3 |
| TNSL S | Mar. 31, 2008 | 17 | 10 | 0 | 0 | Anti-IgM (Fab')2, CD4OL, BAFF | Negative | Screening discontinued: negative at week 3 |

TABLE 11-continued

Summary of data on isolation of immortalized human B cells secreting monoclonal antibodies reactive with PLGF

| Sample | Date received | # of B cells (×107) | # of plates | # of sub-cloned wells | # of possible clones | Treatment for inducing B cell differentiation | PLGF specific IgG | Status |
| --- | --- | --- | --- | --- | --- | --- | --- | --- |
| TNSL V | May 2, 2008 | 8 | 9 | 0 | 0 | Anti-IgM (Fab')2, CD4OL, BAFF | Negative | Screening discontinued: negative at week 2 |
| TNSL W | May 14, 2008 | 14 | 10 | 1 | 1 | Anti-IgM (Fab')2, CD4OL, BAFF | Positive | 1 subclone, 5 plates: (TW 1E12)Weak reactivity in 215 plates |
| TNSL X | May 19, 2008 | 11 | 10 | 0 | 0 | Anti-IgM (Fab')2, CD4OL, BAFF | Negative | Screening discontinued: negative at week 2 |
| TNSL Y | Jun. 2, 2008 | 7 | 10 | 0 | 0 | Anti-IgM (Fab')2, CD4OL, BAFF | Negative | Screening discontinued: negative at day 10 |
| TNSL Z | Jun. 2, 2008 | 12.5 | 10 | 2 | 2 | Anti-IgM (Fab')2, CD4OL, BAFF | Positive | 2 subclones, 2 plates each: (TZ 3B10, TZ 5F9) |
| TNSL α | Jun. 6, 2008 | 7 | 10 | 0 | 0 | Anti-IgM (Fab')2, CD4OL, BAFF | Negative | Screening discontinued: negative at week 2 |
| TNSL β | Jun. 11, 2008 | 11 | 10 | 0 | 0 | Anti-IgM (Fab')2, CD4OL, BAFF | Negative | Screening discontinued: negative at week 2 |
| TNSL γ | Jun. 18, 2008 | 12 | 10 | 0 | 0 | Anti-IgM (Fab')2, CD4OL, BAFF | Negative | Screening discontinued: negative at week 2 |
| TNSL G | Nov. 19, 2007 | 6.5 | 2 × 24-well | 0 | 0 | Anti-IgM (Fab')2, CD4OL, BAFF | Negative | Screening discontinued: negative at week 2 |
| TNSL H | Nov. 19, 2007 | 5.2 | 2 × 24-well | 0 | 0 | Anti-101 (Fab')2, CD4OL, BAFF | Negative | Screening discontinued: negative at week 2 |
| TNSL I | Dec. 10, 2007 | 5.0 | 2 × 24-well | 0 | 0 | Anti-IgM (Fab')2, CD4OL, BAFF | Negative | Screening discontinued: negative at week 2 |

TABLE 13

Summary of data on isolation of immortalized human B cells secreting monoclonal antibodies reactive with ricin B chain

| Sample | Date received | # of B cells (×107) | # of plates | # of sub-cloned wells | # of possible clones | Treatment for inducing B cell differentiation | Ricin B specific IgG | Status |
| --- | --- | --- | --- | --- | --- | --- | --- | --- |
| TNSL R | Mar. 31, 2008 | 21 | 10 | 0 | 0 | Anti-IgM (Fab')2, CD40L, BAFF | Negative | Screening discontinued: negative at week 3 |
| TNSL TABLE 13-continued Summary of data on isolation of immortalized human B cells secreting monoclonal antibodies reactive with ricin B chain

| Sample | Date received | # of B cells (×10⁷) | # of plates | # of sub-cloned wells | # of possible clones | Treatment for inducing B cell differentiation | Ricin B specific IgG | Status |
|---|---|---|---|---|---|---|---|---|
| TNSL γ | Jun. 18, 2008 | 12 | 10 | 0 | 0 | Anti-IgM (Fab')2, CD40L, BAFF | Negative | Screening discontinued: negative at week 2 |
| TNSL G | Nov. 19, 2007 | 6.5 | 2 × 24-well | 0 | 0 | Anti-IgM (Fab')2 CD40L, BAFF | Negative | Screening discontinued: negative at week 2 |
| TNSL H | Nov. 19, 2007 | 5.2 | 2 × 24-well | 0 | 0 | Anti-IgM (Fab')2 CD40L, BAFF | Negative | Screening discontinued: negative at week 2 |
| TNSL I | Dec. 10, 2007 | 5.0 | 2 × 24-well | 0 | 0 | Anti-IgM (Fab')2 CD40L, BAFF | Negative | Screening discontinued: negative at week 2 |

TABLE 15

Summary of data on isolation of immortalized human B cells secreting monoclonal antibodies reactive with IL-6

| Sample | Date received | # of B cells (×10⁷) | # of plates | # of sub-cloned wells | # of possible clones | Treatment for inducing B cell differentiation | IL-6 specific IgG | Status |
|---|---|---|---|---|---|---|---|---|
| TNSL R | Mar. 31, 2008 | 21 | 10 | 0 | 0 | Anti-IgM (Fab')2, CD40L, BAFF | Negative | Screening discontinued: negative at week 3 |
| TNSL S | Mar. 31, 2008 | 17 | 10 | 0 | 0 | Anti-IgM (Fab')2, CD40L, BAFF | Negative | Screening discontinued: negative at week 3 |
| TNSL β | Jun. 11, 2008 | 11 | 10 | 0 | 0 | Anti-IgM (Fab')2, CD40L, BAFF | Negative | Screening discontinued: negative at week 2 |
| TNSL γ | Jun. 18, 2008 | 12 | 10 | 0 | 0 | Anti-IgM (Fab')2, CD40L, BAFF | Negative | Screening discontinued: negative at week 2 |

Figures 37A, 37B, 37C:
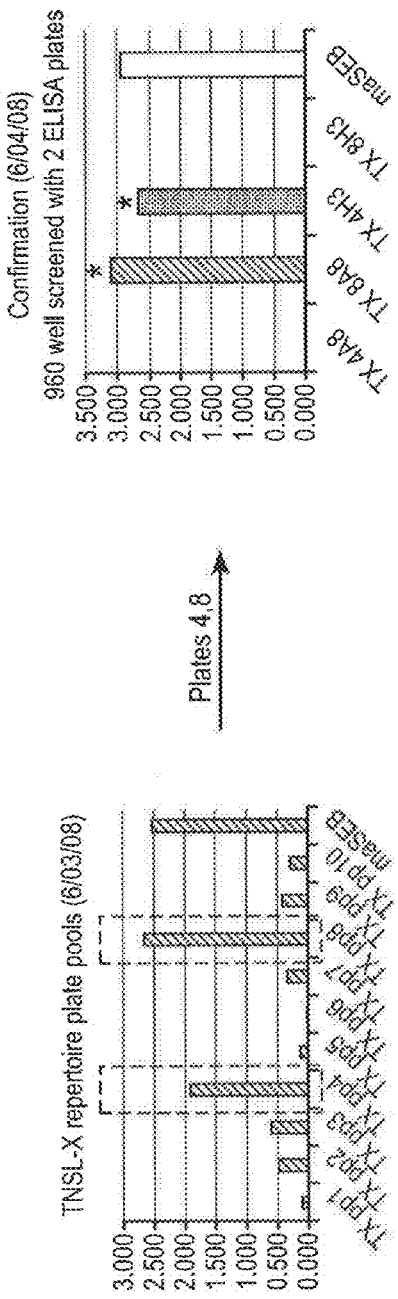
FIGS. 37A-C Rapid screening strategy for SE Bre activity in tonsil X repertoire. Tonsil repertoire TNSL-X was immortalized as summarized in Table 7 and cultured in 10 96-well plates.

Isolation of SEB reactive immortalized cell lines. Culture supernatants for all 11 new tonsil repertoires were screened for SEB reactivity between 10 d and 18 d subsequent to immortalization (summarized in Table 7). An example of the rapid screening strategy used to detect wells with reactive IgG is shown in FIG. 37. Tonsil repertoire TNSL-X (TX) supernatants from 10 96-well plates containing a total of 960 wells were screened with 2 ELISAs containing pooled supernatants from corresponding wells on each of the 10 plates, e.g., well A1 pools, (FIG. 37A), and pooled supernatants from all of the wells on each plate (plate pools, FIG. 37B). FIG. 37A indicated that cells in wells A8 and H3 on one of the 10 plates was reactive with SEB. FIG. 37B indicated that TX plates 2 and 4 contained cells that were SEB reactive. Combining these data in FIG. 37C, the inventors tested wells A8 and H3 on TX plates 4 and 8. The results indicated that well A8 on plate 8 (TX-8A8), and well H3 on plate 4 (TX-4H3) contained the activity. These wells were thus chosen for primary subcloning analysis. As can be seen in Table 8, TX-8A8 and TX-4H3 were subcloned initially on Jun. 4, 2008 into 3 96-well plates each, containing 1,000 cells per well.

TABLE 8

Summary of subcloning of immortalized human B cells secreting monoclonal antibodies reactive with SEB.

| Subclone | Origin | Subclone stage | Date subcloned | # of plates | cells/ well | Unique clone | Possible sib clones | Status |
|---|---|---|---|---|---|---|---|---|
| TS 2B1 | TNSL-S 2B1 | primary | Apr. 29, 2008 | 1 | 100 | yes | none | Lost reactivity |
| TS 8B12 | TNSL-S 8B12 | primary | Apr. 29, 2008 | 1 | 100 | yes | none | Lost reactivity |

TABLE 8-continued

Summary of subcloning of immortalized human B cells secreting monoclonal antibodies reactive with SEB.

| Subclone | Origin | Subclone stage | Date subcloned | # of plates | cells/well | Unique clone | Possible sib clones | Status |
|---|---|---|---|---|---|---|---|---|
| TS 7C2 | TNSL-S 7C2 | primary | Apr. 29, 2008 | 1 | 100 | yes | none | Lost reactivity |
| TR 9D8 | TNSL-R 9D8 | primary | Apr. 29, 2008 | 1 | 100 | yes | none | Lost reactivity |
| TV 6F7 | TNSL-V 6F7 | primary | May 29, 2008 | 3 | 1000 | yes | none | Moderate reactivity in 3/3 plates, 3 wells subloned 6123/08 |
| TV 6F7 2H6 | TNSL-V 6F7 2H6 | secondary | Jun. 23, 2008 | 2 | 50 | no | 3E2, 3E4 | Characterization underway |
| TV 6F7 3E2 | TNSL-V 6F7 3E2 | secondary | Jun. 23, 2008 | 2 | 50 | no | 2H6, 3E4 | Characterization underway |
| TV 6F7 3E4 | TNSL-V 6F7 3E4 | secondary | Jun. 23, 2008 | 2 | 50 | no | 2H6, 3E2 | Characterization underway |
| TX 8A8 | TNSL-X 8A8 | primary | Jun. 4, 2008 | 3 | 1000 | yes | none | Strong reactivity in 3/3 plates 3 wells subcloned |
| TX 8A8 1C6 | TNSL-X 8A8 1C6 | secondary | Jun. 23, 2008 | 2 | 50 | no | 3F4, 3D7 | Characterization underway |
| TX 8A8 3F4 | TNSL-X 8A8 3F4 | secondary | Jun. 23, 2008 | 2 | 50 | no | 1C6, 3D7 | Characterization underway |
| TX 8A8 3D7 | TNSL-X 8A8 3D7 | secondary | Jun. 23, 2008 | 2 | 50 | no | 1C6, 3F4 | Characterization underway |
| TX 4H3 | TNSL-X 4H3 | primary | Jun. 4, 2008 | 3 | 1000 | yes | none | Strong confirmed reactivity in 3/3 plates, 3 secondary subclones made |
| TX 4H3 1E7 | TNSL-X 4H3 1E7 | secondary | Jun. 21, 2008 | 2 | 50 | no | 3C6, 3D8 | Characterization underway |
| TX 4H3 3C6 | TNSL-X 4H3 3C6 | secondary | Jun. 21, 2008 | 2 | 50 | no | 1E7, 3D8 | Characterization underway |
| TX 4H3 3D8 | TNSL-X 4H3 3D8 | secondary | Jun. 21, 2008 | 2 | 50 | no | 1E7, 3C6 | Characterization underway |

As can be seen in FIG. 38B, after 8 days in culture each of these plates contained SEB reactive cells. After 2 weeks in culture, individual wells from each plate were tested for SEB reactivity (FIG. 40 and FIG. 41). Three TX-4H3 wells with the highest reactivity (TX-1E7, -3C6, -3D8, FIG. 40) were chosen for a secondary round of subcloning on Jun. 23, 2008, in which 2 plates were created containing 50 cells per well (Table 8). In addition, three TX-8A8 wells with the highest reactivity (TX-8A8-1C6, -3D7, -3F4, FIG. 41) were chosen for a secondary round of subcloning on Jun. 23, 2008, in which 2 plates were created containing 50 cells per well (Table 8). Cells are currently growing to sufficient levels to test for SEB reactive IgG in individual wells. As can be seen in Table 7 and FIG. 38A, SEB reactive cells were detected in three other repertoires (TNSL-R, -S, -V). Wells containing the reactive cells (TS-2B1, -8B12, TS-7C2, TR-9D8, TV-6F7) were subcloned, and reactivity was detected in cells from the TV-6F7 plates, but was lost from the TS-8B12, TS-7C2 and TR-9D8 cell lines (FIG. 38B). Three TV6F7 wells with the highest reactivity (TV-6F7-2H6, -3E2, -3E4, FIG. 39) were chosen for a secondary round of subcloning on Jun. 23, 2008, in which 2 plates were created containing 50 cells per well (Table 8). Cells are currently growing to sufficient levels to test for SEB reactive IgG in individual wells.

Figure 42A:
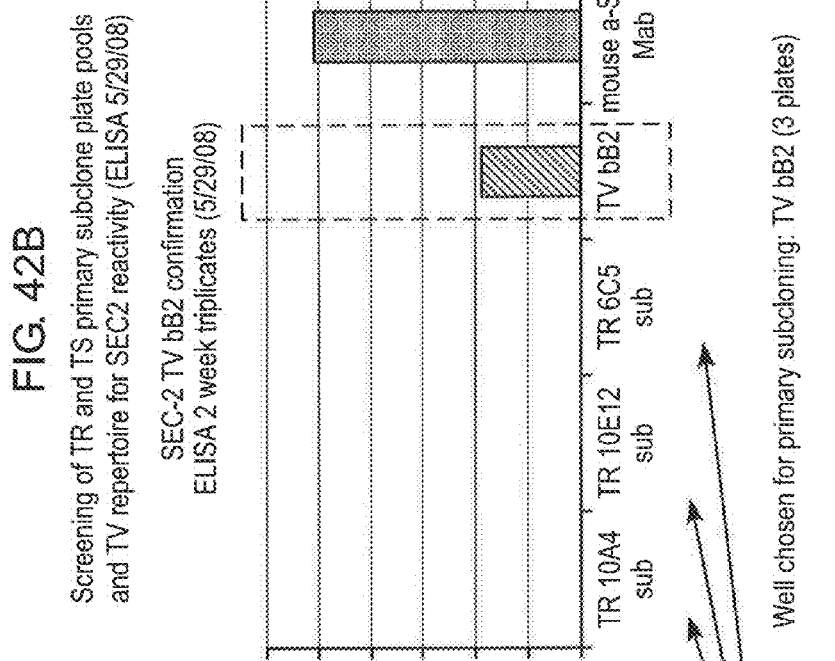
FIGS. 42A-B Confirmation of repertoire SEC2 reactivity and screening of primary subclone plate pools.
Figure 42B:
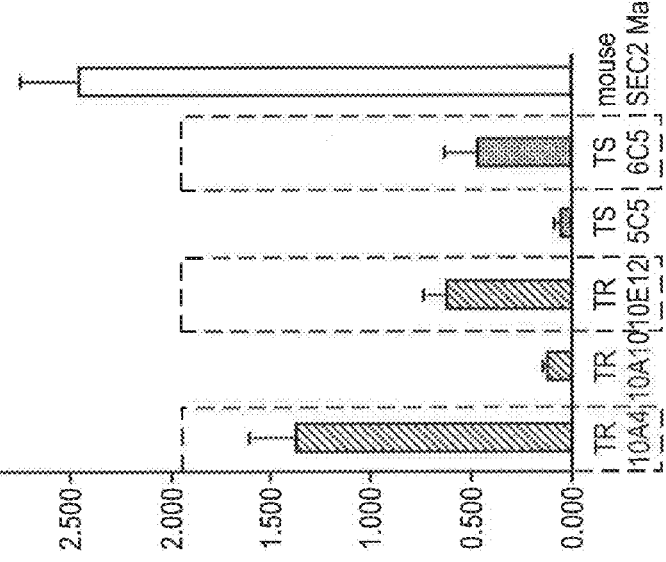
Figure 43A:
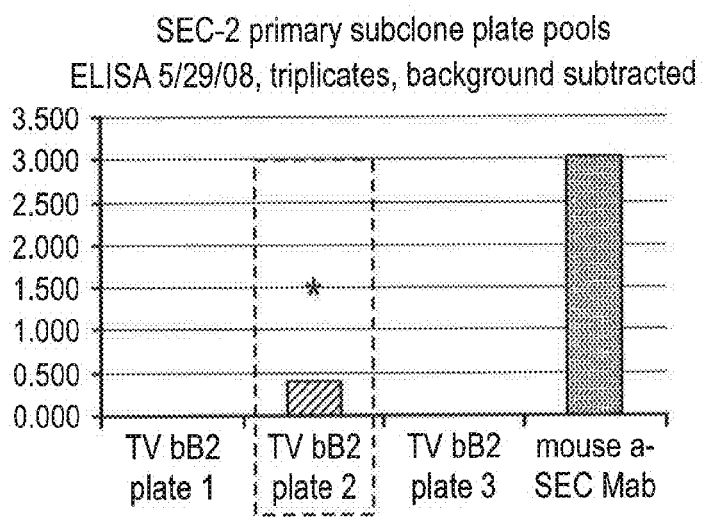

Isolation of SEC2 reactive immortalized cell lines. As can be seen in Table 9 and FIG. 42, SEC2 reactive cells were detected in three tonsil repertoires (TNSL-R, -S, and -V). Wells containing the reactive cells (TR-10A4, TR-10E12, TS-6C5, and TV-bB2) were subcloned, and reactivity was detected in cells from 1 of 3 of the TV-bB2 plates (FIG. 43A), but was lost from the TR-10A4, TR-10E12, TS-6C5 plates (FIG. 42B). Two TV6F7 wells with the highest reactivity (TVbB2 2E1, 2F2, FIG. 43B) were chosen for a secondary round of subcloning on Jun. 23, 2008, in which 2 plates were created containing 50 cells per well (Table 10).

TABLE 10

Summary of subcloning of immortalized human B cells secreting monoclonal antibodies reactive with SEC₂

| Subclone | Origin | Subclone stage | Date subcloned | # of plates | cells/ well | Unique clone | Possible sib clones | Status |
|---|---|---|---|---|---|---|---|---|
| TR 10A4 | TNSL-R 10A4 | primary | Apr. 29, 2008 | 1 | 100 | yes | none | Lost reactivity |
| TR 10E12 | TNSL-R 10E12 | primary | Apr. 29, 2008 | 1 | 100 | yes | none | Lost reactivity |
| TS 6C5 | TNSL-S 6C5 | primary | Apr. 29, 2008 | 1 | 100 | yes | none | Lost reactivity |
| TV bB2 | TNSL-V bB2 | primary | May 29, 2008 | 3 | 500 | yes | none | Weak reactivity in 1/3 plate pools, 2 secondary |
| TV bB2 2E1 | TNSL-V bB2 2E1 | secondary | Jun. 23, 2008 | 2 | 50 | no | 2F2 | Characterization underway |
| TV bB2 2F2 | TNSL-V bB2 2F2 | secondary | Jun. 23, 2008 | 2 | 50 | no | 2E1 | Characterization underway |

Figure 45A:
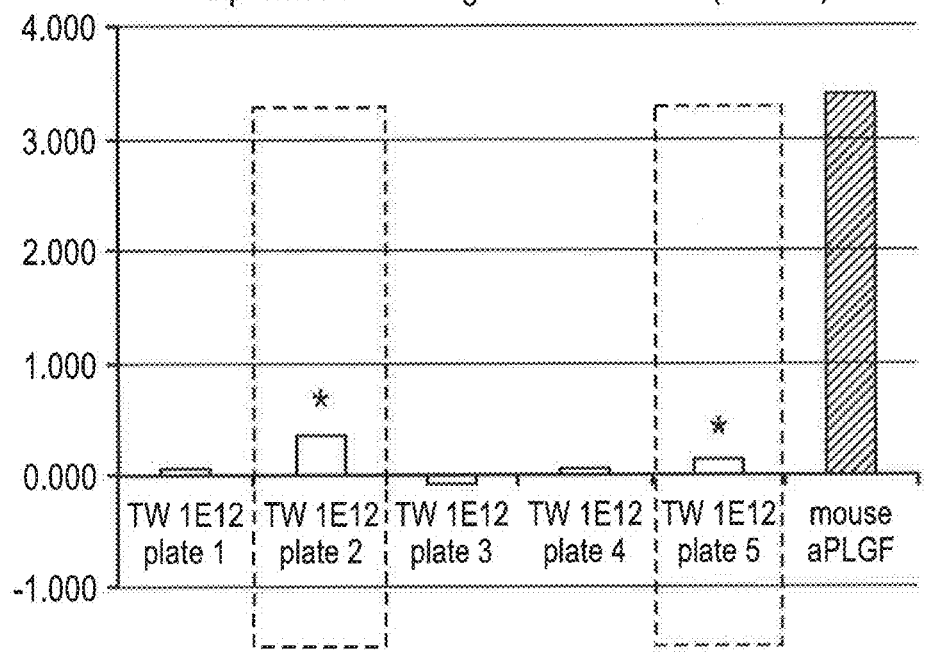

Isolation of PLGF reactive immortalized cell lines. As can be seen in Table 11 and FIG. 44 and FIG. 46, PLGF reactive cells were detected in two tonsil repertoires (TNSL-W, and -Z). Wells containing the reactive cells (TW-1E12, FIG. 44; TZ-3B10 and TZ-5F9, FIG. 46) were subcloned. Two of 5 subcloned TW-1E12 plates were PLGF reactive (FIG. 45A). Individual wells on these plates were screened and 3 wells with the highest reactivity (TW 2E3, 2G9, 5A10) were chosen for a secondary round of subcloning on Jun. 23, 2008, in which 2 plates were created for each containing 50 cells per well (Table 12). Cells are currently growing to sufficient levels to test for PLGF reactive IgG in individual wells.

TABLE 12

Summary of subcloning of immortalized human B cells secreting monoclonal antibodies reactive with PLGF.

| Subclone | Origin | Subclone stage | Date subcloned | # of plates | cells/ well | Unique clone | Possible sib clones | Status |
|---|---|---|---|---|---|---|---|---|
| TW 1E12 | TNSL-W 1E12 | primary | May 29, 2008 | 5 | 1000 | yes | none | Weak reactivity in 2/5 plate pools, 3 secondary |
| TW 1E12 2E3 | TNSL-W 1E12 2E3 | secondary | Jun. 23, 2008 | 2 | 50 | no | TW 1E12 2G9, TVV 1E12 5A10 | Characterization underway |
| TW 1E12 2G9 | TNSL-W 1E12 2G9 | secondary | Jun. 23, 2008 | 2 | 50 | no | TVV 1E12 2E3, TW 1E12 5A10 | Characterization underway |
| TW 1E12 5A10 | TNSL-W 1E12 5A10 | secondary | Jun. 23, 2008 | 2 | 50 | no | TW 1E12 2G9, TW 1E12 2E3 | Characterization underway |
| TZ 3B10 | TNSL-Z 3B10 | primary | Jun. 13, 2008 | 3 | 1000 | yes | none | Characterization underway |
| TZ 5F9 | TNSL-Z 5F9 | primary | Jun. 13, 2008 | 3 | 1000 | yes | none | Characterization underway |

Figure 49:
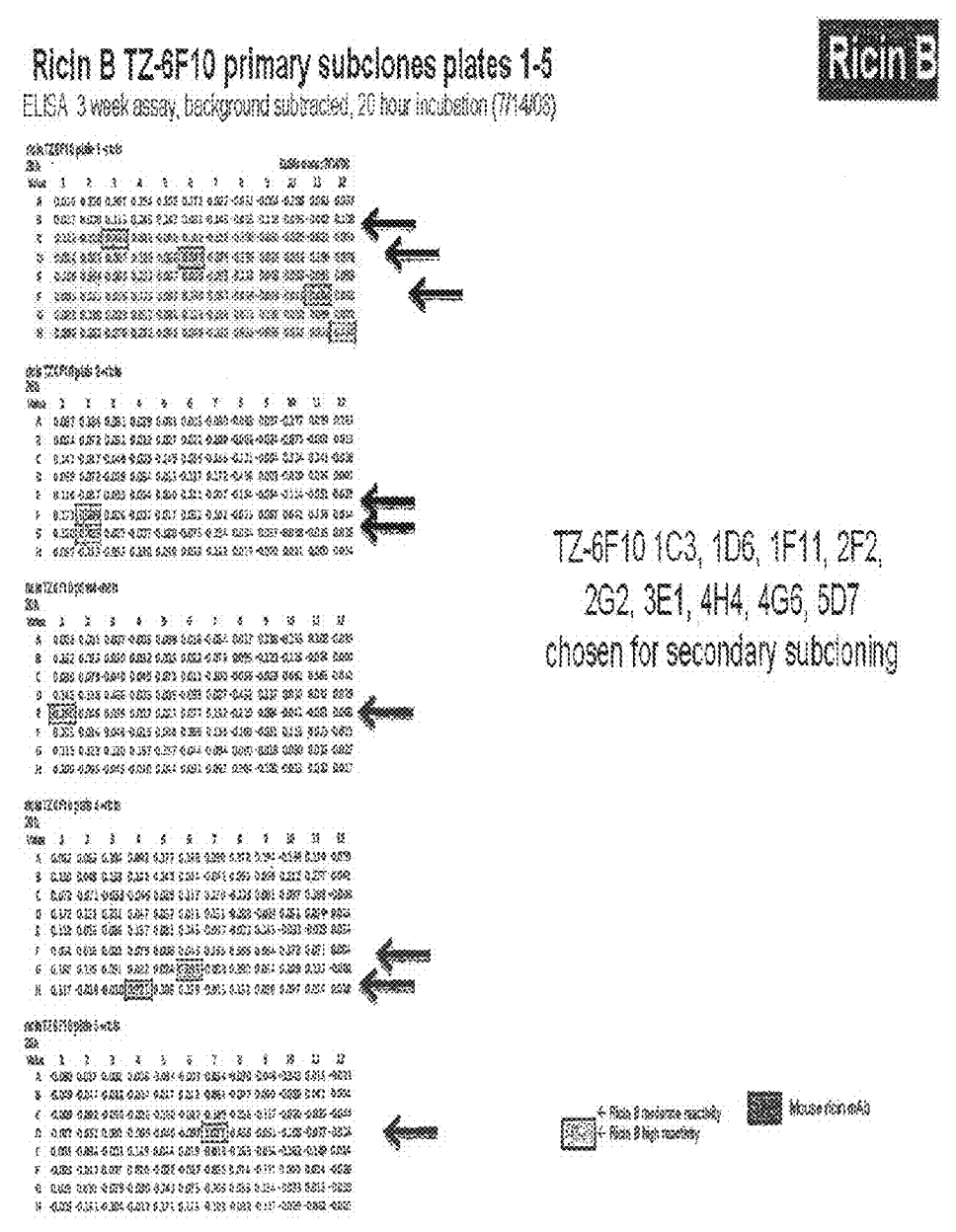

Isolation of ricin subunit B reactive immortalized cell lines. As can be seen in Table 13 and FIG. 47C, ricin subunit B reactive cells were detected in two wells of tonsil repertoire TNSL-Z (TZ-7B8 and TZ-6F10). Wells containing the reactive cells were subcloned on Jun. 21, 2008, 5 96-well plates each containing 50 cells per well (Table 14). Individual wells on these plates were screened on Jul. 14, 2008 and wells with the highest reactivity (TZ-7B8-1A12, -1E3, -2A1, -2A3, -4A1, FIG. 48) and (TZ-6F10 1C3, 1D6, 1F 11, 2F2, 2G2, 3E1, 4H4, 4G6 5D7, FIG. 49) were chosen for a secondary round of subcloning, and for sequencing.

TABLE 14

Summary of subcloning of immortalized human B cells secreting monoclonal antibodies reactive with ricin B chain.

| Subclone | Origin | Subclone stage | Date subcloned | # of plates | cells/ well | Unique clone | Possible sib clones | Status |
|---|---|---|---|---|---|---|---|---|
| TZ 7B8 | TNSL-Z 7B8 | primary | Jun. 21, 2008 | 5 | 50 | yes | none | Positive wells detected on 3/5 plates, screened Jul. 14, 2008 |
| TZ 6F10 | TNSL-Z 6F10 | primary | Jun. 21, 2008 | 5 | 50 | yes | none | Positive wells detected on 4/5 plates, screened Jul. 14, 2008 |

Figure 12:
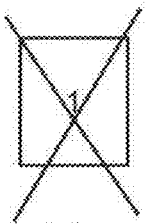
FIG. 12. Subcloning strategy of H5 HA specific B cells found in plate 2 well D11, from PBMC A1 sample. EBV-immortalized B cells from PBMC A1 were stimulated to produce IgG with IL-4, IL-6, BAFF and anti-human IgM (Fab')$_2$ (see Example 1), and cultured in three 96-well plates ($10^4$ cells per well). H5 HA binding was determined as described in Example 1. Culture supernatants from all wells on each plate were collected (150 µl per well), and 50 µl per well were pooled and assayed for H5 HA binding. All plates contained H5 HA-reactive IgG after two weeks and culture supernatant from individual rows on these plates were pooled and assayed on week 3. Plate 1 row E, Plate 2 rows C, D and E, and Plate 3 row D had significant H5 HA binding. Culture supernatants from dual adjacent wells on each reactive row were assayed on week 4, identifying wells 5 and 6 on Plate 1, row E, and wells 11 and 12, on Plate 2, row D as having H5 HA binding. On week 5, reactive well D11 on Plate 2 was identified in a similar manner, and cells from this well were subcloned by limiting dilution analysis in 96-well plates containing 1, 10, 100, or 1000 cells per well. At weekly intervals thereafter, culture supernatants from all wells on each plate were pooled and tested by ELISA for H5 HA binding. Identification of a potentially clonal population secreting IgG reactive with H5 HA was isolated from well D11 of the plate containing 1 cell per well on week 8. The isolation strategy is summarized.
Figure 59A2:
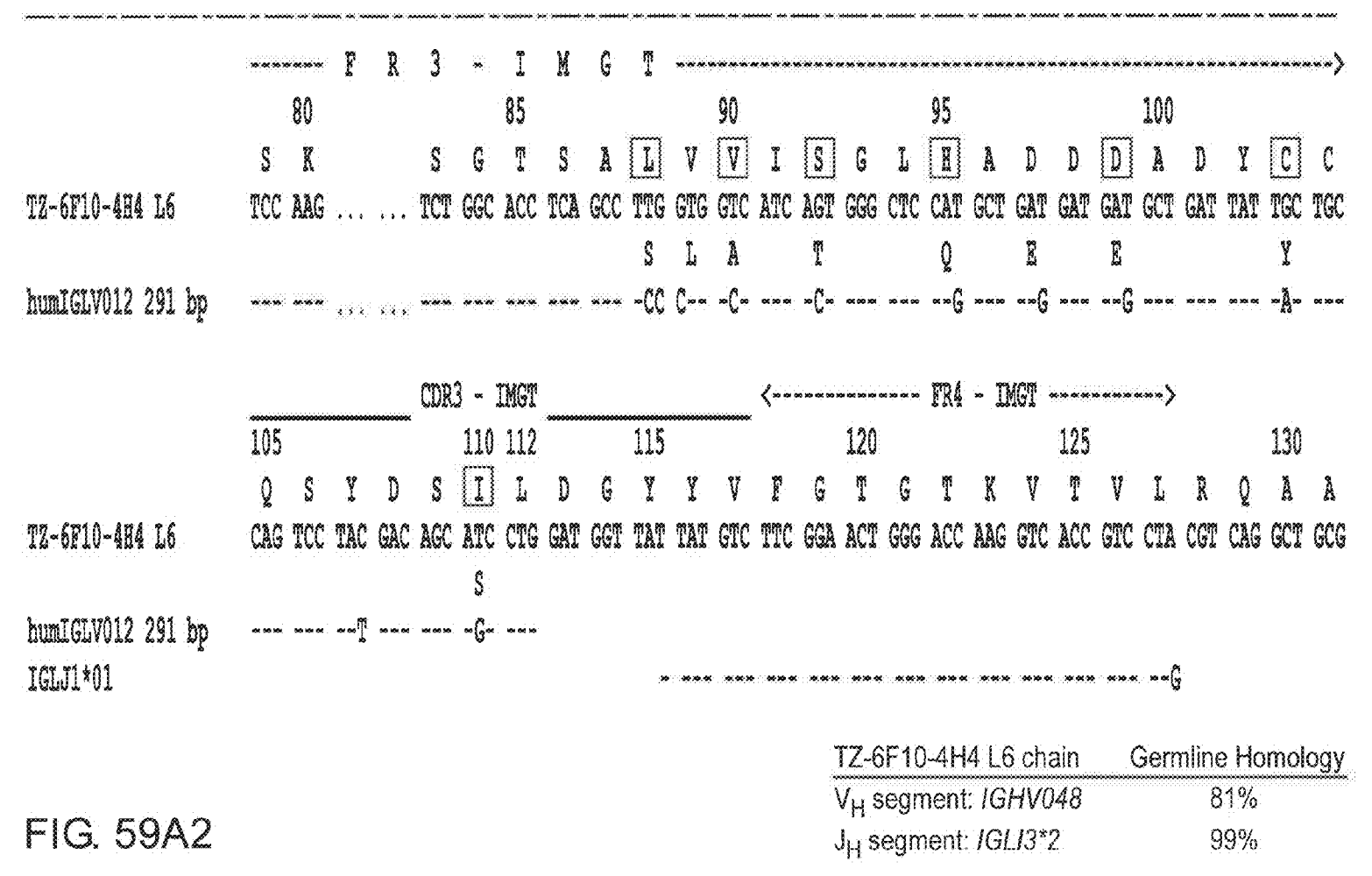

Characterization of Ricin subunit B reactive cells TZ-6F10$^{-4}$H4 and TZ 7B8-2A3. Two weeks after the secondary round of subcloning (25-500 cells per well), culture supernatant from individual wells was tested in triplicate for Ricin subunit B reactivity by ELISA. As can be seen in FIG. 58A, 12/20 wells containing secondary subcloned cells had variable levels of ricin B reactivity. Cells in wells TZ-6F10-4H4 and TZ-7B8-2A3 were chosen for immunoglobulin sequencing analysis. RT-PCR was performed using the primers described in FIG. 54A, as described previously. In each well, 2 light chain and heavy chain sequences were identified, consisting of λ1/3 and λ6, $V_{H1}$ and $V_{H3}$. PCR amplification products were sequenced. Sequencing indicated that the light chain immunoglobulin variable region for TZ-6F10-4H4 was composed of IGLV048 and IGLJ03*2 gene segments (FIG. 59A) (SEQ ID NOS:41 and 42). The $V_{H3}$ heavy chain immunoglobulin variable region was composed of IGHV035 (FIG. 59B) (SEQ ID NOS:45 and 46). While the light chain region had >99% homology to germline sequences, the heavy chain region was hypermutated with 89% $V_H$ germline homology; the obtained sequences were compared against the germline sequences and are presented in FIGS. 59A and B. The complentarity determining regions of the heavy and light chains are identified in FIG. 59F. Sequencing indicated that the λ3 light chain immunoglobulin variable region for TZ-7B8-2A3 was composed of IGLV063 and IGLJ03*2 gene segments (FIG. 59C) (SEQ ID NOS:49 and 50). A second λ6 light chain sequence was identified in cells in well TZ-7B8-2A3, composed of ILGVO48 and IGLJ3*02 gene segments (FIG. 59D) (SEQ ID NOS:52 and 53). The $V_{H1}$ heavy chain immunoglobulin variable region was composed of IGHV157, IGHD3-10*2, IGHJ04*2 (FIG. 59E) (SEQ ID NOS:57 and 58). While the light chain regions had >98% homology to germline sequences, the heavy chain region was hypermutated with 96% $V_H$ germline homology, 46% $D_H$ and 81% $J_H$ homology to germline; the obtained sequences compared against the germline sequences are presented in FIGS. 59C-E. The complentarity determining regions of the heavy and light chains are identified in FIG. 59F (SEQ ID NOS:60, 61, 62, 63, and 64).

Screening for IL6 reactive immortalized cell lines. As can be seen in Table 15, four immortalized cell lines were tested for IL6 reactivity, and so far there have been no IL6 specific cell lines detected.

Example 5

Materials & Methods for Human B-Cells Secreting Antibodies Reactive with H5 HA

Generation and analysis of tonsil and peripheral blood derived B cell repertoires. Generation of concentrated EBV stocks and preparation of B cells from tonsil tissue and peripheral blood samples have been described previously. For induction of differentiation of EBV immortalized B cells, complete RPMI medium containing soluble CD40 ligand (5 ng/ml), BAFF (10 ng/ml), and goat anti-human IgM F(ab')$_2$ (1.62 ng/ml) were used, as previously described.

Sample collection for ELISA analysis. Collection and screening of sample culture supernatants for H5 HA reactivity by ELISA have been modified as follows. Culture supernatants were collected into corresponding wells on a 96-well plate on day 10 post-transduction at 100 μl from each well, and aliquots were pooled (30 μl of supernatant from all wells on each plate) and screened by ELISA for H5 HA reactivity. The culture supernatant was replaced with 100 μl fresh RPMI medium containing CD40L, BAFF and anti-human IgM(Fab')$_2$. If H5 HA reactivity was detected in pooled wells, each of the individual wells contributing to the pool was subcloned into 5 new wells to preserve viability while the identity of the positive well was confirmed by additional ELISA experiments. Once an individual well containing H5 HA reactive IgG had been identified in the rapid screening strategy, cells from that well were counted, and 50-80% of them were subcloned into 96-well plates (~500 cells per well, depending upon the count), while the remainder were frozen. At various times after subcloning, supernatants were collected as outlined above and rapid screening analysis was repeated. This was followed by additional rounds of limiting dilution subcloning and screening. Clonality was assumed when at the lowest dilution, all wells on the plate were producing anti-H5 HA reactive IgG.

H5 HA and HIS-tagged H5 HA ELISA. His tagged recombinant H5 HA (strain H5N1 A/Vietnam/1203/2004) was obtained from Immune Technology Corp (# IT-003-0051p). This protein (H5 a.a. 18-530) has N-terminal 6 histidine (6×His) tag and a deletion at the HA cleavage site (ΔRRRKKR). His-tagged H5 HA was prepared in a neutral pH binding buffer (1×DPBS, pH 7.2) at 2 μg/ml for coating wells of 96-well ELISA plates (50 μl per well); sealed plates were allowed to bind overnight at 4° C. Non-specific binding for each sample and control was evaluated in triplicate by comparing results obtained from H5 HA coated wells vs. an equal number of uncoated wells that received binding buffer only. Next day, the plates were washed, blocked with a neutral pH blocking solution (SuperBlock-TBS, pH 7.4, from Pierce) plus 0.1% Tween 20, and incubated with samples or controls (100 μl per well) in triplicate wells. Controls consisted of human serum from volunteer (V5), previously found to be H5 HA reactive (diluted 1:500 in RPMI culture medium), and nonreactive purified human IgG (500 ng per 0.1 ml RPMI culture medium, Sigma). After extensive washes, alkaline phosphatase-labeled goat anti-human IgG (Southern) was added to each well, followed by colorimetric substrate reaction and detection. Average $OD_{405}$ values±standard deviations (n=3) for H5 HA binding (with average non-specific binding subtracted) are shown in all graphs.

Enrichment of cell populations expressing anti-H5 HA Ig using magnetic beads coupled to HIS-tagged H5 HA. Two different bead systems were employed. Amounts of reagents are given per $1 \times 10^6$ cells to be screened, and were changed accordingly with different cell numbers. For THE™ Anti-His MagBeads (GenScript Corporation, #L00275), 0.5 mg (50 μl of stock) beads were washed 3× with 2 ml cold DPBS, and re-suspended in 0.2 ml cold Washing Buffer 1 (DPBS plus 0.2% BSA and 20 mM EDTA). Washed beads were mixed on ice with 0.5 μg of HIS-tagged H5 HA and incubated on ice with shaking for 1 hour, then washed twice with WB1. For the MagnaBead® Biotin Binder (Invitrogen, #110.47), 15 μl of beads (at $4 \times 10^8$ beads per ml) are washed 3× with cold DPBS and re-suspended in 0.2 ml cold WB1. Beads are mixed on ice with 1 μg of THE™ Anti-His mAb[biotin] (GenScript, #A00613) and 1 μg HIS-tagged H5 HA and incubated on ice with shaking for 1 hour, then washed twice with WB1. For either bead::his-H5 HA complex, $1 \times 10^6$ cells that have been washed 3× with DPBS are resuspended in 0.2 ml of WB1 and combined with the bead complex. The tube is shaken on ice for 30 minutes. The suspension is brought to 10 ml with ice-cold WB1 and placed in the EasySep magnet for a 3 min separation. The supernatant containing unbound cells (referred to as flow-through or FT) is collected, and the bead-cell retentate is washed twice with 10 ml of WB1. Next, 3 ml of room-temperature trypsin-EDTA solution (Mediatech Cellgro #21-053-C1) is added and incubated for 5 min at RT. Then, 7 ml of complete culture media is added to inactivate trypsin, and the cells no longer attached to beads (trypsin wash fraction) are collected. The beads are washed twice with 10 ml WB1, and re-suspended in 1 ml of complete culture media (trypsin bead fraction). The FT and trypsin wash fractions are counted, centrifuged for 7 min at 1600 rpm, re-suspended in complete RPMI media, and dispensed into wells of a 96-well plate at $1 \times 10^4$ to $5 \times 10^4$ cells per well.

Identification of IgG subtypes. TN-6G7-7F8-2G7 culture supernatants were collected and dispensed into wells of a 96-well ELISA plate pre-coated with anti-human IgG and blocked with SuperBlock plus 0.1% Tween-20, as described in previous sections. After blocking, plates were washed extensively, then incubated with 100 μl of one of the four subtype-specific alkaline phoshatase-labeled murine monoclonal antibodies: anti-Hu $IgG_1$ (Invitrogen 05-3322), anti-Hu $IgG_2$ (Invitrogen 05-3522), anti-Hu $IgG_3$ (Invitrogen 05-3622), and anti-Hu $IgG_4$ (Invitrogen 05-3722). All antibodies were diluted in the block solution at 1:250. One hour incubation with antibodies was followed by colorimetric substrate reaction and detection. Average $OD_{405}$ values±standard deviations (n=3) were reported.

Analysis of the heavy and light chain variable region sequences of clone TN-6G7-7F8-2G7. Total RNA was extracted from approximately $10^5$-$10^6$ cells using RNEasy protocol (Qiagen, #74104) with QIAshredder columns (Qiagen, #79654). RNA was converted to cDNA with the High Capacity cDNA Reverse Transcription Kit according to manufacturer's instructions (Applied Biosystems, #4368813) and analyzed by PCR for light and heavy chain type content using a set of primers adapted from Welschof et al. (1995) (see Figure×A). All forward primers incorporated an XbaI restriction site, while the reverse primers incorporated a SalI restriction site. PCR products were analyzed on 1% agarose gel (Figure×B). Reactions that resulted in detectable product were scaled up using the proofreading Accuzyme™ Mix kit (Bioline, # BIO-25027). PCR products were gel-purified using QIAquick Gel Extraction Kit (Qiagen, #28704), and a portion of each was submitted for sequencing to the MUSC DNA Core Facility with the original forward and reverse PCR primers. The remainder of each product was digested with XbaI and SalI (New England Biolabs), and cloned into XbaI/SalI digested a similarly digested pSP73 plasmid (Promega, # P2221) for subsequent subcloning into mammalian expression vectors. Forward and reverse DNA sequences were aligned using VectorNTI (Invitrogen) ALIGN function, and combined corrected sequences were generated. These were analyzed using VBASE2 online software (Retter et al., 2005). Sequence numbering and motif alignments were performed according to Kabat standards (Johnson and Wu, 2000).

Example 6

Results for Human B-Cells Secreting Antibodies Reactive with H5 HA

Derivation of TN-6G7-7F8-2G7 cells. Human tonsil derived immortalized B cell repertoires were created as summarized in Table 16. All were screened for H5N1 hemagglutinin (H5 HA) reactivity at 10-14 days post-infection with Epstein-Barr virus (EBV). TN-6G7-7F8-2G7 cells were derived from tonsil repertoire TNSL-N (highlighted in yellow on Table 16). Culture supernatants were screened using the rapid screening ELISA method comprised of testing plate pools (pooled aliquots of culture supernatants derived from all wells in a single plate) and well pools (pooled aliquots from a particular well in same location on all 10 plates). As shown in FIG. 50, correlation of these data allowed for rapid identification of individual positive wells. As seen in FIG. 50A, ELISA analysis of culture supernatant from pooled wells indicated that H5 HA reactive IgG was found in well G7 on at least one of the 10 plates. FIG. 50B indicated that the reactivity was highest on plate 6. Verification of reactivity in culture supernatant from positive wells was conducted the following day. The ELISA was performed in triplicate with background binding to the plate (in the absence of H5 HA antigen) subtracted from the results. FIG. 50C indicated that plate 6 well G7 had the highest reactivity; thus, cells from well 6G7 were subcloned at 500 cells/well into ten 96-well plates, referred to as the primary round of subcloning. Two weeks later, culture supernatants from the subcloned cells were screened for H5 HA reactivity using a similar rapid screening strategy (FIG. 51). As can be seen in FIG. 51A, H5 HA reactivity was identified in multiple wells, with C8 and F8 having the highest reactivity. FIG. 51B indicated that significant H5 HA reactivity was detected on plates 2, 3, 5, 7 and 8; therefore culture supernatants from wells C8 and F8 were tested on each of these plates. As can be seen in FIG. 51C, wells 2C8, 8C8, and 7F8 contained the activity, with well 7F8 having the highest reactivity. Cells from that well were therefore subcloned at 500 cells per well into two plates, referred to as the secondary round of subcloning. Three weeks later, culture supernatants from wells pools from both plates were screened by ELISA for H5 HA reactivity. As can be seen in FIG. 52A, multiple wells were positive, with well G7 having the highest reactivity. FIG. 52B indicated that the strongest reactivity derived from culture supernatant in plate 2 well G7; thus, cells from this well were subcloned at 50 cells per well into two 96-well plates, referred to as the tertiary round of subcloning. Fungal contamination four weeks later necessitated that the process be repeated using an aliquot of frozen cells derived from the same well. Four weeks later, it was found that all wells on both subcloned plates were H5 HA reactive, indicative of clonality FIG. 53A. The subcloning strategy was summarized in Table 17.

TABLE 16

Summary of data on isolation of immortalized human B cells secreting antibodies reactive with H5 HA

| Sample | Date received | # of B cells (×107) | # of plates | # of sub-cloned wells | # of possible clones | Treatment for inducing B cell differentiation | H5 HA specific IgG | Status |
|---|---|---|---|---|---|---|---|---|
| PBMC A1 | Jan. 16, 2007 | 0.2 | 3 | 1 | 0 | Anti-IgM (Fab)2, IL-4, IL6 | Positive originally | Subcloned 1 well: PA1-2D11 lost reactivity |
| PBMC B | Feb. 16, 2007 | 0.2 | 3 | 0 | 0 | Anti-19M (Fab')2, IL-4, IL6 | Negative | Screening discontinued: negative at week 3 |
| PBMC A2 | Mar. 14, 2007 | 0.6 | 6 | 3 | 0 | Anti-IgM (Fab)2, CD4OL, BAFF | Positive originally | Subcloned 3 wells; lost reactivity |
| PBMC C | Sep. 22, 2007 | 3 | 10 | 1 | 1 | Anti-IgM (Fab)2, CD4OL, BAFF | Positive originally | Subcloned 1 well (PC-9F9) lost reactivity |
| PBMC A3 | Jan. 28, 2008 | 4 | 10 | 2 | 2 | Anti-IgM (Fab')2, CD4OL, BAFF | Positive originally | Subcloned 2 wells: (PA3-4F5, PA3-3F2) lost reactivity |
| TNSL A | Jan. 22, 2007 | 20 | 10 | 2 | 0 | Anti-IgM (Fab')2, IL-4, IL6 | Positive lost | Screening discontinued: week 3 fungal contamination |
| TNSL B | Mar. 26, 2007 | 20 | 10 | 0 | 0 | Anti-IgM (Fab)2. CD4OL, BAFF | Negative | Screening discontinued: negative at week 4 |
| TNSL C | Apr. 16, 2007 | 22 | 10 | 0 | 0 | Anti-IgM (Fab')2. CD4OL, BAFF | Negative | Screening discontinued: negative at week 3 |
| TNSL D | Apr. 23, 2007 | 15 | 10 | 1 | 0 | Anti-IgM (Fal: 02, CD4OL, BAFF | Positive originally | Subcloned 1 well; lost reactivity |
| TNSL E | May 14, 2007 | 4 | 4 | 1 | 2 | Anti-IgM (Fab')2, CD4OL, BAFF | Positive | Subcloned 1 well, 2 clones: (TE-3A10-E3A5, TE-3A10-C7F6) |
| TNSL F | Sep. 24, 2007 | 20 | 10 | 0 | 0 | Anti-IgM (Fab')2, CD4OL, BAFF | Negative | Screening discontinued: negative at week 3 |
| TNSL G | Nov. 19, 2007 | 13 | 10 | 0 | 0 | Anti-IgM (Fab)2, CD4OL, BAFF | Negative | Screening discontinued: negative at week 3 |
| TNSL H | Nov. 19, 2007 | 12.5 | 10 | 0 | 0 | Anti-IgM (Fab')2, CD4OL, BAFF | Negative | Screening discontinued: negative at week 3 |
| TNSL I | Dec. 10, 2007 | 10 | 10 | 0 | 0 | Anti-IgM (Fab.)2, CD4OL, BAFF | Negative | Screening discontinued: negative at week 4 |
| TNSL J | Jan. 07, 2008 | 11 | 10 | 2 | 2 | Anti-IgM (Fab12, CD4OL, BAFF | Positive | Subcloned 2 wells: (TJ-1G6, TJ-1C8) 2 tertiary subclones underway |
| TNSL K | Jan. 14, 2008 | 13.5 | 10 | 0 | 0 | Anti-IgM (Fab)2, CD4OL, BAFF | Negative | Screening discontinued: negative at week 3 |
| TNSL L | Feb. 01, 2008 | 8 | 10 | 0 | 0 | Anti-IgM (Fab)2, CD4OL, BAFF | Negative | Screening discontinued: negative at week 3 |
| TNSL M | Feb. 05, 2008 | 17 | 10 | 2 | 2 | Anti-IgM (Fab')2, CD4OL, BAFF | Positive originally | Subcloned 2 wells: (TM-7C2, TM-7F8) reactivity lost |
| TNSL N | Feb. 05, 2008 | 5 | 10 | 1 | 1 | Anti-IgM (Fab)2 CD4OL, BAFF | Positive | Subcloned 1 well (TN-6G7) Isolated clone TN-6G7-7F8-2G7 |
| TNSL 0 | Feb. 06, 2008 | 23 | 10 | 0 | 0 | Anti-IgM (Fab)2, CD4OL, BAFF | Negative | Screening discontinued: negative at week 2 |
| TNSL P | Mar. 11, 2008 | 27 | 10 | 1 | 1 | Anti-IgM (Fab)2, CD4OL, BAFF | Positive | Subcloned 1 well: (TP-2C2) secondary subclones underway |
| TNSL Q | Mar. 18, 2008 | 18.8 | 10 | 0 | 0 | Anti-IgM (Fab)2, CD4OL, BAFF | Negative | Screening discontinued: negative at week 2 |
| TNSL R | Mar. 31, 2008 | 21 | 10 | 1 | 1 | Anti-I9M (Fab)2, CD4OL, BAFF | Positive originally | Subcloned 1 well; (TR-8E9) lost reactivity |
| TNSL S | Mar. 31, 2008 | 17 | 10 | 2 | 2 | Anti-IgM (Fab')2, CD4OL, BAFF | Positive originally | Subcloned 2 wells (TS-801, TS-1A8); lost reactivity |
| TNSL V | May 2, 2008 | 8 | 10 | 0 | 0 | Anti-IgM (Fab2,') CD4OL, BAFF | Negative | Bead assay used; Screening discontinued: negative at week 3 |
| TNSL W | May 14, 2008 | 14 | 10 | 0 | 0 | Anti-IgM (Fab)2. CD4OL, BAFF | Negative | Screening discontinued: negative at week 2 |
| TNSL X | May 19, 2008 | 11 | 10 | 0 | 0 | Anti-19M (Fab')2, CD4OL, BAFF | Negative | Screening discontinued: negative at week 2 |
| TNSL Z | Jun. 2, 2008 | 12.5 | 10 | 3 | 3 | Anti-IgM (Fab')2, CD4OL, BAFF | Positive | Subcloned 3 wells: (TZ-4F12, TZ-1001, TZ-10G9) |

TABLE 16-continued Summary of data on isolation of immortalized human B cells secreting antibodies reactive with H5 HA

| Sample | Date received | # of B cells (×107) | # of plates | # of sub-cloned wells | # of possible clones | Treatment for inducing B cell differentiation | H5 HA specific IgG | Status |
|---|---|---|---|---|---|---|---|---|
| TNSL α | Jun. 6, 2008 | 7 | 10 | 1 | 1 | Anti-IgM (Fab')2, CD4OL, BAFF | Positive | Subcloned 1 well: (TGt-6G8) |
| TNSL β | Jun. 11, 2008 | 11 | 10 | 0 | 0 | Anti-IgM (Fab.)2, CD4OL, BAFF | Negative | Screening discontinued: negative at week 2 |
| TNSL γ | Jun. 18, 2008 | 12 | 10 | TBD | TBD | Anti-19M (Fab)2, CD4OL, BAFF | TBD | Screening underway (Jun. 29, 2008) |

TABLE 17

Summary of subcloning of TN-6G7 immortalized human B cells secreting antibodies reactive with H5 HA

| Subclone | Origin/Well | Subclone stage | Date subcloned | # of plates | cells/ well | Clonal | Status |
|---|---|---|---|---|---|---|---|
| TN-6G7 | TNSL-N/ well 6G7 | primary | Mar. 5, 2008 | 10 | 500 | no | 3 wells identified with H5 HA reactivity: 2C8, 808, 7F8 (3120108) |
| TN-6G7-7F8 | TNSL-N/ well 607 | secondary | Apr. 01, 2008 | 2 | 500 | no | Well 2G7 identified with H5 HA reactivity (412108) |
| TN-607-7F8-2G7 | TNSL-N/ well 6G7/ well 7F8 | tertiary | 06110108 | 2 | 50 | yes | All wells identified with H5 HA reactivity (Jun. 25, 2008); Ig genes sequenced |

Characterization of TN-6G7-7F8-2G7 cells.Subtyping of IgG in culture supernatant from TN-6G7-7F8-2G7 cells indicated that the cells secreted $IgG_1$ (FIG. 53B). This was confirmed and further analyzed by RT-PCR analysis (FIG. 54), which indicated that the cells expressed λ1 light chain and $V_{H3}$ heavy chain (FIG. 54B). Sequencing of the PCR amplification product indicated that the light chain immunoglobulin variable region was composed of IGLV015 and IGLJ2*01 gene segments (FIG. 55A) (SEQ ID NOS:32 and 33). The heavy chain immunoglobulin variable region was composed of IGHV318, IGHD4-23*1, and IGHJ4*3 (FIG. 55B) (SEQ ID NOS:36 and 37). While the light chain region had >99% homology to germline sequences, the heavy chain region was hypermutated with 92% $V_H$ germline homology, 56% $D_H$ and 80% $J_H$ homology to germline; the obtained sequences compared against the germline sequences are presented in FIGS. 55A and 55B. The complentarity determining regions of the heavy and light chains are identified in FIG. 55C (SEQ ID NOS:39 and 40).

Example 7

Determination of Dissociation Constants ($K_d$) for TE-3A10-E3A5 Monoclonal Antibody by Competition ELISA Dissociation constants are a measure of the affinity of antibody for the antigen. The lower the dissociation constant, the higher the affinity. Generally, antibodies with Kd less than $10^{-8}$ are considered in the therapeutic range. In order to calculate the antibody dissociation constant for E3A5 monoclonal antibody, the investigators needed to know the antigen-antibody complex concentration at equilibrium, the total antibody concentration, and the amount of antigen sites at equilibrium. These were then used to generate a Scatchard plot. The Scatchard equation is $[x]/[Ag]=([AbT]-[x])/K_d$, where [x] and [Ag] are antibody-antigen complex and antigen concentrations at equilibrium, respectively, and [AbT] is the total antibody concentration. The investigators used the method presented by Friguet et al. (1985), where the antigen-antibody equilibrium is pre-established prior to exposure to coated antigen. If the coated antigen interacts with only a small fraction of free antibody (10% or less), it will not significantly shift the equilibrium, thus ensuring that the true affinity is being measured. The reciprocal of the affinity constant then yields the dissociation constant, $K_d$, where $K_a=1/K_d$.

Determination of the amount of antibody interacting with the coated antigen. As mentioned above, it was crucial that no more than 10% of antibody binds to antigen on the plate. To determine if that condition was met, the wells in two identical 96-well plates were coated with his-H5 HA, 100 μl per well at 500 ng/ml in DPBS, overnight at 4° C. Next day, a 2-fold dilution series of E3A5 was set up, using RPMI 1640 complete media as diluent. After the plates were washed and blocked according to standard H5 HA ELISA protocols, the antibody dilutions were placed in the wells in triplicate, 100 μl per well of plate 1 and incubated for 15 min at room temperature. Next, the contents of all the wells on plate 1 were transferred to their exact counterparts on plate 2, followed by a second 15 min incubation. Subsequently, both plates were washed and exposed for 1 hour to alkaline phosphatase-coupled goat anti-human IgG Fc detection antibody diluted 1:10,000 in blocking buffer, at 100 μl per well. Following a colorimetric substrate reaction and detection, average $OD_{405}$ values±standard deviations (n=3) were obtained and plotted against the relevant antibody concentrations. Lines were fitted to the data points, and line slopes for plate 1 ($S_1$) and 2 ($S_2$) were determined. Level of antibody binding to coated antigen was calculated by the formula $S_1-S_2/S_1$. A value of 0.1 or less indicates that 10% or less of the antibody bound to the antigen coating the plate.

Determination of Kd. A 96-well plate coated with H5 HA antigen was prepared as described. Solutions containing E3A5 at 18 ng/ml were prepared with complete media. His-H5 HA (75 kDa) was prepared at 10 different concentration as a serial 2-fold dilution, from $1.3 \times 10^{-7}$ M to $1.3 \times 10^{-10}$ M. Equal volumes of antibody solutions and each of the antigen dilutions were mixed together and allowed to equilibrate at room temperature overnight. The next day, the pre-incubated antibody-antigen solutions were added to washed wells of the prepared plate at 100 μl per well. Following a 15 min incubation, the rest of the steps followed the protocol described above precisely.

The following equations were utilized in making $K_d$ calculations: $[Ab]=[AbT] (A/A_o)$; $[x]=[AbT] (A_o-A)/A_o$; $[Ag]=[AgT]-[x]$. Where $A_o$ is absorbance in the absence of soluble antigen, and A is absorbance at a particular antigen concentration. A graph plotting v/[Ag] versus v, where v=[x]/[AbT] was generated. From the slope of the graph, the affinity constant, $K_a$, and its reciprocal, $K_d$ for E3A5, were calculated. As can be seen in FIG. 56, the average Kd calculated from two replicate plates for E3A5 binding to H5 HA was $1.625 \times 10^{-9}$, with standard error of $3.75 \times 10^{-10}$.

Example 8

Production of Full-Length Ig Chains from TE-3A10-E3A5 and -C7F6 Cells, and Construction of Recombinant Retrovirus Expression Vectors In order to create cell lines producing the recombinant Ig genes isolated from clones E3A5 and C7F6, the full length heavy and light chain Ig genes were amplified from their cDNA. The variable regions were approximately 400 bp, while full length light chains were about 700 bp, and full length heavy chains were about 1400 bp (FIG. XXXA). In order to create the primers, a BLAST search of Genbank was performed using the cloned variable region sequences, to identify leader peptide sequences, for new primer design. Reverse primers for the C-termini of the constant regions of the heavy and light chains were derived from published sequences of those genes. The Primers used were: L-VλE3 (5'AAAAAAAAGCGGCCGCCATGGAATACCTATTGC-CTACGGCA3') (SEQ ID NO:41) and L-VλC7 (5'AAAAAAAGCGGCCGCCATGGCCTGGTCTC-CTCTCCTCCTC3') (SEQ ID NO:42) in combination with reverse primer CT-Cλ(5'AAAAAAAGGATCCTAWGAR CATTCTGYAGGGGCCACTGT3') (SEQ ID NO:43) for amplification of IgG light chains from E3A5 and C7F6 cDNAs, respectively. Similarly, L-Vh1 (5'AAAAAAGCG-GCCGCCATGGAGTTTGGGCT GAGCTGGGTTTTC3') (SEQ ID NO:44) and L-Vh3 (5'AAAAAAAGCGGCCGC-CATGGAGTTTGGGCTG AGCTGGCTTTTTC3') (SEQ ID NO:45) with reverse primer CT-CIgG1 (5'AAAAAAAGGATCCTCATTTACCCRGAGACA-GGGAGAGGC3') (SEQ ID NO:46) were used to amplify the heavy chains of C7F6 and E3A5, respectively. PCR reactions were performed using the AccuPrime Taq DNA polymerase (Invitrogen, #12339-016) with the provided PCR buffer I, and with primers at the final concentration of 1 μM each.

Full length heavy and light chains from both E3A5 and C7F6 cells were isolated (FIG. 57A).

Restriction enzyme sites incorporated into the forward and reverse primers allowed for direct insertion into expression vectors. Retroviral vectors were chosen for delivery of full length E3A5 and C7F6 Ig genes to CHO, 293 and myeloma cell lines, because retrovirus vectors integrate into the cell's DNA, allowing for rapid establishment of stable cell lines. In order to construct the retrovirus vectors, pQCXIN retrovirus vector (Clontech) were modified by replacing the neomycin resistance gene ($neo^R$) with a gene for enhanced green fluorescent protein (EGFP) to create pQCXIG (FIG. 57B). E3A5 and C7F6 Ig gene PCR products were purified using Qiagen spin columns, digested overnight with EcoR1 and Not1 restriction endonucleases (in EcoR1 buffer), and ligated with retroviral expression vector plasmids also digested with EcoR1 and Not1. Light chains were inserted into pQCXIN, to generate pQC.E3A5-LC.IN and pQC.C7F6-LC.IN, while heavy chains were cloned into pQCXIG, to generate pQC.E3A5-HC.IG and pQC.C7F6-HC.IG, as described in FIG. 57B.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,024,946
U.S. Patent Publn. 2006/0252124
Atherton et al., *Biol. Reprod.*, 32(1):155-171, 1985.
Audige et al., *J. Immunol.*, 177:6227-6237, 2006.
Bourke et al., *Blood*, 102:956-963, 2003.
Dholakia et al, *J. Biol. Chem.*, 264(34):20638-20642, 1989.
EP 0 161 941
EP 0 218 158
Friguet et al., *J. Immunol. Methods*, 77:305-319, 1985.
Hamilton-Williams et al., *J. Immunol.*, 174:1159-1163, 2005.
Johnson and Wu, *Nucleic Acids Res.*, 28(1):214-218, 2000.
Kanbe and Zhang, *Blood Cells Mol. Dis.*, 33:64-67, 2004.
Khatoon et al., *Ann. Neurol*, 26(2):210-215, 1989.
King et al., *J. Biol. Chem.*, 264(17):10210-10218, 1989.
Lanzavecchia et al., *Immunol. Rev.*, 211:303-309, 2006.
Miller and Lipman, *Proc. Natl. Acad. Sci. USA*, 70:190-194, 1973.
O'Doherty et al., *J. Virol.*, 74:10074-10080, 2000.
Owens and Haley, *Biochem. Biophys. Res Commun.*, 142 (3):964-971, 1987.
Potter and Haley, *Methods Enzymol*, 91:613-633, 1983.
Retter et al., *Nucleic Acids Res.*, 33:D671-674, 2005.
Speck et al., *J. Gen. Viral.*, 80:2193-2203, 1999.
Takekoshi et al., *J. Biochem.*, 130:299-303, 2001.
Traggia et al., *Nat. Med.*, 10(8):871-875, 2004.
Welschof et al, *J. Immunol. Methods*, 179:203-214, 1995.

The invention claimed is:

1. A method of producing an immortalized human B-cell repertoire comprising:
   (a) obtaining a population of human B cells;
   (b) centrifuging said B cells with Epstein-Barr virus (EBV) to infect said human B cells;
   (c) resuspending said B cells; and
   (d) culturing said B cells to produce an immortalized human B-cell repertoire.

2. The method of claim 1, wherein about 50%-99% of the B cells are immortalized by EBV infection.

3. The method of claim 2, wherein about 95%-99% of the B cells are immortalized by EBV infection.

4. The method of claim 1, further comprising isolating an immortalized human B cell from the cultured B cells.

5. The method of claim 1, wherein step (b) further comprises the use of concentrated EBV.

6. The method of claim 5, wherein the EBV is concentrated 10-fold.

7. The method of claim 6, wherein the EBV is concentrated by ultrafiltration.

8. The method of claim 5, wherein the centrifugation is performed at 900×G for 1 hour.

9. The method of claim 5, wherein about 50%-99% of the B cells are immortalized by EBV infection.

10. The method of claim 9, wherein about 95%-99% of the B cells are immortalized by EBV infection.

11. The method of claim 1, wherein the B cells of step (a) are primary B cells.

12. The method of claim 1, wherein the B cells of step (a) are an established B cell line.

13. A method of producing a monoclonal antibody comprising culturing the isolated immortalized B cell of claim 4, and screening for a monoclonal antibody secreted by said immortalized B cell.

14. The method of claim 13, further comprising isolating a nucleic acid encoding an entire antibody heavy and/or light chain from the B cell.

15. A method of producing a monoclonal antibody comprising:
   (a) transferring the nucleic acid of claim 14 into a cell, and
   (b) expressing the heavy and/or light chain.

16. The method of claim 4, further comprising isolating a nucleic acid encoding a heavy and/or light chain antigen-binding region from the B cell.

17. A method of producing a monoclonal antibody comprising:
   (a) transferring the nucleic acid of claim 16 into a cell, and
   (b) expressing the heavy and/or light chain.

18. The method of claim 4, wherein said immortalized human B-cell secretes an antibody which binds a viral antigen, a bacterial antigen, a fungal antigen, a parasite antigen, a toxin antigen, a cellular receptor antigen for virus entry, a cellular receptor for bacterial entry, a cellular receptor for fungus entry, a cellular receptor mediating parasite entry, a cellular receptor mediating toxin entry, a tumor antigen, a cytokine/chemokine/growth factor receptor antigen, an antigen on molecules mediating inflammation, an antigen on molecules mediating pain, an antigen on molecules mediating tissue injury/damage, an antigen on activation molecules/ligands/receptors, an antigen on molecules mediating innate immunity, an antigen on cellular adhesion molecules, an antigen on cellular adhesion molecule receptors, an antigen on over-expressed/under-glycosylated/oxidized/misfolded/mutated cellular proteins ("altered self"antigens) associated with a disease state, an antigen on molecules/ligands/receptors mediating cell apoptosis, an antigen on growth inhibitory molecules, H5N1hemagglutinin (H5 HA), cancer angiogenic molecular placenta induced growth factor (PLGF), cancer and autoimmunity associated factor interleukin-6 (IL6), *Staphylococcal* enterotoxins B (SEB), *Staphylococcal* enterotoxins C2 (SEC2), ricin subunit B, anthrax toxin, an Ebola virus antigen, ricin A chain, a *Yersinia pestis* antigen, a Marburg virus antigen, a MDR *Staphylococcus* antigen, cholera toxin, a herpes B virus antigen, or a hemorrhagic fever virus antigen.

* * * * *

SEQUENCE LISTING

<160> NUMBER OF SEQ ID NOS: 71

<210> SEQ ID NO 1
<211> LENGTH: 33
<212> TYPE: DNA
<213> ORGANISM: Artificial
<220> FEATURE:
<223> OTHER INFORMATION: Synthetic primer

<400> SEQUENCE: 1
tctagacagt ctgtgytgac kcagccgccc tca       33

<210> SEQ ID NO 2
<211> LENGTH: 33
<212> TYPE: DNA
<213> ORGANISM: Artificial
<220> FEATURE:
<223> OTHER INFORMATION: Synthetic primer

<400> SEQUENCE: 2
tctagacagt ctgcgctgac tcarccgscc tct       33

<210> SEQ ID NO 3
<211> LENGTH: 31
<212> TYPE: DNA
<213> ORGANISM: Artificial
<220> FEATURE:
<223> OTHER INFORMATION: Synthetic primer

<400> SEQUENCE: 3
tctagatcct atgaactgac tcagccaccy t       31

<210> SEQ ID NO 4
<211> LENGTH: 29
<212> TYPE: DNA
<213> ORGANISM: Artificial
<220> FEATURE:
<223> OTHER INFORMATION: Synthetic primer

<400> SEQUENCE: 4
tctagatctg aactgactca gccdscctc       29

<210> SEQ ID NO 5
<211> LENGTH: 30
<212> TYPE: DNA
<213> ORGANISM: Artificial
<220> FEATURE:
<223> OTHER INFORMATION: Synthetic primer

<400> SEQUENCE: 5
tctagatctg aactgactca ggaccctgyt       30

<210> SEQ ID NO 6
<211> LENGTH: 33
<212> TYPE: DNA
<213> ORGANISM: Artificial
<220> FEATURE:
<223> OTHER INFORMATION: Synthetic primer

<400> SEQUENCE: 6
tctagaratt ttatgctgac tcagccccac tct       33

<210> SEQ ID NO 7
<211> LENGTH: 30
<212> TYPE: DNA
<213> ORGANISM: Artificial

<220> FEATURE:
<223> OTHER INFORMATION: Synthetic primer

<400> SEQUENCE: 7
gtcgacagag gasggyggga acagagtgac          30

<210> SEQ ID NO 8
<211> LENGTH: 27
<212> TYPE: DNA
<213> ORGANISM: Artificial
<220> FEATURE:
<223> OTHER INFORMATION: Synthetic primer

<400> SEQUENCE: 8
tctagacatc srgatgaccc agtctcc          27

<210> SEQ ID NO 9
<211> LENGTH: 32
<212> TYPE: DNA
<213> ORGANISM: Artificial
<220> FEATURE:
<223> OTHER INFORMATION: Synthetic primer

<400> SEQUENCE: 9
tctagatatt gtgatgacyc agwctccact ct          32

<210> SEQ ID NO 10
<211> LENGTH: 28
<212> TYPE: DNA
<213> ORGANISM: Artificial
<220> FEATURE:
<223> OTHER INFORMATION: Synthetic primer

<400> SEQUENCE: 10
tctagaaatt gtrwtgacrc agtctcca          28

<210> SEQ ID NO 11
<211> LENGTH: 30
<212> TYPE: DNA
<213> ORGANISM: Artificial
<220> FEATURE:
<223> OTHER INFORMATION: Synthetic primer

<400> SEQUENCE: 11
gtcgacgaag acagatggtg cagccacagt          30

<210> SEQ ID NO 12
<211> LENGTH: 27
<212> TYPE: DNA
<213> ORGANISM: Artificial
<220> FEATURE:
<223> OTHER INFORMATION: Synthetic primer

<400> SEQUENCE: 12
tctagasagg tgcagctggt gcagtct          27

<210> SEQ ID NO 13
<211> LENGTH: 26
<212> TYPE: DNA
<213> ORGANISM: Artificial
<220> FEATURE:
<223> OTHER INFORMATION: Synthetic primer

<400> SEQUENCE: 13
tctagacagg trcagctgca gsagtc          26

<210> SEQ ID NO 14
<211> LENGTH: 25
<212> TYPE: DNA
<213> ORGANISM: Artificial
<220> FEATURE:
<223> OTHER INFORMATION: Synthetic primer

<400> SEQUENCE: 14
tctagaggtg cagctgktgg agtct    25

<210> SEQ ID NO 15
<211> LENGTH: 24
<212> TYPE: DNA
<213> ORGANISM: Artificial
<220> FEATURE:
<223> OTHER INFORMATION: Synthetic primer

<400> SEQUENCE: 15
gtcgacsgat gggcccttgg tgga    24

<210> SEQ ID NO 16
<211> LENGTH: 122
<212> TYPE: PRT
<213> ORGANISM: Artificial
<220> FEATURE:
<223> OTHER INFORMATION: Synthetic primer
<220> FEATURE:
<221> NAME/KEY: misc_feature
<222> LOCATION: (122)..(122)
<223> OTHER INFORMATION: Xaa can be any naturally occurring amino acid

<400> SEQUENCE: 16

Val Leu Thr Gln Pro Pro Ser Ala Ser Gly Thr Pro Gly Gln Arg Val
1               5                   10                  15

Thr Ile Ser Cys Ser Gly Ser Ser Asn Ile Gly Ser Asn Thr Val
            20                  25                  30

Asn Trp Tyr Gln Gln Leu Pro Gly Thr Ala Pro Lys Leu Leu Ile Tyr
        35                  40                  45

Ser Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Ser Leu Asn Gly
                85                  90                  95

Pro Val Phe Gly Gly Gly Thr Lys Leu Thr Val Leu Gly Asn Pro Lys
            100                 105                 110

Ala Ala Pro Ser Val Thr Leu Phe Pro Xaa
        115                 120

<210> SEQ ID NO 17
<211> LENGTH: 365
<212> TYPE: DNA
<213> ORGANISM: Artificial
<220> FEATURE:
<223> OTHER INFORMATION: Synthetic primer

<400> SEQUENCE: 17
gtgttgacgc agccgccctc agcgtctggg accccggggc agagggtcac catctcttgt    60
tctggaagca gctccaacat cggaagtaat actgtaaact ggtaccagca gctcccagga    120
acggccccca aactcctcat ctatagtaat aatcagcggc cctcaggggt ccctgaccga    180
ttctctggct ccaagtctgg cacctcagcc tccctggcca tcagtgggct ccagtctgag    240

```
gatgaggctg attattactg tgcagcatgg gatgacagcc tgaatggtcc ggtgttcggc    300
ggaaccaagc tgaccgtcct aggtcagccc aaggctgccc cctcggtcac tctgttcccg    360
ccctc                                                                 365
```

```
<210> SEQ ID NO 18
<211> LENGTH: 287
<212> TYPE: DNA
<213> ORGANISM: Artificial
<220> FEATURE:
<223> OTHER INFORMATION: Synthetic primer

<400> SEQUENCE: 18
```

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtataatca gcggccctca ggggtccctg   180
accgattctc tggctccaag tctggcacct cagcctccct ggccatcagt gggctccagt   240
ctgaggatga ggctgattat tactgtgcag catgggatga cagcctg                  287
```

```
<210> SEQ ID NO 19
<211> LENGTH: 128
<212> TYPE: PRT
<213> ORGANISM: Artificial
<220> FEATURE:
<223> OTHER INFORMATION: Synthetic primer
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid

<400> SEQUENCE: 19

Leu Thr Gln Pro Pro Ser Val Ser Gly Ala Pro Gly Gln Lys Val Thr
1               5                   10                  15

Ile Ser Cys Thr Gly Ser Gln Ser Val Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr His Cys Gln Ser Tyr Asp Ser Ser
                85                  90                  95

Leu Asn Gly Tyr Tyr Val Phe Gly Thr Gly Thr Lys Val Thr Val Leu
            100                 105                 110

Gly Gln Pro Lys Ala Asn Pro Thr Val Thr Leu Phe Xaa Pro Ser Xaa
        115                 120                 125
```

```
<210> SEQ ID NO 20
<211> LENGTH: 374
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (366)..(366)
```

<223> OTHER INFORMATION: n is a, c, g, or t

<400> SEQUENCE: 20

```
gttgacgcag ccgccctcag tgtctggggc cccagggcag aaggtcacca tctcctgcac    60
tgggagcagc tccaacatcg ggcaggttta tgatgtacac tggtaccagc agcttccagg   120
aacagccccc aaactcctca tctatggtaa cagcaatcgg ccctcagggg tccctgaccg   180
attctctggc tccaagtctg gcacctcagc ctccctggcc atcactgggc tccaggctga   240
ggatgaggct gattatcact gccagtccta cgacagcagc ctgaatggtt attatgtctt   300
cggaactggg accaaggtca ccgtcctagg tcagcccaag ccaaccccca ctgtcactct   360
gttccncccct cctc                                                    374
```

<210> SEQ ID NO 21
<211> LENGTH: 291
<212> TYPE: DNA
<213> ORGANISM: Artificial
<220> FEATURE:
<223> OTHER INFORMATION: Synthetic primer

<400> SEQUENCE: 21

```
cagtctgtgc tgacgcagcc gccctcagtg tctggggccc cagggcagaa ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctacg acagcagcct g            291
```

<210> SEQ ID NO 22
<211> LENGTH: 117
<212> TYPE: PRT
<213> ORGANISM: Artificial
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: Xaa can be any naturally occurring amino acid

<400> SEQUENCE: 22

```
Arg Xaa Gly Gly Gly Leu Val Gln Pro Gly Gly Ser Leu Arg Leu Ser
 1               5                  10                  15
Cys Ala Ala Ser Arg Phe Thr Phe Ser Arg Tyr Ala Met Asn Trp Val
                20                  25                  30
Arg Gln Ala Pro Gly Lys Gly Leu Glu Trp Val Ser Ser Ile Thr Gly
            35                  40                  45
Ser Gly Gly Arg Thr Phe Tyr Ala Asp Ser Val Lys Gly Arg Phe Thr
        50                  55                  60
Ile Ser Arg Asp Asn Ser Lys Asn Thr Leu Tyr Leu Gln Met Asn Ser
65                  70                  75                  80
Leu Arg Ala Glu Asp Thr Ala Leu Tyr Tyr Cys Ala Lys Pro Pro Thr
                85                  90                  95
Val Thr Thr Gly Asp Pro Phe Asp Ile Trp Gly Gln Gly Thr Met Val
            100                 105                 110
Thr Val Ser Ser Pro
        115
```

<210> SEQ ID NO 23
<211> LENGTH: 352

<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or t

<400> SEQUENCE: 23

```
gccggggngg gggaggcttg gtacagcctg gggggtccct gagactctcc tgtgcagcct    60
ctagattcac ctttagcaga tatgccatga actgggtccg ccaggctcca gggaaggggc   120
tggagtgggt ctcatctatt actggtagtg gtggtaggac atttatgca gactccgtga   180
agggccgctt caccatctcc agagacaatt ccaagaacac attgtatctg caaatgaaca   240
gcctgagagc cgaggacacg gccctttatt actgtgcgaa accccctacg gtgactacgg   300
ggatcctttt gatatctggg gccaagggac aatggtcacc gtctcttcac cc            352
```

<210> SEQ ID NO 24
<211> LENGTH: 294
<212> TYPE: DNA
<213> ORGANISM: Artificial
<220> FEATURE:
<223> OTHER INFORMATION: Synthetic primer

<400> SEQUENCE: 24

```
gaggtgcagc tggtggagtc tgggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaa          294
```

<210> SEQ ID NO 25
<211> LENGTH: 134
<212> TYPE: PRT
<213> ORGANISM: Artificial
<220> FEATURE:
<223> OTHER INFORMATION: Synthetic primer

<400> SEQUENCE: 25

```
Glu Val Gln Leu Val Gln Ser Gly Gly Gly Leu Ile Gln Pro Gly Gly
 1               5                  10                  15

Ser Leu Arg Leu Ser Cys Ala Ala Ser Gly Phe Thr Val Ser Asn Asn
            20                  25                  30

Tyr Ile Ser Trp Val Arg Gln Ala Pro Gly Lys Gly Leu Glu Trp Val
        35                  40                  45

Ser Val Ile Tyr Ser Gly Gly Ser Arg Tyr Tyr Pro Glu Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Tyr Glu Asp Thr Ala Val Tyr Tyr Cys Ala
                85                  90                  95

Arg Val Ser Cys Asn Ser Thr Ser Cys His Pro Val Tyr Val Arg Thr
            100                 105                 110

Thr Val Trp Thr Ser Gly Ala Lys Gly Pro Gln Ser Pro Ser Pro Gln
        115                 120                 125

Pro Pro Pro Arg Ala His
    130
```

<210> SEQ ID NO 26
<211> LENGTH: 403
<212> TYPE: DNA
<213> ORGANISM: Artificial
<220> FEATURE:
<223> OTHER INFORMATION: Synthetic primer

<400> SEQUENCE: 26

```
gaggtgcagc tggtgcagtc tggaggaggc ttgatccagc cggggggtc cctaagactc      60 tcctgtgcag cctctgggtt caccgtcagt aacaactaca tcagctgggt ccgccaggct     120
ccagggaagg ggctggagtg gtctcagtt atttatagcg gtggtagtag atactaccca     180
gagtccgtga agggccgatt caccatctcc agagacaatt ccaagaacac gctgtatctt    240
caaatgaaca gcctgagagt cgaggacacg cccgtgtatt actgtgcgag ggtttcttgt    300
aatagtacca gctgtcatcc cgtgtacgta cgtactacgg tatggacgtc tggggccaag    360
ggaccacagt caccgtctcc tcagcctcca ccaagggccc atc                      403
```

<210> SEQ ID NO 27
<211> LENGTH: 291
<212> TYPE: DNA
<213> ORGANISM: Artificial
<220> FEATURE:
<223> OTHER INFORMATION: Synthetic primer

<400> SEQUENCE: 27

```
gaggtgcagc tggtggagtc tggaggaggc ttgatccagc ctggggggtc cctgagactc     60
tcctgtgcag cctctggctt caccgtcagt agcaactaca tgagctgggt ccgccaggct    120
ccagggaagg ggctgcagtg gtctcagtt atttatagcg gtggtagcac atactacgca    180
gactccgtga agggccgatt caccatctcc agagacaatt ccaagaacac gctgtatctt    240
caaatgaaca gcctgagagc cgaggacacg cccgtgtatt actgtgcgag a             291
```

<210> SEQ ID NO 28
<211> LENGTH: 22
<212> TYPE: PRT
<213> ORGANISM: Artificial
<220> FEATURE:
<223> OTHER INFORMATION: Synthetic primer

<400> SEQUENCE: 28

Ser Ser Asn Ile Gly Ser Asn Thr Ser Asn Asn Ala Ala Trp Asp Asp
1               5                   10                  15
Ser Leu Asn Gly Pro Val
            20

<210> SEQ ID NO 29
<211> LENGTH: 24
<212> TYPE: PRT
<213> ORGANISM: Artificial
<220> FEATURE:
<223> OTHER INFORMATION: Synthetic primer

<400> SEQUENCE: 29

Ser Ser Asn Ile Gly Ala Gly Tyr Asp Gly Asn Ser Gln Ser Tyr Asp
1               5                   10                  15
Ser Ser Leu Asn Gly Tyr Tyr Val
            20

<210> SEQ ID NO 30

```
<211> LENGTH: 31
<212> TYPE: PRT
<213> ORGANISM: Artificial
<220> FEATURE:
<223> OTHER INFORMATION: Synthetic primer

<400> SEQUENCE: 30

Arg Phe Thr Phe Ser Arg Tyr Ala Ile Thr Gly Ser Gly Gly Arg Thr
1               5                   10                  15

Ala Lys Pro Pro Thr Val Thr Thr Gly Asp Pro Phe Asp Ile Trp
            20                  25                  30

<210> SEQ ID NO 31
<211> LENGTH: 48
<212> TYPE: PRT
<213> ORGANISM: Artificial
<220> FEATURE:
<223> OTHER INFORMATION: Synthetic primer

<400> SEQUENCE: 31

Gly Phe Thr Val Ser Asn Asn Tyr Ile Tyr Ser Gly Ser Arg Ala
1               5                   10                  15

Arg Val Ser Cys Asn Ser Thr Ser Cys His Pro Val Tyr Val Arg Thr
            20                  25                  30

Thr Val Trp Thr Ser Gly Ala Lys Gly Pro Gln Ser Pro Ser Pro Gln
        35                  40                  45

<210> SEQ ID NO 32
<211> LENGTH: 121
<212> TYPE: PRT
<213> ORGANISM: Artificial
<220> FEATURE:
<223> OTHER INFORMATION: Synthetic primer

<400> SEQUENCE: 32

Val Ser Ala Ala Pro Gly Gln Lys Pro Thr Ile Ser Cys Ser Gly Ser
1               5                   10                  15

Ser Ser Asn Ile Gly Thr Asp Tyr Val Ser Trp Gln Gln Leu Pro Gly
            20                  25                  30

Thr Ala Pro Lys Leu Ile Tyr Asp Asn Asn Lys Arg Pro Ser Gly Met
        35                  40                  45

Pro Asp Arg Phe Ser Ser Lys Ser Gly Thr Ser Ala Thr Leu Gly Ile
50                  55                  60

Thr Gly Leu Gln Thr Gly Asp Glu Ala Asp Tyr Tyr Gly Thr Trp Asp
65                  70                  75                  80

Ser Ser Leu Asn Gly Pro Val Val Phe Gly Gly Thr Lys Leu Thr
                85                  90                  95

Val Leu Gly His His Ala Ala Ala Ser Val Thr Leu Phe Leu Pro Ser
                100                 105                 110

Ser Pro Asp Val Thr Ile Lys Ile Lys
        115                 120

<210> SEQ ID NO 33
<211> LENGTH: 366
<212> TYPE: DNA
<213> ORGANISM: Artificial
<220> FEATURE:
<223> OTHER INFORMATION: Synthetic primer

<400> SEQUENCE: 33
gtgtctgcgg cccccaggaca gaaggtcacc atctcctgct ctggaagcag ctccaacatt    60
```

```
gggactgatt atgtatcctg gtaccagcag ctcccaggaa cagcccccaa actcatctat    120
gataataata agcgaccctc agggatgcct gaccgattct cttccaagtc tggcacctca    180
gccaccctgg gcatcaccgg actccagact ggggatgagg ctgattatta cggaacatgg    240
gatagcagcc tgaatggtcc tgtggtattc ggcggaggga ccaagctgac cgtcctaggt    300
catcatgctg ccgcctccgt cactctgttt ctgccatcct ctgttgacgt ctttattaaa    360
attaaa                                                               366
```

<210> SEQ ID NO 34
<211> LENGTH: 109
<212> TYPE: PRT
<213> ORGANISM: Artificial
<220> FEATURE:
<223> OTHER INFORMATION: Synthetic primer

<400> SEQUENCE: 34

Gln Ser Val Leu Thr Gln Phe Pro Ser Val Ala Ala Pro Gly Gln
1               5                   10                  15

Lys Pro Thr Ile Ser Cys Ser Gly Ser Ser Asn Ile Gly Asn Met
            20                  25                  30

Val Ser Trp Gln Gln Leu Pro Gly Thr Ala Pro Lys Leu Ile Tyr Leu
        35                  40                  45

Asn Asn Lys Arg Pro Ser Gly Ile Pro Asp Arg Phe Ser Ser Lys Ser
    50                  55                  60

Gly Thr Ser Ala Thr Leu Gly Ile Thr Gly Leu Gln Thr Gly Asp Glu
65                  70                  75                  80

Ala Asp Tyr Tyr Gly Thr Trp Asp Ser Ser Leu Asn Gly Pro Val Val
                85                  90                  95

Phe Gly Gly Gly Thr Lys Leu Thr Val Leu Gly His His
            100                 105

<210> SEQ ID NO 35
<211> LENGTH: 333
<212> TYPE: DNA
<213> ORGANISM: Artificial
<220> FEATURE:
<223> OTHER INFORMATION: Synthetic primer

<400> SEQUENCE: 35

```
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag ccccccaaact catctatgaa aataataagc gacgctcagg gattcctgac   180
cgattctctt ccaagtctgg cacgtcagcc accctgggca tcaccggact ccagactggg   240
gacgaggccg attattacgg aacatgggat agcagcctga atggtcctgt ggtattcggc   300
ggagggacca agctgaccgt cctaggtcat cat                                 333
```

<210> SEQ ID NO 36
<211> LENGTH: 95
<212> TYPE: PRT
<213> ORGANISM: Artificial
<220> FEATURE:
<223> OTHER INFORMATION: Synthetic primer

<400> SEQUENCE: 36

Ser Ser Ala Phe Ser Ser Leu Ala Met Ser Trp Val Arg Gln Ala Pro
1               5                   10                  15

Gly Gln Gly Leu Glu Trp Val Ser Ala Ile Ile Gly Ser Gly Gly Ser

```
            20                  25                  30
Thr Tyr Tyr Ala Asp Ser Val Lys Gly Asp Phe Thr Ile Ser Arg Asp
         35                  40                  45

Asn Ser Lys Asn Thr Pro Leu Gln Met Asn Ser Leu Arg Ala Glu Asp
 50                  55                  60

Thr Ala Pro Tyr Tyr Cys Leu Lys Thr Pro Thr Cys Thr Thr Gly Val
 65                  70                  75                  80

Leu Leu Asp Tyr Cys Gly Gln Gly Thr Leu Val Ser Val Ser Ser
                 85                  90                  95
```

<210> SEQ ID NO 37
<211> LENGTH: 289
<212> TYPE: DNA
<213> ORGANISM: Artificial
<220> FEATURE:
<223> OTHER INFORMATION: Synthetic primer

<400> SEQUENCE: 37

```
tagcagcgcc ttcagcagct tggccatgag ctgggtccgc caggctccag ggcaggggct   60
ggagtgggtg tcagctatca ttggtagtgg tggtagcaca tattatgcag actctgtgaa  120
gggccgcttc accatctcca gagacaattc caagaacaca ccgtatcttc aaatgaacag  180
cctgagagcc gaggacacgg ccgtgtatta ctgtttgaaa accctacgt gcactacggg   240
ggttctctta gactactgcg gccaggggac cctggtctcc gtctcctcc              289
```

<210> SEQ ID NO 38
<211> LENGTH: 288
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (75)..(75)
<223> OTHER INFORMATION: n is a, c, g, or t

<400> SEQUENCE: 38

```
tcaacacaac ggttcccagt tacatccatg ttgtttcaaa cagcggggtc cctgagagtc   60
tcgtgtgcag cgtcnggatt caccttagc agctatgcca tgagctgggt ccgccaggct  120
ccagggaagg ggctggagtg gtctctcagct attagtggta gtggtggtag cacatactac  180
gcagactccg tgaagggccg gttcacgatc tccagagaca attccaagaa cacgctgtat  240
ctgcaaatga acagcctgag agccgaggac acggcggtat attactgt              288
```

<210> SEQ ID NO 39
<211> LENGTH: 23
<212> TYPE: PRT
<213> ORGANISM: Artificial
<220> FEATURE:
<223> OTHER INFORMATION: Synthetic primer

<400> SEQUENCE: 39

```
Ser Ser Asn Ile Gly Thr Asp Tyr Asp Asn Asn Gly Thr Trp Asp Ser
  1               5                  10                  15
Ser Leu Asn Gly Pro Cys Val
                 20
```

<210> SEQ ID NO 40
<211> LENGTH: 35
<212> TYPE: PRT
<213> ORGANISM: Artificial

<220> FEATURE:
<223> OTHER INFORMATION: Synthetic primer

<400> SEQUENCE: 40

Ser Ser Ala Phe Ser Ser Leu Ala Ile Ile Gly Ser Gly Gly Ser Thr
1               5                   10                  15

Leu Lys Thr Pro Thr Cys Thr Thr Gly Val Leu Leu Asp Tyr Cys Gly
            20                  25                  30

Gln Gly Thr
        35

<210> SEQ ID NO 41
<211> LENGTH: 41
<212> TYPE: DNA
<213> ORGANISM: Artificial
<220> FEATURE:
<223> OTHER INFORMATION: Synthetic primer

<400> SEQUENCE: 41
aaaaaaaagc ggccgccatg gaatacctat tgcctacggc a                    41

<210> SEQ ID NO 42
<211> LENGTH: 40
<212> TYPE: DNA
<213> ORGANISM: Artificial
<220> FEATURE:
<223> OTHER INFORMATION: Synthetic primer

<400> SEQUENCE: 42
aaaaaaagcg gccgccatgg cctggtctcc tctcctcctc                      40

<210> SEQ ID NO 43
<211> LENGTH: 39
<212> TYPE: DNA
<213> ORGANISM: Artificial
<220> FEATURE:
<223> OTHER INFORMATION: Synthetic primer

<400> SEQUENCE: 43
aaaaaaagga tcctawgarc attctgyagg ggccactgt                       39

<210> SEQ ID NO 44
<211> LENGTH: 42
<212> TYPE: DNA
<213> ORGANISM: Artificial
<220> FEATURE:
<223> OTHER INFORMATION: Synthetic primer

<400> SEQUENCE: 44
aaaaaagcgg ccgccatgga gtttgggctg agctgggttt tc                   42

<210> SEQ ID NO 45
<211> LENGTH: 43
<212> TYPE: DNA
<213> ORGANISM: Artificial
<220> FEATURE:
<223> OTHER INFORMATION: Synthetic primer

<400> SEQUENCE: 45
aaaaaagcgg ccgccatgga gtttgggctg agctggcttt ttc                  43

<210> SEQ ID NO 46
<211> LENGTH: 39
<212> TYPE: DNA
<213> ORGANISM: Artificial

<220> FEATURE:
<223> OTHER INFORMATION: Synthetic primer

<400> SEQUENCE: 46
aaaaaaagga tcctcattta cccrgagaca gggagaggc                    39

<210> SEQ ID NO 47
<211> LENGTH: 107
<212> TYPE: PRT
<213> ORGANISM: Artificial
<220> FEATURE:
<223> OTHER INFORMATION: Synthetic peptide

<400> SEQUENCE: 47

Val Ser Gly Ala Pro Gly Gln Lys Val Thr Ile Ser Cys Ser Gly Ser
1               5                   10                  15

Ser Ser Asn Ile Gly Ala Gly Tyr Asp Val His Cys Tyr Gln Leu Leu
            20                  25                  30

Gln Gly Thr Ala Pro Lys Leu Leu Ile Tyr Gly Asn Ser Tyr Arg Pro
        35                  40                  45

Ser Gly Val Asp Asp Arg Phe Cys Gly Ser Lys Ser Gly Thr Ser Ala
    50                  55                  60

Leu Val Val Ile Ser Gly Leu His Ala Asp Asp Ala Asp Tyr Cys
65                  70                  75                  80

Cys Gln Ser Tyr Asp Ser Ile Leu Asp Gly Tyr Tyr Val Phe Gly Thr
                85                  90                  95

Gly Thr Lys Val Thr Val Leu Arg Gln Ala Ala
            100                 105

<210> SEQ ID NO 48
<211> LENGTH: 321
<212> TYPE: DNA
<213> ORGANISM: Artificial
<220> FEATURE:
<223> OTHER INFORMATION: Synthetic primer

<400> SEQUENCE: 48
gtgtctgggg ccccagggca gaaggtcacc atctcctgct ctggaagcag ctccaacatc    60
ggggctggtt atgatgtaca ctgctaccag ctgcttcaag gaacagcccc caaactcctc   120
atttatggta acagctatcg gccctcaggg gtcgatgacc gattctgtgg ctccaagtct   180
ggcacctcag ccttggtggt catcagtggg ctccatgctg atgatgatgc tgattattgc   240
tgccagtcct acgacagcat cctggatggt tattatgtct tcggaactgg gaccaaggtc   300
accgtcctac gtcaggctgc g                                             321

<210> SEQ ID NO 49
<211> LENGTH: 97
<212> TYPE: PRT
<213> ORGANISM: Artificial
<220> FEATURE:
<223> OTHER INFORMATION: Synthetic peptide

<400> SEQUENCE: 49

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

```
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
                85                  90                  95
Leu
```

```
<210> SEQ ID NO 50
<211> LENGTH: 291
<212> TYPE: DNA
<213> ORGANISM: Artificial
<220> FEATURE:
<223> OTHER INFORMATION: Synthetic primer

<400> SEQUENCE: 50
cagtctgtcg tgacgcagcc gccctcagtg tctggggccc cagggcagag ggtcaccatc    60
tcctgcactg ggagcagctc caacatcggg gcaggttatg atgtacactw ctaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct g            291
```

```
<210> SEQ ID NO 51
<211> LENGTH: 97
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 51

Xaa Leu Lys Pro Phe Xaa Ala Glu Val Lys Lys Pro Gly Ala Ser Val
1               5                   10                  15
Lys Val Ser Cys Lys Ala Ser Gly Tyr Thr Phe Thr Ser Tyr Cys Ile
                20                  25                  30
Trp Trp Val Arg Gln Ala Pro Gly Gln Gly Leu Glu Trp Met Gly Ser
            35                  40                  45
Ile Asn Pro Ile Asp Gly Ala Ile Asn Tyr Ala Gln Lys Phe Gln Gly
    50                  55                  60
Lys Val Thr Ile Ser Ala Asp Lys Ser Ile Ser Thr Ala Tyr Met Gln
65                  70                  75                  80
Leu Ser Ser Leu Lys Ala Glu Asp Thr Ala Val Tyr Tyr Cys Ala Arg
                85                  90                  95
Glu
```

```
<210> SEQ ID NO 52
<211> LENGTH: 289
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (15)..(15)
```

<223> OTHER INFORMATION: n is a, c, g, or t

<400> SEQUENCE: 52

```
tttaaagcct tcanggcag aggtgaagaa gcctggggcc tctgtgaagg tctcctgcaa      60
ggcttctgga tacaccttca ccagctattg tatcaactgg gtgcgacagg cgcctggaca    120
agggctggag tggatgggaa gcatcaatcc tattgacggt gcaacaaact acgcacagaa    180
gttccagggc aaagtcacca tttcagcgga caagtccatc agcacagcct acatgcagtt    240
gagcagcctg aaagctgagg acacggccgt gtattactgt gcgagagag                289
```

<210> SEQ ID NO 53
<211> LENGTH: 97
<212> TYPE: PRT
<213> ORGANISM: Artificial
<220> FEATURE:
<223> OTHER INFORMATION: Synthetic peptide

<400> SEQUENCE: 53

```
Gln Val Gln Val Gln Ser Gly Ala Glu Val Lys Lys Pro Gly Ser Ser
1               5                   10                  15

Val Lys Val Ser Cys Lys Ala Ser Gly Gly Thr Phe Ser Ser Tyr Ala
            20                  25                  30

Ile Ser Trp Val Arg Gln Ala Pro Gly Gln Gly Leu Glu Trp Met Gly
        35                  40                  45

Arg Ile Ile Pro Ile Leu Gly Ile Ala Asn Tyr Ala Gln Lys Phe Gln
    50                  55                  60

Gly Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg
```

<210> SEQ ID NO 54
<211> LENGTH: 294
<212> TYPE: DNA
<213> ORGANISM: Artificial
<220> FEATURE:
<223> OTHER INFORMATION: Synthetic primer

<400> SEQUENCE: 54

```
caggtccagc tggtgcagtc tggggctgag gtgaagaagc ctgggtcctc ggtgaaggtc      60
tcctgcaagg cttctggagg cacccttcagc agctatgcta tcagctgggt gcgacaggcc   120
cctggacaag ggcttgagtg gatgggaagg atcatcccta tccttggtat agcaaactac   180
gcacagaagt tccagggcag agtcacgatt accgcggaca atccacgag cacagcctac    240
atggagctga gcagcctgag atctgaggac acggccgtgt attactgtgc gaga          294
```

<210> SEQ ID NO 55
<211> LENGTH: 122
<212> TYPE: PRT
<213> ORGANISM: Artificial
<220> FEATURE:
<223> OTHER INFORMATION: Synthetic peptide

<400> SEQUENCE: 55

```
Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
                100                 105                 110

Pro Lys Ala Ala Pro Ser Val Thr Leu Phe
                115                 120

<210> SEQ ID NO 56
<211> LENGTH: 366
<212> TYPE: DNA
<213> ORGANISM: Artificial
<220> FEATURE:
<223> OTHER INFORMATION: Synthetic primer

<400> SEQUENCE: 56
tcctatgaac tgactcagcc accttcagcg tctgggaccc ccgggcagag ggtcaccatc    60
tcttgttctg gaagcagctc aacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggtccggtg   300
ttcggcggag ggaccaagct gaccgtccta ggtcagccca aggctgcccc ctcggtcact   360
ctgttc                                                               366

<210> SEQ ID NO 57
<211> LENGTH: 96
<212> TYPE: PRT
<213> ORGANISM: Artificial
<220> FEATURE:
<223> OTHER INFORMATION: Synthetic peptide

<400> SEQUENCE: 57

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

<210> SEQ ID NO 58
<211> LENGTH: 288
<212> TYPE: DNA
<213> ORGANISM: Artificial
<220> FEATURE:
<223> OTHER INFORMATION: Synthetic primer
```

<400> SEQUENCE: 58

```
cagtctgtgc tgactcagcc accctcagcg tctgggaccc ccggggcagag ggtcaccatc    60
tcttgttctg gaagcagctc caacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctg                288
```

<210> SEQ ID NO 59
<211> LENGTH: 108
<212> TYPE: PRT
<213> ORGANISM: Artificial
<220> FEATURE:
<223> OTHER INFORMATION: Synthetic peptide

<400> SEQUENCE: 59

```
Val Ser Glu Ser Pro Gly Lys Thr Val Thr Ile Ser Cys Thr Arg Ser
1               5                  10                  15
Ser Gly Ser Ile Ala Ser Asn Tyr Val Gln Trp Tyr Gln Gln Arg Pro
            20                  25                  30
Gly Ser Ser Pro Thr Thr Val Ile Tyr Glu Asp Asn Gln Arg Pro Ser
        35                  40                  45
Gly Val Pro Asp Arg Phe Ser Gly Ser Ile Asp Ser Ser Ser Asn Ser
    50                  55                  60
Ala Ser Leu Thr Ile Ser Gly Leu Lys Thr Glu Asp Glu Ala Asp Tyr
65                  70                  75                  80
Tyr Cys Gln Ser Tyr Asp Ser Ser Asn Trp Val Phe Gly Gly Gly Thr
                85                  90                  95
Lys Leu Thr Val Leu Ser Gln Pro Lys Ala Ala Pro
            100                 105
```

<210> SEQ ID NO 60
<211> LENGTH: 324
<212> TYPE: DNA
<213> ORGANISM: Artificial
<220> FEATURE:
<223> OTHER INFORMATION: Synthetic primer

<400> SEQUENCE: 60

```
gtgtcggagt ctccggggaa gacggtaacc atctcctgca cccgcagcag tggcagcatt    60
gccagcaact atgtgcagtg gtaccagcag cgcccgggca gttcccccac cactgtgatc   120
tatgaggata ccaaagacc ctctggggtc cctgatcggt tctctggctc catcgacagc   180
tcctccaact ctgcctccct caccatctct ggactgaaga ctgaggacga ggctgactac   240
tactgtcagt cttatgatag cagcaattgg gtgttcggcg agggaccaa gctgaccgtc   300
ctaagtcagc ccaaggctgc cccc                                          324
```

<210> SEQ ID NO 61
<211> LENGTH: 98
<212> TYPE: PRT
<213> ORGANISM: Artificial
<220> FEATURE:
<223> OTHER INFORMATION: Synthetic peptide

<400> SEQUENCE: 61

```
Asn Phe Met Leu Thr Gln Pro His Ser Val Ser Glu Ser Pro Gly Lys
1               5                  10                  15
Thr Val Thr Ile Ser Cys Thr Arg Ser Ser Gly Ser Ile Ala Ser Asn
```

```
                    20                  25                  30
Tyr Val Gln Trp Tyr Gln Gln Arg Pro Gly Ser Ser Pro Thr Thr Val
                35                  40                  45

Ile Tyr Glu Asp Asn Gln Arg Pro Ser Gly Val Pro Asp Arg Phe Ser
         50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn

<210> SEQ ID NO 62
<211> LENGTH: 294
<212> TYPE: DNA
<213> ORGANISM: Artificial
<220> FEATURE:
<223> OTHER INFORMATION: Synthetic primer

<400> SEQUENCE: 62
aattttatgc tgactcagcc ccactctgtg tcggagtctc cggggaagac ggtaaccatc      60
tcctgcaccc gcagcagtgg cagcattgcc agcaactatg tgcagtggta ccagcagcgc     120
ccgggcagtt cccccaccac tgtgatctat gaggataacc aaagacccctc tggggtccct    180 gatcggttct ctggctccat cgacagctcc tccaactctg cctccctcac catctctgga    240
ctgaagactg aggacgaggc tgactactac tgtcagtctt atgatagcag caat          294

<210> SEQ ID NO 63
<211> LENGTH: 126
<212> TYPE: PRT
<213> ORGANISM: Artificial
<220> FEATURE:
<223> OTHER INFORMATION: Synthetic peptide

<400> SEQUENCE: 63

Glu Val Gln Leu Val Gln Ser Gly Gly Gly Leu Val Gln Pro Gly Glu
 1               5                  10                  15

Ser Leu Arg Leu Ser Cys Ala Ala Ser Gly Phe Thr Phe Ser Ser His
                20                  25                  30

Pro Met Ser Trp Val Arg Gln Ala Pro Gly Lys Gly Leu Glu Trp Val
                35                  40                  45

Ser Ala Ile Ser Gly Ser Gly Asp Asp Thr Tyr Tyr Ala Asp Ser Val
         50                  55                  60

Thr Gly Arg Phe Ile Ile Ser Arg Asp Asn Ser Glu Asn Thr Leu Tyr
 65                  70                  75                  80

Leu Gln Met Ser Ser Leu Arg Ala Glu Asp Thr Ala Val Tyr Tyr Cys
                 85                  90                  95

Ala Lys Gly Gly Pro Phe Cys Phe Gly Gly Gln Gly Thr Leu Val Thr
                100                 105                 110

Val Ser Ser Ala Ser Thr Lys Gly Pro Ser Val Asp Phe Phe
                115                 120                 125

<210> SEQ ID NO 64
<211> LENGTH: 378
<212> TYPE: DNA
<213> ORGANISM: Artificial
<220> FEATURE:
<223> OTHER INFORMATION: Synthetic primer

<400> SEQUENCE: 64
```

-continued

```
gaggtgcagc tggtgcagtc tgggggaggc ttggtacagc ctggggagtc cctgagactc      60
tcctgtgcag cctctggatt cacctttagc agccatccca tgagctgggt ccgccaggct     120
ccagggaagg ggctggagtg ggtctcagct attagtggta gtggtgatga cacatactac     180
gcagactccg tgacgggccg gttcatcatc tccagagaca attccgagaa tacgctgtat     240
ctgcaaatga gcagcctgag agccgaggac acggccgtat attactgtgc gaaggggggg     300 ccgtttttgct tcgggggcca gggaaccctg gtcaccgtct cctcagcctc caccaagggc     360
ccatcgtgcg acttttttt                                                    378
```

<210> SEQ ID NO 65
<211> LENGTH: 98
<212> TYPE: PRT
<213> ORGANISM: Artificial
<220> FEATURE:
<223> OTHER INFORMATION: Synthetic peptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 66
<211> LENGTH: 294
<212> TYPE: DNA
<213> ORGANISM: Artificial
<220> FEATURE:
<223> OTHER INFORMATION: Synthetic primer

<400> SEQUENCE: 66

```
gaggtgcagc tggtggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaa           294
```

<210> SEQ ID NO 67
<211> LENGTH: 24
<212> TYPE: PRT
<213> ORGANISM: Artificial
<220> FEATURE:
<223> OTHER INFORMATION: Synthetic peptide

<400> SEQUENCE: 67

Ser Ser Asn Ile Gly Ala Gly Tyr Asp Gly Asn Ser Gln Ser Tyr Asp
1               5                   10                  15

Ser Ile Leu Asp Gly Tyr Tyr Val

```
<210> SEQ ID NO 68
<211> LENGTH: 22
<212> TYPE: PRT
<213> ORGANISM: Artificial
<220> FEATURE:
<223> OTHER INFORMATION: Synthetic peptide

<400> SEQUENCE: 68

Ser Ser Asn Ile Gly Ser Asn Thr Ser Asn Asn Ala Ala Trp Asp Asp
1               5                   10                  15

Ser Leu Asn Gly Pro Val
            20

<210> SEQ ID NO 69
<211> LENGTH: 20
<212> TYPE: PRT
<213> ORGANISM: Artificial
<220> FEATURE:
<223> OTHER INFORMATION: Synthetic peptide

<400> SEQUENCE: 69

Ser Gly Ser Ile Ala Ser Asn Tyr Glu Asp Asn Gln Ser Tyr Asp Ser
1               5                   10                  15

Ser Asn Trp Val
            20

<210> SEQ ID NO 70
<211> LENGTH: 18
<212> TYPE: PRT
<213> ORGANISM: Artificial
<220> FEATURE:
<223> OTHER INFORMATION: Synthetic peptide

<400> SEQUENCE: 70

Gly Tyr Thr Phe Thr Ser Tyr Cys Ile Asn Pro Ile Asp Gly Ala Thr
1               5                   10                  15

Ala Arg

<210> SEQ ID NO 71
<211> LENGTH: 27
<212> TYPE: PRT
<213> ORGANISM: Artificial
<220> FEATURE:
<223> OTHER INFORMATION: Synthetic peptide

<400> SEQUENCE: 71

Gly Phe Thr Phe Ser Ser His Pro Ile Ser Gly Ser Gly Asp Asp Thr
1               5                   10                  15

Ala Lys Gly Gly Pro Phe Cys Phe Gly Gly Gln
            20                  25
```